United States Patent
Bilcer et al.

(10) Patent No.: US 11,667,645 B2
(45) Date of Patent: Jun. 6, 2023

(54) GRANZYME B DIRECTED IMAGING AND THERAPY

(71) Applicant: CytoSite Biopharma Inc., Sudbury, MA (US)

(72) Inventors: Geoffrey Malcolm Bilcer, Shorewood, MN (US); Terence Alfred Kelly, Ridgefield, CT (US)

(73) Assignee: CytoSite Biopharma Inc., Sudbury, MA (US)

( * ) Notice: Subject to any disclaimer, the term of this patent is extended or adjusted under 35 U.S.C. 154(b) by 0 days.

(21) Appl. No.: 16/969,823

(22) PCT Filed: Feb. 13, 2019

(86) PCT No.: PCT/US2019/017802
§ 371 (c)(1),
(2) Date: Aug. 13, 2020

(87) PCT Pub. No.: WO2019/160916
PCT Pub. Date: Aug. 22, 2019

(65) Prior Publication Data
US 2020/0369673 A1 Nov. 26, 2020

Related U.S. Application Data

(60) Provisional application No. 62/724,433, filed on Aug. 29, 2018, provisional application No. 62/629,949, filed on Feb. 13, 2018.

(51) Int. Cl.
| | | |
|---|---|---|
| *A61K 31/55* | (2006.01) | |
| *A61K 38/06* | (2006.01) | |
| *A61K 49/04* | (2006.01) | |
| *A61K 51/04* | (2006.01) | |
| *A61P 37/00* | (2006.01) | |
| *A61P 37/02* | (2006.01) | |
| *C07K 5/08* | (2006.01) | |
| *C07D 487/06* | (2006.01) | |
| *C07D 498/06* | (2006.01) | |
| *A61B 6/03* | (2006.01) | |

(52) U.S. Cl.
CPC ........ *C07D 487/06* (2013.01); *A61K 51/0468* (2013.01); *C07D 498/06* (2013.01); *A61B 6/037* (2013.01)

(58) Field of Classification Search
CPC ........ A61K 31/55; A61K 38/06; A61K 49/04; A61K 51/0468; A61P 37/00; A61P 37/02; A61B 6/037; C07K 5/0808; C07D 487/06
See application file for complete search history.

(56) References Cited

U.S. PATENT DOCUMENTS

| | | |
|---|---|---|
| 9,605,021 B2 | 3/2017 | Cameron |
| 2006/0019945 A1 | 1/2006 | Chapman et al. |
| 2010/0190688 A1 | 7/2010 | Chao et al. |
| 2014/0056964 A1 | 2/2014 | Hiebert et al. |

FOREIGN PATENT DOCUMENTS

| | | |
|---|---|---|
| WO | WO 02/070544 A2 | 9/2002 |
| WO | WO 2014/139014 A1 | 9/2014 |
| WO | WO 2018/005926 A1 | 1/2018 |
| WO | 2019/160916 A1 | 8/2019 |

OTHER PUBLICATIONS

Kim et al., Approaches to design non-covalent inhibitors for human granzyme B (hGrB). Org Biomol Chem. Nov. 28, 2014;12(44):8952-65.
Willoughby et al., Discovery of potent, selective human granzyme B inhibitors that inhibit CTL mediated apoptosis. Bioorg Med Chem Lett. Aug. 19, 2002;12(16):2197-200.
U.S. Appl. No. 17/430,180, filed Aug. 11, 2021, Bilcer et al.

*Primary Examiner* — Brenda L Coleman
(74) *Attorney, Agent, or Firm* — McDermott Will & Emery LLP

(57) ABSTRACT

Provided herein are heterocyclic compounds useful for imaging Granzyme B. Methods of imaging Granzyme B, combination therapies, and kits comprising the Granzyme B imaging agents are also provided.

14 Claims, No Drawings

GRANZYME B DIRECTED IMAGING AND THERAPY

CROSS-REFERENCE TO RELATED APPLICATIONS

This application is a U.S. National Stage Application under 35 U.S.C. § 371 of International Patent Application No. PCT/US2019/017802, filed Feb. 13, 2019, which claims the benefit of U.S. Provisional Application No. 62/629,949, filed on Feb. 13, 2018 and U.S. Provisional Application No. 62/724,433, filed on Aug. 29, 2018, each of which are incorporated herein by reference.

RELATED APPLICATIONS

This application claims the benefit of U.S. Provisional Application No. 62/629,949, filed on Feb. 13, 2018 and U.S. Provisional Application No. 62/724,433, filed on Aug. 29, 2018, the entire contents of both, which are incorporated herein by reference.

TECHNICAL FIELD

This disclosure relates to compounds useful for imaging techniques, and more particularly to compounds that are useful for imaging Granzyme B using medical imaging, including positron emission tomography.

BACKGROUND

Granzyme B is a serine-protease released through exocytosis by cytotoxic lymphocytes (CTL) during the cellular immune response, and represents one of the two dominant mechanisms, along with the FAS/FASL pathway, by which T-cells mediate cancer-cell death. Granzyme B is released along with the pore-forming protein perforin at the immunological-synapse formed between T-cells and their targets. A portion of the released Granzyme B then enters cancer cells, primarily through perforin-pores, where it activates multiple substrates leading to activation of the caspase cascade.

SUMMARY

The present application provides heterocyclic compounds of Formula I-VIII below and their use as imaging agents or therapy both related to Granzyme B.

In one aspect, this disclosure relates to a compound of Formula I or a pharmaceutically acceptable salt thereof, or a stereoisomer or tautomer thereof:

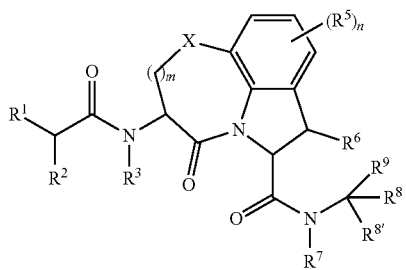

(I)

wherein:
m is 0, 1, or 2;
n is 1, 2, or 3;
$R^1$ and $R^2$ are each independently selected from the group consisting of: hydrogen, $C_{1-6}$ alkyl, $C_{1-6}$ alkoxy, $C_{3-6}$ cycloalkyl, $C_{6-10}$ aryl, HET and $-NR^{10}R^{12}$, wherein each $C_{1-6}$ alkyl, $C_{1-6}$ alkoxy, $C_{3-6}$ cycloalkyl, are optionally substituted with 1, 2, or 3 substituents independently selected from the group consisting of halo and hydroxy, and each $C_{6-10}$ aryl and HET are optionally substituted with 1, 2, or 3 substituents independently selected from the group consisting of oxo, halo, hydroxy, $C_{1-4}$ alkyl and $C_{1-4}$ haloalkyl;
or $R^1$ and $R^2$ may come together, with the carbon atom to which they are attached, to form a 5-6 membered cycloalkyl or 5-6 heterocycloalkyl group, each of which may be optionally substituted with 1, 2, or 3 $R^{10}$ groups;
each $R^3$ and $R^7$ is independently selected from the group consisting of hydrogen, $C_{1-4}$ alkyl and $C_{1-4}$ haloalkyl;
X is selected from the group consisting of $CH_2$, O, S, $SO_2$, and $NR^4$, with the proviso that, when X is $CH_2$, at least one of $R^1$ and $R^2$ is $-NR^{10}R^{12}$, and at least one of $R^{10}$ and $R^{12}$ is $-C(O)C_{6-10}$ aryl, $-C(O)C_{6-10}$ cycloalkyl or $-C(O)$HET;
$R^4$ is selected from the group H, $C_{1-4}$ alkyl and $C_{1-4}$ haloalkyl;
each $R^5$, $R^6$, $R^{8'}$ and $R^8$ is independently selected from the group consisting of hydrogen, halo, COOH, hydroxy, $OC_{1-4}$ alkyl, $C_{1-4}$ alkyl and $C_{1-4}$ haloalkyl;
$R^9$ is $COOR^{13}$, $-O-C_{1-4}$ alkyl, $-O-C_{1-4}$ haloalkyl, $-B(OR^{13})_2$, $-PO(OR^{13''})_2$, or HET, wherein the HET may be optionally substituted with 1, 2, or 3 substituents independently selected from the group consisting of oxo, halo, hydroxy, $C_{1-4}$ alkyl and $C_{1-4}$ haloalkyl;
$R^{10}$ is selected from the group consisting of hydrogen, $C_{1-4}$ alkyl, $-C(O)C_{6-10}$ aryl, $-C(O)C_{6-10}$ cycloalkyl, $-C(O)$HET and $-C(O)C_{1-4}$ alkyl; wherein the $C_{1-4}$ alkyl is optionally substituted with 1, 2, or 3 halo groups; wherein the $-C(O)C_{1-4}$ alkyl is optionally substituted with 1, 2, or 3 substituents independently selected from the group consisting of halo, oxo, $-N(R^{11})_2$, HET, $-O-C_{1-4}$ alkyl and $C_{6-10}$ aryl; wherein the $-O-C_{1-4}$ alkyl may be optionally substituted with 1, 2, or 3 substituents independently selected from the group consisting of halo, oxo, $-N(R^{11})_2$ and $C_{6-10}$ aryl; wherein the $C_{6-10}$ aryl may be optionally substituted with 1, 2, or 3 halo groups; and wherein the $-C(O)C_{6-10}$ aryl, $-C(O)C_{6-10}$ cycloalkyl and $-C(O)$HET may be optionally substituted with 1, 2, or 3 substituents independently selected from the group consisting of $C_{1-4}$ alkyl, $C_{1-4}$ haloalkyl, $-O-C_{1-4}$ alkyl, $-O-C_{1-4}$ haloalkyl and halo groups;
each HET is an independently selected mono- or bicyclic 5-10-membered heteroaryl or a mono- or bicyclic 5-10 membered heterocycloalkyl group, wherein each HET comprises 1, 2, 3, or 4 heteroatoms selected from O, S and N and is optionally substituted with 1 or 2 substituents independently selected from the group consisting of $C_{1-4}$ alkyl, $C_{1-4}$ haloalkyl, $-O-C_{1-4}$ alkyl, $-O-C_{1-4}$ haloalkyl, halo, hydroxy and oxo groups;
$R^{11}$ is selected from hydrogen, $C_{1-4}$ alkyl and $C_{1-4}$ haloalkyl;
$R^{12}$ is selected from the group consisting of hydrogen, $C_{1-4}$ alkyl, $-C(O)C_{6-10}$ aryl, $-C(O)C_{6-10}$ cycloalkyl, $-C(O)$HET and $-C(O)C_{1-4}$ alkyl; wherein the $C_{1-4}$ alkyl is optionally substituted with 1, 2, or 3 halo groups; wherein the $-C(O)C_{1-4}$ alkyl is optionally substituted with 1, 2, or 3 substituents independently selected from the group consisting of halo, oxo, $-N(R^{11})_2$, HET, $-O-C_{1-4}$ alkyl and $C_{6-10}$ aryl; wherein the $-O-C_{1-4}$ alkyl may be optionally substituted with 1, 2, or 3 substituents independently selected from the group consisting of halo, oxo, —N(R$^{11}$)$_2$ and C$_{6-10}$ aryl; wherein the C$_{6-10}$ aryl may be optionally substituted with 1, 2, or 3 halo groups; and wherein the —C(O)C$_{6-10}$ aryl, —C(O)C$_{6-10}$ cycloalkyl and —C(O)HET may be optionally substituted with 1, 2, or 3 substituents independently selected from the group consisting of C$_{1-4}$ alkyl, C$_{1-4}$ haloalkyl, —O—C$_{1-4}$ alkyl, —O—C$_{1-4}$ haloalkyl and halo groups; and each of R$^{13}$, R$^{13'}$, and R$^{13''}$, independently, is selected from the group consisting of hydrogen, C$_{1-6}$ alkyl, C$_{1-6}$ cycloalkyl and HET.

In one aspect, this disclosure relates to a compound of Formula II or a pharmaceutically acceptable salt thereof, or a stereoisomer or tautomer thereof:

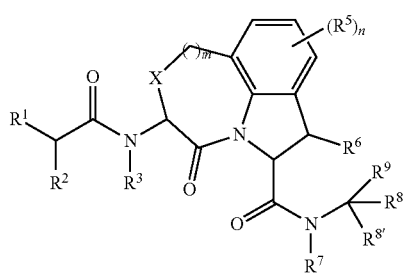

(II)

wherein:
all variables as defined in Formula (I).

In one aspect, this disclosure relates to a compound of Formula III or a pharmaceutically acceptable salt thereof, or a stereoisomer or tautomer thereof:

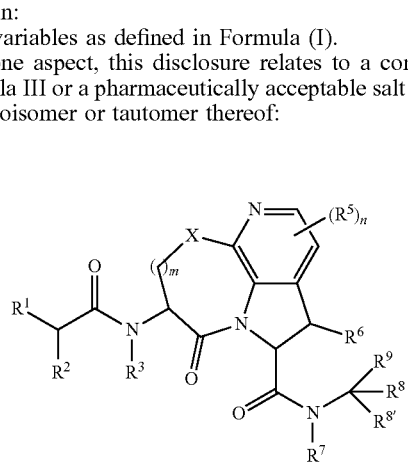

(III)

wherein:
n is 1 or 2 and all other variables as defined in Formula (I).

In one aspect, this disclosure relates to a compound of Formula IV or a pharmaceutically acceptable salt thereof, or a stereoisomer or tautomer thereof:

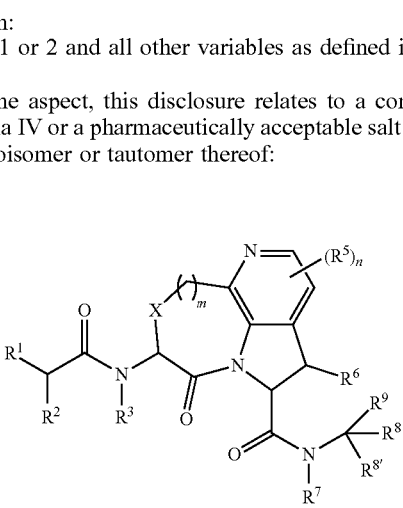

(IV)

wherein:
n is 1 or 2 and all other variables as defined in Formula (I).

In one aspect, this disclosure relates to a compound of Formula V or a pharmaceutically acceptable salt thereof, or a stereoisomer or tautomer thereof:

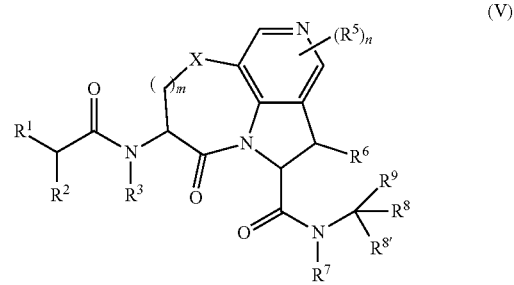

(V)

wherein:
n is 1 or 2 and all other variables as defined in Formula (I).

In one aspect, this disclosure relates to a compound of Formula VI or a pharmaceutically acceptable salt thereof, or a stereoisomer or tautomer thereof:

(VI)

wherein:
n is 1 or 2 and all other variables as defined in Formula (I).

In one aspect, this disclosure relates to a compound of Formula VII or a pharmaceutically acceptable salt thereof, or a stereoisomer or tautomer thereof:

(VII)

wherein:
n is 1 or 2 and all other variables as defined in Formula (I).

In one aspect, this disclosure relates to a compound of Formula VIII or a pharmaceutically acceptable salt thereof, or a stereoisomer or tautomer thereof:

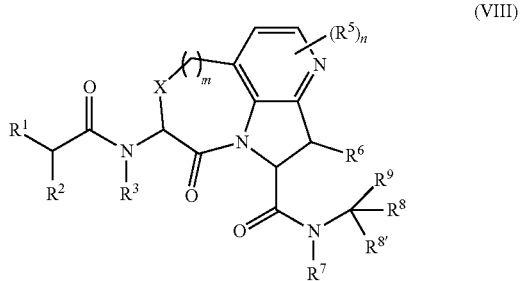

(VIII)

wherein:

n is 1 or 2 and all other variables as defined in Formula (I).

In some aspects, this disclosure relates to a compound of any one of Formula I-VIII or a pharmaceutically acceptable salt thereof, wherein X is $CH_2$; at least one of $R^1$ and $R^2$ is $-NR^{10}R^{12}$; at least one of $R^{10}$ and $R^{12}$ is $-C(O)C_{1-4}$ alkyl, $-C(O)C_{6-10}$ aryl, $C(O)C_{6-10}$ cycloalkyl or $-C(O)HET$, wherein the $-C(O)C_{1-4}$ alkyl, $-C(O)C_{6-10}$ aryl, $C(O)C_{6-10}$ cycloalkyl and $-C(O)HET$ are optionally substituted with 1, 2, or 3 substituents independently selected from the group consisting of halo, oxo, $-N(R^{11})_2$, HET, $-O-C_{1-4}$ alkyl and $C_{6-10}$ aryl; wherein the $-O-C_{1-4}$ alkyl may be optionally substituted with 1, 2, or 3 substituents independently selected from the group consisting of halo, oxo, $-N(R^{11})_2$ and $C_{6-10}$ aryl; wherein the $C_{6-10}$ aryl may be optionally substituted with 1, 2, or 3 halo groups.

In other aspects, this disclosure relates to a compound of any one of Formula I-VIII or a pharmaceutically acceptable salt thereof, wherein X is O, S, $SO_2$, and $NR^4$; $R^{10}$ is selected from the group consisting of hydrogen, $C_{1-4}$ alkyl and $-C(O)C_{1-4}$ alkyl; wherein the $C_{1-4}$ alkyl is optionally substituted with 1, 2, or 3 halo groups; wherein the $-C(O)C_{1-4}$ alkyl is optionally substituted with 1, 2, or 3 substituents independently selected from the group consisting of halo, oxo, $-N(R^{11})_2$, HET, $-O-C_{1-4}$ alkyl and $C_{6-10}$ aryl; wherein the $O-C_{1-4}$ alkyl may be optionally substituted with 1, 2, or 3 substituents independently selected from the group consisting of halo, oxo, $-N(R^{11})_2$ and $C_{6-10}$ aryl; wherein the $C_{6-10}$ aryl may be optionally substituted with 1, 2, or 3 halo groups; $R^{12}$ is selected from the group consisting of hydrogen, $C_{1-4}$ alkyl and $-C(O)C_{1-4}$ alkyl; wherein the $C_{1-4}$ alkyl is optionally substituted with 1, 2, or 3 halo groups; wherein the $-C(O)C_{1-4}$ alkyl is optionally substituted with 1, 2, or 3 substituents independently selected from the group consisting of halo, oxo, $-N(R^{11})_2$, HET, $-O-C_{1-4}$ alkyl and $C_{6-10}$ aryl; wherein the $-O-C_{1-4}$ alkyl may be optionally substituted with 1, 2, or 3 substituents independently selected from the group consisting of halo, oxo, $-N(R^{11})_2$ and $C_{6-10}$ aryl; wherein the $C_{6-10}$ aryl may be optionally substituted with 1, 2, or 3 halo groups. Preferably at least one of $R^1$, $R^2$, $R^5$ and $R^9$ of the compound of Formula I-VIII or a pharmaceutically acceptable salt thereof, comprises an imaging agent, such as a paramagnetic ion, an x-ray imaging agent, a fluorophore, and a radioisotope.

In some aspects, the paramagnetic ion is selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

In some aspects, the x-ray imaging agent is selected from the group consisting of lanthanum (III), gold (III), lead (II), bismuth (III), and an iodinated x-ray imaging agent.

In some aspects, the fluorophores is selected from the group consisting of Alexa 350, Alexa 430, AMCA, BODIPY 630/650, BODIPY 650/665, BODIPY-FL, BODPY-R6G, 13BODLPY-TMR, BODLPY-TRX, cascade blue, Cy3, Cy5, 6-FAM, fluorescein isothiocyanate, HEX, 6-JOE, oregon green 488, oregon green 500, oregon green 514, quantum dots, pacific blue, REG, rhodamine green, rhodamine red, renographin, ROX, TAMRA, TET, tetramethylrhodamine, Texas Red, AF 350, 405, AF532, AF488, AF647, AF680, AF750, Cy5, Cy5.5, Cy7, indocyanine green (ICG), green fluorescent protein (GFP), red fluorescent protein (RFP), and dsRED. In some embodiments, at least one of $R^1$, $R^2$, $R^5$ and $R^9$ of the compound of Formula I-VIII or a pharmaceutically acceptable salt thereof, comprises 1, 2, or 3 independently selected fluorophores.

In some aspects, the radioisotope is selected from the group consisting of $^3H$, $^{11}C$, $^{14}C$, $^{18}F$, $^{32}P$, $^{35}S$, $^{36}Cl$, $^{51}Cr$, $^{52}Fe$, $^{57}Co$, $^{58}Co$, $^{59}Fe$, $^{64}Cu$, $^{67}Cu$, $^{67}Ga$, $^{68}Ga$, $^{75}Se$, $^{76}Br$, $^{77}Br$, $^{89}Zr$, $^{90}Y$, $^{99m}Tc$, $^{111}In$, $^{123}I$, $^{124}I$, $^{125}I$, $^{131}I$, $^{152}Eu$, $^{153}Sm$, $^{166}Ho$, $^{177}Lu$, $^{186}Re$, $^{188}Re$, $^{201}Tl$, $^{203}Pb$, $^{210}At$, $^{211}At$, $^{212}Bi$, $^{213}Bi$, and, $^{225}Ac$.

In preferred aspects, at least one of $R^1$, $R^2$, $R^5$ and $R^9$ of the compound of Formula I-VIII or a pharmaceutically acceptable salt thereof, comprises $^{18}F$.

In some aspects, at least one of $R^1$, $R^2$, $R^5$ and $R^9$ of the compound of Formula I-VIII or a pharmaceutically acceptable salt thereof, comprises an imaging agent selected from the group consisting of a PET imaging agent, a SPECT imaging agent, and a computed tomography imaging agent.

In some embodiments, at least one of $R^1$, $R^2$, $R^5$ and $R^9$ of the compound of Formula I-VIII or a pharmaceutically acceptable salt thereof is a PET or SPECT imaging agent.

In some aspects, at least one of $R^1$, $R^2$, $R^5$ and $R^9$ of the compound of Formula I-VIII or a pharmaceutically acceptable salt thereof, is a PET or SPECT imaging agent comprising a radioisotope selected from the group consisting of $^3H$, $^{11}C$, $^{14}C$, $^{18}F$, $^{35}S$, $^{52}Fe$, $^{58}Co$, $^{64}Cu$, $^{68}Ga$, $^{76}Br$, $^{77}Br$, $^{89}Zr$ $^{111}In$, $^{123}I$, $^{124}I$, $^{125}I$, $^{131}I$, $^{186}Re$, $^{188}Re$, $^{201}Tl$.

In a preferred aspect, at least one of $R^1$, $R^2$, $R^5$ and $R^9$ of the compound of Formula I-VIII or a pharmaceutically acceptable salt thereof, contains a PET imaging agent comprising $^{18}F$.

In some aspects, at least one of $R^1$, $R^2$, $R^5$ and $R^9$ of the compound of Formula I-VIII or a pharmaceutically acceptable salt thereof, further comprises a chelating agent.

In some embodiments, the chelating agent is selected from the group consisting of 1,4,7-triazacyclononanetriacetic acid (NOTA), 1,4,7-triazacyclononane-4,7-diacetic acid (NODA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetraacetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), and 1,4,8,11-tetraazacyclotetradecane-N,N',N'', N'''-tetraacetic acid (TETA), 1,4,7,10-tetraaza-1,4,7,10-tetra-(2-carbamoyl methyl)-cyclododecane (TCMC), and Desferrioxamine B (DFO). In some embodiments, the chelating agent is selected from the group consisting of 1,4,7-triazacyclononanetriacetic acid (NOTA), 1,4,7-triazacyclononane-4,7-diacetic acid (NODA), 1,4,7,10-tetraazacyclododecane-1,4,7,10-tetraacetic acid (DOTA), and 1,4,7-triazacyclononane-1-glutaric acid-4,7-diacetic acid (NODAGA). In some embodiments, the chelating agent is 1,4,7-triazacyclononanetriacetic acid (NOTA).

In some aspects, at least one of $R^1$, $R^2$, $R^5$ and $R^9$ of the compound of Formula I-VIII or a pharmaceutically acceptable salt thereof, contains an imaging agent comprising one or more of a paramagnetic ion, an x-ray imaging agent, a fluorophore, and a radioisotope and that, the compound of Formula I-VIII or a pharmaceutically acceptable salt thereof, binds Granzyme B.

In some aspects, at least one of $R^1$, $R^2$, $R^5$ and $R^9$ of the compound of Formula I-VIII or a pharmaceutically acceptable salt thereof, comprises a radioisotope and that, the compound of Formula I-VIII or a pharmaceutically acceptable salt thereof, binds Granzyme B.

In preferred aspects, at least one of $R^1$, $R^2$, $R^5$ and $R^9$ of the compound of Formula I-VIII or a pharmaceutically acceptable salt thereof, comprises $^{18}F$ and that, the compound of Formula I-VIII or a pharmaceutically acceptable salt thereof, binds Granzyme B.

In one aspect, the compound of Formula I-VIII or a pharmaceutically acceptable salt thereof, binds Granzyme B.

In other aspect, the compound of Formula I-VIII or a pharmaceutically acceptable salt thereof, is an irreversible binder of Granzyme B.

In some aspect, the compound of Formula I-VIII or a pharmaceutically acceptable salt thereof, is an inhibitor of Granzyme B.

The present application further provides a method of imaging Granzyme B in a subject comprising:
 i) administering to the subject an effective amount of compound of Formula I-VIII or a pharmaceutically acceptable salt thereof, wherein at least one of $R^1$, $R^2$, $R^5$ and $R^9$ of the compound of Formula I-VIII or a pharmaceutically acceptable salt thereof, comprises an imaging agent and
 ii) imaging the subject with a suitable imaging technique, thereby imaging Granzyme B in the subject.

The present application further provides a method of imaging immune response in a cell or tissue sample, comprising:
 i) contacting the cell or tissue sample with an effective amount of compound of Formula I-VIII or a pharmaceutically acceptable salt thereof, wherein at least one of $R^1$, $R^2$, $R^5$ and $R^9$ of the compound of Formula I-VIII or a pharmaceutically acceptable salt thereof, comprises an imaging agent and
 ii) imaging the cell or tissue sample with a suitable imaging technique, thereby imaging the immune response in the cell or tissue.

The present application further provides a method of imaging immune response in a subject, comprising:
 i) administering to the subject an effective amount of compound of Formula I-VIII or a pharmaceutically acceptable salt thereof, wherein at least one of $R^1$, $R^2$, $R^5$ and $R^9$ of the compound of Formula I-VIII or a pharmaceutically acceptable salt thereof, comprises an imaging agent and
 ii) imaging the subject with a suitable imaging technique, thereby imaging the immune response in the subject.

The present application further provides a method of monitoring treatment of a disease in a subject, comprising:
 i) administering to the subject an effective amount of compound of Formula I-VIII or a pharmaceutically acceptable salt thereof, wherein at least one of $R^1$, $R^2$, $R^5$ and $R^9$ of the compound of Formula I-VIII or a pharmaceutically acceptable salt thereof, comprises an imaging agent and
 ii) imaging the subject with a suitable imaging technique.

The present application further provides a method of monitoring an immune response in the treatment of a disease in a subject, comprising:
 i) administering to the subject an effective amount of compound of Formula I-VIII or a pharmaceutically acceptable salt thereof, wherein at least one of $R^1$, $R^2$, $R^5$ and $R^9$ of the compound of Formula I-VIII or a pharmaceutically acceptable salt thereof, comprises an imaging agent and
 ii) imaging the subject with a suitable imaging technique.

In some embodiments, the method further comprises administering a therapeutic agent, typically prior to step i). In some embodiments, administration of the therapeutic agent induces an immune response cell or tissue sample or subject.

In some embodiments, the therapeutic agent is selected from the group consisting of an anti-inflammatory agent, a steroid, an immunotherapy agent, a chemotherapeutic agent, and a therapeutic antibody. In some embodiments, the therapeutic agent is a chemotherapeutic agent.

In some embodiments, the disease is selected from the group consisting of an autoimmune disorder, an inflammatory disorder, a skin disorder, cancer, and a cardiovascular disorder. In some embodiments, the disease is a cancer. In some embodiments, the cancer is selected from the group consisting of brain cancer, breast cancer, cervical cancer, colorectal cancer, lung cancer, lymphoma, melanoma, bladder cancer, renal cell carcinoma, multiple myeloma, pancreatic cancer, and prostate cancer. In some embodiments, the cancer is colon cancer. In some embodiments, the cancer is melanoma.

In some embodiments, the disease is selected from the group consisting of graft-versus-host disease, rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, rheumatic fever, post-infectious glomerulonephritis, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia, alopecia senilis by preventing epilation, alopecia senilis by providing hair germination and/or promoting hair generation and hair growth, muscular dystrophy, pyoderma, Sezary's syndrome, Addison's disease, ischemia-reperfusion injury of organs, transplantation disease, ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, aging, carcinogenesis, metastasis of carcinoma and hypobaropathy, histamine or leukotriene-C4 release associated diseases, Behcet's disease, autoimmune hepatitis, primary biliary cirrhosis, sclerosing cholangitis, partial liver resection, acute liver necrosis, necrosis caused by toxin, viral hepatitis, shock, anoxia, B-virus hepatitis, non-A/non-B hepatitis, cirrhosis, alcoholic cirrhosis, hepatic failure, fulminant hepatic failure, late-onset hepatic failure, acute-on-chronic liver failure, cytomegalovirus infection, HCMV infection, AIDS, senile dementia, trauma, chronic bacterial infection, malignancy of lymphoid origin, acute lymphocytic leukemia, chronic lymphocytic leukemia, acute lymphocytic lymphoma, and chronic lymphocytic lymphoma. In some embodiments, the disease is selected from the group consisting of systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, asthma, schleroderma and Sjogren's syndrome. In some embodiments, the disease is selected from the group consisting of bone marrow rejection, organ transplant rejection, and graft-versus-host disease.

DETAILED DESCRIPTION

Cancer immunotherapies have represented a significant advance in cancer therapy over recent years. Antibodies directed against immune checkpoints such as programmed cell death protein 1 (PD-1) and cytotoxic t lymphocyte-associated protein 4 (CTLA-4) have been approved with positive outcomes for some patients. Research into the field of immune-oncology continues, with strategies including CAR-T cells, vaccines, small molecules, and antibodies under development. Despite the promise of these therapies, they are not a panacea. These immunotherapies can be associated with significant adverse events, which are costly, and the response rates are typically 20-50%, meaning the majority of patients do not respond to therapy. Furthermore, determining an individual patient's response to therapy can be challenging using conventional methods, as response is frequently associated with an immune-cell infiltrate that can make responding tumors appear to grow on anatomic imaging (e.g., CT, MRI), and demonstrate increased avidity with FDG-PET imaging due to the influx of metabolically active immune cells. Given the constraints of current imaging technologies, clinical studies for cancer immunotherapies typically employ overall survival as their study endpoint as opposed to progression-free survival.

Granzyme B, a downstream marker of cytotoxic T-cell activity, could serve as a novel biomarker to assess cancer immunotherapy efficacy. Granzyme B expression within a tumor can be assessed not only for CTL presence or absence, but as an effector protein released by active T-cells that also integrates a measure of CTL activity, thus accounting for issues of T-cell exhaustion that make assessment of CTL presence difficult to accomplish. Accordingly, the present application provides novel Granzyme B specific imaging agents.

Compounds

This disclosure relates to compounds that bind Granzyme B and can be used for diagnostic and therapeutic purposes, in particular as imaging agents. The compounds are of Formula I-VIII or a pharmaceutically acceptable salt thereof.

The compound of Formula I or a pharmaceutically acceptable salt thereof, is as follows:

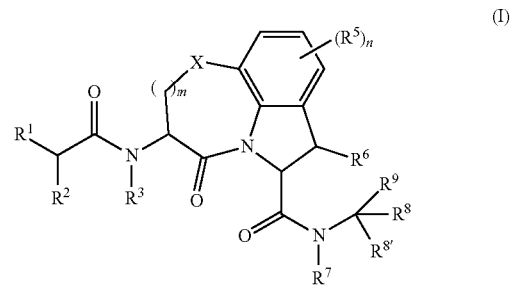

(I)

wherein:

m is 0, 1, or 2;

n is 1, 2, or 3;

$R^1$ and $R^2$ are each independently selected from the group consisting of: hydrogen, $C_{1-6}$ alkyl, $C_{1-6}$ alkoxy, $C_{3-6}$ cycloalkyl, $C_{6-10}$ aryl, HET and $-NR^{10}R^{12}$, wherein each $C_{1-6}$ alkyl, $C_{1-6}$ alkoxy, $C_{3-6}$ cycloalkyl, are optionally substituted with 1, 2, or 3 substituents independently selected from the group consisting of halo and hydroxy, and each $C_{6-10}$ aryl and HET are optionally substituted with 1, 2, or 3 substituents independently selected from the group consisting of oxo, halo, hydroxy, $C_{1-4}$ alkyl and $C_{1-4}$ haloalkyl;

or $R^1$ and $R^2$ may come together, with the carbon atom to which they are attached, to form a 5-6 membered cycloalkyl or 5-6 heterocycloalkyl group, each of which may be optionally substituted with 1, 2, or 3 $R^{10}$ groups;

each $R^3$ and $R^7$ is independently selected from the group consisting of hydrogen, $C_{1-4}$ alkyl and $C_{1-4}$ haloalkyl;

X is selected from the group consisting of $CH_2$, O, S, $SO_2$, and $NR^4$, with the proviso that, when X is $CH_2$, at least one of $R^1$ and $R^2$ is $-NR^{10}R^{12}$, and at least one of $R^{10}$ and $R^{12}$ is $-C(O)C_{6-10}$ aryl, $-C(O)C_{6-10}$ cycloalkyl or $-C(O)$ HET;

$R^4$ is selected from the group H, $C_{1-4}$ alkyl and $C_{1-4}$ haloalkyl;

each $R^5$, $R^6$, $R^{8'}$ and $R^8$ is independently selected from the group consisting of hydrogen, halo, COOH, hydroxy, $OC_{1-4}$ alkyl, $C_{1-4}$ alkyl and $C_{1-4}$ haloalkyl;

$R^9$ is $COOR^{13}$, $-O-C_{1-4}$ alkyl, $-O-C_{1-4}$ haloalkyl, $-B(OR^{13'})_2$, $-PO(OR^{13''})_2$, or HET, wherein the HET may be optionally substituted with 1, 2, or 3 substituents independently selected from the group consisting of oxo, halo, hydroxy, $C_{1-4}$ alkyl and $C_{1-4}$ haloalkyl;

$R^{10}$ is selected from the group consisting of hydrogen, $C_{1-4}$ alkyl, —C(O)$C_{6-10}$ aryl, —C(O)$C_{6-10}$ cycloalkyl, —C(O)HET and —C(O)$C_{1-4}$ alkyl; wherein the $C_{1-4}$ alkyl is optionally substituted with 1, 2, or 3 halo groups; wherein the —C(O)$C_{1-4}$ alkyl is optionally substituted with 1, 2, or 3 substituents independently selected from the group consisting of halo, oxo, —N($R^{11}$)$_2$, HET, —O—$C_{1-4}$ alkyl and $C_{6-10}$ aryl; wherein the —O—$C_{1-4}$ alkyl may be optionally substituted with 1, 2, or 3 substituents independently selected from the group consisting of halo, oxo, —N($R^{11}$)$_2$ and $C_{6-10}$ aryl; wherein the $C_{6-10}$ aryl may be optionally substituted with 1, 2, or 3 halo groups and wherein the —C(O)$C_{6-10}$ aryl, —C(O)$C_{6-10}$ cycloalkyl and —C(O)HET may be optionally substituted with 1, 2, or 3 substituents independently selected from the group consisting of $C_{1-4}$ alkyl, $C_{1-4}$ haloalkyl, —O—$C_{1-4}$ alkyl, —O—$C_{1-4}$ haloalkyl and halo groups;

each HET is an independently selected mono- or bicyclic 5-10-membered heteroaryl or a mono- or bicyclic 5-10 membered heterocycloalkyl group, wherein each HET comprises 1, 2, 3, or 4 heteroatoms selected from O, S and N and is optionally substituted with 1 or 2 substituents independently selected from the group consisting of $C_{1-4}$ alkyl, $C_{1-4}$ haloalkyl, —O—$C_{1-4}$ alkyl, —O—$C_{1-4}$ haloalkyl, halo, hydroxy and oxo groups;

$R^{11}$ is selected from hydrogen, $C_{1-4}$ alkyl and $C_{1-4}$ haloalkyl;

$R^{12}$ is selected from the group consisting of hydrogen, $C_{1-4}$ alkyl, —C(O)$C_{6-10}$ aryl, —C(O)$C_{6-10}$ cycloalkyl, —C(O)HET and —C(O)$C_{1-4}$ alkyl; wherein the $C_{1-4}$ alkyl is optionally substituted with 1, 2, or 3 halo groups; wherein the —C(O)$C_{1-4}$ alkyl is optionally substituted with 1, 2, or 3 substituents independently selected from the group consisting of halo, oxo, —N($R^{11}$)$_2$, HET, —O—$C_{1-4}$ alkyl and $C_{6-10}$ aryl; wherein the —O—$C_{1-4}$ alkyl may be optionally substituted with 1, 2, or 3 substituents independently selected from the group consisting of halo, oxo, —N($R^{11}$)$_2$ and $C_{6-10}$ aryl; wherein the $C_{6-10}$ aryl may be optionally substituted with 1, 2, or 3 halo groups and wherein the —C(O)$C_{6-10}$ aryl, —C(O)$C_{6-10}$ cycloalkyl and —C(O)HET may be optionally substituted with 1, 2, or 3 substituents independently selected from the group consisting of $C_{1-4}$ alkyl, $C_{1-4}$ haloalkyl, —O—$C_{1-4}$ alkyl, —O—$C_{1-4}$ haloalkyl and halo groups; and each of $R^{13}$, $R^{13'}$ and $R^{13''}$, independently, is selected from the group consisting of hydrogen, $C_{1-6}$ alkyl, $C_{1-6}$ cycloalkyl and HET.

The compound of Formula II or a pharmaceutically acceptable salt thereof, is as follows:

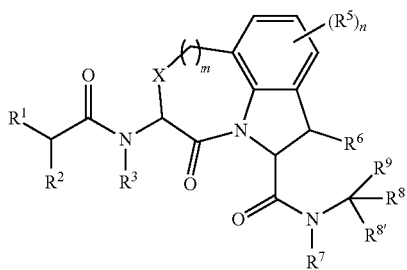

(II)

wherein:

all variables as defined in Formula (I).

The compound of Formula III or a pharmaceutically acceptable salt thereof, is as follows:

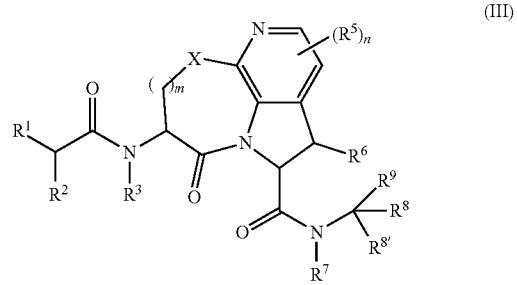

(III)

wherein:

n is 1 or 2 and all other variables as defined in Formula (I).

The compound of Formula IV or a pharmaceutically acceptable salt thereof, is as follows:

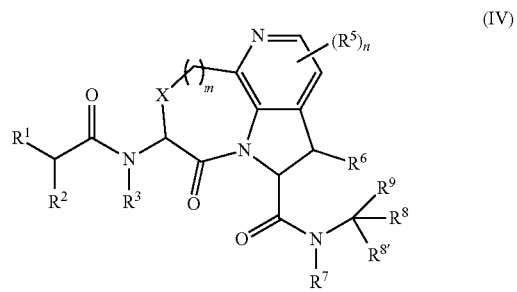

(IV)

wherein:

n is 1 or 2 and all other variables as defined in Formula (I).

The compound of Formula V or a pharmaceutically acceptable salt thereof, is as follows:

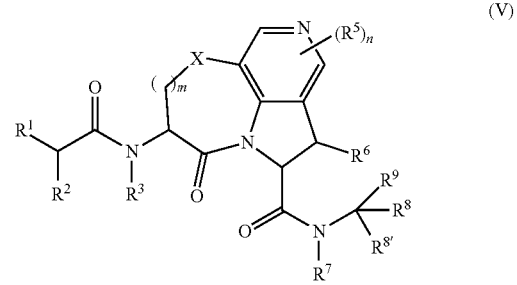

(V)

wherein:

n is 1 or 2 and all other variables as defined in Formula (I).

The compound of Formula VI or a pharmaceutically acceptable salt thereof, is as follows:

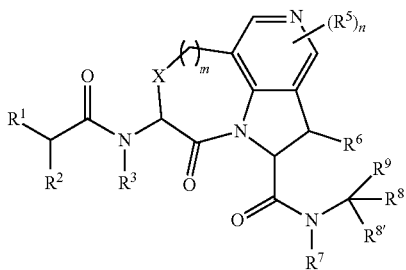

(VI)

wherein:

n is 1 or 2 and all other variables as defined in Formula (I).

The compound of Formula VII or a pharmaceutically acceptable salt thereof, is as follows:

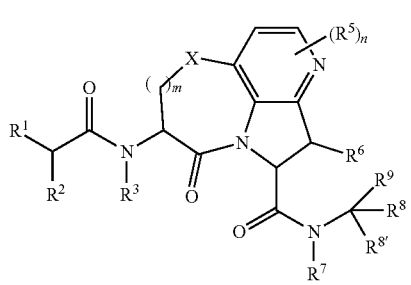

(VII)

wherein:

n is 1 or 2 and all other variables as defined in Formula (I).

The compound of Formula VIII or a pharmaceutically acceptable salt thereof, is as follows:

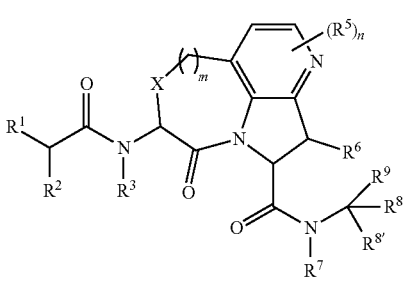

(VIII)

wherein:

n is 1 or 2 and all other variables as defined in Formula (I).

In some embodiments of Formulas I-VIII, m is 0 and n is 0; m is 0 and n is 1, 2 or 3; m is 1 and n is 1, 2 or 3; m is 2 and n is 1, 2, or 3; m is 1 or 2 and n is 0; m is 1 or 2 and n is 2; or m is 1 or and n is 3.

In some embodiments, $R^1$ and $R^2$ are each independently selected from the group consisting of hydrogen, $C_{1-6}$ alkyl, $C_{1-6}$ alkoxy, $C_{3-6}$ cycloalkyl, $C_{6-10}$ aryl, HET and $-N(R^{10}R^{12})$, wherein each $C_{1-6}$ alkyl, $C_{1-6}$ alkoxy, $C_{3-6}$ cycloalkyl are optionally substituted with 1, 2, or 3 substituents independently selected from the group consisting of halo and hydroxy, and each $C_{6-10}$ aryl and HET are optionally substituted with 1, 2, or 3 substituents independently selected from the group consisting of oxo, halo, hydroxy, $C_{1-4}$ alkyl and $C_{1-4}$ haloalkyl.

In some embodiments, $R^1$ and $R^2$ are each independently selected from the group consisting of $C_{1-6}$ alkyl, $C_{1-6}$ alkoxy, $C_{3-6}$ cycloalkyl, phenyl, HET and $-NR^{10}R^{12}$, wherein each $C_{1-6}$ alkyl, $C_{1-6}$ alkoxy, $C_{3-6}$ cycloalkyl are optionally substituted with 1, 2, or 3 substituents independently selected from the group consisting of halo and hydroxy, and each phenyl and HET are optionally substituted with 1, 2, or 3 substituents independently selected from the group consisting of oxo, halo, hydroxy, $C_{1-4}$ alkyl and $C_{1-4}$ haloalkyl.

In some embodiments, $R^1$ and $R^2$ are each independently selected from the group consisting of $C_{1-6}$ alkyl, $C_{3-6}$ cycloalkyl, phenyl, pyridyl, 2-oxopyrrolidine and $-NR^{10}R_{12}$, wherein the $C_{1-6}$ alkyl and $C_{3-6}$ cycloalkyl are each optionally substituted with 1, 2, or 3 groups independently selected from the group consisting of halo and hydroxy and the phenyl, pyridyl and 2-oxopyrrolidine optionally substituted with 1, 2, or 3 groups independently selected from the group consisting of halo, hydroxy, and $C_{1-4}$ alkyl, optionally substituted with 1, 2, or 3 halo groups.

In some embodiments, $R^1$ and $R^2$ are each independently selected from the group consisting of $C_{1-6}$ alkyl, $C_{3-6}$ cycloalkyl, phenyl, pyridyl, 2-oxopyrrolidine and $-N(R^{10}R^{12})$, wherein the $C_{1-6}$ alkyl and $C_{3-6}$ cycloalkyl are each optionally substituted with 1, 2, or 3 groups independently selected from the group consisting of halo and hydroxy and the phenyl, pyridyl and 2-oxopyrrolidine optionally substituted with 1, 2, or 3 groups independently selected from the group consisting of halo, hydroxy, and $C_{1-4}$ alkyl, optionally substituted with 1, 2, or 3 halo groups.

In some embodiments, $R^1$ and $R^2$ may come together, with the carbon atom to which they are attached, to form a 5-6 membered cycloalkyl or 5-6 heterocycloalkyl group, each of which may be optionally substituted with 1, 2, or 3 $R^{10}$ groups;

In some embodiments, $R^3$ is selected from the group consisting of H, $C_{1-4}$ alkyl and $C_{1-4}$ haloalkyl. In some embodiments, $R^3$ is H. In some embodiments, $R^3$ is $C_{1-4}$ alkyl. In some embodiments, $R^3$ is $C_{1-4}$ haloalkyl.

In some embodiments, each $R^4$ is selected from the group consisting of H, halo, $C_{1-6}$ alkyl and $C_{1-4}$ haloalkyl. In some embodiments, each $R^4$ is independently H or $C_{1-4}$ alkyl. In some embodiments, each $R^4$ is H.

In some embodiments, each $R^5$ is selected from the group consisting of H, halo, COOH, hydroxy, $OC_{1-4}$ alkyl, $C_{1-4}$ alkyl and $C_{1-4}$ haloalkyl. In some embodiments, each $R^5$ is independently H or $C_{1-4}$ alkyl. In some embodiments, each $R^5$ is H.

In some embodiments, each $R^6$ is selected from the group consisting of H, halo, COOH, hydroxy, $OC_{1-4}$ alkyl, $C_{1-4}$ alkyl and $C_{1-4}$ haloalkyl. In some embodiments, each $R^6$ is independently H or $C_{1-4}$ alkyl. In some embodiments, each $R^6$ is H.

In some embodiments, each $R^7$ is selected from the group consisting of H, $C_{1-4}$ alkyl and $C_{1-4}$ haloalkyl. In some embodiments, $R^7$ is H. In some embodiments, $R^7$ is $C_{1-4}$ alkyl. In some embodiments, $R^7$ is $C_{1-4}$ haloalkyl.

In some embodiments, each $R^{8'}$, $R^8$ is selected from the group consisting of H, halo, COOH, hydroxy, $OC_{1-4}$ alkyl, $C_{1-4}$ alkyl and $C_{1-4}$ haloalkyl. In some embodiments, In some embodiments, each $R^{8'}$, $R^8$ is independently H or $C_{1-4}$ alkyl. In some embodiments, each $R^{8'}$, $R^8$ is H.

In some embodiments, each $R^3$, $R^4$, $R^5$, $R^6$, $R^7$, $R^{8'}$ and $R^8$ is H.

In some embodiments, $R^9$ is $COOR^{13}$, $-O-C_{1-4}$ alkyl, $-O-C_{1-4}$ haloalkyl, $-B(OR^{13'})_2-PO(OR^{13''})_2$, or HET group. In some embodiments, $R^9$ is an unsubstituted HET group. In some embodiments, $R^9$ is a HET group, wherein the HET may optionally be substituted with 1, 2 or 3 substituents independently selected from oxo, halo, hydroxy, $C_{1-4}$ alkyl and $C_{1-4}$ haloalkyl. In some embodiments, $R^9$ is selected from the group consisting of is selected from the group consisting of pyridyl, pyrimidyl, pyrazinyl, pyridazinyl, imidazolyl, pyrazolyl, thiazolyl, oxazolyl, oxadiazolyl, isoxazolyl, 1,2,4-triazolyl, 1,2,3-triazolyl, and tetrazolyl. In some embodiments, $R^9$ is selected from the group consisting of pyridyl, pyrimidyl, pyrazinyl, pyridazinyl, imidazolyl, pyrazolyl, thiazolyl, oxazolyl, oxadiazolyl, isoxazolyl, 1,2,4-triazolyl, 1,2,3-triazolyl, and tetrazolyl, each optionally substituted with 1, 2, or 3 substituents independently selected from the group consisting of halo, hydroxy, $C_{1-4}$ alkyl and $C_{1-4}$ haloalkyl.

In some embodiments, $R^{10}$ is selected from the group consisting of hydrogen, $C_{1-4}$ alkyl and —C(O)$C_{1-4}$ alkyl, the $C_{1-4}$ alkyl is optionally substituted with 1, 2, or 3 halo groups. Preferably, the $C_{1-4}$ alkyl is optionally substituted with 1, 2, or 3 fluoro groups.

In some embodiments, $R^{10}$ is selected from the group consisting of hydrogen, $C_{1-4}$ alkyl and —C(O)$C_{1-4}$ alkyl, the —C(O)$C_{1-4}$ alkyl optionally substituted with N($R^{11}$)$_2$, pyrrolidinyl, piperidinyl, morpholinyl, benzothiophenyl, and phenyl, the phenyl optionally substituted with 1, 2, or 3 halo groups.

In some embodiments, $R^{10}$ is selected from the group consisting of hydrogen, $C_{1-4}$ alkyl and —C(O)$C_{1-4}$ alkyl; wherein the —C(O)$C_{1-4}$ alkyl is optionally substituted with 1, 2, or 3 substituents independently selected from the group consisting of halo, oxo, N($R^{11}$)$_2$, HET, —O—$C_{1-4}$ alkyl and $C_{6-10}$ aryl; wherein the —O—$C_{1-4}$ alkyl may be optionally substituted with 1, 2, or 3 substituents independently selected from the group consisting of halo, oxo, —N($R^{11}$)$_2$ and $C_{6-10}$ aryl and wherein the $C_{6-10}$ aryl may be optionally substituted with 1, 2, or 3 halo groups. Preferably, the —C(O)$C_{1-4}$ alkyl is optionally substituted with 1, 2, or 3 fluoro groups. Preferably, the —C(O)$C_{1-4}$ alkyl is optionally substituted with 1, 2, or 3 oxo groups. Preferably, the —C(O)$C_{1-4}$ alkyl is optionally substituted with 1, 2, or 3 fluoro groups and with 1, 2, or 3 oxo groups. In particular embodiments, $R^{10}$ is —C(O)CH$_2$—O—CH$_2$—CH$_2$—F.

In some embodiments, $R^{10}$ is —C(O)$C_{6-10}$ aryl, —C(O)$C_{6-10}$ cycloalkyl or —C(O)HET and wherein the —C(O)$C_{6-10}$ aryl, —C(O)$C_{6-10}$ cycloalkyl and —C(O)HET may be optionally substituted with substituents independently selected from the group consisting of $C_{1-4}$ alkyl, $C_{1-4}$ haloalkyl, —O—$C_{1-4}$ alkyl, —O—$C_{1-4}$ haloalkyl and 1, 2, or 3 halo groups. In such embodiments, HET is preferably a 5 to 10 membered heterocycloalkyl or a 5 to 10 membered heteroaryl, that is optionally substituted as described herein.

In some embodiments, $R^{11}$ is selected from hydrogen, $C_{1-4}$ alkyl and $C_{1-4}$ haloalkyl.

In some embodiments, $R^{12}$ is selected from the group consisting of hydrogen, $C_{1-4}$ alkyl and —C(O)$C_{1-4}$ alkyl, the $C_{1-4}$ alkyl optionally substituted with 1, 2, or 3 halo groups. Preferably, the $C_{1-4}$ alkyl is optionally substituted with 1, 2, or 3 fluoro groups.

In some embodiments, $R^{12}$ is selected from the group consisting of hydrogen, $C_{1-4}$ alkyl and —C(O)$C_{1-4}$ alkyl, the —C(O)$C_{1-4}$ alkyl optionally substituted with N($R^{11}$)$_2$, pyrrolidinyl, piperidinyl, morpholinyl, benzothiophenyl, and phenyl, the phenyl optionally substituted with 1, 2, or 3 halo groups.

In some embodiments, $R^{12}$ is selected from the group consisting of hydrogen, $C_{1-4}$ alkyl and —C(O)$C_{1-4}$ alkyl; wherein the —C(O)$C_{1-4}$ alkyl is optionally substituted with 1, 2, or 3 substituents independently selected from the group consisting of halo, oxo, N($R^{11}$)$_2$, HET, —O—$C_{1-4}$ alkyl and $C_{6-10}$ aryl; wherein the —O—$C_{1-4}$ alkyl may be optionally substituted with 1, 2, or 3 substituents independently selected from the group consisting of halo, oxo, —N($R^{11}$)$_2$ and $C_{6-10}$ aryl and wherein the $C_{6-10}$ aryl may be optionally substituted with 1, 2, or 3 halo groups. Preferably, the —C(O)$C_{1-4}$ alkyl is optionally substituted with 1, 2, or 3 fluoro groups. Preferably, the —C(O)$C_{1-4}$ alkyl is optionally substituted with 1, 2, or 3 oxo groups. Preferably, the —C(O)$C_{1-4}$ alkyl is optionally substituted with 1, 2, or 3 fluoro groups and with 1, 2, or 3 oxo groups. In particular embodiments, $R^{12}$ is —C(O)CH$_2$—O—CH$_2$—CH$_2$—F.

In some embodiments, $R^{12}$ is —C(O)$C_{6-10}$ aryl, —C(O)$C_{6-10}$ cycloalkyl or —C(O)HET and wherein the —C(O)$C_{6-10}$ aryl, —C(O)$C_{6-10}$ cycloalkyl and —C(O)HET may be optionally substituted with 1, 2, or 3 substituents independently selected from the group consisting of $C_{1-4}$ alkyl, $C_{1-4}$ haloalkyl, —O—$C_{1-4}$ alkyl, —O—$C_{1-4}$ haloalkyl and halo groups. In such embodiments, HET is preferably a 5 to 10 membered heterocycloalkyl or a 5 to 10 membered heteroaryl, that is optionally substituted as described herein.

In some embodiments, each of $R^{13}$, $R^{13'}$ and $R^{13''}$, independently, is selected from the group consisting of hydrogen, $C_{1-6}$ alkyl, $C_{1-6}$ cycloalkyl and HET. In some embodiments, each of $R^{13}$, $R^{13'}$ and $R^{13''}$ is H.

In some embodiments, X is CH$_2$; at least one of $R^1$ and $R^2$ is —NR$^{10}$R$^{12}$; and at least one of $R^{10}$ and $R^{12}$ is —C(O)$C_{6-10}$ aryl, —C(O)$C_{6-10}$ cycloalkyl or —C(O)HET.

In some embodiments, each HET is an independently selected monocyclic 5-6 membered heteroaryl, 8-10 membered bicyclic heteroaryl, a monocyclic 4-6 membered heterocycloalkyl, or a bicyclic 8-10 membered heterocycloalkyl group, each comprising 1, 2, 3, or 4 heteroatoms selected from O, S and N, and optionally substituted with 1, 2, or 3 substituents independently selected from the group consisting of $C_{1-4}$ alkyl, $C_{1-4}$ haloalkyl, —O—$C_{1-4}$ alkyl, —O—$C_{1-4}$ haloalkyl, halo, hydroxy and oxo groups.

In some embodiments, each HET is independently selected from the group consisting of benzimidazolyl, benzofuranyl, benzopyrazolyl, benzotriazolyl, benzothiophenyl, benzoxazolyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, tetrazolyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, tetrahydrofuranyl, and tetrahydrothienyl, each optionally substituted with 1, 2, or 3 substituents independently selected from the group consisting of $C_{1-4}$ alkyl, $C_{1-4}$ haloalkyl, —O—$C_{1-4}$ alkyl, —O—$C_{1-4}$ haloalkyl, halo, hydroxy and oxo groups.

It is preferred that, in the compound of Formula I-VIII or a pharmaceutically acceptable salt thereof, at least one of $R^1$, $R^2$, $R^5$ and $R^9$ comprises an imaging agent. If desired, two, three or all of $R^1$, $R^2$, $R^5$ and $R^9$ can comprises an imaging agent.

Suitable imaging agents are selected from the group consisting of a paramagnetic ion, an x-ray imaging agent, a fluorophore, and a radioisotope.

Suitable paramagnetic ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), and erbium (III). The paramagnetic ions are either directly or indirectly (e.g., through a chelator) bound to the compounds of Formula I-VIII or a pharmaceutically acceptable salt thereof, provided herein.

Suitable x-ray imaging agents include lanthanum (III), gold (III), lead (II), bismuth (III), and iodinated x-ray imaging agents (e.g, diatrizoate, ioxaglate, metrizoate, iopamidol, iohexol, ioxilan, iopromide, iodixanol, and ioversol).

Suitable fluorophores include Alexa 350, Alexa 430, AMCA, BODIPY 630/650, BODIPY 650/665, BODIPY-FL, BODPY-R6G, 13BODLPY-TMR, BODLPY-TRX, cascade blue, Cy3, Cy5, 6-FAM, fluorescein isothiocyanate, HEX, 6-JOE, oregon green 488, oregon green 500, oregon green 514, quantum dots, pacific blue, REG, rhodamine green, rhodamine red, renographin, ROX, TAMRA, TET, tetramethylrhodamine, Texas Red, AF 350, 405, AF532, AF488, AF647, AF680, AF750, Cy5, Cy5.5, Cy7, indocyanine green (ICG), green fluorescent protein (GFP), red fluorescent protein (RFP), and dsRED.

The radioisotopes provided herein are useful as imaging agents in one or more of the methods provided herein. In addition, the radioistopes provided herein may also be useful in one or more therapeutic applications, for example, when administered to a subject in a therapeutically effective amount. For example, $^{131}I$ and $^{64}Cu$ may be useful as imaging agents (e.g., as non-toxic and/or non-therapeutic radioisotopes) when administered to the subject at low concentrations (e.g., 5 mCi) and may also be useful as therapeutic agents (i.e., as toxic radioisotopes and/or therapeutic radioisotopes) when administered to the subject at a higher concentration.

Suitable radioisotopes include $^{3}H$, $^{11}C$, $^{14}C$, $^{18}F$, $^{32}P$, $^{35}S$, $^{36}Cl$, $^{51}Cr$, $^{52}Fe$, $^{57}Co$, $^{58}Co$, $^{59}Fe$, $^{64}Cu$, $^{67}Cu$, $^{67}Ga$, $^{68}Ga$, $^{75}Se$, $^{76}Br$, $^{77}Br$, $^{89}Zr$, $^{90}Y$, $^{99m}Tc$, $^{111}In$, $^{123}I$, $^{124}I$, $^{125}I$, $^{131}I$, $^{152}Eu$, $^{153}Sm$, $^{166}Ho$, $^{177}Lu$, $^{186}Re$, $^{188}Re$, $^{201}Tl$, $^{203}Pb$, $^{210}At$, $^{211}At$, $^{212}Bi$, $^{213}Bi$, and $^{225}Ac$. The radioisotopes are either directly or indirectly (e.g., through a chelator) bound to the compounds of Formula I-VIII or a pharmaceutically acceptable salt thereof, provided herein.

In preferred aspects of the disclosure, at least one of $R^1$, $R^2$, $R^5$ and $R^9$ of the compound of Formula I-VIII or a pharmaceutically acceptable salt thereof, contains $^{18}F$.

In some embodiments, at least one of $R^1$, $R^2$, $R^5$ and $R^9$ of the compound of Formula I-VIII or a pharmaceutically acceptable salt thereof, comprises an imaging agent selected from the group consisting of a positron emission tomography (PET) imaging agent, a single-photon emission computed tomography (SPECT) imaging agent, and a computed tomography imaging agent.

In some embodiments, the compound of Formula I-VIII or a pharmaceutically acceptable salt thereof, is a PET or SPECT imaging agent. In some embodiments, the compound of Formula I-VIII or a pharmaceutically acceptable salt thereof, is a PET imaging agent. In some embodiments, the compound of Formula I-VIII or a pharmaceutically acceptable salt thereof, is a SPECT imaging agent. In some embodiments, the compound of Formula I-VIII or a pharmaceutically acceptable salt thereof, is a computed tomography imaging agent. In some embodiments, the compound of Formula I-VIII or a pharmaceutically acceptable salt thereof, is a radioisotopic computed tomography imaging agent.

In some embodiments, the compound of Formula I-VIII or a pharmaceutically acceptable salt thereof, is a PET or SPECT imaging agent, wherein at least one of $R^1$, $R^2$, $R^5$ and $R^9$ of the compound of Formula I-VIII or a pharmaceutically acceptable salt thereof, comprises one or more radioisotopes selected from the group consisting of $^{3}H$, $^{11}C$, $^{14}C$, $^{18}F$, $^{32}P$, $^{35}S$, $^{52}Fe$, $^{58}CD$, $^{64}Cu$, $^{68}Ga$, $^{76}Br$, $^{77}Br$, $^{89}Zr$, $^{111}In$, $^{123}I$, $^{124}I$, $^{125}I$, $^{131}I$, $^{186}Re$, $^{188}Re$, and $^{201}Tl$.

In some embodiments, the compound of Formula I-VIII or a pharmaceutically acceptable salt thereof, is a PET or SPECT imaging agent, wherein at least one of $R^1$, $R^2$, $R^5$ and $R^9$ of the compound of Formula I-VIII or a pharmaceutically acceptable salt thereof, comprises 1, 2, or 3 radioisotopes selected from the group consisting of $^{3}H$, $^{11}C$, $^{14}C$, $^{18}F$, $^{32}P$, $^{35}S$, $^{52}Fe$, $^{58}Co$, $^{64}Cu$, $^{68}Ga$, $^{76}Br$, $^{77}Br$, $^{89}Zr$, $^{111}In$, $^{123}I$, $^{124}I$, $^{125}I$, $^{131}I$, $^{186}Re$, $^{188}Re$, and $^{201}Tl$.

In some embodiments, the compound of Formula I-VIII or a pharmaceutically acceptable salt thereof, is a PET or SPECT imaging agent, wherein at least one of $R^1$, $R^2$, $R^5$ and $R^9$ of the compound of Formula I-VIII or a pharmaceutically acceptable salt thereof, comprises one radioisotope selected from the group consisting of $^{3}H$, $^{11}C$, $^{14}C$, $^{18}F$, $^{32}P$, $^{35}S$, $^{52}Fe$, $^{58}Co$, $^{64}Cu$, $^{68}Ga$, $^{76}Br$, $^{77}Br$, $^{89}Zr$, $^{111}In$, $^{123}I$, $^{124}I$, $^{125}I$, $^{131}I$, $^{186}Re$ $^{188}Re$, and $^{201}Tl$.

In some embodiments, the compound of Formula I-VIII or a pharmaceutically acceptable salt thereof, is a PET or SPECT imaging agent, wherein at least one of $R^1$, $R^2$, $R^5$ and $R^9$ of the compound of Formula I-VIII or a pharmaceutically acceptable salt thereof, comprises $^{68}Ga$.

In a preferred embodiment, the compound of Formula I-VIII or a pharmaceutically acceptable salt thereof, is a PET imaging agent, wherein at least one of $R^1$, $R^2$, $R^5$ and $R^9$ of the compound of Formula I-VIII or a pharmaceutically acceptable salt thereof, comprises $^{18}F$.

In some embodiments, at least one of $R^1$, $R^2$, $R^5$ and $R^9$ of the compound of Formula I-VIII or a pharmaceutically acceptable salt thereof, further comprises one or more chelating agents.

Suitable chelating agents include, but are not limited to, 1,4,7-triazacyclononanetriacetic acid (NOTA), 1,4,7-triazacyclononane-4,7-diacetic acid (NODA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), and 1,4,8,11-tetraazacyclotetradecane-N,N',N'',N'''-tetraacetic acid (TETA), 1,4,7,10-tetraaza-1,4,7,10-tetra-(2-carbamoyl methyl)-cyclododecane (TCMC), and Desferrioxamine B (DFO). In some embodiments, the chelating agent is selected from the group consisting of 1,4,7-triazacyclononanetriacetic acid (NOTA), 1,4,7-triazacyclononane-4,7-diacetic acid (NODA), 1,4,7,10-tetraazacyclododecane-1,4,7,10-tetraacetic acid (DOTA), 1,4,7-triazacyclononane-1-glutaric acid-4,7-diacetic acid (NODAGA), ethylene diamine tetra-acetic acid (EDTA), diethylene triaminepentaacetic acid (DTPA), cyclohexyl-1,2-diaminetetraacetic acid (CDTA), ethyleneglycol-O,O'-bis(2-aminoethyl)-N,N,N',N'-tetraacetic acid (EGTA), N,N-bis(hydroxybenzyl)-ethylenediamine-N,N'-diacetic acid (HBED), triethylene tetramine hexaacetic acid (TTHA), hydroxyethyidiamine triacetic acid (HEDTA), and 1,4,8,11-tetraazacyclotetradecane-N,N',N'',N'''-tetraacetic acid (TETA), 1,4,7,10-tetraaza-1,4,7,10-tetra-(2-carbamoyl methyl)-cyclododecane (TCMC), and Desferrioxamine B (DFO). In some embodiments, the chelating agent is selected from the group consisting of 1,4,7-triazacyclononanetriacetic acid (NOTA), 1,4,7-triazacyclononane-4,7-diacetic acid (NODA), 1,4,7, 10-tetraazacyclododecane-1,4,7,10-tetraacetic acid (DOTA), and 1,4,7-triazacyclononane-1-glutaric acid-4,7-diacetic acid (NODAGA). In some embodiments, the chelating agent is 1,4,7-triazacyclononanetriacetic acid (NOTA).

Synthesis

As will be appreciated, the compounds provided herein, including salts thereof, can be prepared using known organic synthesis techniques and can be synthesized according to any of numerous possible synthetic routes.

The compound of Formula I-VIII or a pharmaceutically acceptable salt thereof, provided herein can be prepared by the routes described in the following Schemes. Appropriate protective groups for use in such syntheses will be found in the above texts, as well as in McOmie, *Protective Groups in Organic Chemistry*, (1973):98.

Additional reactions may be necessary, as described elsewhere, to form intramolecular linkages to restrain conformation.

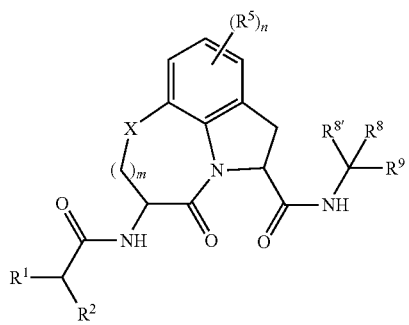

4

Some compounds of the disclosure could be synthesized following the general Scheme I wherein Compound 1 could be coupled with an appropriate protected amino acid and followed with cyclization onto the indole nitrogen to form Compound 2. The ester of Compound 2 could then be hydrolyzed followed by amide formation to form Compound 3. Boc deprotection of Compound 3 could be followed by amide bond formation using an appropriate acid to form final Compound 4.

Scheme I

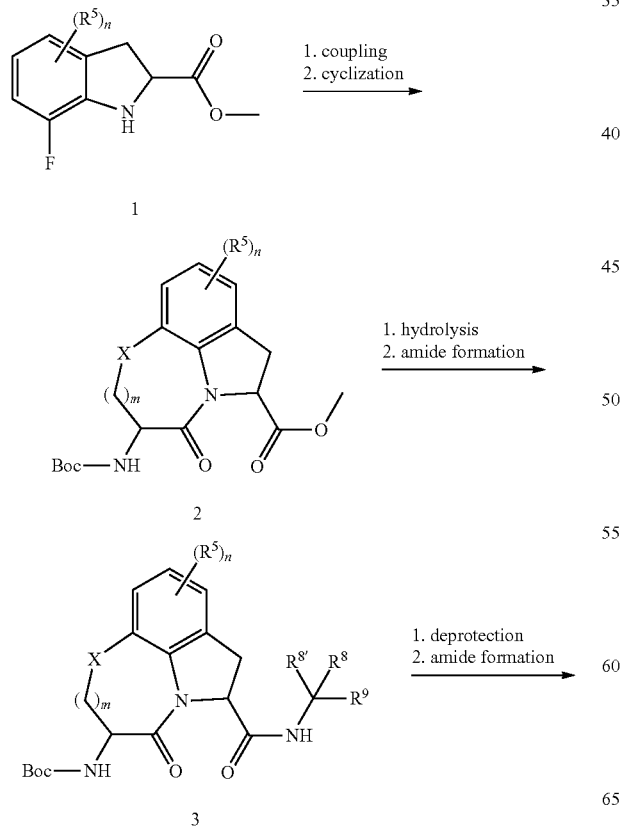

Scheme II

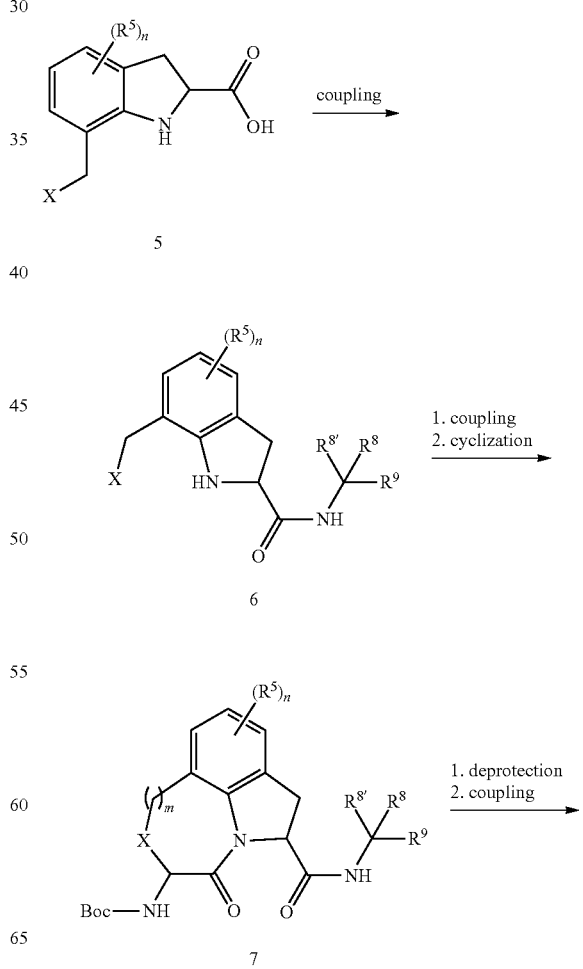

-continued

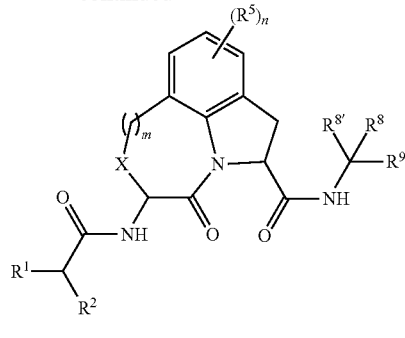

8

Other compound of the disclosure could be synthesized following general Scheme II wherein Compound 5 could be coupled with an appropriate amine to form Compound 6. Compound 6 could then be coupled to an appropriate protected amino acid which could then be cyclized to form Compound 7. Deprotection of Compound 7 followed by coupling with an appropriate acid could be performed to afford final Compound 8.

Imaging Agents

Many appropriate imaging agents are known in the art (see, for e.g., U.S. Pat. Nos. 5,021,236; 4,938,948; and 4,472,509, the disclosure of each of which is incorporated herein by reference in its entirety). Radioactively labeled compounds of Formula I-VIII or a pharmaceutically acceptable salt thereof, provided herein may be prepared according to well-known methods in the art. As an example, compounds of Formula I-VIII or a pharmaceutically acceptable salt thereof, provided herein may be labeled with $^{68}$Ga by radiometalation of a bifunctional chelator provided herein (e.g., NOTA, NODA, DOTA, or NODAGA) or a similar derivative thereof.

Synthetic methods for incorporating radioisotopes into organic compounds are well known in the art, and one of ordinary skill in the art will readily recognize other methods applicable for the compounds provided herein.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^{1}$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Definitions

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms. In some embodiments, the $C_{1-4}$ alkyl group is optionally substituted with 1, 2, or 3 halo groups. Preferably, the $C_{1-4}$ alkyl group is optionally substituted with 1, 2, or 3 fluoro groups As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cycloheptyl, or adamantyl. In some embodiments, the cycloalkyl has 6-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "halo" or "halogen" refers to F, Cl, Br, or I, or their isotopes. In some embodiments, a halo or halogen is F, Cl, or Br, or their isotopes. Preferably, the halo or halogen is F or $^{18}$F.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "HET" refers to a heteroaryl and a heterocycloalkyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

As used herein, the term "hydroxy" refers to a group of formula —OH.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "oxo" refers to a double-bonded oxygen (i.e., =O).

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of Formula I-VIII depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Unless specifically defined, compounds provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}$C], [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

All compounds of Formula I-VIII or a pharmaceutically acceptable salt thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

Methods of Use

The present application further provides methods of imaging Granzyme B using a compound of Formula I-VIII or a pharmaceutically acceptable salt thereof.

In some embodiments, the method of imaging is performed in a cell, a tissue, a cell sample, a tissue sample, or a subject.

As used herein, the term "subject," refers to any animal, including mammals and invertebrates. For example, mice, rats, other rodents, rabbits, dogs, cats, swine, cattle, sheep, horses, primates, fish, and humans. In some embodiments, the subject is a human. In some embodiments, the subject is a mouse. In some embodiments, the subject is a fish (e.g., a zebra fish).

In some embodiments, the method comprises administering to the subject an effective amount of a compound of Formula I-VIII or a pharmaceutically acceptable salt thereof. In some embodiments, the method is an in vitro method. In some embodiments, the method is an in vivo method.

The present application further provides a method of imaging Granzyme B in a cell or tissue, comprising:
i) contacting the cell or tissue with an effective amount of a compound of Formula I-VIII or a pharmaceutically acceptable salt thereof, and
ii) imaging the cell or tissue with a suitable imaging technique, thereby imaging Granzyme B in the cell or tissue, wherein:
at least one of $R^1$, $R^2$, $R^5$ and $R^9$ of the compound of Formula I-VIII or a pharmaceutically acceptable salt thereof, comprises an imaging agent.

The present application further provides a method of imaging Granzyme B in a cell sample or tissue sample, comprising:
i) contacting the cell sample or tissue sample with effective amount of a compound of Formula I-VIII or a pharmaceutically acceptable salt thereof, and
ii) imaging the cell sample or tissue sample with a suitable imaging technique, thereby imaging Granzyme B in the cell sample or tissue sample, wherein:
at least one of $R^1$, $R^2$, $R^5$ and $R^9$ of the compound of Formula I-VIII or a pharmaceutically acceptable salt thereof, comprises an imaging agent.

The present application further provides a method of imaging Granzyme B in a subject, comprising:
i) administering to the subject an effective amount of a compound of Formula I-VIII or a pharmaceutically acceptable salt thereof, and
ii) imaging the subject with a suitable imaging technique, thereby imaging Granzyme B in the subject, wherein:
at least one of $R^1$, $R^2$, $R^5$ and $R^9$ of the compound of Formula I-VIII or a pharmaceutically acceptable salt thereof, comprises an imaging agent.

The present application further provides a method of imaging an immune response in a cell or tissue sample, comprising:
i) contacting the cell or tissue sample with an effective amount of a compound of Formula I-VIII or a pharmaceutically acceptable salt thereof, and
ii) imaging the cell or tissue sample with a suitable imaging technique, thereby imaging the immune response in the cell or tissue sample, wherein:
at least one of $R^1$, $R^2$, $R^5$ and $R^9$ of the compound of Formula I-VIII or a pharmaceutically acceptable salt thereof, comprises an imaging agent.

The present application further provides a method of imaging an immune response in a subject, comprising:
i) administering to the subject an effective amount of a compound of Formula I-VIII or a pharmaceutically acceptable salt thereof, and
ii) imaging the subject with a suitable imaging technique, thereby imaging the immune response in the subject, wherein:
at least one of $R^1$, $R^2$, $R^5$ and $R^9$ of the compound of Formula I-VIII or a pharmaceutically acceptable salt thereof, comprises an imaging agent.

The present application further provides a method of monitoring treatment of a disease in a subject, comprising:
i) administering to the subject an effective amount of a compound of Formula I-VIII or a pharmaceutically acceptable salt thereof, and
ii) imaging the subject with a suitable imaging technique, wherein:
at least one of $R^1$, $R^2$, $R^5$ and $R^9$ of the compound of Formula I-VIII or a pharmaceutically acceptable salt thereof, comprises an imaging agent.

The present application further provides a method of monitoring an immune response in the treatment of a disease in a subject, comprising:
i) administering to the subject an effective amount of a compound of Formula I-VIII or a pharmaceutically acceptable salt thereof, and
ii) imaging the subject with a suitable imaging technique, wherein:
at least one of $R^1$, $R^2$, $R^5$ and $R^9$ of the compound of Formula I-VIII or a pharmaceutically acceptable salt thereof, comprises an imaging agent.

In some embodiments, the methods provided herein further comprise waiting a time sufficient to allow the compound of Formula I-VIII or a pharmaceutically acceptable salt thereof, to accumulate at a cell or tissue site (e.g., a cell or tissue site in a subject) associated with the disease, prior to imaging.

In some embodiments, the methods provided herein further comprise waiting a time sufficient to allow the compound of Formula I-VIII or a pharmaceutically acceptable salt thereof, to bind Granzyme B at a cell or tissue site (e.g., a cell or tissue site in a subject) associated with the disease, prior to imaging.

In some embodiments, the time sufficient is from about 30 seconds to about 24 hours, for example, about 30 seconds to about 24 hours, about 30 seconds to about 12 hours, about 30 seconds to about 6 hours, about 30 seconds to about 2 hours, about 30 seconds to about 1 hour, about 30 seconds to about 30 minutes, about 30 seconds to about 10 minutes, about 10 minutes to about 24 hours, about 10 minutes to about 12 hours, about 10 minutes to about 6 hours, about 10 minutes to about 2 hours, about 10 minutes to about 1 hour, about 10 minutes to about 30 minutes, about 30 minutes to about 24 hours, about 30 minutes to about 12 hours, about 30 minutes to about 6 hours, about 30 minutes to about 2 hours, about 30 minutes to about 1 hour, about 1 hour to about 24 hours, about 1 hour to about 12 hours, about 1 hour to about 6 hours, about 1 hour to about 2 hours, about 2 hours to about 24 hours, about 2 hours to about 12 hours, about 2 hours to about 6 hours, about 6 hours to about 24 hours, about 6 hours to about 12 hours, or about 12 hours to about 24 hours.

In some embodiments, the suitable imaging technique is a non-invasive imaging technique. In some embodiments, the suitable imaging technique is a minimally invasive imaging technique. As used herein, the term "minimally invasive imaging technique" comprises imaging techniques employing the use of an internal probe or injection of a compound of Formula I-VIII or a pharmaceutically acceptable salt thereof, or radiotracer via syringe.

Example imaging techniques include, but are not limited to, fluoroscopic imaging, x-ray imaging, magnetic resonance imaging (MRI), ultrasound imaging, photoacoustic imaging, thermographic imaging, tomographic imaging, echocardiographic imaging, positron emission tomography (PET) imaging, PET with computed tomography (CT) imaging, PET-MRI, single-photon emission computed tomography (SPECT), and ultrasound imaging. In some embodiments, the suitable imaging technique is selected from the group consisting of PET imaging, PET-CT, PET-MRI, and SPECT.

In some embodiments, the suitable imaging technique is selected from the group consisting of positron emission tomography (PET) imaging, positron emission tomography (PET) with computed tomography imaging, and positron emission tomography (PET) with magnetic resonance imaging (MRI). In some embodiments, the suitable imaging technique is selected positron emission tomography (PET) imaging.

In some embodiments, a disease as described herein is selected from the group consisting of an autoimmune disorder, an inflammatory disorder, a skin disorder, cancer, and a cardiovascular disorder.

In some embodiments, the disease is a cancer. In some embodiments, the cancer comprises a solid tumor. In some embodiments, the cancer is a hematological cancer (e.g., leukemia, lymphoma, and the like). In some embodiments, the cancer is selected from the group consisting of brain, breast cancer, cervical cancer, colorectal cancer, lung cancer, lymphoma, melanoma, bladder cancer, renal cell carcinoma, multiple myeloma, pancreatic cancer, and prostate cancer. In some embodiments, the cancer is selected from the group consisting of Hairy-cell leukemia, Kaposi's sarcoma, follicular lymphoma, chronic myeloid leukemia, cutaneous T-cell lymphoma, peripheral T-cell lymphoma, T-cell prolymphocytic leukemia, Classical Hodgkin's lymphoma, B-cell non-Hodgkin's lymphoma, chronic lymphocytic leukemia, acute myeloid leukemia, myelodysplastic syndrome, primary myelofibrosis, post-essential thrombocytheia myelofibrosis, post-polycythemia vera myelofibrosis, melanoma, renal cell carcinoma, prostate cancer, non-small cell lung cancer, small cell lung cancer, glioblastoma, hepatocellular carcinoma, urothelial carcinoma, esophageal carcinoma, gastroesophageal carcinoma, gastric cancer, multiple myeloma, colon cancer, rectal cancer, squamous cell carcinoma of the head and neck, epithelial ovarian cancer (EOC), primary peritoneal cancer, fallopian tube carcinoma, HER2+ breast cancer, ER+/PR+/HER2−breast cancer, triple-negative breast cancer, gastric cancer, pancreatic cancer, bladder cancer, Merkel cell cancer, nasopharyngeal cancer, adrenocortical carcinoma, meningioma, neuroblastoma, retinoblastoma, osteosarcoma, rhabdomyosarcoma, Ewing's sarcoma, liposarcoma, fibrosarcoma, leiomyosarcoma, peripheral primitive neuroectodermal tumor, squamous cell carcinoma of the cervix, squamous cell carcinoma of the vagina, and squamous cell carcinoma of the vulva. In some embodiments, the cancer is colon cancer.

In some embodiments, the disease is selected from the group consisting of graft-versus-host disease, rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, rheumatic fever, post-infectious glomerulonephritis, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia, alopecia senilis by preventing epilation, alopecia senilis by providing hair germination and/or promoting hair generation and hair growth, muscular dystrophy, pyoderma, Sezary's syndrome, Addison's disease, ischemia-reperfusion injury of organs, transplantation disease, ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, aging, carcinogenesis, metastasis of carcinoma and hypobaropathy, histamine or leukotriene-C4 release associated diseases, Behcet's disease, autoimmune hepatitis, primary biliary cirrhosis, sclerosing cholangitis, partial liver resection, acute liver necrosis, necrosis caused by toxin, viral hepatitis, shock, anoxia, B-virus hepatitis, non-A/non-B hepatitis, cirrhosis, alcoholic cirrhosis, hepatic failure, fulminant hepatic failure, late-onset hepatic failure, acute-on-chronic liver failure, cytomegalovirus infection, HCMV infection, AIDS, senile dementia, trauma, chronic bacterial infection, malignancy of lymphoid origin, acute lymphocytic leukemia, chronic lymphocytic leukemia, acute lymphocytic lymphoma, and chronic lymphocytic lymphoma.

In some embodiments, the disease is selected from the group consisting of systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, asthma, schleroderma and Sjogren's syndrome.

In some embodiments, the disease is selected from the group consisting of bone marrow rejection, organ transplant rejection, and graft-versus-host disease.

As used herein, the phrase "therapeutically effective amount" refers to the amount of active compound of Formula I-VIII or a pharmaceutically acceptable salt thereof, or pharmaceutical agent that elicits the biological or medicinal response that is being sought in a tissue, system, animal, individual or human by a researcher, veterinarian, medical doctor or other clinician.

In some embodiments, the dosage of the compound of Formula I-VIII or a pharmaceutically acceptable salt thereof, administered to a subject or individual is about 1 µg to about 2 g, for example, about 1 μg to about 2 g, about 1 μg to about 1000 mg, about 1 μg to about 500 mg, about 1 μg to about 100 mg, about 1 μg to about 50 mg, about 1 μg to about 1 mg, about 1 μg to about 500 μg, about 1 μg to about 100 μg, about 1 μg to about 10 μg, about 10 μg to about 2 g, for example, about 10 μg to about 2 g, about 10 μg to about 1000 mg, about 10 μg to about 500 mg, about 10 μg to about 100 mg, about 10 μg to about 50 mg, about 10 μg to about 1 mg, about 10 μg to about 500 μg, about 10 μg to about 100 μg, about 100 μg to about 2 g, for example, about 100 μg to about 2 g, about 100 μg to about 1000 mg, about 100 μg to about 500 mg, about 100 μg to about 100 mg, about 100 μg to about 50 mg, about 100 μg to about 1 mg, about 100 μg to about 500 μg, about 500 μg to about 2 g, for example, about 500 μg to about 2 g, about 500 μg to about 1000 mg, about 500 μg to about 500 mg, about 500 μg to about 100 mg, about 500 μg to about 50 mg, about 500 μg to about 1 mg, about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

When employed in methods of treating a disease, the compound of Formula I-VIII or a pharmaceutically acceptable salt thereof, provided herein can be administered in combination with one or more of the additional agents provided herein. Example therapeutic agents include, but are not limited to, anti-inflammatory agents, steroids, immunotherapy agents, chemotherapeutic agents, and therapeutic antibodies.

In some embodiments, administration of the therapeutic agent induces an immune response cell or tissue sample or subject. In some embodiments, the therapeutic agent is a compound of Formula I-VIII or a pharmaceutically acceptable salt thereof.

In some embodiments, the therapeutic agent is a compound of Formula I-VIII or a pharmaceutically acceptable salt thereof, wherein at least one of $R^1$, $R^2$, $R^5$ and $R^9$ of the compound of Formula I-VIII or a pharmaceutically acceptable salt thereof, comprises a radioisotope (e.g., a therapeutic radioisotope).

In some embodiments, the therapeutic agent is a compound of Formula I-VIII or a pharmaceutically acceptable salt, wherein at least one of $R^1$, $R^2$, $R^5$ and $R^9$ of the compound of Formula I-VIII or a pharmaceutically acceptable salt thereof, comprises a toxic radioisotope.

Examples of toxic radioisotopes include, but are not limited to, alpha emitters (e.g., $^{211}$At, $^{212}$Pb, $^{212}$Bi, $^{213}$Bi, $^{225}$Ac, $^{227}$Th) and beta emitters (e.g., $^{90}$Y, $^{131}$I and $^{177}$Lu). In some embodiments, the toxic radioisotope is a beta emitter.

In some embodiments, the toxic radioisotope is a beta emitter selected from the group consisting of $^{90}$Y, $^{131}$I and $^{177}$Lu. In some embodiments, the toxic radioisotope is an alpha emitter.

In some embodiments, the toxic radioisotope is an alpha emitter selected from the group consisting of $^{211}$At, $^{212}$Pb, $^{212}$Bi, $^{213}$Bi, $^{225}$Ac, $^{227}$Th.

The present application further provides a method of treating a disease in a subject, comprising:

i) administering to the subject, an effective amount of compound of Formula I-VIII or a pharmaceutically acceptable salt thereof, wherein at least one of $R^1$, $R^2$, $R^5$ and $R^9$ of the compound of Formula I-VIII or a pharmaceutically acceptable salt thereof, comprises a non-toxic imaging agent (e.g., a non-toxic radioisotope); and ii) imaging the subject with a suitable imaging technique, thereby treating the disease in the subject.

The present application further provides a method of treating a disease in a subject, comprising:

i) administering to the subject, an effective amount of compound of Formula I-VIII or a pharmaceutically acceptable salt thereof, wherein at least one of $R^1$, $R^2$, $R^5$ and $R^9$ of the compound of Formula I-VIII or a pharmaceutically acceptable salt thereof, comprises a non-therapeutic imaging agent (e.g., a non-therapeutic radioisotope); and ii) imaging the subject with a suitable imaging technique, thereby treating the disease in the subject.

In some embodiments, at least one of $R^1$, $R^2$, $R^5$ and $R^9$ of the compound of Formula I-VIII or a pharmaceutically acceptable salt thereof, comprises a non-toxic radioisotope selected from the group consisting of $^3$H, $^{11}$C, $^{14}$C, $^{18}$F, $^{35}$S, $^{52}$Fe, $^{58}$Co, $^{64}$Cu, $^{68}$Ga $^{76}$Br, $^{77}$Br, $^{89}$Zr, $^{111}$In, $^{123}$I, $^{124}$I, $^{125}$I, $^{131}$I, $^{186}$Re, $^{188}$Re, $^{201}$Tl.

In a preferred embodiment, at least one of $R^1$, $R^2$, $R^5$ and $R^9$ of the compound of Formula I-VIII or a pharmaceutically acceptable salt thereof, comprises $^{18}$F.

In some embodiments, at least one of $R^1$, $R^2$, $R^5$ and $R^9$ of the compound of Formula I-VIII or a pharmaceutically acceptable salt thereof, comprises a toxic radioisotope selected from the group consisting of $^{211}$At, $^{212}$Pb, $^{212}$Bi, $^{213}$Bi, $^{225}$Ac, $^{227}$Th, $^{90}$Y $^{131}$I and $^{177}$Lu.

In some embodiments, the subject has been identified and/or diagnosed as having the disease to be treated prior to step i). In some embodiments, the subject is identified and/or diagnosed as having the disease to be treated after step ii). For example, the disease to be treated is selected from the group consisting of: an autoimmune disorder, an inflammatory disorder, a skin disorder, cancer, and a cardiovascular disorder as described herein.

In some embodiments, the subject has been treated with one or more immunotherapeutic agents prior to step i). In some embodiments, the disease has been determined to be resistant to the one or more immunotherapeutic agents administered prior to step i).

In some embodiments, the method further comprises:

iii) administering one or more immunotherapeutic agents after the administration of an effective amount of the compound of Formula I-VIII or a pharmaceutically acceptable salt thereof. In some embodiments, steps i)-iii) are repeated multiple times.

In some embodiments, the disease to be treated is selected from the group consisting of an autoimmune disorder, an inflammatory disorder, a skin disorder, cancer, and a cardiovascular disorder as described herein. In some embodiments, the disease is a cancer described herein.

In some embodiments, the compound of Formula I-VIII or a pharmaceutically acceptable salt thereof, is administered to the subject in a therapeutically effective amount.

In some embodiments, the methods provided herein further comprise administering a therapeutic agent prior to step i). In some embodiments, the methods provided herein further comprise administering a therapeutic agent after step ii).

In some embodiments, the methods provided herein further comprise the steps of:

iii) administering a therapeutically effective amount of a therapeutic agent after step ii); and iv) repeating steps i) and ii) of the methods provided herein.

In some embodiments, the therapeutic agent is a compound other than a compound of Formula I-VIII, or a pharmaceutically acceptable salt thereof, provided herein.

In some embodiments, steps i)-iv) are repeated multiple times.

In some embodiments, the compound of Formula I-VIII or a pharmaceutically acceptable salt thereof, provided herein and the one or more additional therapeutic agents are administered according to a dosing regimen over a period of time. In some embodiments, the cell, cell sample, tissue, tissue sample, or subject are imaged with an appropriate imaging technique after administration of an effective amount of compound of Formula I-VIII or a pharmaceutically acceptable salt thereof, provided herein. In some embodiments, the cell, cell sample, tissue, tissue sample, or subject are imaged with an appropriate imaging technique after administration of the additional therapeutic agent.

In some embodiments, the present application provides a method of treating a disease in a subject, comprising:

i) administering to the subject an effective amount of a compound of Formula I-VIII or a pharmaceutically acceptable salt thereof, wherein at least one of $R^1$, $R^2$, $R^5$ and $R^9$ of the compound of Formula I-VIII or a pharmaceutically acceptable salt thereof, comprises a non-toxic imaging agent (e.g., a non-toxic radioisotope);

ii) imaging the subject with a suitable imaging technique;

iii) administering to the subject a therapeutic agent, thereby treating the disease in the subject.

In some embodiments, the present application provides a method of treating a disease in a subject, comprising:

i) administering to the subject an effective amount of a compound of Formula I-VIII or a pharmaceutically acceptable salt thereof, wherein at least one of $R^1$, $R^2$, $R^5$ and $R^9$ of the compound of Formula I-VIII or a pharmaceutically acceptable salt thereof, comprises a non-therapeutic imaging agent (e.g., a non-therapeutic radioisotope);

ii) imaging the subject with a suitable imaging technique;

iii) administering to the subject a therapeutic agent, thereby treating the disease in the subject.

In some embodiments, the method further comprises determining if the compound of Formula I-VIII or a pharmaceutically acceptable salt thereof, binds to a cell or tissue of the subject to be treated prior to step iii). In some embodiments, the method further comprises determining if the compound of Formula I-VIII or a pharmaceutically acceptable salt thereof, binds to Granzyme B, prior to the administration of step iii).

In some embodiments, the subject has been identified and/or diagnosed as having the disease to be treated prior to step i). In some embodiments, the subject is identified and/or diagnosed as having the disease to be treated after step ii).

In some embodiments, the subject has been treated with one or more immunotherapeutic agents prior to step i). In some embodiments, the disease has been determined to be resistant to the one or more immunotherapeutic agents administered prior to step i).

In some embodiments, the method further comprises:

iv) administering one or more immunotherapeutic agents after the administration of the therapeutic agent of step iii). In some embodiments, steps i)-iv) are repeated multiple times.

In some embodiments, the additional therapeutic agent is administered to the subject in a therapeutically effective amount.

In some embodiments, the therapeutic agent is an antibody. Example antibodies for use in combination therapy include but are not limited to trastuzumab (e.g. anti-HER2), ranibizumab (e.g. anti-VEGF-A), bevacizumab (e.g. anti-VEGF), panitumumab (e.g. anti-EGFR), cetuximab (e.g. anti-EGFR), rituxan (anti-CD20), antibodies directed to c-MET, and antibody inhibitors of Granzyme B (e.g., Clone GB11, Clone GrB-7, and NCL-L-Gran-B), ipilimumab (anti-CTLA-4), nivolumab (anti-PD-1), pembrolizumab (anti-PD-1), atezolizumab (anti-PD-1), elotuzumab (anti-SLAM7), and daratumumab (anti-CD38).

In some embodiments, the therapeutic agent is a steroid. Example steroids include corticosteroids such as cortisone, dexamethasone, hydrocortisone, methylprednisolone, prednisolone, and prednisone. In some embodiments, the additional agent is a corticosteroid.

In some embodiments, the therapeutic agent is an anti-inflammatory compound. Example anti-inflammatory compounds include aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

In some embodiments, the therapeutic agent is chemotherapeutic agent. Example chemotherapeutic agents include, but are not limited to, a cytostatic agent, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, SCH 66336, R115777, L778,123, BMS 214662, gefitinib, erlotinib hydrochloride, antibodies to EGFR, imatinib mesylate, intron, ara-C, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, vinorelbine, porfimer, erbitux, liposomal, thiotepa, altretamine, melphalan, trastuzumab, fulvestrant, exemestane, ifosfamide, rituximab, C225, alemtuzumab, clofarabine, cladribine, aphidicolin, sunitinib, dasatinib, tezacitabine, Sml1, triapine, didox, trimidox, amidox, 3-AP, MDL-101,731, bendamustine, ofatumumab, and GS-1101 (also known as CAL-101).

In some embodiments, the chemotherapeutic agent is selected from the group consisting of an alkylating agent (e.g., busulfan, chlorambucil, cisplatin, cyclophosphamide (cytoxan), dacarbazine, ifosfamide, mechlorethamine (mustargen), and melphalan), a nitrosourea (e.g., carmustine, lomustine, semustine, and streptozocin), a triazine (e.g., dacarbazine) an anti-metabolite (e.g., 5-fluorouracil (5-FU), cytarabine (Ara-C), fludarabine, gemcitabine, and methotrexate), a purine analog (e.g., 6-mercaptopurine, 6-thioguanine, and pentostatin (2-deoxycoformycin)), a mitotic inhibitor (e.g., docetaxel, etoposide (VP16), teniposide, paclitaxel, taxol, vinblastine, vincristine, and vinorelbine), an anti-tumor antibiotic (e.g., bleomycin, dactinomycin, daunorubicin, doxorubicin, mitomycin, plicamycin, and idarubicin), a platinum chemotherapeutic agent (e.g., cisplatin and carboplatin), an anthracenedione (e.g., mitoxantrone), a toxin (e.g., ricin A-chain (Burbage, *Leukemia research,* 21.7 (1997): 681-690), diphtheria toxin A (Massuda et al., *Proceedings of the National Academy of Sciences,* 94.26 (1997): 14701-14706; Lidor, *American journal of obstetrics and gynecology,* 177.3 (1997): 579-585), pertussis toxin A subunit, E. colienterotoxin toxin A subunit, cholera toxin A subunit and *Pseudomonas* toxin c-terminal), and a gene therapy vector (e.g., a signal transducing protein (e.g., Src, Abl, and Ras), Jun, Fos, and Myc).

In some embodiments, the therapeutic agent is an immunotherapeutic agent. An immunotherapeutic agent generally triggers immune effector cells and molecules to target and destroy cells (e.g., cancer cells). The immune effector may be, for example, an antibody specific for a marker on the surface of a cell (e.g. a tumor cell). The antibody alone may serve as an effector of therapy or it may recruit other cells to effect cell killing. Various effector cells include, but are not limited to, cytotoxic T cells and NK cells.

Example immunotherapeutic agents include, but are not limited to, azathioprine, chlorambucil, cyclophosphamide, cyclosporine, daclizumab, infliximab, methotrexate, tacrolimus, immune stimulators (e.g., IL-2, IL-4, IL-12, GM-CSF, tumor necrosis factor; interferons alpha, beta, and gamma; F42K and other cytokine analogs; a chemokine such as MIP-1, MIP-1β, MCP-1, RANTES, IL-8; or a growth factor such FLT3 ligand), an antigenic peptide, polypeptide or protein, or an autologous or allogenic tumor cell composition (see e.g., Ravindranath & Morton, *International reviews of immunology,* 7.4 (1991): 303-329), hormonal therapy, adrenocorticosteroids, progestins (e.g., hydroxyprogesterone caproate, medroxyprogesterone acetate, and megestrol acetate), estrogens (e.g., diethylstilbestrol and ethinyl estradiol), anti-estrogens (e.g., testosterone propionate and fluoxymesterone), anti-androgens (e.g., flutamide), and gonadotropin-releasing hormone analogs (e.g., leuprolide). Additional immunotherapeutic agents are known in the art, and can be found, for example, in Rosenberg et al, *New England Journal of Medicine,* 319.25 (1988): 1676-1680; and Rosenberg et al, *Annals of surgery,* 210.4 (1989): 474).

The therapeutic agents provided herein can be effective over a wide dosage range and are generally administered in an effective amount. It will be understood, however, that the amount of the therapeutic agent actually administered will usually be determined by a physician, according to the relevant circumstances, including the condition to be imaged, the chosen route of administration, the actual compound administered, the age, weight, and response of the individual subject, the severity of the subject's symptoms, and the like.

Pharmaceutical Compositions

When employed as pharmaceuticals, the compound of Formula I-VIII or a pharmaceutically acceptable salt thereof, and therapeutic agents provided herein can be administered in the form of pharmaceutical compositions. These compositions can be prepared as described herein or elsewhere, and can be administered by a variety of routes, depending upon whether local or systemic treatment is desired and upon the area to be treated.

Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral.

Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump.

In some embodiments, the compound of Formula I-VIII or a pharmaceutically acceptable salt thereof, provided herein is suitable for parenteral administration. In some embodiments, the compound of Formula I-VIII or a pharmaceutically acceptable salt thereof, is suitable for intravenous administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

In some embodiments, the pharmaceutical compositions provided herein are suitable for parenteral administration. In some embodiments, the pharmaceutical compositions provided herein are suitable for intravenous administration.

Also provided are pharmaceutical compositions which contain, as the active ingredient, a compound provided herein, or a pharmaceutically acceptable salt thereof, in combination with one or more pharmaceutically acceptable carriers (excipients).

In making the pharmaceutical compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient.

Thus, the pharmaceutical compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The pharmaceutical formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

Kits

The present application further provides a kit comprising a compound of Formula I-VIII or a pharmaceutically acceptable salt thereof. In some embodiments, the kit further comprises one or more additional therapeutic agents provided herein.

In some embodiments, the kit comprises one or more components of the compounds provided herein (e.g., one or more imaging agents, one or more chelating agents, one or more linking groups, or compounds of Formula I-VIII or a pharmaceutically acceptable salt thereof, that bind Granzyme B).

In some embodiments, each component of the kit (is stored within the kit in a separate container (e.g., a separate vial). In some embodiments, the components of the kits may be packaged either in aqueous media or in lyophilized form.

In some embodiments, the kit further comprises instructions, for example, as inserts or as labels, indicating quantities of the composition to be administered, guidelines for administration, and/or guidelines for mixing components of the kit to prepare a compound of Formula I-VIII, or a pharmaceutically acceptable salt thereof. In some embodiments, the instructions further comprise instructions for performing one or more of the methods provided herein.

The kits provided herein can further include, if desired, one or more conventional pharmaceutical kit components, such as, for example, containers with one or more pharmaceutically acceptable carriers, additional containers, etc., as will be readily apparent to those skilled in the art.

The compounds of Formula I-VIII described above can be tested using the human Granzyme B biochemical assay provided below.

Assay Parameters:

TABLE 1

Specific assay parameters.

| | |
|---|---|
| Enzyme: Granzyme B (human lymphocytes) | 5 nM |
| Substrate: Ac-IETD-AFC | 200 µM |
| Cpd incubation with enzyme | 30 mins |
| Assay temperature | 22° C. |
| Read time | 60 mins |
| Std inhibitor | C006 |
| Reader | EnVision multimode plate reader 2104 |

Materials:
1. Granzyme B (human lymphocytes) Enzyme: Enzo Lifesciences, Cat #ALX-200-602-0010
2. Substrate (Ac-IETD-AFC): Enzo Lifesciences, Cat #ALX-260-110-M010
3. Standard inhibitor (Compound 20-Isomer3): Synthesized internally in TCG
4. Dimethyl sulfoxide (DMSO): Sigma-Aldrich, Cat #41639
5. HEPES: Gibco, Cat #15630-080
6. Calcium chloride: Sigma-Aldrich, Cat #C-5080
7. Distilled water: Gibco, Cat #15230-162
8. Bovine serum albumin (BSA): Sigma-Aldrich, Cat #A3059
9. Black, clear bottom PDL plate (384 wells): Greiner bio-one, Cat #781946
10. Polypropylene plate (384 wells): Corning, Cat #3657

Assay Buffer Composition:

TABLE 2

Specific assay buffer compositions.

| Components | Concentration |
|---|---|
| HEPES | 50 mM |
| CaCl$_2$ | 10 mM |
| In distilled water pH adjusted to 7.5 with 5(N) NaOH | |

Compound Preparation:
1. DMSO is added to the respective compound vial to make 10 mM Compound stock solution, which is stored at −20° C.
2. 10 mM Compound stock solution is thawed and 1 mM DMSO stock solution is prepared by adding 45 µl of DMSO to 5 µl of 10 mM compound stock solution.
3. 1 mM DMSO stock solution is serially diluted (3.16 fold) by adding 10 µl of 1 mM DMSO stock to 21.6 µl of DMSO and mixed well. 10 µl of the resulting solution is then added to 21.6 µl of DMSO and mixed well. This process is continued to create 11 dilution points for the assay standard inhibitor and 8 dilution points for test compounds in 384 well polypropylene plate.
4. 2 µl of each dilution are dispensed in assay ready plate.
5. Each well is then diluted 25 fold by adding 48 µl of assay buffer to 2 µl of compound in assay ready plate to make Compound working stock.

Enzyme Preparation:
1. Supplied Granzyme B (human lymphocytes) enzyme is reconstituted to 1 mg/ml (about 31.25 µM) and 1 µl aliquots are kept in −80° C.
2. 1 µl aliquot is diluted to 625 nM by adding 49 µl of assay buffer containing 0.1% BSA and gently mixed.
3. 10 nM enzyme working stock is prepared by adding assay buffer containing 0.1% BSA.

Substrate Preparation:
1. Supplied substrate (Ac-IETD-AFC) is reconstituted by adding DMSO to make 10 mM stock, aliquoted and stored in −80° C.
2. 4 mM substrate mid stock is prepared by adding DMSO.
3. Substrate working stock i.e. 800 µM is prepared by adding assay buffer.

Assay Protocol:
1. 10 µl of serially diluted Compound working stock (start dose 40 µM) is added from assay ready plate to assay plate according to the plate map.
2. Positive control (40 µM of standard inhibitor) and negative control (4% DMSO buffer) are added to the respective wells.
3. 20 µl of Enzyme working stock is added to assay plate and gently mixed.
4. The plate is incubated at 22° C. for 30 mins and spun at 130 g for 1 minute.
5. After incubation, 10 µl of Substrate working stock is added to respective wells and mixed (Assay plate is maintained in dark after substrate addition).
6. The plate is incubated at 22° C. for 60 mins and spun at 130 g for 1 minute.
7. Fluorescence read (RFU) (Ex: 400 nm/Em: 505 nm) is taken after 60 mins in EnVision Multimode plate reader.

Final Assay Concentration:

TABLE 3

Specific final assay concentrations.

| Reagent | Final concentration | Volume added |
|---|---|---|
| Compound/Std/Controls | Starting from 10 µM, 3.16 fold serial dilution | 10 µl |
| Enzyme | 5 nM | 20 µl |
| Substrate | 200 µM | 10 µl |

Data Analysis:

1. The RFU read is analyzed to calculate percent inhibition by normalizing with positive and negative controls taken as 100% and 0% effect respectively in Microsoft excel.
2. Graph is generated by putting the analyzed data in GraphPad prism 5.0 software to get $IC_{50}$ value for each compound.

In addition, compounds of Formula I-VIII described above are also tested in the metabolic stability assay using liver microsomes, as provided below.

Experimental Summary

TABLE 4

Summary of experimental protocol.

| Test system | Metabolic stability |
|---|---|
| Test | 1 µM, n = 2 |
| Liver microsomes | Human/Rat/Mouse liver microsomes (0.4 mg/ml) |
| Cofactor | NADPH Regeneration System (NRS) |
| Incubation | 0 and 30 min, or 0, 5, 10, 20, 30 and 60 minutes with NRS at 37° C. |
| Detection | LC-MS/MS |
| Reference | Atenolol, Propranolol, Diclofenac, Verapamil |
| Data | % Parent compound remaining/T-half/Clearance |

Protocol

Buffer pH7.4: Prepare 1 (M) $KH_2PO_4$ and 1 (M) $K_2HPO_4$. Titrate 1(M) $K_2HPO_4$ with 1 (M) $KH_2PO_4$ to obtain pH 7.40. Dilute this buffer 10 fold in Water (30 ml buffer+270 ml of water) to obtain 100 mM phosphate buffer. Adjust pH to 7.40±0.02 using 5(N) HCl or 5(N) NaOH.

NADPH Regeneration System (NRS): Prepare a solution containing 13 mM NADP, 33 mM Glucose-6-phosphate, 33 mM $MgCl_2$ and 4 U/ml Glucose-6-phosphate dehydrogenase in buffer.

Liver Microsome (LM) suspension: Thaw LM vial on ice, then mix 1.0 ml LM (20 mg/ml) with 19 ml buffer [final LM Conc: 1 mg/ml]

LM+NRS suspension: Mix 5.0 ml NRS with 20 ml LM suspension [final LM Conc: 0.8 mg/ml]

System suitability standard: a synthesized compound having Mol wt 686.2 used as System suitability standard. Dissolve this compound in ice-cold acetonitrile to obtain concentration of 0.1 µg/ml and store at 4° C.

Compound Dilution:

Compound Stock: 10 mM in DMSO

Sub stock (100 µM): 4 µl of 10 mM Compound Stock+398 µl Acetonitrile

Working plate (2 µM): 10 µl of 100 µM Sub stock+490 µl buffer

Assay Procedure

Incubate all plastic materials including tips at 37° C. overnight.

Incubate LM suspension and NRS at 37° C. for 15 min before use.

Add 40 µl buffer to the wells of blank plate.

Add 40 µl compound (from working plate) to 0, 5, 10, 20, 30 and 60 min plates.

Initiate reaction by adding 40 µl of LM+NRS suspension in each plate.

Terminate reaction by adding 240 µl ice-cold acetonitrile containing system suitability standard at designated time points. For T=0 add 240 µl ice-cold acetonitrile containing system suitability standard before LM+NRS addition.

Centrifuge (3500 rpm, 20 min and 15° C.) the plates.

Mix 110 µl supernatant with 110 µl water and quantitate amount of Compound in the solution using LC-MS/MS.

Calculation $$\% \text{ Remaining at } t =$$
$$x \text{ min} = 100 \times ([LC-MS/MS \text{ peak area of analyte}]_{t=x \, min})/$$
$$([LC-MS/MS \text{ peak area of analyte}]_{t=0 \, min})$$

$T_{1/2} = \ln 2 / -(\text{slope of the ln}(\% \text{ Remaining}) \text{ vs. time plot}) = \text{minutes}$ $$CLint, app = \ln 2 \cdot \frac{1}{T1/2(\text{min})} \cdot \frac{\text{mL incubation}}{\text{mg } LM \text{ protein}} \cdot \frac{1000 \, \mu L}{\text{mL}} = \mu L/\text{min/mg}$$

For Scaled CLint & Predicted CL use the relevant physiological parameters, as applicable.

Note that in this assay:

(1) Source of LM:

Human LM: Corning, Cat #25117

Rat LM: Corning, Cat #452501

Mouse LM: Xenotech, Cat #M1000

(2) Volumes mentioned in the protocol are representative values and may change depending on number of test compounds.

(3) It is assumed that the compounds are chemically stable in the assay system/buffer. This study does not carry any information on chemical stability or instability.

The metabolic stability assay described above can be performed using different test concentrations, LM Concentrations, or time points.

Without further elaboration, it is believed that one skilled in the art can, based on the above description, utilize the present disclosure to its fullest extent. The following specific examples are therefore to be construed as merely illustrative, and not limitative of the remainder of the disclosure in any way whatsoever. All publications cited herein are incorporated by reference in their entirety.

Shown in the table below are the structures and names of certain exemplary compounds. These compounds were found to inhibit Granzyme B to various degrees as indicated by their $IC_{50}$ values included in Table 5 below. Among the symbols in the table, "++++" indicates an $IC_{50}$ value of 0.001-0.300 µM, "+++" indicates an $IC_{50}$ value of 0.301-1.000 µM, "++" indicates an $IC_{50}$ value of 1.001-5 µM, "+" indicates an $IC_{50}$ value of greater than 5 µM, and "nd" indicates not determined.

TABLE 5

Compounds and IC$_{50}$ Values

| Compound Number | Structure | Name | IC$_{50}$ |
|---|---|---|---|
| C001 | 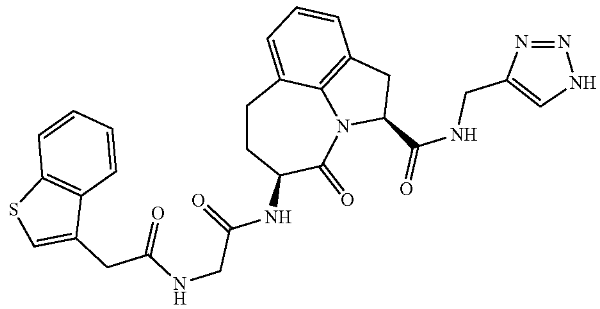 [SMILES: O=C(Cc1csc2ccccc12)NCC(=O)N[C@H]1CCc2cccc3c2N(C1=O)[C@H](C(=O)NCc1c[nH]nn1)C3] | (2S,5S)-5-[2-(2-Benzo[b]thiophen-3-yl-acetylamino)-acetylamino]-4-oxo-1,2,4,5,6,7-hexahydro-azepino[3,2,1-hi]indole-2-carboxylic acid (1H-[1,2,3]triazol-4-ylmethyl)-amide | + |
| C002 | 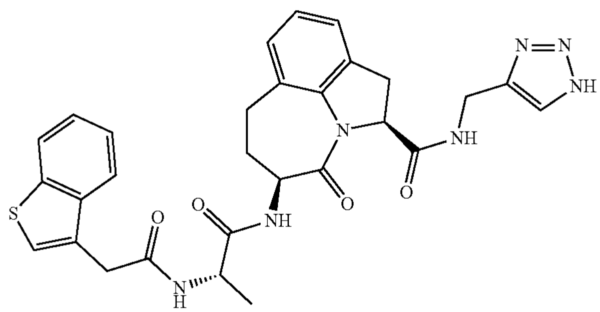 [SMILES: C[C@H](NC(=O)Cc1csc2ccccc12)C(=O)N[C@H]1CCc2cccc3c2N(C1=O)[C@H](C(=O)NCc1c[nH]nn1)C3] | (2S,5S)-5-[(S)-2-(2-Benzo[b]thiophen-3-yl-acetylamino)propionylamino]-4-oxo-1,2,4,5,6,7-hexahydro-azepino[3,2,1-hi]indole-2-carboxylic acid (1H-[1,2,3]triazol-4-ylmethyl)amide | ++ |
| C003 | 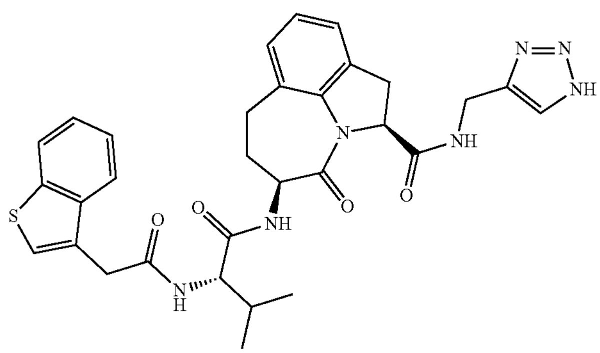 [SMILES: CC(C)[C@H](NC(=O)Cc1csc2ccccc12)C(=O)N[C@H]1CCc2cccc3c2N(C1=O)[C@H](C(=O)NCc1c[nH]nn1)C3] | (2S,5S)-5-[(S)-2-(2-Benzo[b]thiophen-3-yl-acetylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide | +++++ |
| C004 | 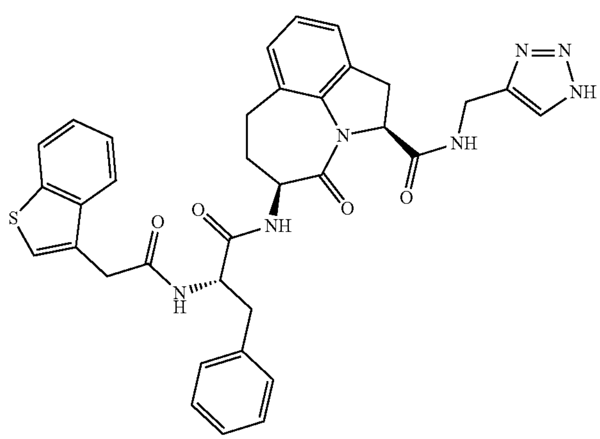 [SMILES: O=C(Cc1csc2ccccc12)N[C@@H](Cc1ccccc1)C(=O)N[C@H]1CCc2cccc3c2N(C1=O)[C@H](C(=O)NCc1c[nH]nn1)C3] | (2S,5S)-5-[(S)-2-(2-Benzo[b]thiophen-3-yl-acetylamino)-3-phenyl-propionylamino]-4-oxo-1,2,4,5,6,7-hexahydro-azepino[3,2,1-hi]indole-2-carboxylic acid (1H-[1,2,3]triazol-4-ylmethyl)-amide | + |

TABLE 5-continued

Compounds and IC$_{50}$ Values

| Compound Number | Structure | Name | IC$_{50}$ |
|---|---|---|---|
| C005 | 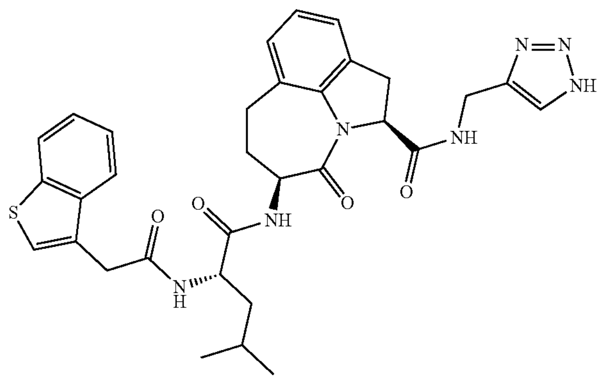 [SMILES: CC(C)C[C@H](NC(=O)Cc1csc2ccccc12)C(=O)N[C@H]1CCc2cccc3c2N(C1=O)[C@H](C(=O)NCc1c[nH]nn1)C3] | (2S,5S)-5-[(S)-2-(2-Benzo[b]thiophen-3-yl-acetylamino)-4-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide | ++ |
| C006 | 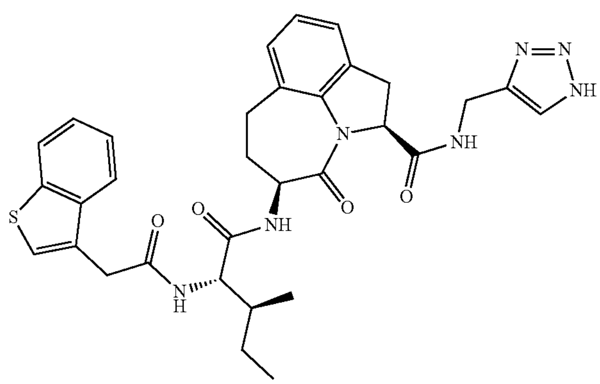 [SMILES: CC[C@H](C)[C@H](NC(=O)Cc1csc2ccccc12)C(=O)N[C@H]1CCc2cccc3c2N(C1=O)[C@H](C(=O)NCc1c[nH]nn1)C3] | (2S,5S)-5-[(2S,3S)-2-(2-Benzo[b]thiophen-3-yl-acetylamino)-3-methyl-pentanoylamino]-4-oxo-1,2,4,5,6,7-hexahydro-azepino[3,2,1hi]indole-2-carboxylic acid (1H-[1,2,3]triazol-4-ylmethyl)-amide | ++++ |
| C007 | 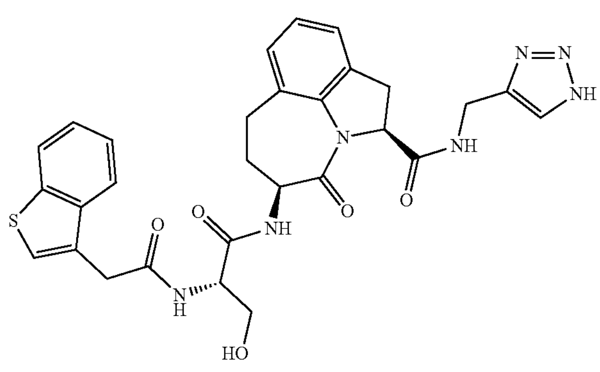 [SMILES: O=C(Cc1csc2ccccc12)N[C@@H](CO)C(=O)N[C@H]1CCc2cccc3c2N(C1=O)[C@H](C(=O)NCc1c[nH]nn1)C3] | (2S,5S)-5-[(S)-2-(2-Benzo[b]thiophen-3-yl-acetylamino)-3-hydroxy-propionylamino]-4-oxo-1,2,4,5,6,7-hexahydro-azepino[3,2,1-hi]indole-2-carboxylic acid (1H-[1,2,3]triazol-4-ylmethyl)-amide | + |

TABLE 5-continued

Compounds and IC$_{50}$ Values

| Compound Number | Structure | Name | IC$_{50}$ |
|---|---|---|---|
| C008 | 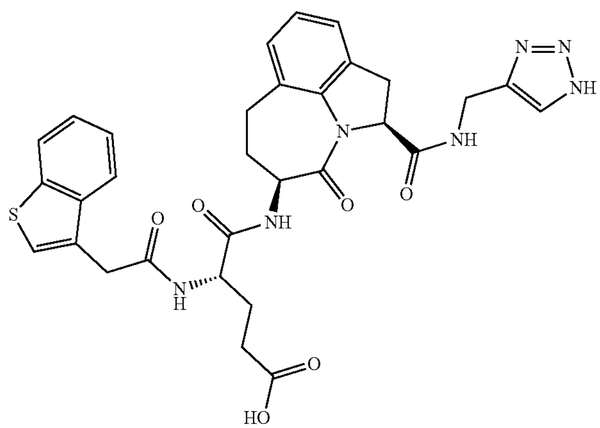 [SMILES: O=C(O)CC[C@H](NC(=O)Cc1csc2ccccc12)C(=O)N[C@H]1CCc2cccc3c2N(C1=O)[C@H](C(=O)NCc1c[nH]nn1)C3] | (S)-4-(2-Benzo[b]thiophen-3-yl-acetylamino)-4-{(2S,5S)-4-oxo-2-[(1H-[1,2,3]triazol-4-ylmethyl)-carbamoyl]-1,2,4,5,6,7-hexahydro-azepino[3,2,1-hi]indol-5-ylcarbamoyl}butyric acid | + |
| C009 | 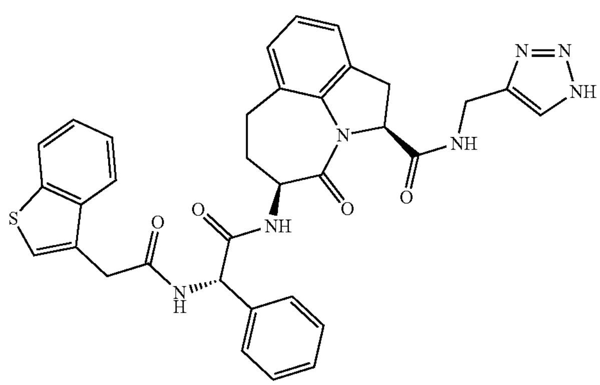 [SMILES: O=C(Cc1csc2ccccc12)N[C@H](C(=O)N[C@H]1CCc2cccc3c2N(C1=O)[C@H](C(=O)NCc1c[nH]nn1)C3)c1ccccc1] | (2S,5S)-5-[(S)-2-(2-Benzo[b]thiophen-3-yl-acetylamino)-2-phenyl-acetylamino]-4-oxo-1,2,4,5,6,7-hexahydro-azepino[3,2,1-hi]indole-2-carboxylic acid (1H-[1,2,3]triazol-4-ylmethyl)-amide | + |
| C010 | 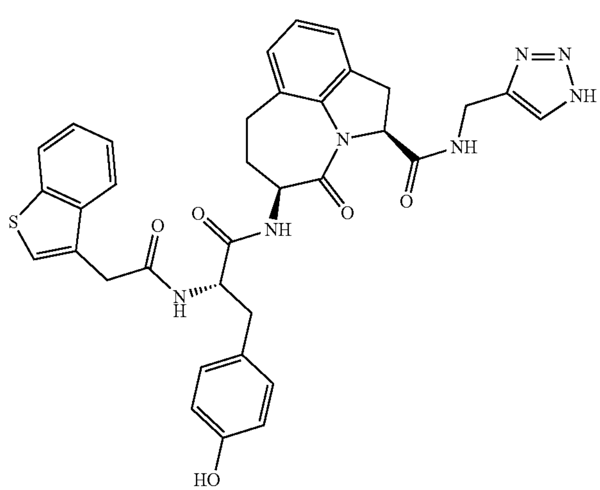 [SMILES: O=C(Cc1csc2ccccc12)N[C@@H](Cc1ccc(O)cc1)C(=O)N[C@H]1CCc2cccc3c2N(C1=O)[C@H](C(=O)NCc1c[nH]nn1)C3] | (2S,5S)-5-[(S)-2-(2-Benzo[b]thiophen-3-yl-acetylamino)-3-(4-hydroxy-phenyl)-propionylamino]-4-oxo-1,2,4,5,6,7-hexahydro-azepino[3,2,1-hi]indole-2-carboxylic acid (1H-[1,2,3]triazol-4-ylmethyl)-amide | + |

TABLE 5-continued

Compounds and IC$_{50}$ Values

| Compound Number | Structure | Name | IC$_{50}$ |
|---|---|---|---|
| C011 | 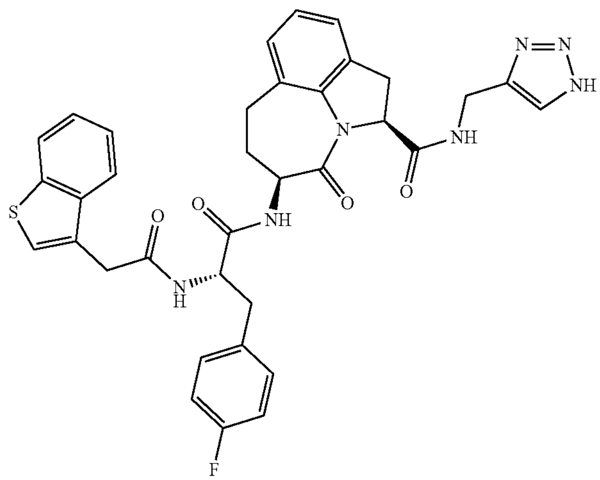 [SMILES: O=C(Cc1csc2ccccc12)N[C@@H](Cc1ccc(F)cc1)C(=O)N[C@H]1CCc2cccc3c2N(C1=O)[C@H](C(=O)NCc1c[nH]nn1)C3] | (2S,5S)-5-[(S)-2-(2-Benzo[b]thiophen-3-yl-acetylamino)-3-(4fluoro-phenyl)-propionylamino]-4-oxo-1,2,4,5,6,7-hexahydro-azepino[,3,2,1-hi]indole-2-carboxylic acid (1H-[1,2,3]triazol-4-ylmethyl)-amide | + |
| C012 | 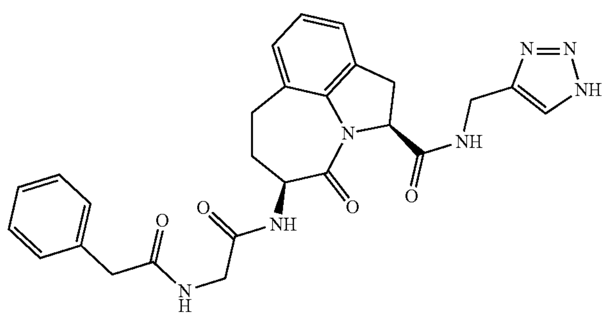 [SMILES: O=C(Cc1ccccc1)NCC(=O)N[C@H]1CCc2cccc3c2N(C1=O)[C@H](C(=O)NCc1c[nH]nn1)C3] | (2S,5S)-4-Oxo-5-(2-phenylacetylamino-acetylamino)-1,2,4,5,6,7-hexahydro-azepino[3,2,1-hi]indole-2-carboxylic acid (1H-[1,2,3]triazol-4-ylmethyl)-amide | + |
| C013 | 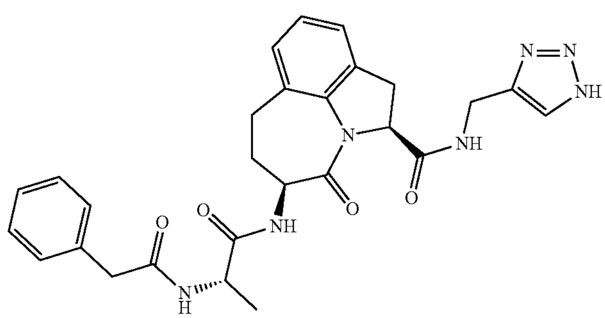 [SMILES: C[C@H](NC(=O)Cc1ccccc1)C(=O)N[C@H]1CCc2cccc3c2N(C1=O)[C@H](C(=O)NCc1c[nH]nn1)C3] | (2S,5S)-4-Oxo-5-((S)-2-phenylacetylamino-propionylamino)-1,2,4,5,6,7-hexahydro-azepino[3,2,1-hi]indole-2-carboxylic acid (1H-[1,2,3]triazol-4-ylmethyl)-amide | + |
| C014 | 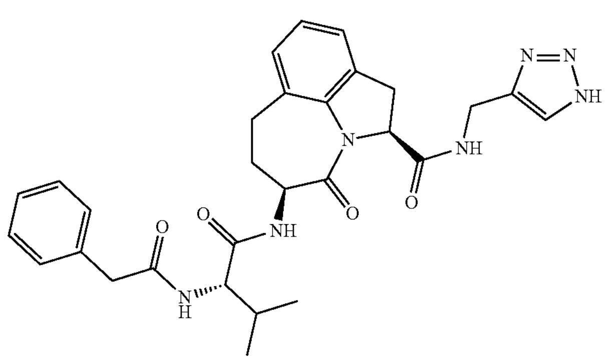 [SMILES: CC(C)[C@H](NC(=O)Cc1ccccc1)C(=O)N[C@H]1CCc2cccc3c2N(C1=O)[C@H](C(=O)NCc1c[nH]nn1)C3] | (2S,5S)-5-((S)-3-Methyl-2-phenylacetylamino-butyrylamino)-4-oxo-1,2,4,5,6,7-hexahydro-azepino[3,2,1-hi]indole-2-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C015 | 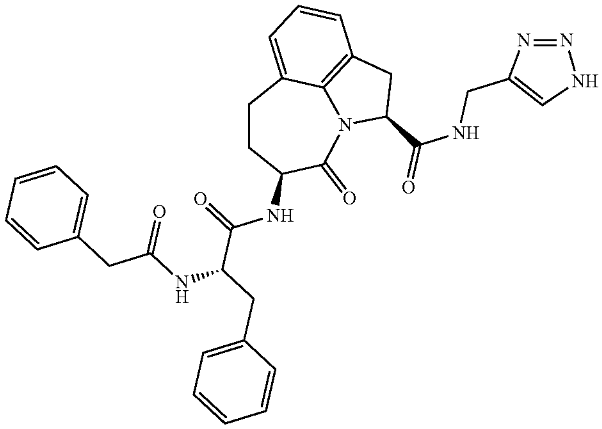 [SMILES: O=C(Cc1ccccc1)N[C@@H](Cc1ccccc1)C(=O)N[C@H]1CCc2cccc3c2N(C1=O)[C@H](C(=O)NCc1c[nH]nn1)C3] | (2S,5S)-4-Oxo-5-((S)-3-phenyl-2-phenylacetylamino-propionylamino)-1,2,4,5,6,7-hexahydro-azepino[3,2,1-hi]indole-2-carboxylic acid (1H-[1,2,3]triazol-4-ylmethyl)-amide | ++ |
| C016 | 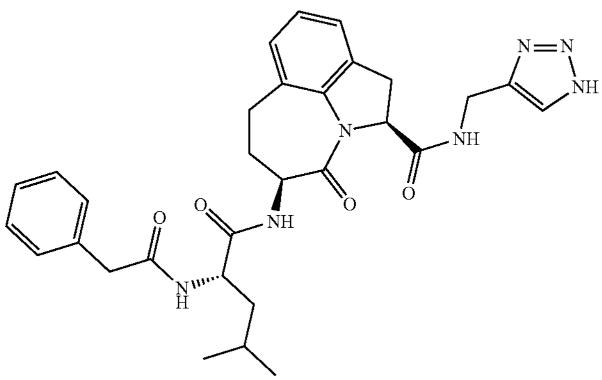 [SMILES: CC(C)C[C@H](NC(=O)Cc1ccccc1)C(=O)N[C@H]1CCc2cccc3c2N(C1=O)[C@H](C(=O)NCc1c[nH]nn1)C3] | (2S,5S)-5-((S)-4-Methyl-2-phenylacetylamino-pentanoylamino)-4-oxo-1,2,4,5,6,7-hexahydro-azepino[3,2,1-hi]indole-2-carboxylic acid (1H-[1,2,3]triazol-4-ylmethyl)-amide | ++ |
| C017 | 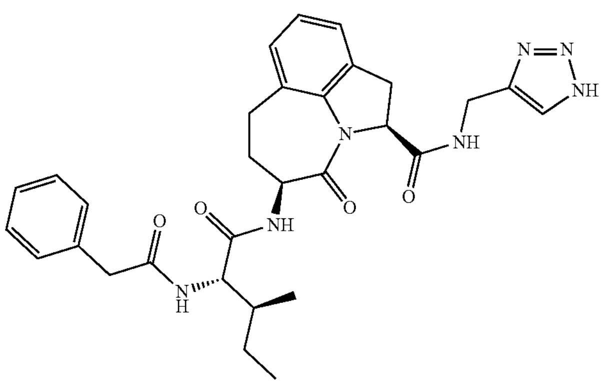 [SMILES: CC[C@H](C)[C@H](NC(=O)Cc1ccccc1)C(=O)N[C@H]1CCc2cccc3c2N(C1=O)[C@H](C(=O)NCc1c[nH]nn1)C3] | (2S,5S)-5-((2S,3S)-3-Methyl-2-phenylacetylamino-pentanoylamino)-4-oxo-1,2,4,5,6,7-hexahydro-azepino[3,2,1-hi]indole-2-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C018 | 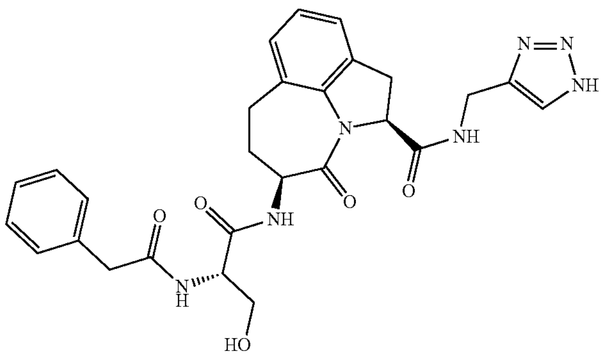 [SMILES: O=C(Cc1ccccc1)N[C@@H](CO)C(=O)N[C@H]1CCc2cccc3c2N(C1=O)[C@H](C(=O)NCc1c[nH]nn1)C3] | (2S,5S)-5-((S)-3-Hydroxy-2-phenylacetylamino-propionylamino)-4-oxo-1,2,4,5,6,7-hexahydro-azepino[3,2,1-hi]indole-2-carboxylic acid (1H-[1,2,3]triazol-4-ylmethyl)-amide | + |
| C019 | 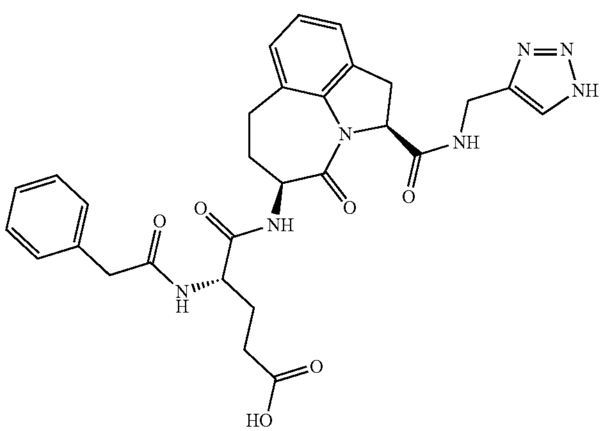 [SMILES: O=C(O)CC[C@H](NC(=O)Cc1ccccc1)C(=O)N[C@H]1CCc2cccc3c2N(C1=O)[C@H](C(=O)NCc1c[nH]nn1)C3] | (S)-4-{(2S,5S)-4-Oxo-2-[(1H-[1,2,3]triazol-4-ylmethyl)-carbamoyl]-1,2,4,5,6,7-hexahydro-azepino[3,2,1-hi]indol-5-ylcarbamoyl}-4-phenylacetylamino-butyric acid | + |
| C020 | 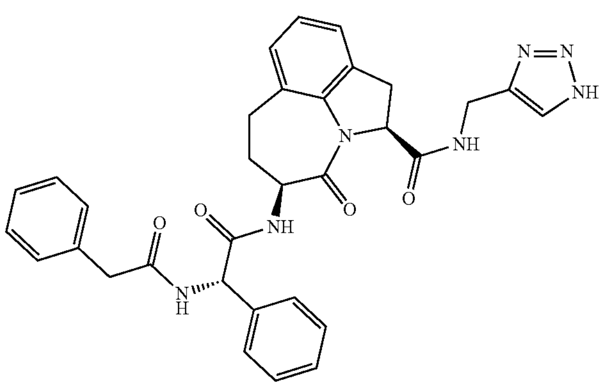 [SMILES: O=C(Cc1ccccc1)N[C@H](C(=O)N[C@H]1CCc2cccc3c2N(C1=O)[C@H](C(=O)NCc1c[nH]nn1)C3)c1ccccc1] | (2S,5S)-4-Oxo-5-((S)-2-phenyl-2-phenylacetylamino-acetylamino)-1,2,4,5,6,7-hexahydro-azepino[3,2,1-hi]indole-2-carboxylic acid (1H-[1,2,3]triazol-4-ylmethyl)-amide | + |

TABLE 5-continued

Compounds and IC$_{50}$ Values

| Compound Number | Structure | Name | IC$_{50}$ |
|---|---|---|---|
| C021 | 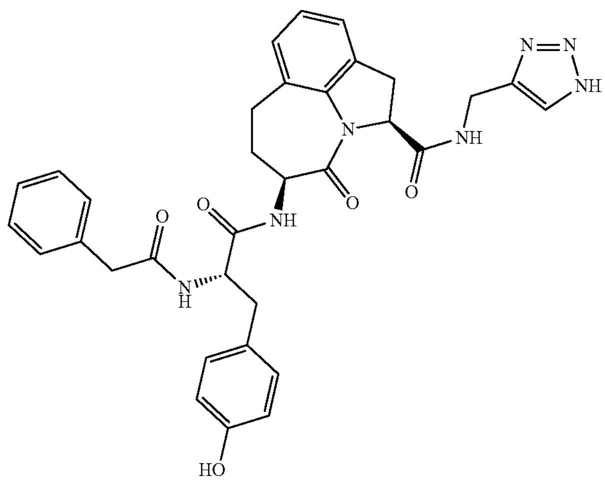 [SMILES: O=C(Cc1ccccc1)N[C@@H](Cc1ccc(O)cc1)C(=O)N[C@H]1CCc2cccc3c2N(C1=O)[C@H](C(=O)NCc1c[nH]nn1)C3] | (2S,5S)-5-[(S)-3-(4-Hydroxy-phenyl)-2-phenylacetylamino-propionylamino]-4-oxo-1,2,4,5,6,7-hexahydro-azepino[3,2,1-hi]indole-2-carboxylic acid (1H-[1,2,3]triazol-4-ylmethyl)-amide | ++ |
| C022 | 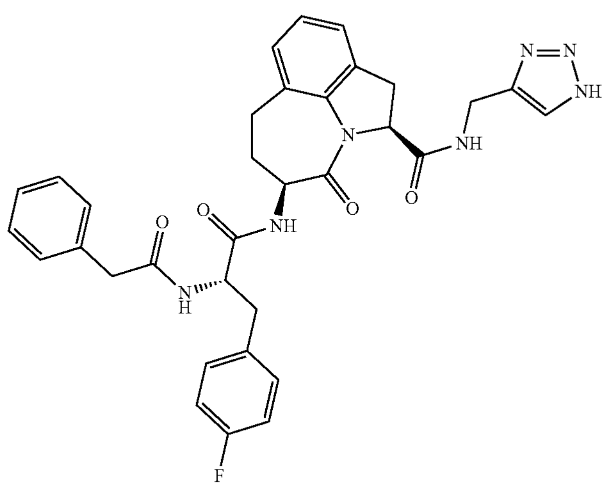 [SMILES: O=C(Cc1ccccc1)N[C@@H](Cc1ccc(F)cc1)C(=O)N[C@H]1CCc2cccc3c2N(C1=O)[C@H](C(=O)NCc1c[nH]nn1)C3] | (2S,5S)-5-[(S)-3-(4-Fluoro-phenyl)-2-phenylacetylamino-propionylamino]-4-oxo-1,2,4,5,6,7-hexahydro-azepino[3,2,1-hi]indole-2-carboxylic acid (1H-[1,2,3]triazol-4-ylmethyl)-amide | + |
| C023 | 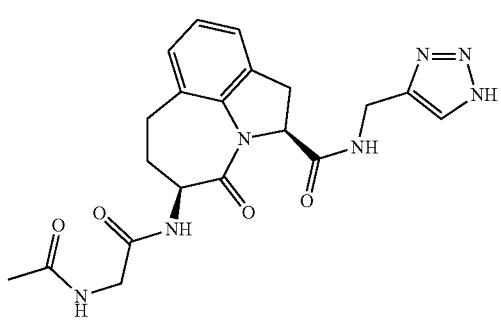 [SMILES: CC(=O)NCC(=O)N[C@H]1CCc2cccc3c2N(C1=O)[C@H](C(=O)NCc1c[nH]nn1)C3] | (2S,5S)-5-(2-Acetylamino-acetylamino)-4-oxo-1,2,4,5,6,7-hexahydro-azepino[3,2,1-hi]indole-2-carboxylic acid (1H-[1,2,3]triazol-4-ylmethyl)-amide | + |

TABLE 5-continued

Compounds and IC$_{50}$ Values

| Compound Number | Structure | Name | IC$_{50}$ |
|---|---|---|---|
| C024 | 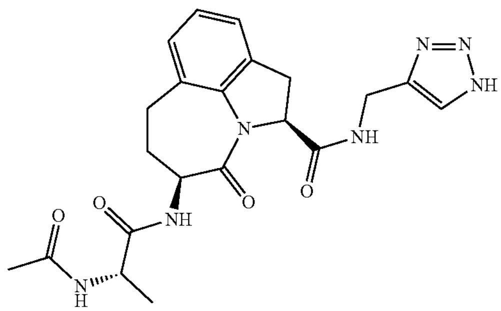 [SMILES: CC(=O)N[C@@H](C)C(=O)N[C@H]1CCc2cccc3c2N(C1=O)[C@H](C(=O)NCc1c[nH]nn1)C3] | (2S,5S)-5-((S)-2-Acetylamino-propionylamino)-4-oxo-1,2,4,5,6,7-hexahydro-azepino[3,2,1-hi]indole-2-carboxylic acid (1H-[1,2,3]triazol-4-ylmethyl)-amide | + |
| C025 | 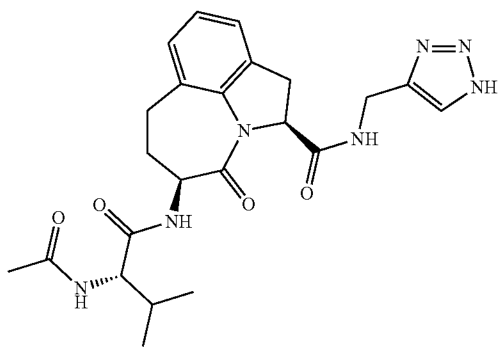 [SMILES: CC(=O)N[C@H](C(=O)N[C@H]1CCc2cccc3c2N(C1=O)[C@H](C(=O)NCc1c[nH]nn1)C3)C(C)C] | (2S,5S)-5-((S)-2-Acetylamino-3-methyl-butyrylamino)-4-oxo-1,2,4,5,6,7-hexahydro-azepino[3,2,1-hi]indole-2-carboxylic acid (1H-[1,2,3]triazol-4-ylmethyl)-amide | ++++ |
| C026 | 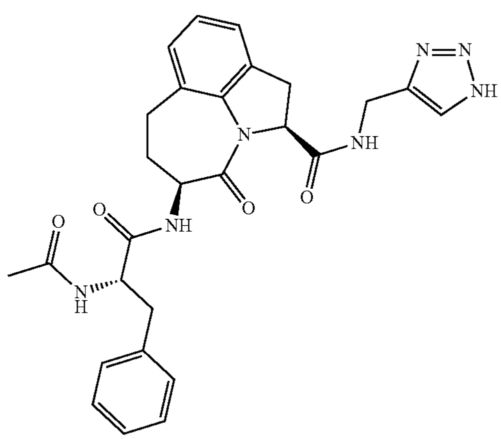 [SMILES: CC(=O)N[C@@H](Cc1ccccc1)C(=O)N[C@H]1CCc2cccc3c2N(C1=O)[C@H](C(=O)NCc1c[nH]nn1)C3] | (2S,5S)-5-((S)-2-Acetylamino-3-phenyl-propionylamino)-4-oxo-1,2,4,5,6,7-hexahydro-azepino[3,2,1-hi]indole-2-carboxylic acid (1H-[1,2,3]triazol-4-ylmethyl)-amide | ++ |
| C027 | 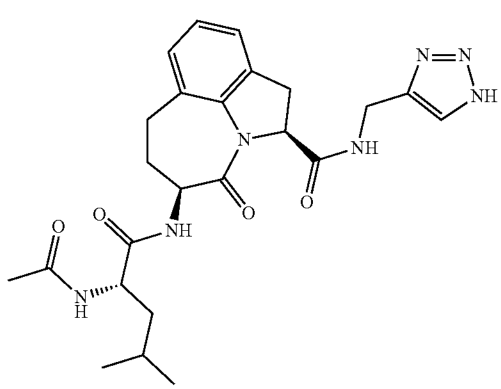 [SMILES: CC(=O)N[C@@H](CC(C)C)C(=O)N[C@H]1CCc2cccc3c2N(C1=O)[C@H](C(=O)NCc1c[nH]nn1)C3] | (2S,5S)-5-((S)-2-Acetylamino-4-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide | ++ |

TABLE 5-continued

Compounds and IC$_{50}$ Values

| Compound Number | Structure | Name | IC$_{50}$ |
|---|---|---|---|
| C028 | 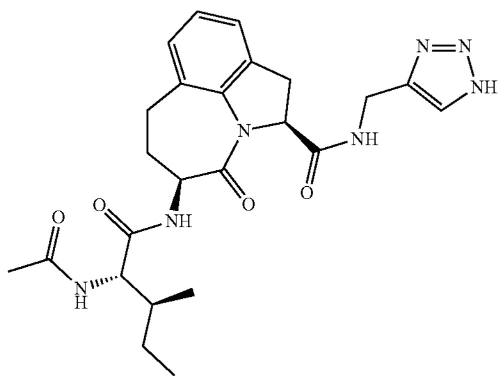 [SMILES: CC[C@H](C)[C@H](NC(C)=O)C(=O)N[C@H]1CCc2cccc3c2N(C1=O)[C@H](C(=O)NCc1c[nH]nn1)C3] | (2S,5S)-5-((2S,3S)-2-Acetylamino-3-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide | ++++ |
| C029 | 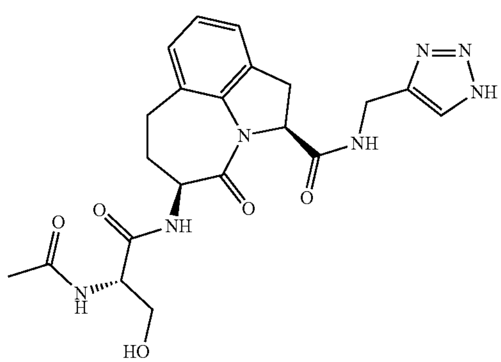 [SMILES: CC(=O)N[C@@H](CO)C(=O)N[C@H]1CCc2cccc3c2N(C1=O)[C@H](C(=O)NCc1c[nH]nn1)C3] | (2S,5S)-5-((S)-2-Acetylamino-3-hydroxy-propionylamino)-4-oxo-1,2,4,5,6,7-hexahydro-azepino[3,2,1-hi]indole-2-carboxylic acid (1H-[1,2,3]triazol-4-ylmethyl)-amide | + |
| C030 | 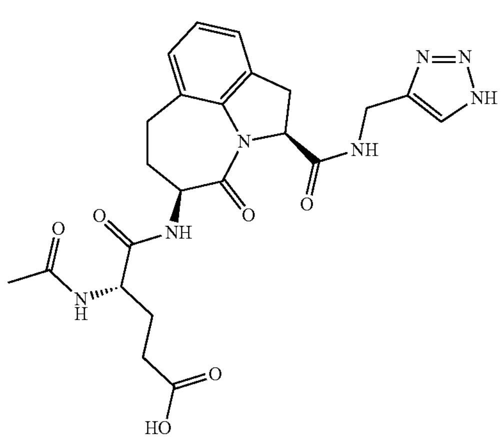 [SMILES: CC(=O)N[C@@H](CCC(=O)O)C(=O)N[C@H]1CCc2cccc3c2N(C1=O)[C@H](C(=O)NCc1c[nH]nn1)C3] | (S)-4-Acetylamino-4-{(2S,5S)-4-oxo-2-[(1H-[1,2,3]triazol-4-ylmethyl)-carbamoyl]-1,2,4,5,6,7-hexahydro-azepino[3,2,1-hi]indol-5-ylcarbamoyl}-butyric acid | + |

TABLE 5-continued

Compounds and IC$_{50}$ Values

| Compound Number | Structure | Name | IC$_{50}$ |
|---|---|---|---|
| C031 | 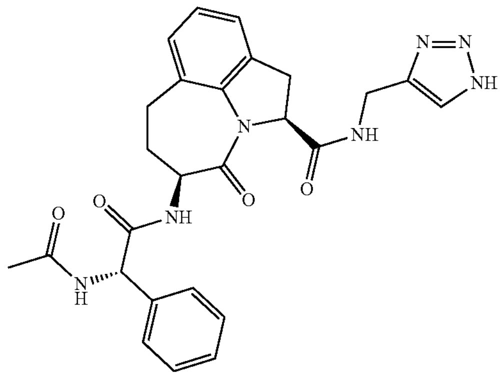 [SMILES: CC(=O)N[C@H](C(=O)N[C@H]1CCc2cccc3c2N(C1=O)[C@H](C(=O)NCc1c[nH]nn1)C3)c1ccccc1] | (2S,5S)-5-((S)-2-Acetylamino-2-phenyl-acetylamino)-4-oxo-1,2,4,5,6,7-hexahydro-azepino[3,2,1-hi]indole-2-carboxylic acid (1H-[1,2,3]triazol-4-ylmethyl)-amide | ++ |
| C032 | 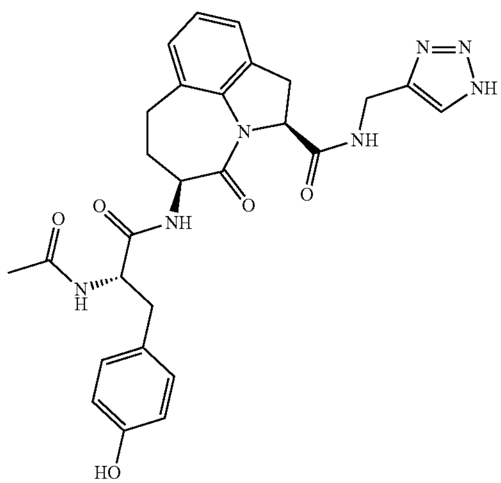 [SMILES: CC(=O)N[C@@H](Cc1ccc(O)cc1)C(=O)N[C@H]1CCc2cccc3c2N(C1=O)[C@H](C(=O)NCc1c[nH]nn1)C3] | (2S,5S)-5-[(S)-2-Acetylamino-3-(4-hydroxy-phenyl)-propionylamino]-4-oxo-1,2,4,5,6,7-hexahydro-azepino[3,2,1-hi]indole-2-carboxylic acid(1H-[1,2,3]triazol-4-ylmethyl)amide | ++ |
| C033 | 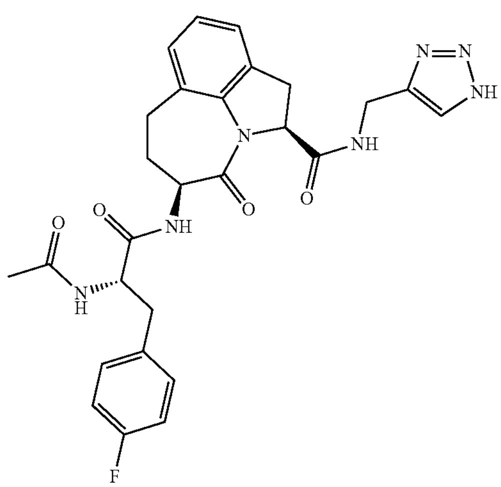 [SMILES: CC(=O)N[C@@H](Cc1ccc(F)cc1)C(=O)N[C@H]1CCc2cccc3c2N(C1=O)[C@H](C(=O)NCc1c[nH]nn1)C3] | (2S,5S)-5-[(S)-2-Acetylamino-3-(4-fluoro-phenyl)-propionylamino]-4-oxo-1,2,4,5,6,7-hexahydro-azepino[3,2,1-hi]indole-2-carboxylic acid (1H-[1,2,3]triazol-4-ylmethyl)-amide | ++ |

TABLE 5-continued

Compounds and IC$_{50}$ Values

| Compound Number | Structure | Name | IC$_{50}$ |
|---|---|---|---|
| C034 | 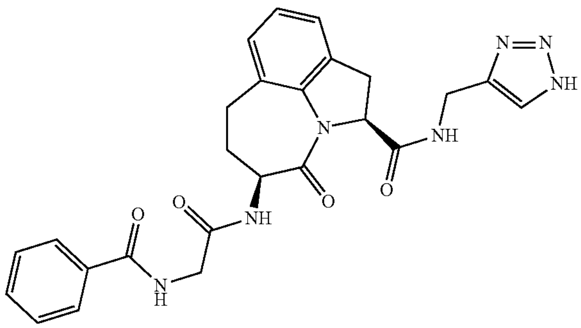 [SMILES: O=C(CNC(=O)c1ccccc1)N[C@H]1CCc2cccc3c2N(C1=O)[C@H](C(=O)NCc1c[nH]nn1)C3] | (2S,5S)-5-(2-Benzoylamino-acetylamino)-4-oxo-1,2,4,5,6,7-hexahydro-azepino[3,2,1-hi]indole-2-carboxylic acid (1H-[1,2,3]triazol-4-ylmethyl)-amide | + |
| C035 | 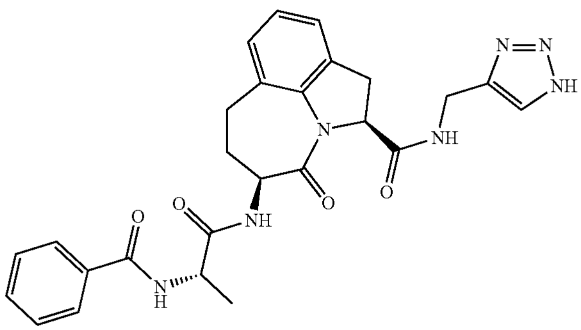 [SMILES: C[C@H](NC(=O)c1ccccc1)C(=O)N[C@H]1CCc2cccc3c2N(C1=O)[C@H](C(=O)NCc1c[nH]nn1)C3] | (2S,5S)-5-((S)-2-Benzoylamino-propionylamino)-4-oxo-1,2,4,5,6,7-hexahydro-azepino[3,2,1-hi]indole-2-carboxylic acid (1H-[1,2,3]triazol-4-ylmethyl)-amide | + |
| C036 | 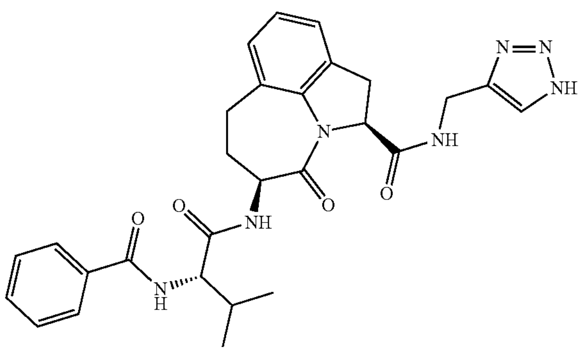 [SMILES: CC(C)[C@H](NC(=O)c1ccccc1)C(=O)N[C@H]1CCc2cccc3c2N(C1=O)[C@H](C(=O)NCc1c[nH]nn1)C3] | (2S,5S)-5-((S)-2-Benzoylamino-3-methyl-butyrylamino)-4-oxo-1,2,4,5,6,7-hexahydro-azepino[3,2,1-hi]indole-2-carboxylic acid (1H-[1,2,3]triazol-4-ylmethyl)-amide | ++++ |
| C037 | 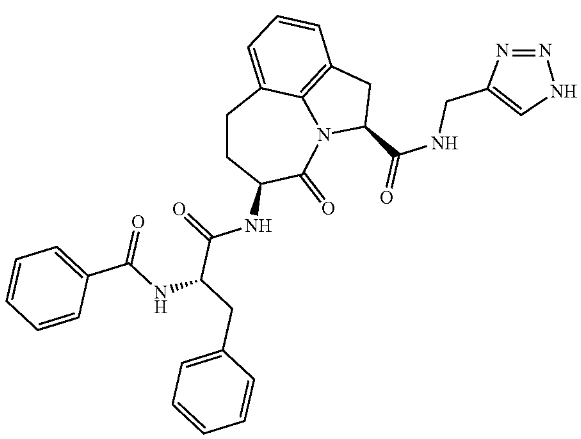 [SMILES: O=C(N[C@@H](Cc1ccccc1)C(=O)N[C@H]1CCc2cccc3c2N(C1=O)[C@H](C(=O)NCc1c[nH]nn1)C3)c1ccccc1] | (2S,5S)-5-(2-Benzoylamino-acetylamino)-4-oxo-1,2,4,5,6,7-hexahydro-azepino[3,2,1-hi]indole-2-carboxylic acid (1H-[1,2,3]triazol-ylmethyl)amide | ++ |

TABLE 5-continued

Compounds and IC$_{50}$ Values

| Compound Number | Structure | Name | IC$_{50}$ |
|---|---|---|---|
| C038 | 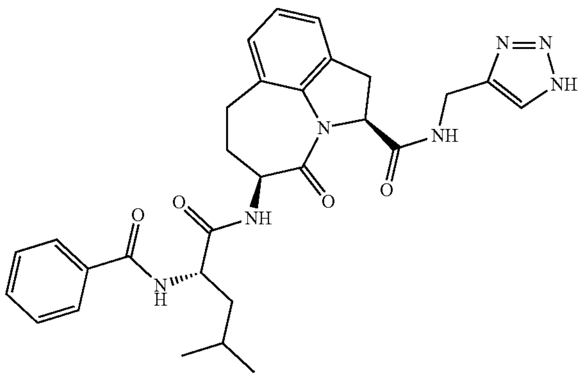 [SMILES: CC(C)C[C@H](NC(=O)c1ccccc1)C(=O)N[C@H]1CCc2cccc3c2N(C1=O)[C@H](C(=O)NCc1c[nH]nn1)C3] | (2S,5S)-5-((S)-2-Benzoylamino-4-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide | +++ |
| C039 | 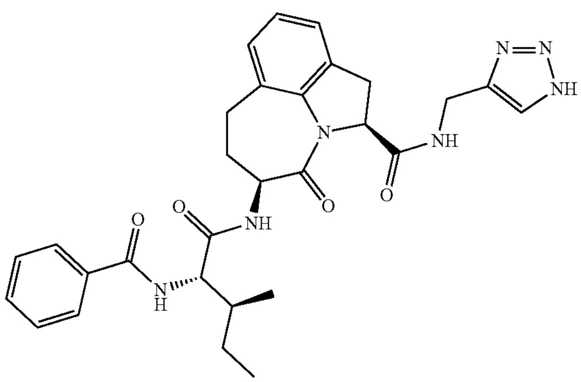 [SMILES: CC[C@H](C)[C@H](NC(=O)c1ccccc1)C(=O)N[C@H]1CCc2cccc3c2N(C1=O)[C@H](C(=O)NCc1c[nH]nn1)C3] | (2S,5S)-5-((2S,3S)-2-Benzoylamino-3-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide | ++++ |
| C040 | 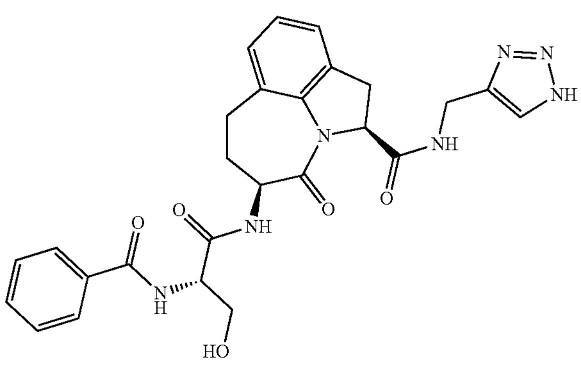 [SMILES: O=C(N[C@@H](CO)C(=O)N[C@H]1CCc2cccc3c2N(C1=O)[C@H](C(=O)NCc1c[nH]nn1)C3)c1ccccc1] | (2S,5S)-5-((S)-2-Benzoylamino-3-hydroxy-propionylamino)-4-oxo-1,2,4,5,6,7-hexahydro-azepino[3,2,1-hi]indole-2-carboxylic acid (1H-[1,2,3]triazol-4-ylmethyl)-amide | + |

TABLE 5-continued

Compounds and IC$_{50}$ Values

| Compound Number | Structure | Name | IC$_{50}$ |
|---|---|---|---|
| C041 | 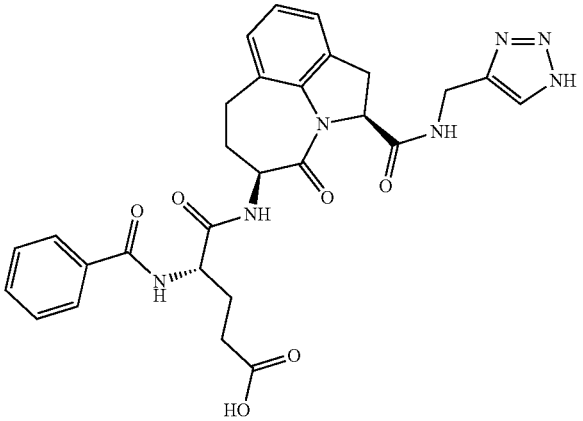 [SMILES: O=C(O)CC[C@H](NC(=O)c1ccccc1)C(=O)N[C@H]1CCc2cccc3c2N(C1=O)[C@H](C(=O)NCc1c[nH]nn1)C3] | (S)-4-Benzoylamino-4-{(2S,5S)-4-oxo-2-[(1H-[1,2,3]triazol-4-ylmethyl)-carbamoyl]-1,2,4,5,6,7-hexahydro-azepino[3,2,1-hi]indol-5-ylcarbamoyl}-butyric acid | + |
| C042 | 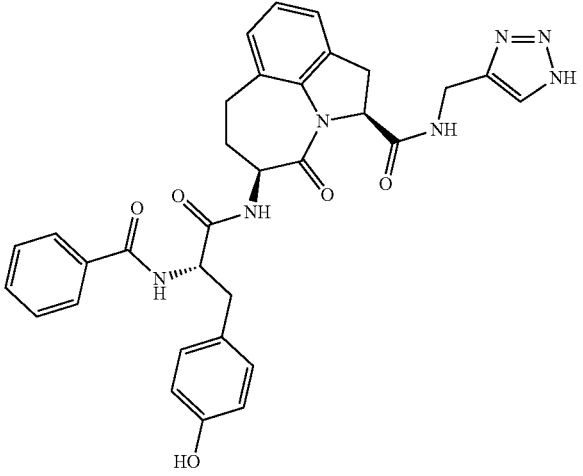 [SMILES: O=C(N[C@@H](Cc1ccc(O)cc1)C(=O)N[C@H]1CCc2cccc3c2N(C1=O)[C@H](C(=O)NCc1c[nH]nn1)C3)c1ccccc1] | (2S,5S)-5-[(S)-2-Benzoylamino-3-(4-hydroxy-phenyl)-propionylamino]-4-oxo,2,4,5,6,7-hexahydro-azepino[3,2,1-hi]indole-2-carboxylic acid (1H-[1,2,3]triazol-4-ylmethyl)-amide | + |
| C043 | 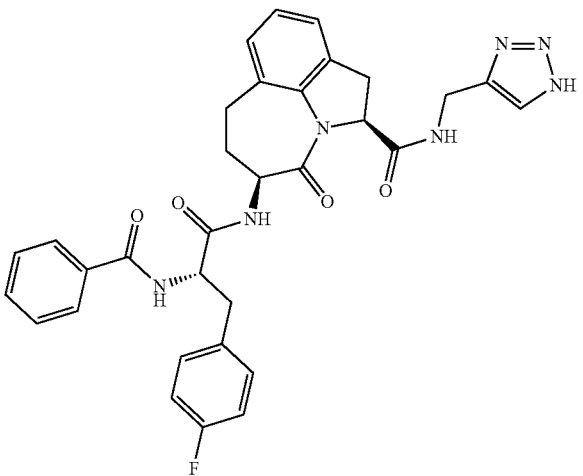 [SMILES: O=C(N[C@@H](Cc1ccc(F)cc1)C(=O)N[C@H]1CCc2cccc3c2N(C1=O)[C@H](C(=O)NCc1c[nH]nn1)C3)c1ccccc1] | (2S,5S)-5-[(S)-2-Benzoylamino-3-(4-fluoro-phenyl)-propionylamino]-4-oxo-1,2,4,5,6,7-hexahydro-azepino[3,2,1-hi]indole-2-carboxylic acid (1H-[1,2,3]triazol-4-ylmethyl)-amide | + |

TABLE 5-continued

Compounds and IC$_{50}$ Values

| Compound Number | Structure | Name | IC$_{50}$ |
|---|---|---|---|
| C044 | 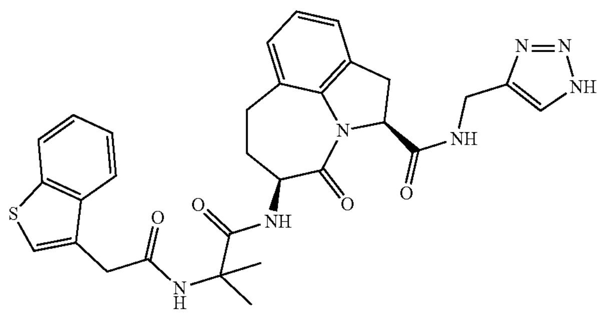 [SMILES: CC(C)(NC(=O)Cc1csc2ccccc12)C(=O)N[C@H]1CCc2cccc3c2N(C1=O)[C@H](C(=O)NCc1c[nH]nn1)C3] | (2S,5S)-5-[2-(2-Benzo[b]thiophen-3-yl-acetylamino)-2-methyl-propionylamino]-4-oxo-1,2,4,5,6,7-hexahydro-azepino[3,2,1-hi]indole-2-carboxylic acid (1H-[1,2,3]triazol-4-ylmethyl)-amide | + |
| C045 | 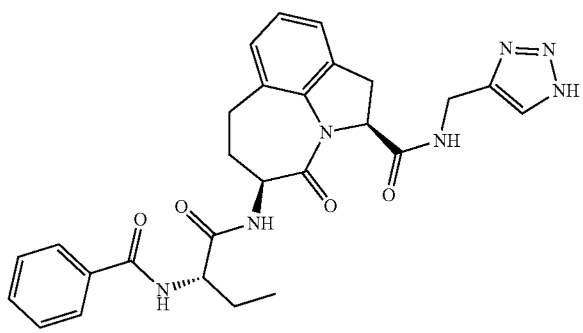 [SMILES: CC[C@H](NC(=O)c1ccccc1)C(=O)N[C@H]1CCc2cccc3c2N(C1=O)[C@H](C(=O)NCc1c[nH]nn1)C3] | (2S,5S)-5-((S)-2-Benzoylamino-butyrylamino)-4-oxo-1,2,4,5,6,7-hexahydro-azepino[3,2,1-hi]indole-2-carboxylic acid (1H-[1,2,3]triazol-4ylmethyl)-amide | ++ |
| C046 | 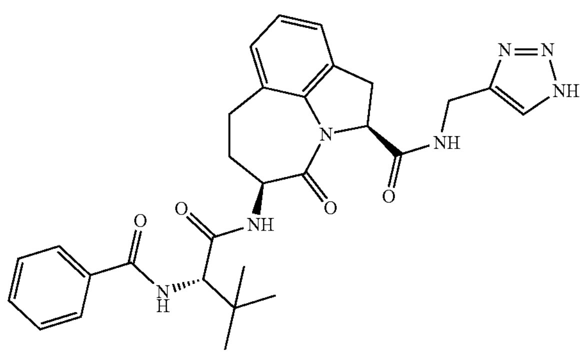 [SMILES: CC(C)(C)[C@H](NC(=O)c1ccccc1)C(=O)N[C@H]1CCc2cccc3c2N(C1=O)[C@H](C(=O)NCc1c[nH]nn1)C3] | (2S,5S)-5-((S)-2-Benzoylamino-3,3-dimethyl-butyrylamino)-4-oxo-1,2,4,5,6,7-hexahydro-azepino[3,2,1-hi]indole-2-carboxylic acid (1H-[1,2,3]triazol-4-ylmethyl)-amide | +++ |
| C047 | 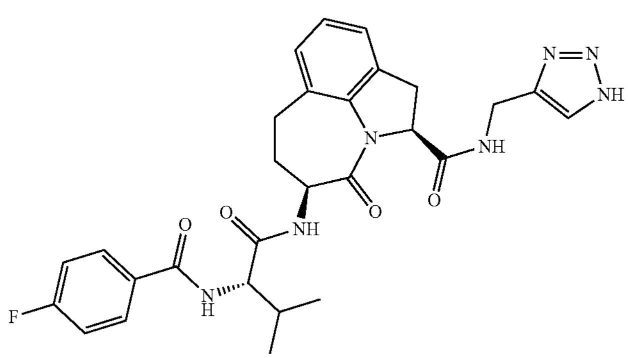 [SMILES: CC(C)[C@H](NC(=O)c1ccc(F)cc1)C(=O)N[C@H]1CCc2cccc3c2N(C1=O)[C@H](C(=O)NCc1c[nH]nn1)C3] | (2S,5S)-5-[(S)-2-(4-Fluoro-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide | +++ |

TABLE 5-continued

Compounds and IC$_{50}$ Values

| Compound Number | Structure | Name | IC$_{50}$ |
|---|---|---|---|
| C048 | 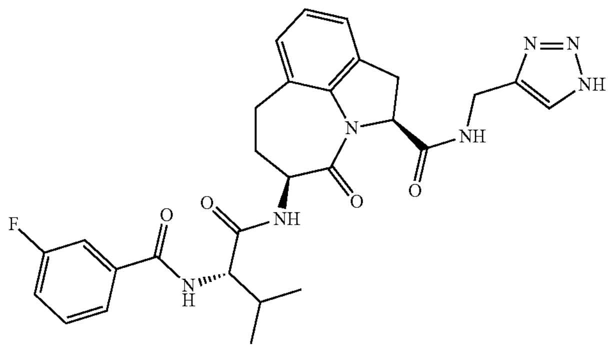 [SMILES: CC(C)[C@H](NC(=O)c1cccc(F)c1)C(=O)N[C@H]1CCc2cccc3c2N(C1=O)[C@H](C(=O)NCc1c[nH]nn1)C3] | (2S,5S)-5-[(S)-2-(3-Fluoro-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide | ++++ |
| C049 | 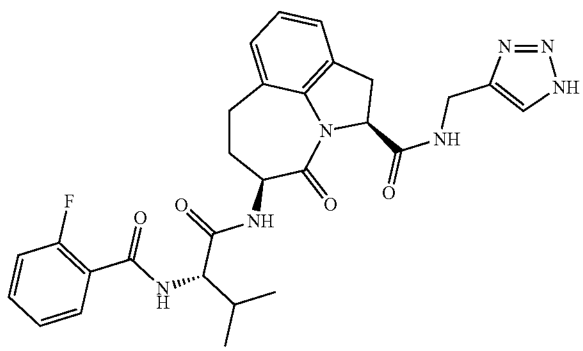 [SMILES: CC(C)[C@H](NC(=O)c1ccccc1F)C(=O)N[C@H]1CCc2cccc3c2N(C1=O)[C@H](C(=O)NCc1c[nH]nn1)C3] | (2S,5S)-5-[(S)-2-(2-Fluoro-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide | +++ |
| C050 | 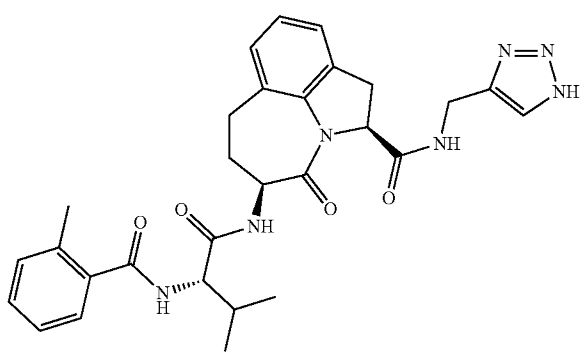 | (2S,5S)-5-[(S)-3-Methyl-2-(2-methyl-benzoylamino)-butyrylamino]-4-oxo-1,2,4,5,6,7-hexahydro-azepino[3,2,1-hi]indole-2-carboxylic acid (1H-[1,2,3]triazol-4-ylmethyl)-amide | ++++ |
| C051 | 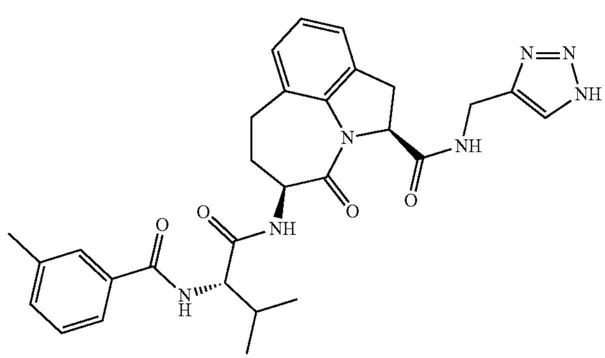 [SMILES: Cc1cccc(C(=O)N[C@H](C(=O)N[C@H]2CCc3cccc4c3N(C2=O)[C@H](C(=O)NCc2c[nH]nn2)C4)C(C)C)c1] | (2S,5S)-5-[(S)-3-Methyl-2-(3-methyl-benzoylamino)-butyrylamino]-4-oxo-1,2,4,5,6,7-hexahydro-azepino[3,2,1-hi]indole-2-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C052 | 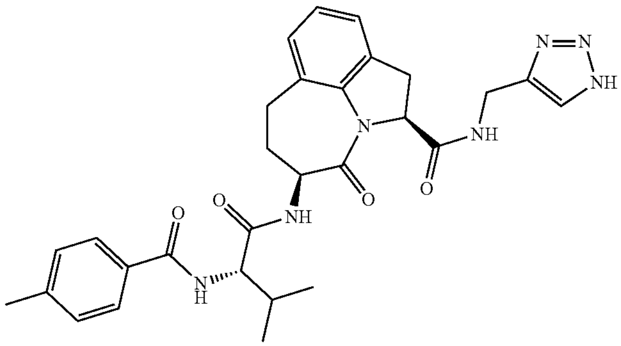 [SMILES: Cc1ccc(C(=O)N[C@H](C(=O)N[C@H]2CCc3cccc4c3N(C2=O)[C@H](C(=O)NCc2c[nH]nn2)C4)C(C)C)cc1] | (2S,5S)-5-[(S)-3-Methyl-2-(4-methyl-benzoylamino)-butyrylamino]-4-oxo-1,2,4,5,6,7-hexahydro-azepino[3,2,1-hi]indole-2-carboxylic acid (1H-[1,2,3]triazol-4-ylmethyl)-amide | ++++ |
| C053 | 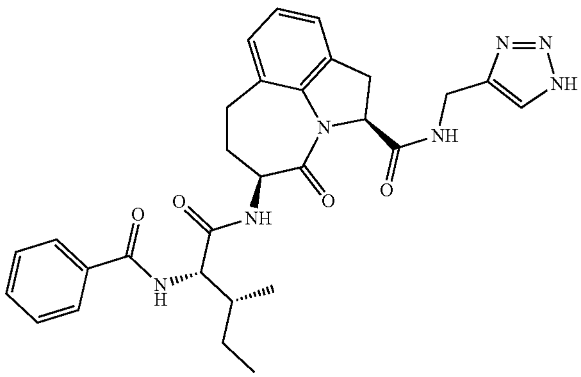 [SMILES: CC[C@@H](C)[C@H](NC(=O)c1ccccc1)C(=O)N[C@H]1CCc2cccc3c2N(C1=O)[C@H](C(=O)NCc1c[nH]nn1)C3] | (2S,5S)-5-((2S,3R)-2-Benzoylamino-3-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide | ++++ |
| C054 | 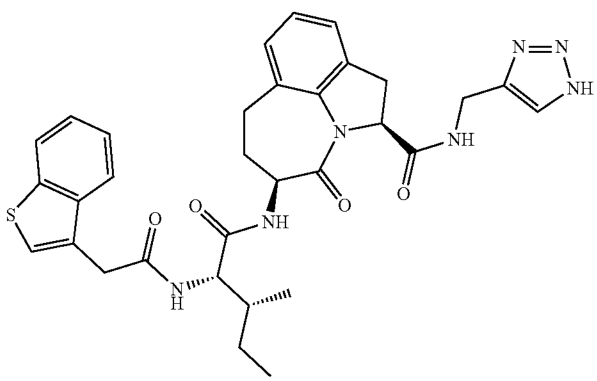 [SMILES: CC[C@@H](C)[C@H](NC(=O)Cc1csc2ccccc12)C(=O)N[C@H]1CCc2cccc3c2N(C1=O)[C@H](C(=O)NCc1c[nH]nn1)C3] | (2S,5S)-5-[(2S,3R)-2-(2-Benzo[b]thiophen-3-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide | ++++ |
| C055 | 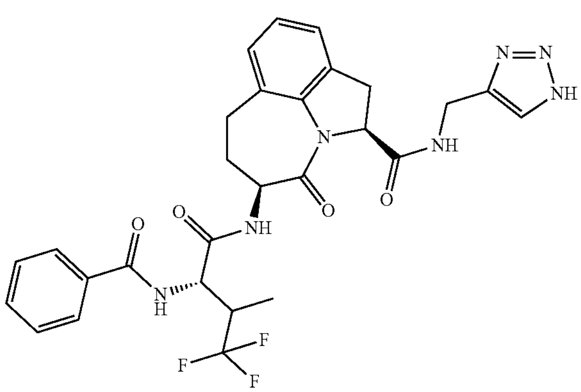 [SMILES: CC([C@H](NC(=O)c1ccccc1)C(=O)N[C@H]1CCc2cccc3c2N(C1=O)[C@H](C(=O)NCc1c[nH]nn1)C3)C(F)(F)F] | (2S,5S)-5-((S)-2-Benzoylamino-4,4,4-trifluoro-3-methyl-butyrylamino)-4-oxo-1,2,4,5,6,7-hexahydro-azepino[3,2,1-hi]indole-2-carboxylic acid (1H-[1,2,3]triazol-4-ylmethyl)-amide | ++++ |

TABLE 5-continued

Compounds and IC₅₀ Values

| Compound Number | Structure | Name | IC₅₀ |
|---|---|---|---|
| C056 | 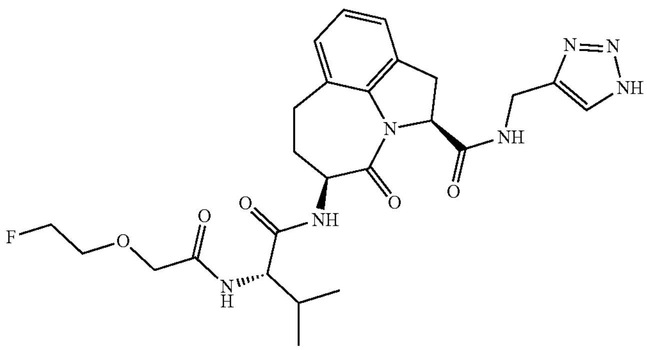 [SMILES: CC(C)[C@H](NC(=O)COCCF)C(=O)N[C@H]1CCc2cccc3c2N(C1=O)[C@H](C(=O)NCc1c[nH]nn1)C3] | (2S,5S)-5-{(S)-2-[2-(2-Fluoro-ethoxy)-acetylamino]-3-methyl-butyrylamino}-4-oxo-1,2,4,5,6,7-hexahydro-azepino[3,2,1-hi]indole-2-carboxylic acid (1H-[1,2,3]triazol-4-ylmethyl)-amide | ++++ |
| C057 | 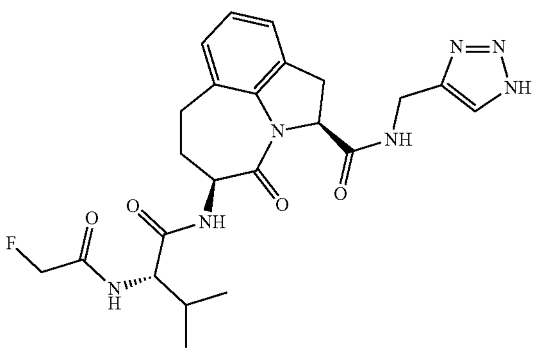 [SMILES: CC(C)[C@H](NC(=O)CF)C(=O)N[C@H]1CCc2cccc3c2N(C1=O)[C@H](C(=O)NCc1c[nH]nn1)C3] | (2S,5S)-5-[(S)-2-(2-Fluoro-acetylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide | ++++ |
| C058 | 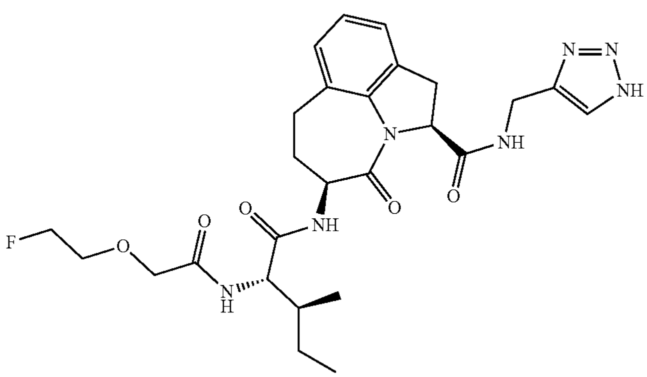 | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (1H-[1,2,3]-triazol-4-ylmethyl)-amide | ++++ |
| C059 | 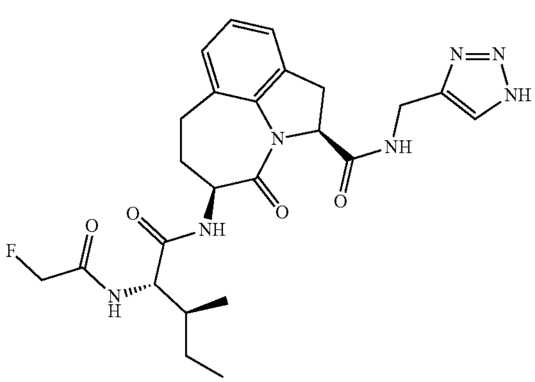 [SMILES: CC[C@H](C)[C@H](NC(=O)CF)C(=O)N[C@H]1CCc2cccc3c2N(C1=O)[C@H](C(=O)NCc1c[nH]nn1)C3] | (2S,5S)-5-[(2S,3S)-2-(2-Fluoro-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C060 | 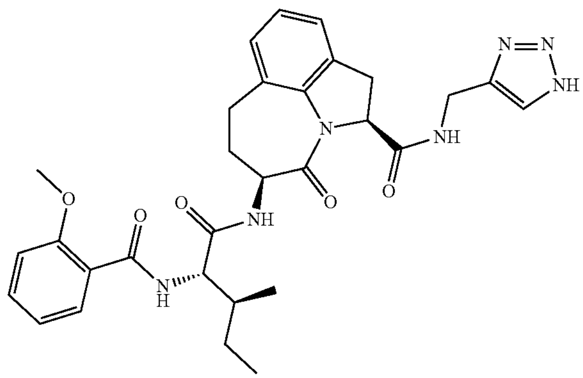 [SMILES: CC[C@H](C)[C@H](NC(=O)c1ccccc1OC)C(=O)N[C@H]1CCc2cccc3c2N(C1=O)[C@H](C(=O)NCc1c[nH]nn1)C3] | (2S,5S)-5-[(2S,3S)-2-(2-Methoxy-benzoylamino)-3-methyl-pentanoylamino]-4-oxo-1,2,4,5,6,7-hexahydro-azepino[3,2,1-hi]indole-2-carboxylic acid(1H-[1,2,3]triazol-4-ylmethyl)-amide | ++++ |
| C061 | 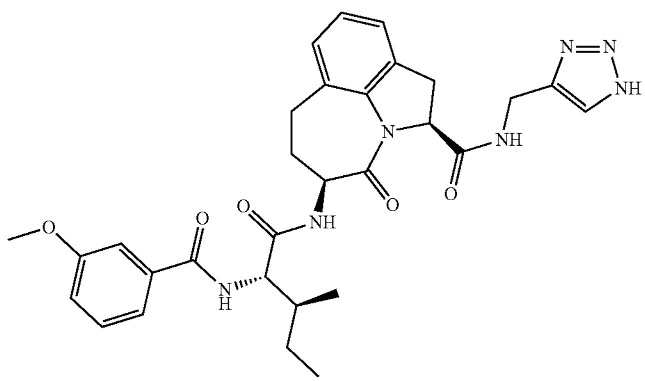 [SMILES: CC[C@H](C)[C@H](NC(=O)c1cccc(OC)c1)C(=O)N[C@H]1CCc2cccc3c2N(C1=O)[C@H](C(=O)NCc1c[nH]nn1)C3] | (2S,5S)-5-[(2S,3S)-2-(3-Methoxy-benzoylamino)-3-methyl-pentanoylamino]-4-oxo-1,2,4,5,6,7-hexahydro-azepino[3,2,1-hi]indole-2-carboxylic acid(1H-[1,2,3]triazol-4-ylmethyl)-amide | ++++ |
| C062 | 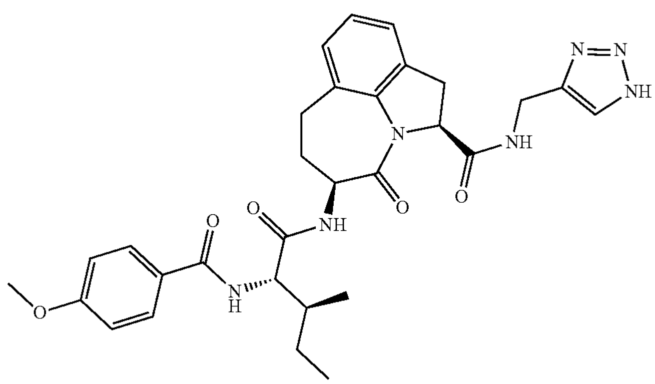 [SMILES: CC[C@H](C)[C@H](NC(=O)c1ccc(OC)cc1)C(=O)N[C@H]1CCc2cccc3c2N(C1=O)[C@H](C(=O)NCc1c[nH]nn1)C3] | (2S,5S)-5-[(2S,3S)-2-(4-Methoxy-benzoylamino)-3-methyl-pentanoylamino]-4-oxo-1,2,4,5,6,7-hexahydro-azepino[3,2,1-hi]indole-2-carboxylic acid(1H-[1,2,3]triazol-4-ylmethyl)-amide | ++++ |
| C063 | 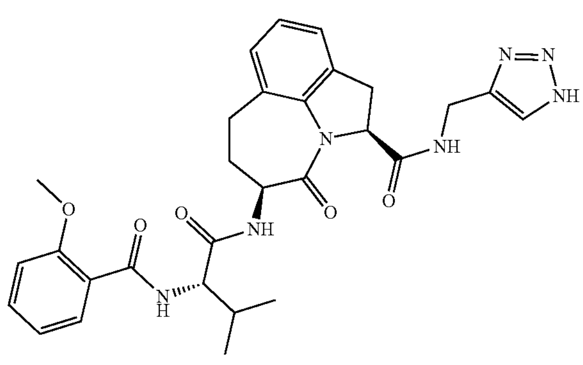 [SMILES: COc1ccccc1C(=O)N[C@H](C(=O)N[C@H]1CCc2cccc3c2N(C1=O)[C@H](C(=O)NCc1c[nH]nn1)C3)C(C)C] | (2S,5S)-5-[(S)-2-(2-Methoxy-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C064 | 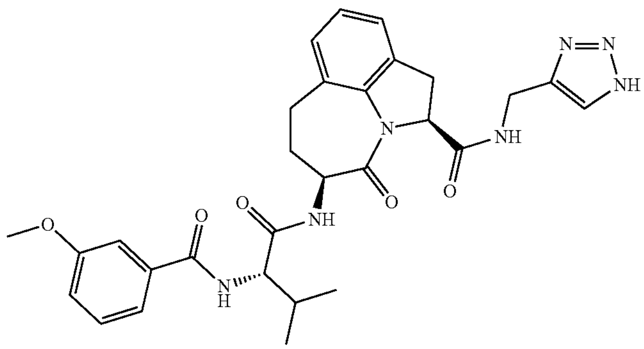 [SMILES: COc1cccc(C(=O)N[C@H](C(=O)N[C@H]2CCc3cccc4c3N(C2=O)[C@H](C(=O)NCc2c[nH]nn2)C4)C(C)C)c1] | (2S,5S)-5-[(S)-2-(3-Methoxy-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide | ++++ |
| C065 | 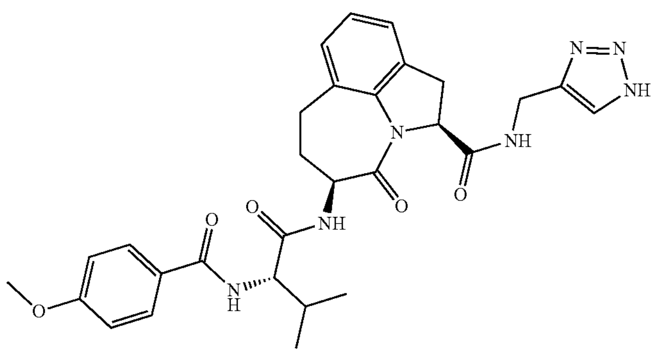 [SMILES: COc1ccc(C(=O)N[C@H](C(=O)N[C@H]2CCc3cccc4c3N(C2=O)[C@H](C(=O)NCc2c[nH]nn2)C4)C(C)C)cc1] | (2S,5S)-5-[(S)-2-(4-Methoxy-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide | ++++ |
| C066 | 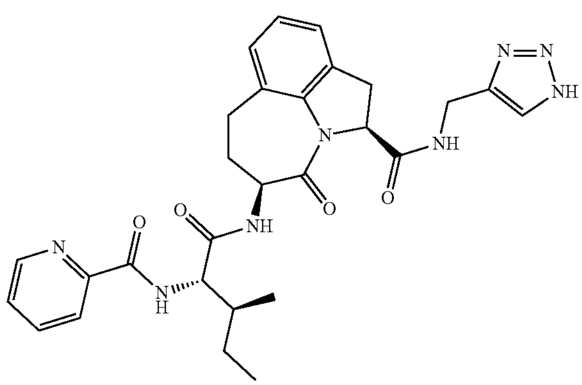 | (2S,5S)-5-{(2S,3S)-3-Methyl-2-[(pyridine-2-carbonyl)-amino]-pentanoylamino}-4-oxo-1,2,4,5,6,7-hexahydro-azepino[3,2,1-hi]indole-2-carboxylicacid (1H-[1,2,3]triazol-4-ylmethyl)-amide | ++++ |
| C067 | 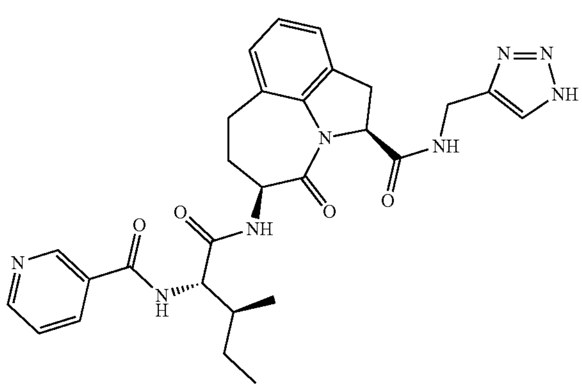 | (2S,5S)-5-{(2S,3S)-3-Methyl-2-[(pyridine-3-carbonyl)-amino]-pentanoylamino}-4-oxo-1,2,4,5,6,7-hexahydro-azepino[3,2,1-hi]indole-2-carboxylicacid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C068 | 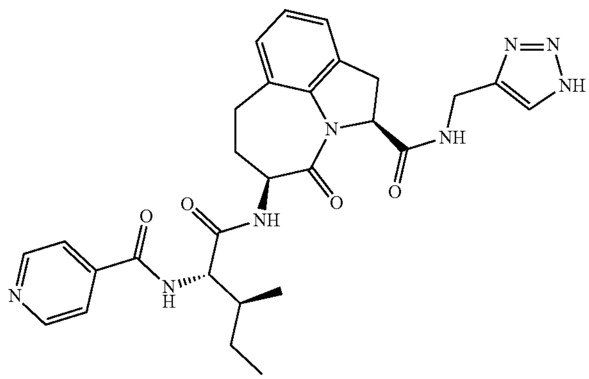 [SMILES: CC[C@H](C)[C@H](NC(=O)c1ccncc1)C(=O)N[C@H]1CCc2cccc3c2N(C1=O)[C@H](C(=O)NCc1c[nH]nn1)C3] | (2S,5S)-5-{(2S,3S)-3-Methyl-2-[(pyridine-4-carbonyl)-amino]-pentanoylamino}-4-oxo-1,2,4,5,6,7-hexahydro-azepino[3,2,1-hi]indole-2-carboxylic acid (1H-[1,2,3]triazol-4-ylmethyl)-amide | ++++ |
| C069 | 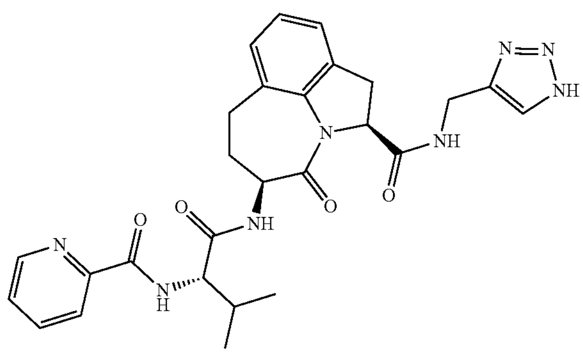 [SMILES: CC(C)[C@H](NC(=O)c1ccccn1)C(=O)N[C@H]1CCc2cccc3c2N(C1=O)[C@H](C(=O)NCc1c[nH]nn1)C3] | (2S,5S)-5-{(S)-3-Methyl-2-[(pyridine-2-carbonyl)-amino]-butyrylamino}-4-oxo-1,2,4,5,6,7-hexahydro-azepino[3,2,1-hi]indole-2-carboxylic acid (1H-[1,2,3]triazol-4-ylmethyl)-amide | ++++ |
| C070 | 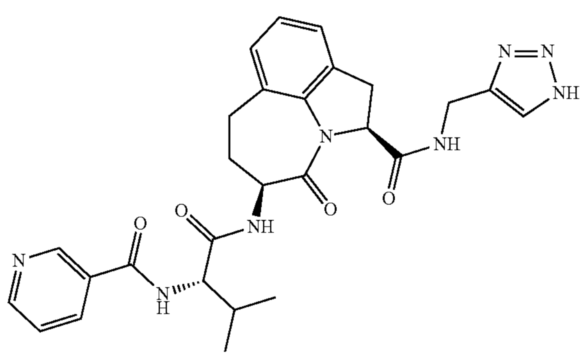 [SMILES: CC(C)[C@H](NC(=O)c1cccnc1)C(=O)N[C@H]1CCc2cccc3c2N(C1=O)[C@H](C(=O)NCc1c[nH]nn1)C3] | (2S,5S)-5-{(S)-3-Methyl-2-[(pyridine-3-carbonyl)-amino]-butyrylamino}-4-oxo-1,2,4,5,6,7-hexahydro-azepino[3,2,1-hi]indole-2-carboxylic acid (1H-[1,2,3]triazol-4-ylmethyl)-amide | ++++ |
| C071 | 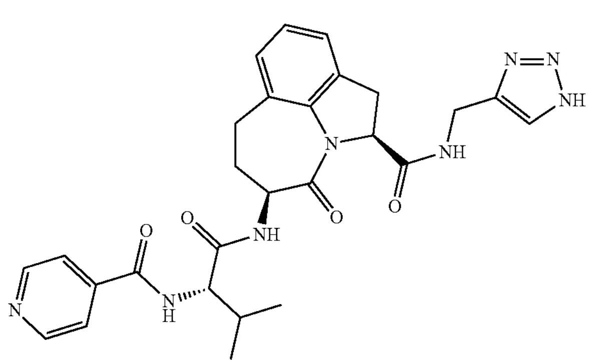 [SMILES: CC(C)[C@H](NC(=O)c1ccncc1)C(=O)N[C@H]1CCc2cccc3c2N(C1=O)[C@H](C(=O)NCc1c[nH]nn1)C3] | (2S,5S)-5-{(S)-3-Methyl-2-[(pyridine-4-carbonyl)-amino]-butyrylamino}-4-oxo-1,2,4,5,6,7-hexahydro-azepino[3,2,1-hi]indole-2-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C072 | 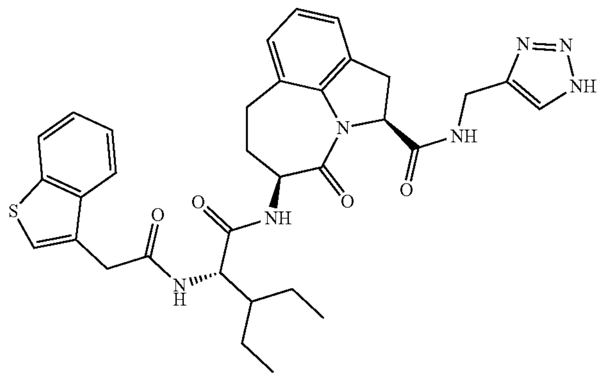 [SMILES: CCC(CC)[C@H](NC(=O)Cc1csc2ccccc12)C(=O)N[C@H]1CCc2cccc3c2N(C1=O)[C@H](C(=O)NCc1c[nH]nn1)C3] | (2S,5S)-5-[(S)-2-(2-Benzo[b]thiophen-3-yl-acetylamino)-3-ethyl-pentanoylamino]-4-oxo-1,2,4,5,6,7-hexahydro-azepino[3,2,1-hi]indole-2-carboxylic acid (1H-[1,2,3]triazol-4-ylmethyl)-amide | +++ |
| C073 | 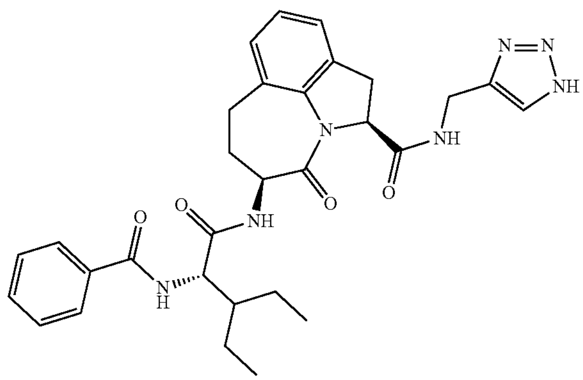 [SMILES: CCC(CC)[C@H](NC(=O)c1ccccc1)C(=O)N[C@H]1CCc2cccc3c2N(C1=O)[C@H](C(=O)NCc1c[nH]nn1)C3] | (2S,5S)-5-((S)-2-Benzoylamino-3-ethyl-pentanoylamino)-4-oxo-1,2,4,5,6,7-hexahydro-azepino[3,2,1-hi]indole-2-carboxylic acid (1H-[1,2,3]triazol-4-ylmethyl)-amide | +++ |
| C074 | 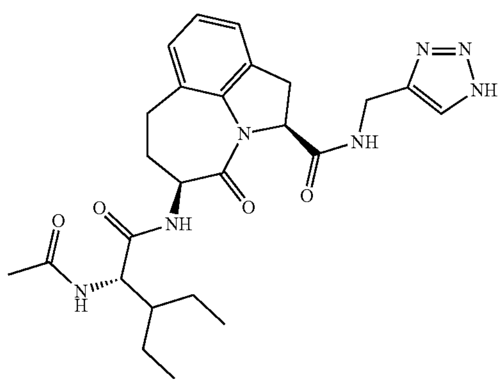 [SMILES: CCC(CC)[C@H](NC(C)=O)C(=O)N[C@H]1CCc2cccc3c2N(C1=O)[C@H](C(=O)NCc1c[nH]nn1)C3] | (2S,5S)-5-((S)-2-Acetylamino-3-ethyl-pentanoylamino)-4-oxo-1,2,4,5,6,7-hexahydro-azepino[3,2,1-hi]indole-2-carboxylic acid (1H-[1,2,3]triazol-4-ylmethyl)-amide | ++++ |
| C075 | 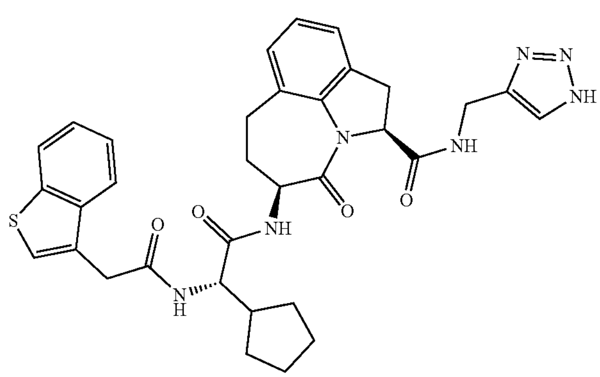 [SMILES: O=C(Cc1csc2ccccc12)N[C@H](C(=O)N[C@H]1CCc2cccc3c2N(C1=O)[C@H](C(=O)NCc1c[nH]nn1)C3)C1CCCC1] | (2S,5S)-5-[(S)-2-(2-Benzo[b]thiophen-3-yl-acetylamino)-2-cyclopentyl-acetylamino]-4-oxo-1,2,4,5,6,7-hexahydro-azepino[3,2,1-hi]indole-2-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C076 | 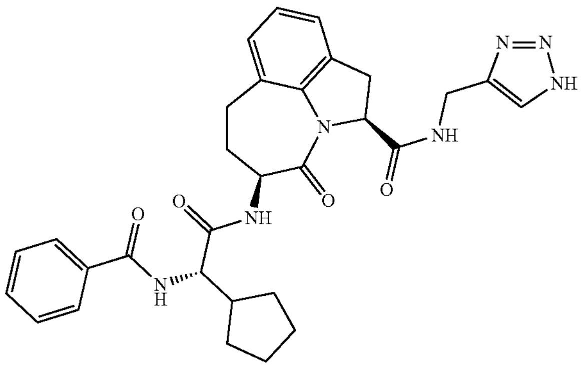 [SMILES: O=C(N[C@H](C(=O)N[C@H]1CCc2cccc3c2N(C1=O)[C@H](C(=O)NCc1c[nH]nn1)C3)C1CCCC1)c1ccccc1] | (2S,5S)-5-((S)-2-Benzoylamino-2-cyclopentyl-acetylamino)-4-oxo-1,2,4,5,6,7-hexahydro-azepino[3,2,1-hi]indole-2-carboxylic acid (1H-[1,2,3]triazol-4-ylmethyl)-amide | ++++ |
| C077 | 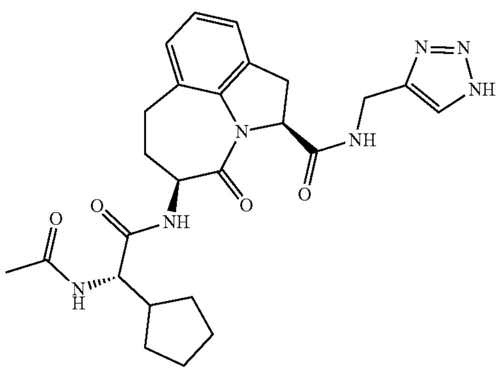 [SMILES: CC(=O)N[C@H](C(=O)N[C@H]1CCc2cccc3c2N(C1=O)[C@H](C(=O)NCc1c[nH]nn1)C3)C1CCCC1] | (2S,5S)-5-((S)-2-Acetylamino-2-cyclopentyl-acetylamino)-4-oxo-1,2,4,5,6,7-hexahydro-azepino[3,2,1-hi]indole-2-carboxylic acid (1H-[1,2,3]triazol-4-ylmethyl)-amide | ++++ |
| C078 | 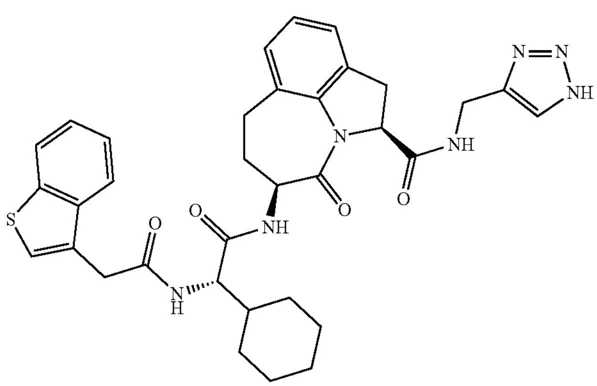 [SMILES: O=C(Cc1csc2ccccc12)N[C@H](C(=O)N[C@H]1CCc2cccc3c2N(C1=O)[C@H](C(=O)NCc1c[nH]nn1)C3)C1CCCCC1] | (2S,5S)-5-[(S)-2-(2-Benzo[b]thiophen-3-yl-acetylamino)-2-cyclohexyl-acetylamino]-4-oxo-1,2,4,5,6,7-hexahydro-azepino[3,2,1-hi]indole-2-carboxylic acid (1H-[1,2,3]triazol-4-ylmethyl)-amide | +++ |
| C079 | 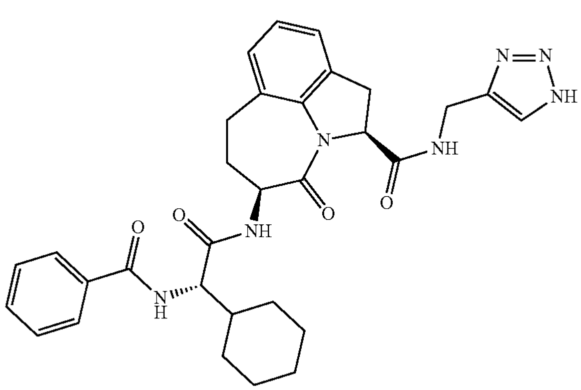 [SMILES: O=C(N[C@H](C(=O)N[C@H]1CCc2cccc3c2N(C1=O)[C@H](C(=O)NCc1c[nH]nn1)C3)C1CCCCC1)c1ccccc1] | (2S,5S)-5-((S)-2-Benzoylamino-2-cyclohexyl-acetylamino)-4-oxo-1,2,4,5,6,7-hexahydro-azepino[3,2,1-hi]indole-2-carboxylic acid (1H-[1,2,3]triazol-4-ylmethyl)-amide | ++ |

TABLE 5-continued

Compounds and IC₅₀ Values

| Compound Number | Structure | Name | IC₅₀ |
|---|---|---|---|
| C080 | 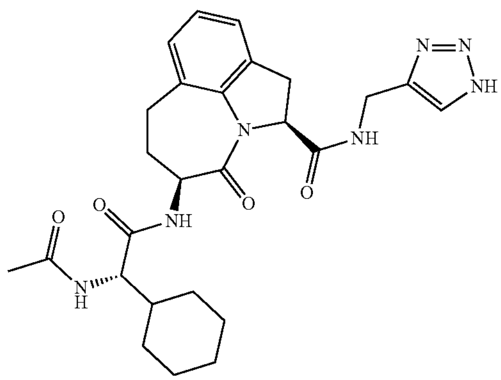 [SMILES: CC(=O)N[C@H](C(=O)N[C@H]1CCc2cccc3c2N(C1=O)[C@H](C(=O)NCc1c[nH]nn1)C3)C1CCCCC1] | (2S,5S)-5-((S)-2-Acetylamino-2-cyclohexyl-acetylamino)-4-oxo-1,2,4,5,6,7-hexahydro-azepino[3,2,1-hi]indole-2-carboxylic acid (1H-[1,2,3]triazol-4-ylmethyl)-amide | +++ |
| C081 | 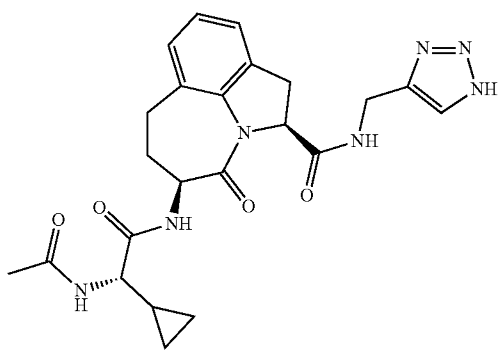 [SMILES: CC(=O)N[C@H](C(=O)N[C@H]1CCc2cccc3c2N(C1=O)[C@H](C(=O)NCc1c[nH]nn1)C3)C1CC1] | (2S,5S)-5-((S)-2-Acetylamino-2-cyclopropyl-acetylamino)-4-oxo-1,2,4,5,6,7-hexahydro-azepino[3,2,1-hi]indole-2-carboxylic acid (1H-[1,2,3]triazol-4-ylmethyl)-amide | +++ |
| C082 | 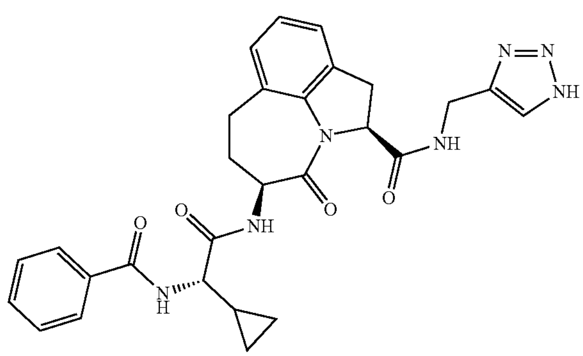 [SMILES: O=C(N[C@H](C(=O)N[C@H]1CCc2cccc3c2N(C1=O)[C@H](C(=O)NCc1c[nH]nn1)C3)C1CC1)c1ccccc1] | (2S,5S)-5-((S)-2-Benzoylamino-2-cyclopropyl-acetylamino)-4-oxo-1,2,4,5,6,7-hexahydro-azepino[3,2,1-hi]indole-2-carboxylic acid (1H-[1,2,3]triazol-4-ylmethyl)-amide | +++ |
| C083 | 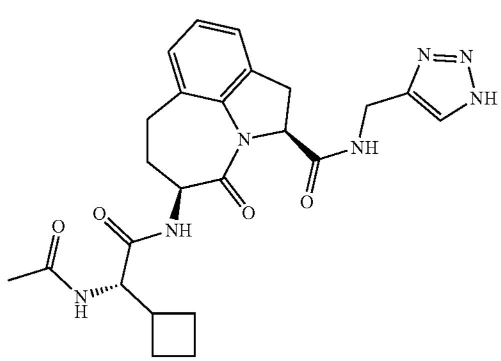 [SMILES: CC(=O)N[C@H](C(=O)N[C@H]1CCc2cccc3c2N(C1=O)[C@H](C(=O)NCc1c[nH]nn1)C3)C1CCC1] | (2S,5S)-5-((S)-2-Acetylamino-2-cyclobutyl-acetylamino)-4-oxo-1,2,4,5,6,7-hexahydro-azepino[3,2,1-hi]indole-2-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C084 | 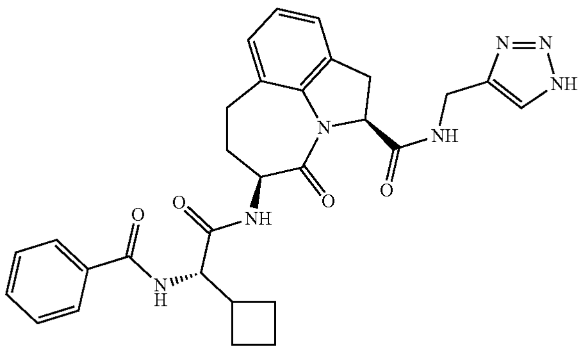 [SMILES: O=C(N[C@H](C(=O)N[C@H]1CCc2cccc3c2N(C1=O)[C@H](C(=O)NCc1c[nH]nn1)C3)C1CCC1)c1ccccc1] | (2S,5S)-5-((S)-2-Benzoylamino-2-cyclobutyl-acetylamino)-4-oxo-1,2,4,5,6,7-hexahydro-azepino[3,2,1-hi]indole-2-carboxylic acid (1H-[1,2,3]triazol-4-ylmethyl)-amide | ++++ |
| C085 | 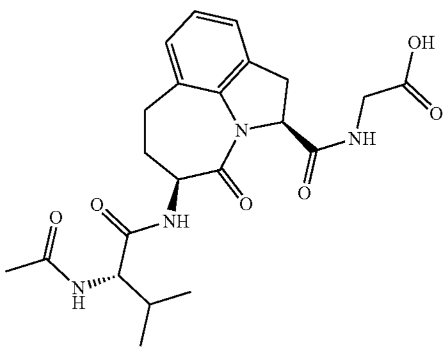 [SMILES: CC(=O)N[C@H](C(=O)N[C@H]1CCc2cccc3c2N(C1=O)[C@H](C(=O)NCC(=O)O)C3)C(C)C] | {[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-acetic acid | ++ |
| C086 | 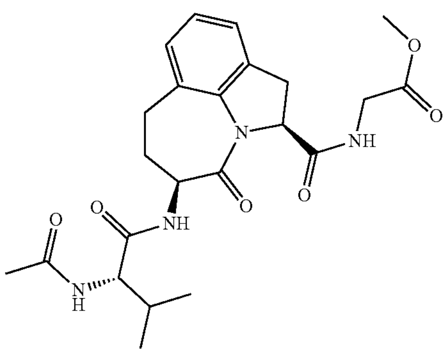 [SMILES: COC(=O)CNC(=O)[C@@H]1Cc2cccc3c2N1C(=O)[C@@H](NC(=O)[C@@H](NC(C)=O)C(C)C)CC3] | {[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-acetic acid methyl ester | + |
| C087 | 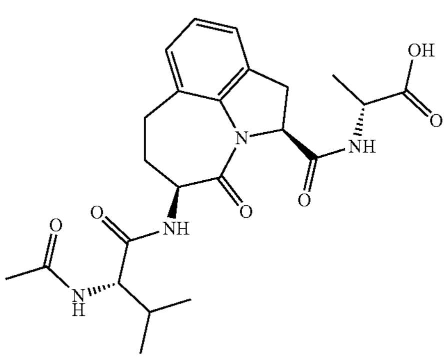 [SMILES: CC(=O)N[C@H](C(=O)N[C@H]1CCc2cccc3c2N(C1=O)[C@H](C(=O)N[C@H](C)C(=O)O)C3)C(C)C] | (R)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-propionicacid | + |

TABLE 5-continued

Compounds and IC$_{50}$ Values

| Compound Number | Structure | Name | IC$_{50}$ |
|---|---|---|---|
| C088 | 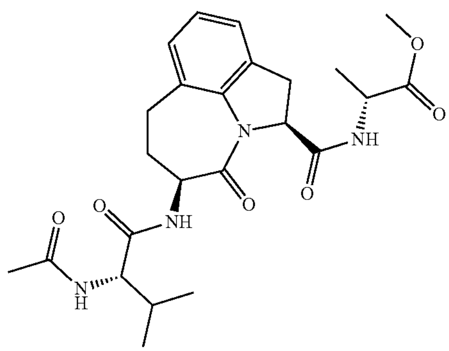 [SMILES: COC(=O)[C@@H](C)NC(=O)[C@@H]1Cc2cccc3c2N1C(=O)[C@@H](NC(=O)[C@@H](NC(C)=O)C(C)C)CC3] | (R)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-propionicacid methyl ester | + |
| C089 | 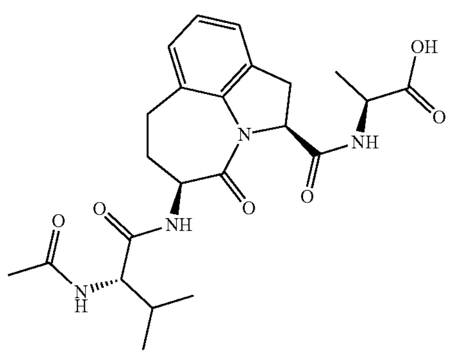 [SMILES: CC(=O)N[C@H](C(=O)N[C@H]1CCc2cccc3c2N(C1=O)[C@H](C(=O)N[C@@H](C)C(=O)O)C3)C(C)C] | (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-propionicacid | + |
| C090 | 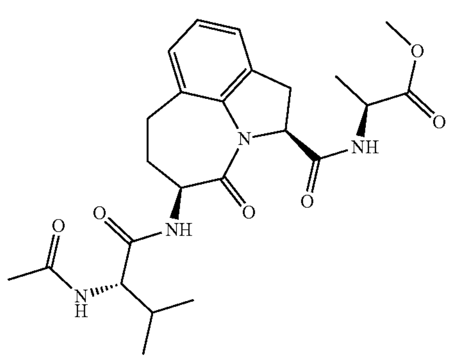 [SMILES: COC(=O)[C@H](C)NC(=O)[C@@H]1Cc2cccc3c2N1C(=O)[C@@H](NC(=O)[C@@H](NC(C)=O)C(C)C)CC3] | (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-propionic acid methyl ester | + |
| C091 | 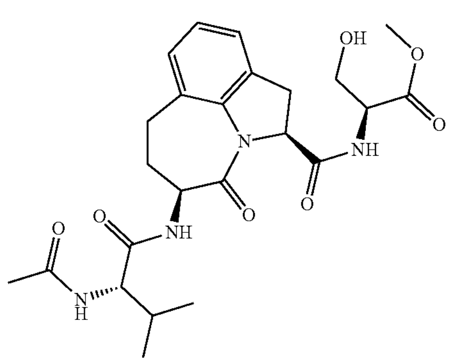 [SMILES: COC(=O)[C@H](CO)NC(=O)[C@@H]1Cc2cccc3c2N1C(=O)[C@@H](NC(=O)[C@@H](NC(C)=O)C(C)C)CC3] | (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-3-hydroxy-propionic acid methyl ester | + |

TABLE 5-continued

Compounds and IC$_{50}$ Values

| Compound Number | Structure | Name | IC$_{50}$ |
|---|---|---|---|
| C092 | 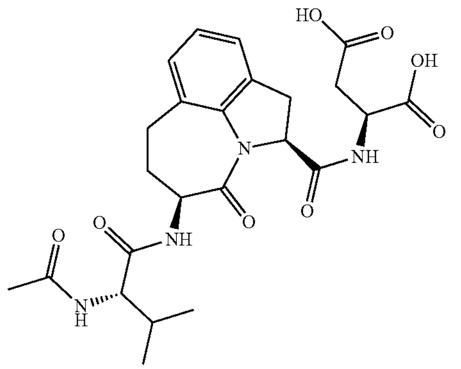 [SMILES: CC(=O)N[C@H](C(=O)N[C@H]1CCc2cccc3c2N(C1=O)[C@H](C(=O)N[C@@H](CC(=O)O)C(=O)O)C3)C(C)C] | (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-succinic acid | + |
| C093 | 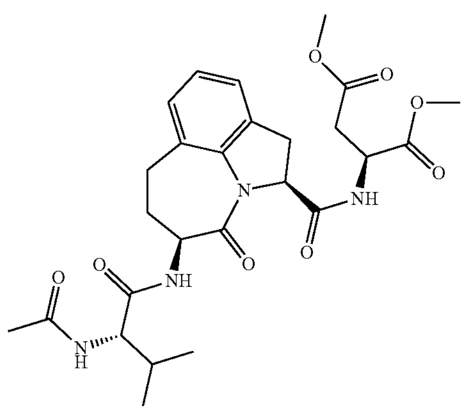 [SMILES: COC(=O)C[C@H](NC(=O)[C@@H]1Cc2cccc3c2N1C(=O)[C@@H](NC(=O)[C@@H](NC(C)=O)C(C)C)CC3)C(=O)OC] | (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-succinic acid dimethyl ester | + |
| C094 | 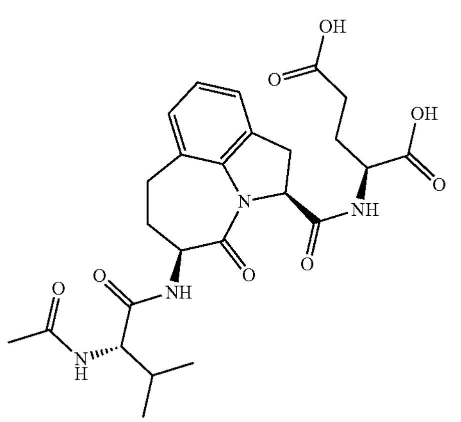 [SMILES: CC(=O)N[C@H](C(=O)N[C@H]1CCc2cccc3c2N(C1=O)[C@H](C(=O)N[C@@H](CCC(=O)O)C(=O)O)C3)C(C)C] | (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-pentanedioic acid | + |

TABLE 5-continued

Compounds and IC$_{50}$ Values

| Compound Number | Structure | Name | IC$_{50}$ |
|---|---|---|---|
| C095 | 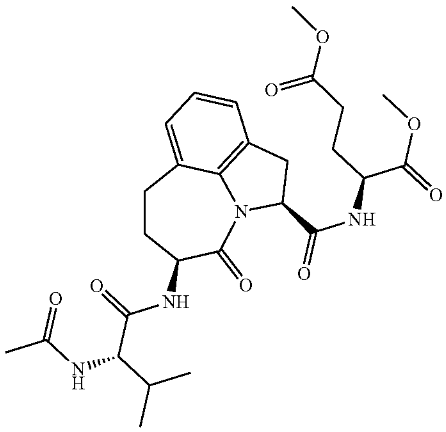 [SMILES: COC(=O)CC[C@H](NC(=O)[C@@H]1Cc2cccc3c2N1C(=O)[C@@H](NC(=O)[C@@H](NC(C)=O)C(C)C)CC3)C(=O)OC] | (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-pentanedioic acid dimethyl ester | + |
| C096 | 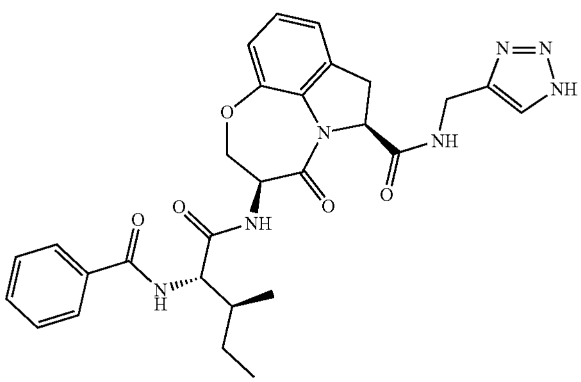 [SMILES: CC[C@H](C)[C@H](NC(=O)c1ccccc1)C(=O)N[C@H]1COc2cccc3c2N(C1=O)[C@H](C(=O)NCc1c[nH]nn1)C3] | (1S,8S)-8-((2S,3S)-2-Benzoylamino-3-methyl-pentanoylamino)-9-oxo-1,2,8,9-tetrahydro-7H-6-oxa-9a-aza-benzo[cd]azulene-1-carboxylic acid (1H-[1,2,3]triazol-4-ylmethyl)-amide | ++++ |
| C097 | 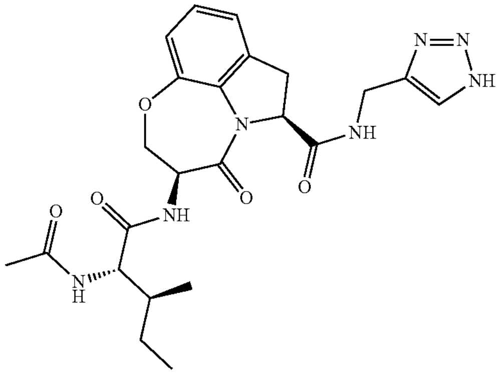 [SMILES: CC[C@H](C)[C@H](NC(C)=O)C(=O)N[C@H]1COc2cccc3c2N(C1=O)[C@H](C(=O)NCc1c[nH]nn1)C3] | (1S,8S)-8-((2S,3S)-2-Acetylamino-3-methyl-pentanoylamino)-9-oxo-1,2,8,9-tetrahydro-7H-6-oxa-9a-aza-benzo[cd]azulene-1-carboxylic acid (1H-[1,2,3]triazol-4-ylmethyl)-amide | ++++ |

TABLE 5-continued

Compounds and IC₅₀ Values

| Compound Number | Structure | Name | IC$_{50}$ |
|---|---|---|---|
| C098 | 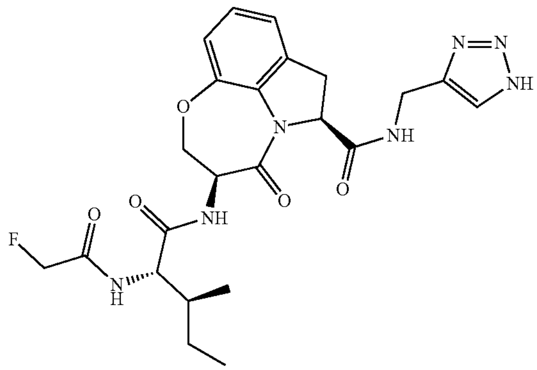 | (1S,8S)-8-[(2S,3S)-2-(2-Fluoro-acetylamino)-3-methyl-pentanoylamino]-9-oxo-1,2,8,9-tetrahydra-7H-6-oxa-9a-aza-benzo[cd]azulene-1-carboxylic acid (1H-[1,2,3]triazol-4-ylmethyl)-amide | ++++ |
| C099 | 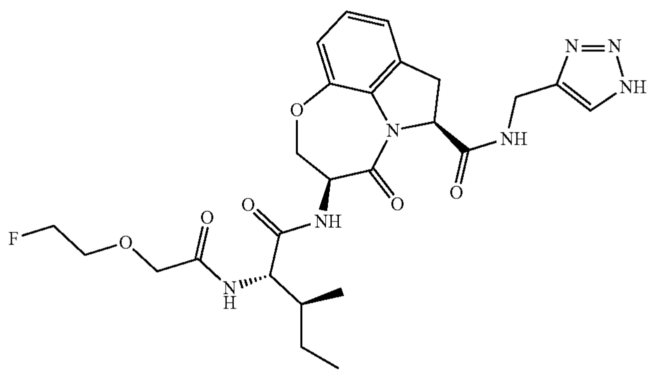 | (1S,8S)-8-{(2S,3S)-2-[2-(2-Fluoro-ethoxy)-acetylamino]-3-methyl-pentanoylamino}-9-oxo-1,2,8,9-tetrahydro-7H-6-oxa-9a-aza-benzo[cd]azulene-1-carboxylic acid (1H-[1,2,3]triazol-4-ylmethyl)-amide | ++++ |
| C100 | 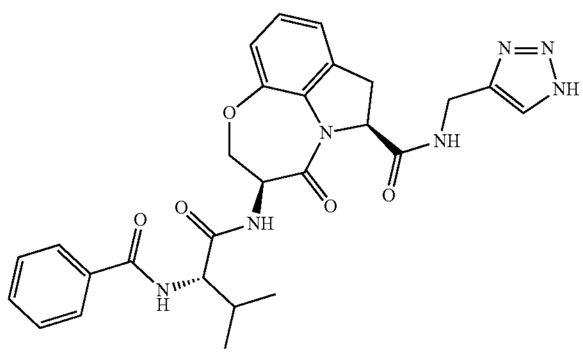 | (1S,8S)-8-((S)-2-Benzoylamino-3-methyl-butyrylamino)-9-oxo-1,2,8,9-tetrahydro-7H-6-oxa-9a-aza-benzo[cd]azulene-1-carboxylic acid (1H-[1,2,3,]triazol-4-ylmethyl)-amide | ++++ |
| C101 | 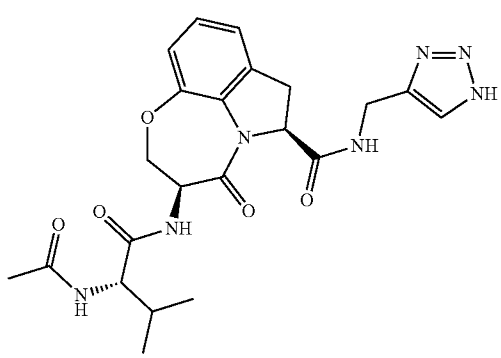 | (1S,8S)-8-((S)-2-Acetylamino-3-methyl-butyrylamino)-9-oxo-1,2,8,9-tetrahydro-7H-6-oxa-9a-aza-benzo[cd]azulene-1-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C102 | 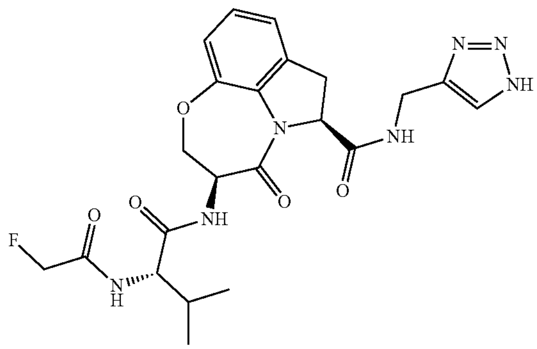 [SMILES: CC(C)[C@H](NC(=O)CF)C(=O)N[C@H]1COc2cccc3c2N(C1=O)[C@H](C(=O)NCc1c[nH]nn1)C3] | (1S,8S)-8-[(S)-2-(2-Fluoro-acetylamino)-3-methyl-butyrylamino]-9-oxo-1,2,8,9-tetrahydro-7H-6-oxa-9a-aza-benzo[cd]azulene-1-carboxylic acid (1H-[1,2,3]triazol-4-ylmethyl)-amide | ++++ |
| C103 | 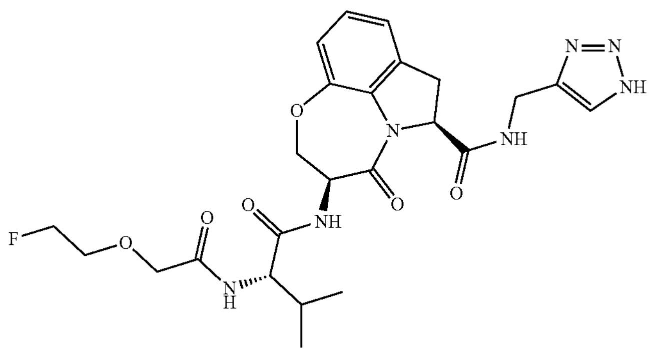 [SMILES: CC(C)[C@H](NC(=O)COCCF)C(=O)N[C@H]1COc2cccc3c2N(C1=O)[C@H](C(=O)NCc1c[nH]nn1)C3] | (1S,8S)-8-{(S)-2-[2-(2-Fluoro-ethoxy)-acetylamino]-3-methyl-butyrylamino}-9-oxo-1,2,8,9-tetrahydro-7H-6-oxa-9a-aza-benzo[cd]azulene-1-carboxylic acid (1H-[1,2,3]triazol-4-ylmethyl)-amide | ++++ |
| C104 | 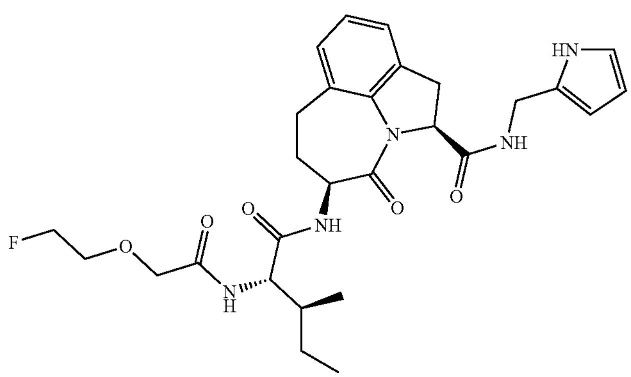 | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (1H-pyrrol-2-ylmethyl)-amide | + |
| C105 | 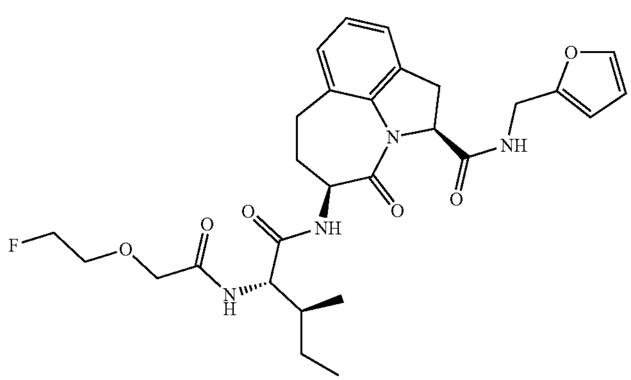 [SMILES: CC[C@H](C)[C@H](NC(=O)COCCF)C(=O)N[C@H]1CCc2cccc3c2N(C1=O)[C@H](C(=O)NCc1cccs1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (furan-2-ylmethyl)-amide | + |

TABLE 5-continued

Compounds and IC$_{50}$ Values

| Compound Number | Structure | Name | IC$_{50}$ |
|---|---|---|---|
| C106 | 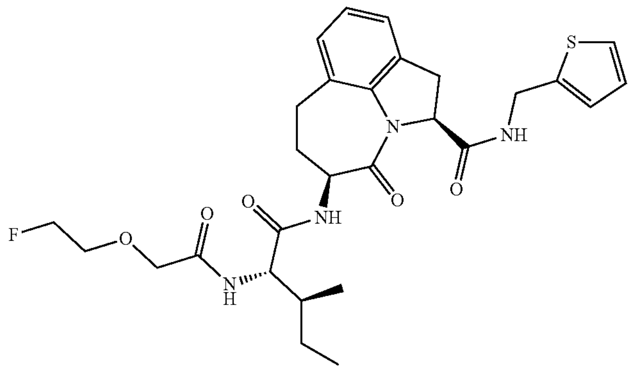 | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (thiophen-2-ylmethyl)-amide | + |
| C107 | 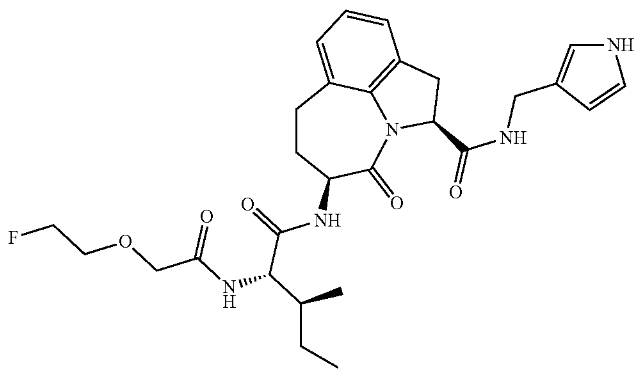 [SMILES: CC[C@H](C)[C@H](NC(=O)COCCF)C(=O)N[C@H]1CCc2cccc3c2N(C1=O)[C@H](C(=O)NCc1cc[nH]c1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (1H-pyrrol-3-ylmethyl)-amide | + |
| C108 | 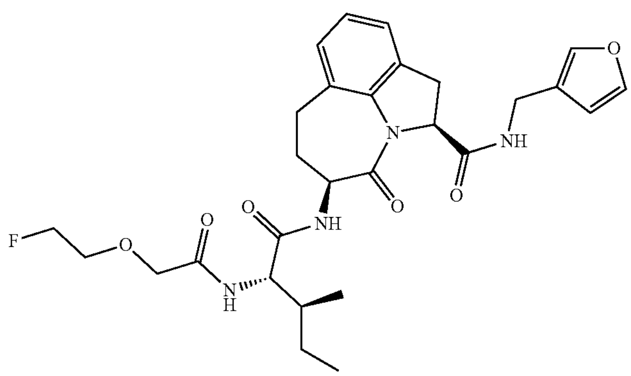 | (2S,5S)-5-{(2S,3R)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (furan-3-ylmethyl)-amide | + |
| C109 | 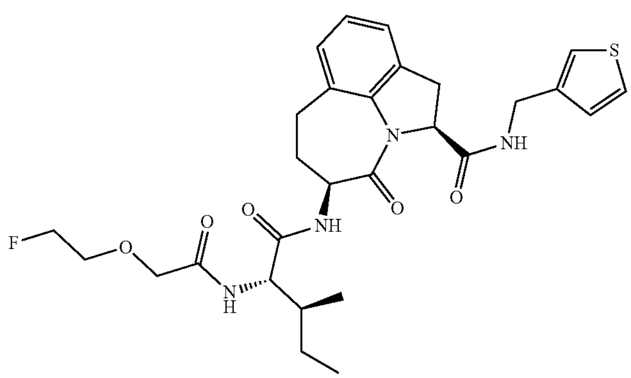 [SMILES: CC[C@H](C)[C@H](NC(=O)COCCF)C(=O)N[C@H]1CCc2cccc3c2N(C1=O)[C@H](C(=O)NCc1ccsc1)C3] | ((2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (thiophen-3-ylmethyl)-amide | + |

TABLE 5-continued

Compounds and IC$_{50}$ Values

| Compound Number | Structure | Name | IC$_{50}$ |
|---|---|---|---|
| C110 | 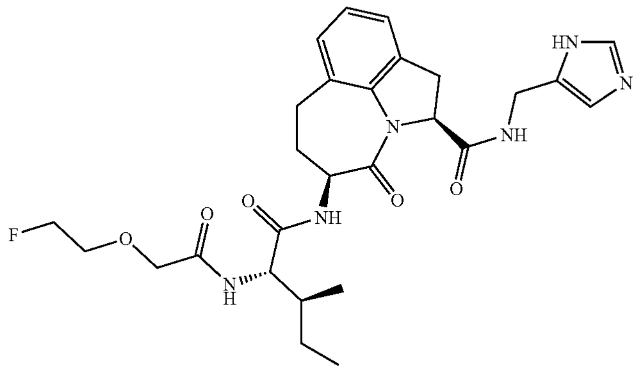 [SMILES: CC[C@H](C)[C@H](NC(=O)COCCF)C(=O)N[C@H]1CCc2cccc3c2N(C1=O)[C@H](C(=O)NCc1cnc[nH]1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (3H-imidazol-4-ylmethyl)-amide | + |
| C111 | 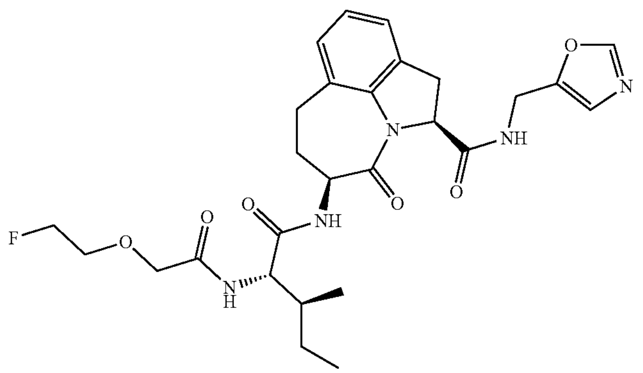 | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (oxazol-5-ylmethyl)-amide | + |
| C112 | 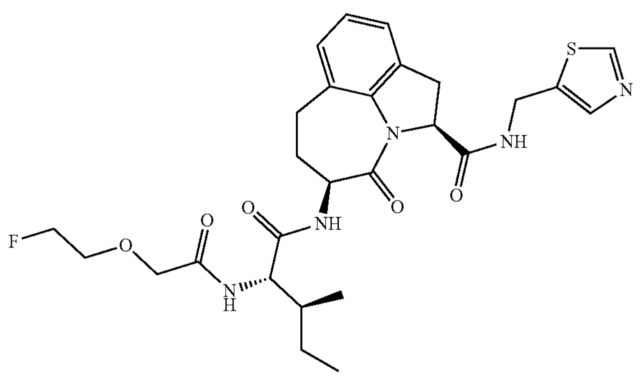 [SMILES: CC[C@H](C)[C@H](NC(=O)COCCF)C(=O)N[C@H]1CCc2cccc3c2N(C1=O)[C@H](C(=O)NCc1cncs1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (thiazol-5-ylmethyl)-amide | + |
| C113 | 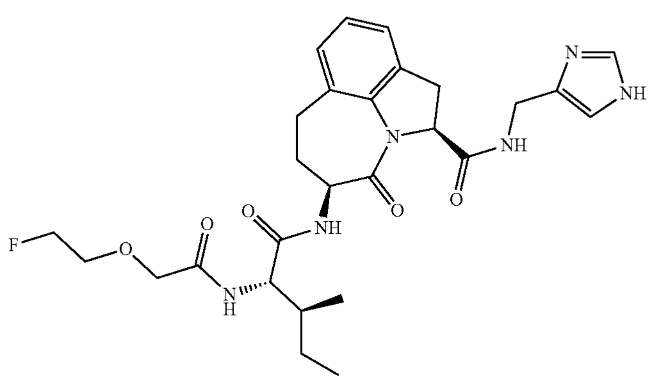 [SMILES: CC[C@H](C)[C@H](NC(=O)COCCF)C(=O)N[C@H]1CCc2cccc3c2N(C1=O)[C@H](C(=O)NCc1c[nH]cn1)C3] | ((2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (1H-imidazol-ylmethyl)-amide | nd |

TABLE 5-continued

Compounds and IC$_{50}$ Values

| Compound Number | Structure | Name | IC$_{50}$ |
|---|---|---|---|
| C114 | 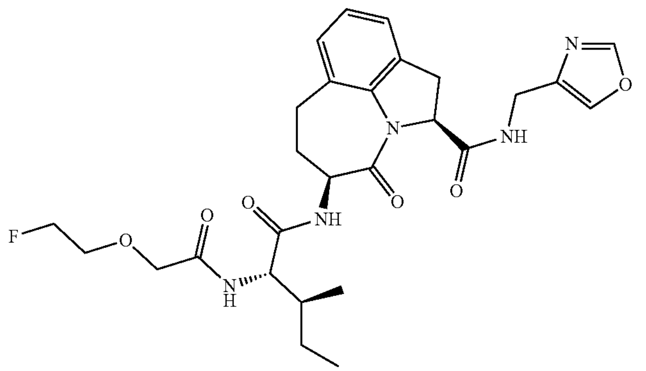 | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (oxazol-4-ylmethyl)-amide | + |
| C115 | 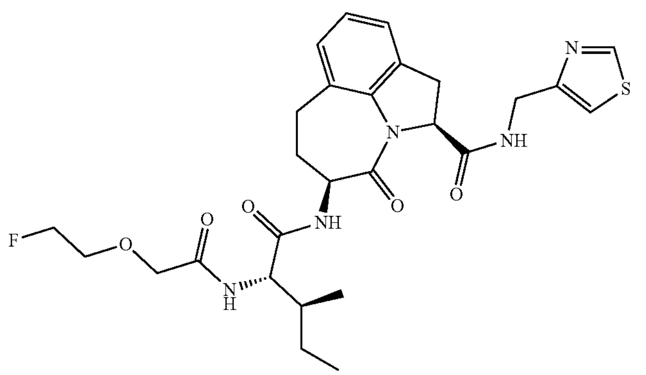 [SMILES: CC[C@H](C)[C@H](NC(=O)COCCF)C(=O)N[C@H]1CCc2cccc3c2N(C1=O)[C@H](C(=O)NCc1cocn1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (thiazol-4-ylmethyl)-amide | + |
| C116 | 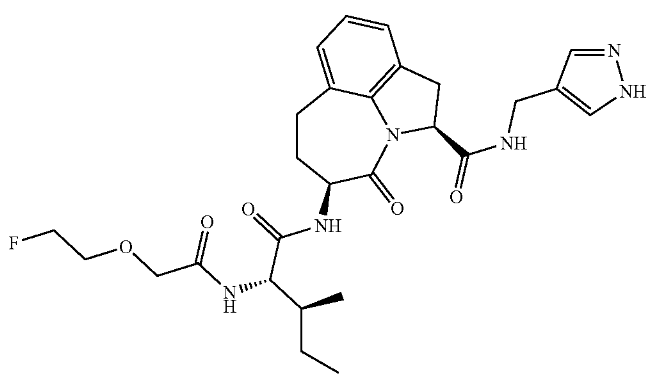 [SMILES: CC[C@H](C)[C@H](NC(=O)COCCF)C(=O)N[C@H]1CCc2cccc3c2N(C1=O)[C@H](C(=O)NCc1cn[nH]c1)C3] | ((2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (1H-pyrazol-4-ylmethyl)-amide | + |
| C117 | 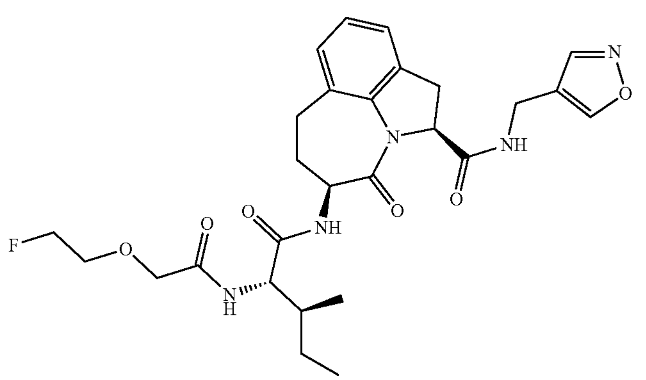 | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (isoxazol-4-ylmethyl)-amide | + |

TABLE 5-continued

Compounds and IC₅₀ Values

| Compound Number | Structure | Name | IC₅₀ |
|---|---|---|---|
| C118 | 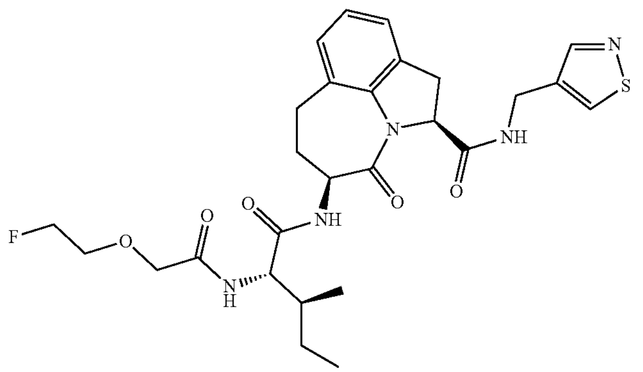 [SMILES: CC[C@H](C)[C@H](NC(=O)COCCF)C(=O)N[C@H]1CCc2cccc3c2N(C1=O)[C@H](C(=O)NCc1cnoc1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (isothiazol-4-ylmethyl)-amide | + |
| C119 | 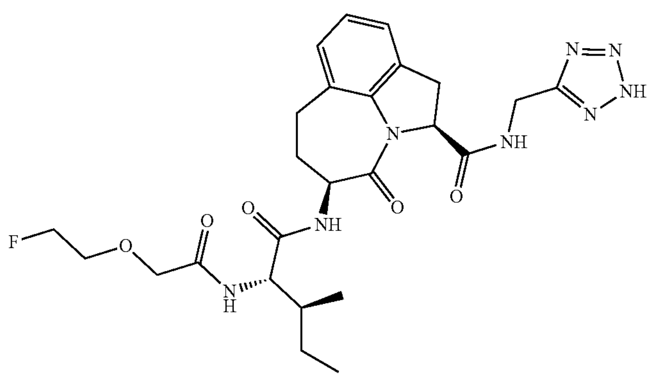 [SMILES: CC[C@H](C)[C@H](NC(=O)COCCF)C(=O)N[C@H]1CCc2cccc3c2N(C1=O)[C@H](C(=O)NCc1nn[nH]n1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (2H-tetrazol-5-ylmethyl)-amide | ++++ |
| C120 | 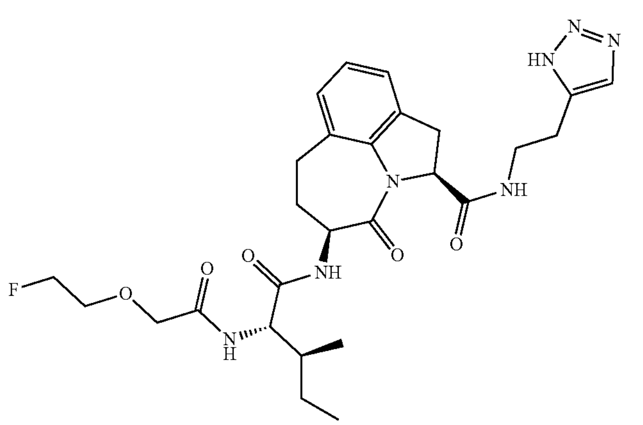 [SMILES: CC[C@H](C)[C@H](NC(=O)COCCF)C(=O)N[C@H]1CCc2cccc3c2N(C1=O)[C@H](C(=O)NCCc1cnn[nH]1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid [2-(3H-[1,2,3]triazol-4-yl)-ethyl]-amide | + |

TABLE 5-continued

Compounds and IC$_{50}$ Values

| Compound Number | Structure | Name | IC$_{50}$ |
|---|---|---|---|
| C121 | 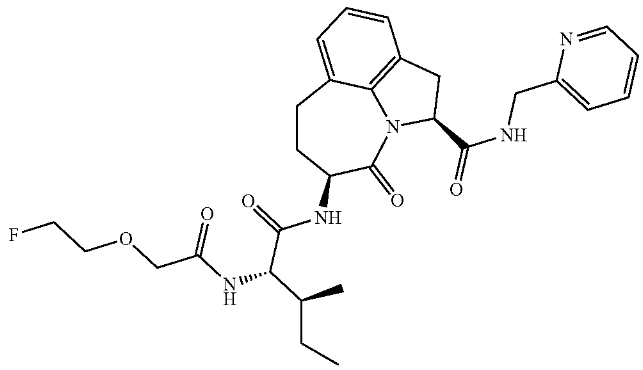 | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (pyridin-2-ylmethyl)-amide | + |
| C122 | 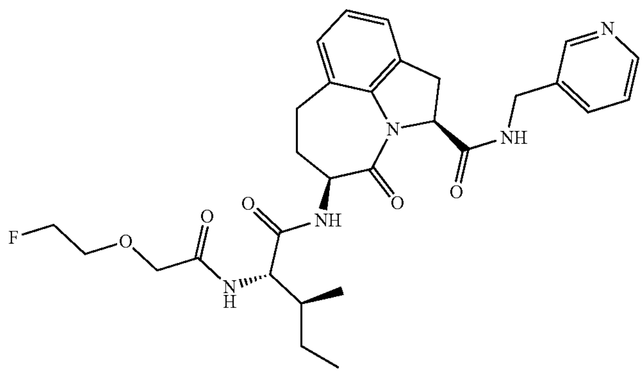 [SMILES: CC[C@H](C)[C@H](NC(=O)COCCF)C(=O)N[C@H]1CCc2cccc3c2N(C1=O)[C@H](C(=O)NCc1cccnc1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (pyridin-3-ylmethyl)-amide | + |
| C123 | 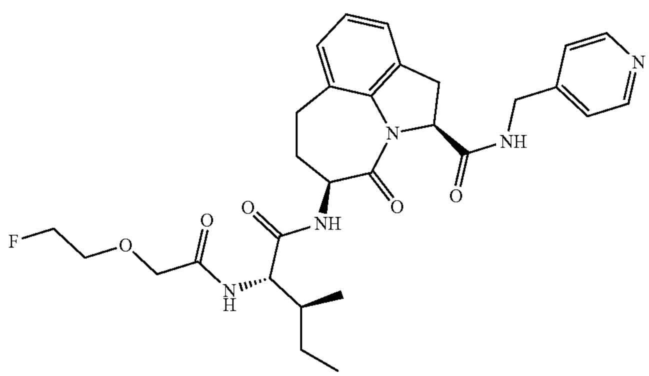 [SMILES: CC[C@H](C)[C@H](NC(=O)COCCF)C(=O)N[C@H]1CCc2cccc3c2N(C1=O)[C@H](C(=O)NCc1ccncc1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (pyridin-4-ylmethyl)-amide | + |
| C124 | 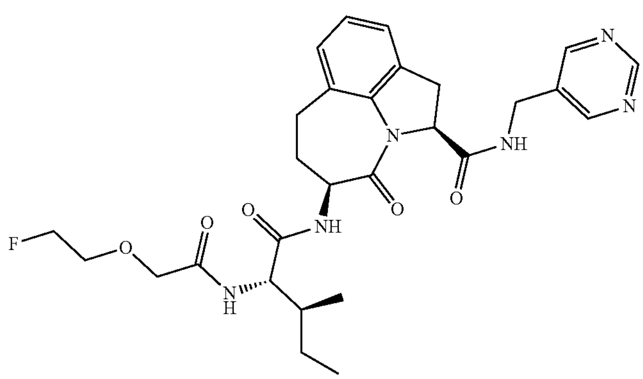 | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (pyrimidin-5-ylmethyl)-amide | nd |

TABLE 5-continued

Compounds and IC$_{50}$ Values

| Compound Number | Structure | Name | IC$_{50}$ |
|---|---|---|---|
| C125 | 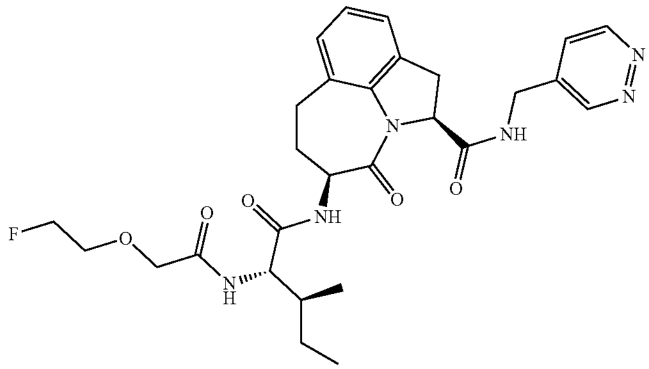 [SMILES: CC[C@H](C)[C@H](NC(=O)COCCF)C(=O)N[C@H]1CCc2cccc3c2N(C1=O)[C@H](C(=O)NCc1ccnnc1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (pyridazin-4-ylmethyl)-amide | nd |
| C126 | 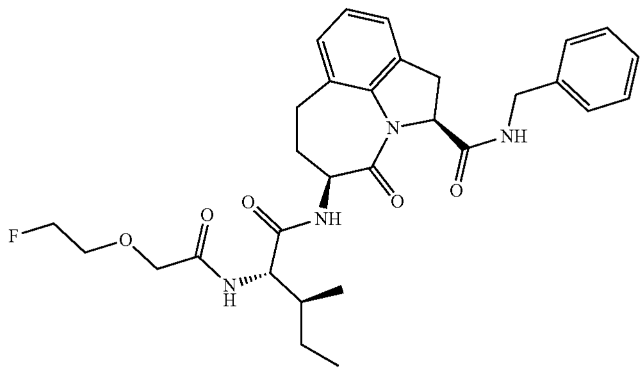 [SMILES: CC[C@H](C)[C@H](NC(=O)COCCF)C(=O)N[C@H]1CCc2cccc3c2N(C1=O)[C@H](C(=O)NCc1ccccc1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid benzylamide | nd |
| C127 | 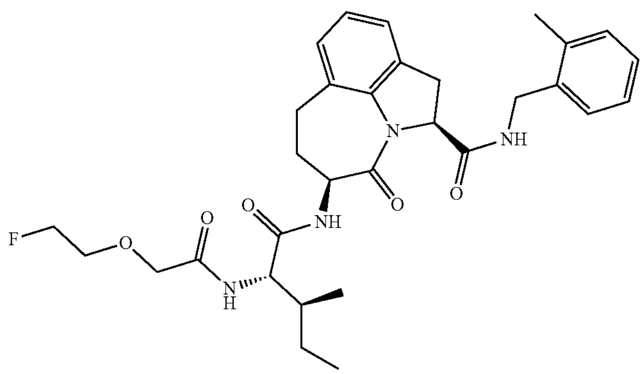 [SMILES: CC[C@H](C)[C@H](NC(=O)COCCF)C(=O)N[C@H]1CCc2cccc3c2N(C1=O)[C@H](C(=O)NCc1ccccc1C)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 2-methyl-benzylamide | + |
| C128 | 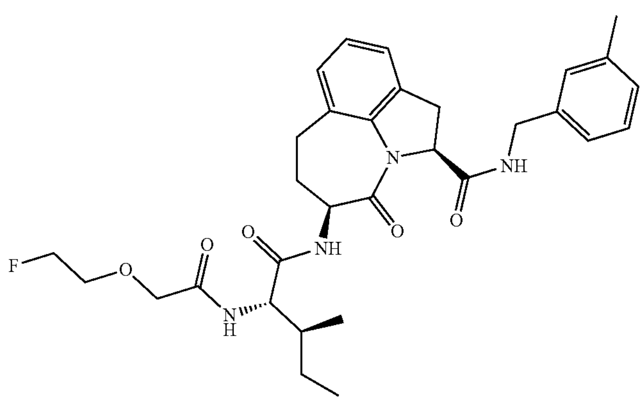 [SMILES: CC[C@H](C)[C@H](NC(=O)COCCF)C(=O)N[C@H]1CCc2cccc3c2N(C1=O)[C@H](C(=O)NCc1cccc(C)c1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 3-methyl-benzylamide | + |

TABLE 5-continued

Compounds and IC$_{50}$ Values

| Compound Number | Structure | Name | IC$_{50}$ |
|---|---|---|---|
| C129 | 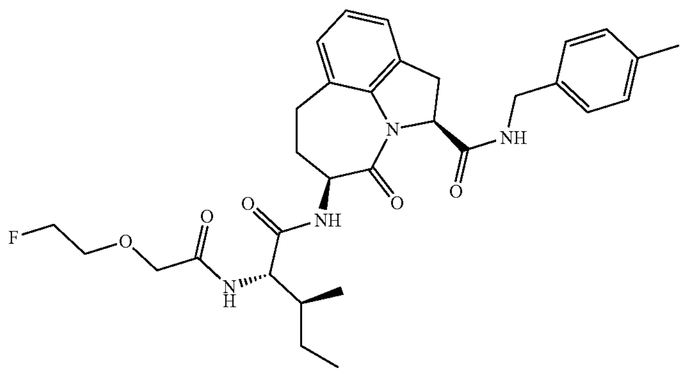 [SMILES: CC[C@H](C)[C@H](NC(=O)COCCF)C(=O)N[C@H]1CCc2cccc3c2N(C1=O)[C@H](C(=O)NCc1ccc(C)cc1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 4-methyl-benzylamide | + |
| C130 | 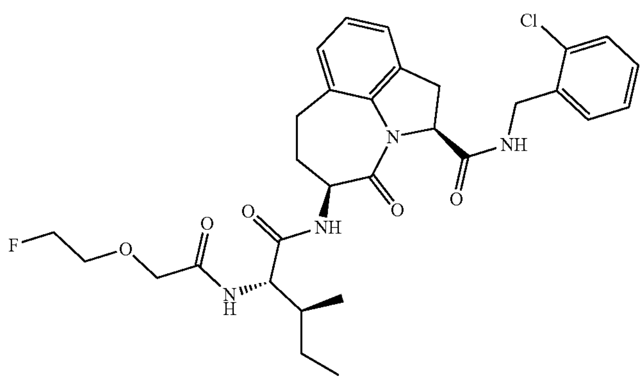 [SMILES: CC[C@H](C)[C@H](NC(=O)COCCF)C(=O)N[C@H]1CCc2cccc3c2N(C1=O)[C@H](C(=O)NCc1ccccc1Cl)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 2-chloro-benzylamide | + |
| C131 | 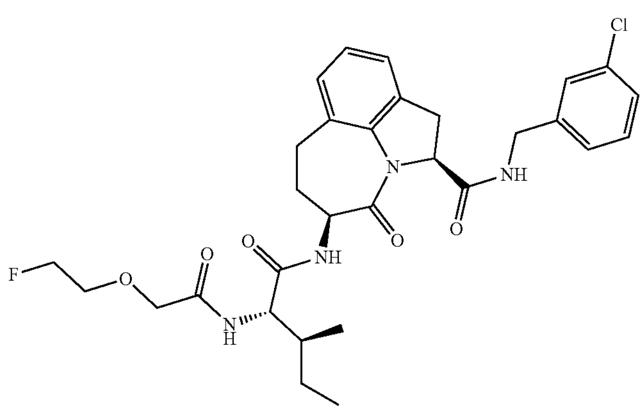 [SMILES: CC[C@H](C)[C@H](NC(=O)COCCF)C(=O)N[C@H]1CCc2cccc3c2N(C1=O)[C@H](C(=O)NCc1cccc(Cl)c1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 3-chloro-benzylamide | + |

TABLE 5-continued

Compounds and IC$_{50}$ Values

| Compound Number | Structure | Name | IC$_{50}$ |
|---|---|---|---|
| C132 | 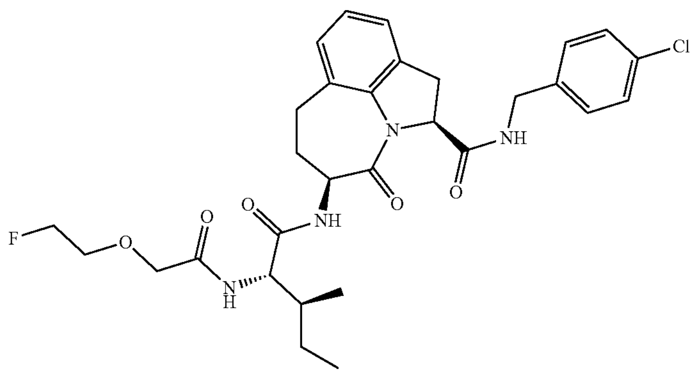 [SMILES: CC[C@H](C)[C@H](NC(=O)COCCF)C(=O)N[C@H]1CCc2cccc3c2N(C1=O)[C@H](C(=O)NCc1ccc(Cl)cc1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 4-chloro-benzylamide | + |
| C133 | 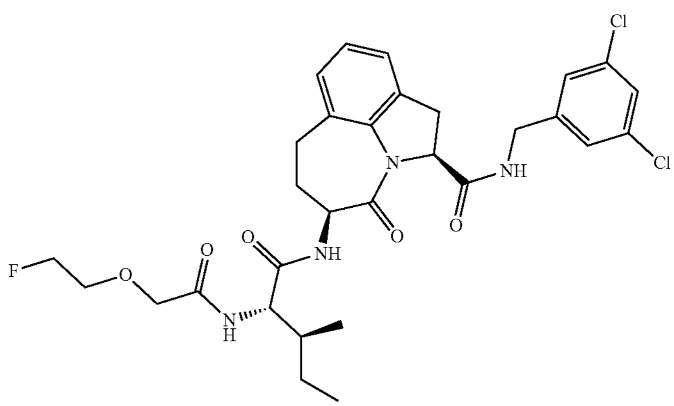 [SMILES: CC[C@H](C)[C@H](NC(=O)COCCF)C(=O)N[C@H]1CCc2cccc3c2N(C1=O)[C@H](C(=O)NCc1cc(Cl)cc(Cl)c1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 3,5-dichloro-benzylamide | + |
| C134 | 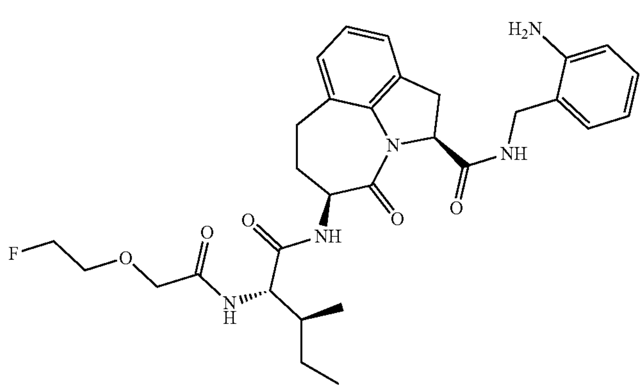 [SMILES: CC[C@H](C)[C@H](NC(=O)COCCF)C(=O)N[C@H]1CCc2cccc3c2N(C1=O)[C@H](C(=O)NCc1ccccc1N)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 2-amino-benzylamide | nd |

TABLE 5-continued

Compounds and IC$_{50}$ Values

| Compound Number | Structure | Name | IC$_{50}$ |
|---|---|---|---|
| C135 | 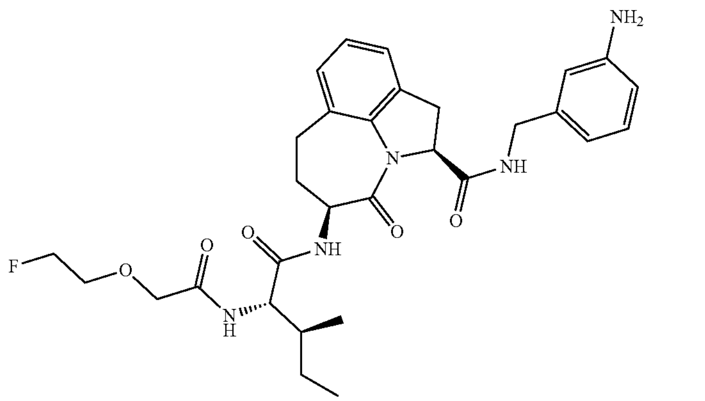 [SMILES: CC[C@H](C)[C@H](NC(=O)COCCF)C(=O)N[C@H]1CCc2cccc3c2N(C1=O)[C@H](C(=O)NCc1cccc(N)c1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 3-amino-benzylamide | nd |
| C136 | 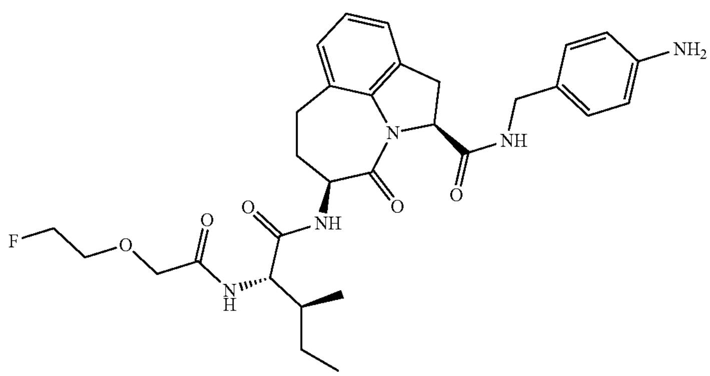 [SMILES: CC[C@H](C)[C@H](NC(=O)COCCF)C(=O)N[C@H]1CCc2cccc3c2N(C1=O)[C@H](C(=O)NCc1ccc(N)cc1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 4-amino-benzylamide | nd |
| C137 | 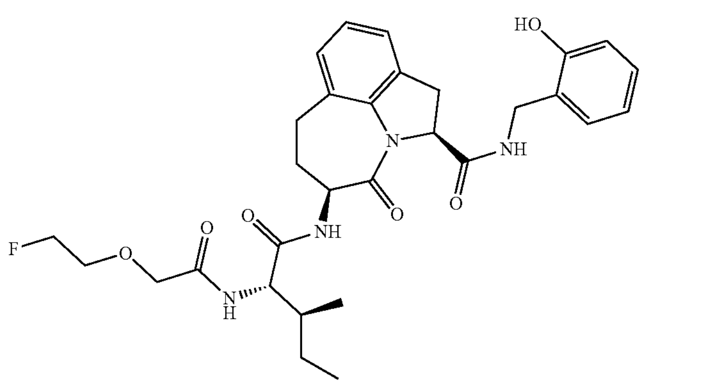 | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 2-hydroxy-benzylamide | nd |

TABLE 5-continued

Compounds and IC$_{50}$ Values

| Compound Number | Structure | Name | IC$_{50}$ |
|---|---|---|---|
| C138 | 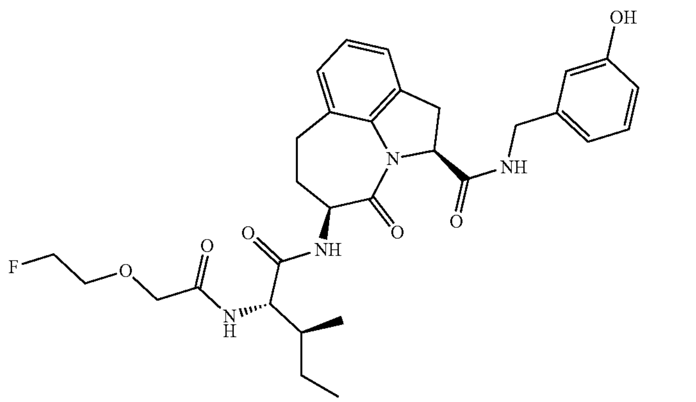 [SMILES: CC[C@H](C)[C@H](NC(=O)COCCF)C(=O)N[C@H]1CCc2cccc3c2N(C1=O)[C@H](C(=O)NCc1cccc(O)c1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 3-hydroxy-benzylamide | nd |
| C139 | 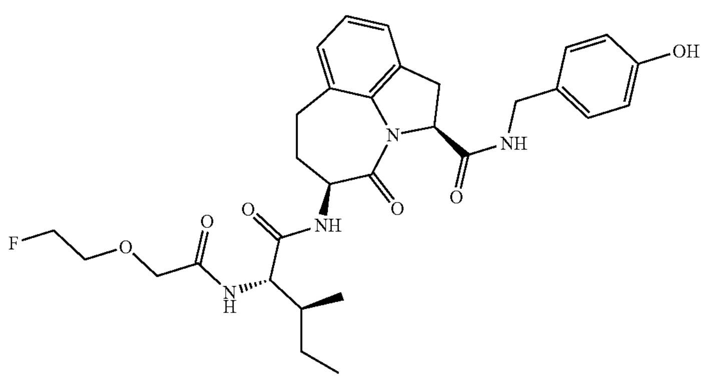 [SMILES: CC[C@H](C)[C@H](NC(=O)COCCF)C(=O)N[C@H]1CCc2cccc3c2N(C1=O)[C@H](C(=O)NCc1ccc(O)cc1)C3] | (2S,5S)-5-{(2S,3R)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 4-hydroxy-benzylamide | nd |
| C140 | 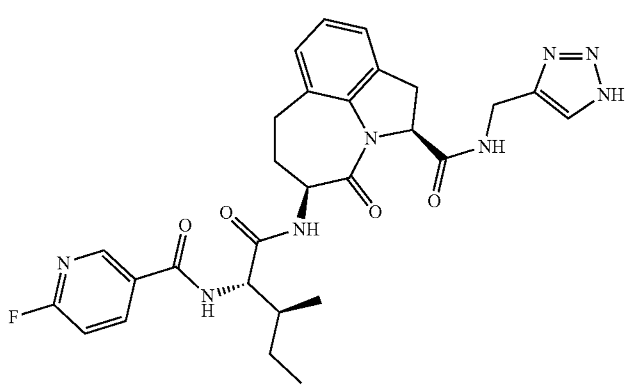 [SMILES: CC[C@H](C)[C@H](NC(=O)c1ccc(F)nc1)C(=O)N[C@H]1CCc2cccc3c2N(C1=O)[C@H](C(=O)NCc1c[nH]nn1)C3] | (2S,5S)-5-{(2S,3S)-2-[(6-Fluoro-pyridine-3-carbonyl)-amino]-3-methyl-pentanoylamino}-4-oxo-1,2,4,5,6,7-hexahydro-azepino[3,2,1-hi]indole-2-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C141 | 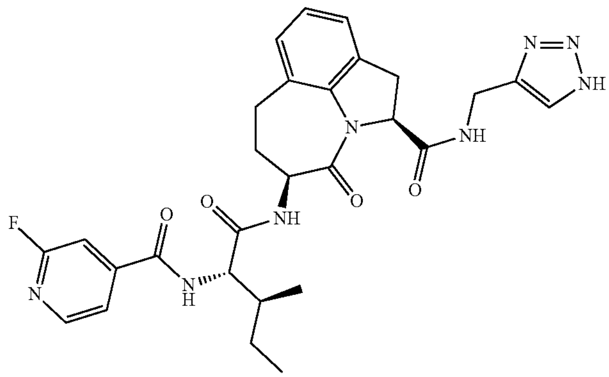 [SMILES: CC[C@H](C)[C@H](NC(=O)c1ccnc(F)c1)C(=O)N[C@H]1CCc2cccc3c2N(C1=O)[C@H](C(=O)NCc1c[nH]nn1)C3] | (2S,5S)-5-{(2S,3S)-2-[(2-Fluoro-pyridine-4-carbonyl)-amino]-3-methyl-pentanoylamino}4-oxo-1,2,4,5,6,7-hexahydro-azepino[3,2,1-hi]indole-2-carboxylic acid (1H-[1,2,3]triazol-4-ylmethyl)-amide | ++++ |
| C142 | 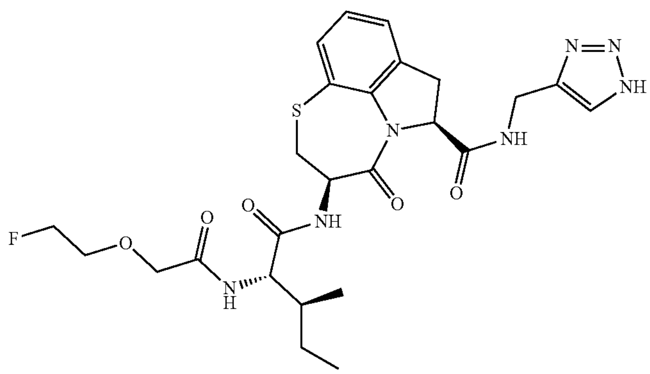 | (1S,8R)-8-{(2S,3S)-2-[2-(2-Fluoro-ethoxy)-acetylamino]-3-methyl-pentanoylamino}-9-oxo-1,2,8,9-tetrahydro-7H-6-thia-9a-aza-benzo[cd]azulene-1-carboxylic acid (1H-[1,2,3]triazol-4-ylmethyl)-amide | nd |
| C143 | 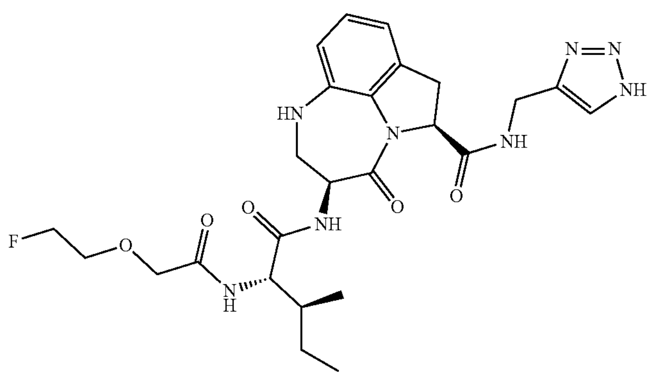 [SMILES: CC[C@H](C)[C@H](NC(=O)COCCF)C(=O)N[C@H]1CNc2cccc3c2N(C1=O)[C@H](C(=O)NCc1c[nH]nn1)C3] | (3S,6S)-3-{(2S,3S)-2-[2-(2-Fluoro-ethoxy)-acetylamino]-3-methyl-pentanoylamino}-4-oxo-1,2,3,4,6,7-hexahydro-[1,4]diazepino[3,2,1-hi]indole-6-carboxylic acid (1H-[1,2,3]triazol-4-ylmethyl)-amide | ++++ |
| C144 | 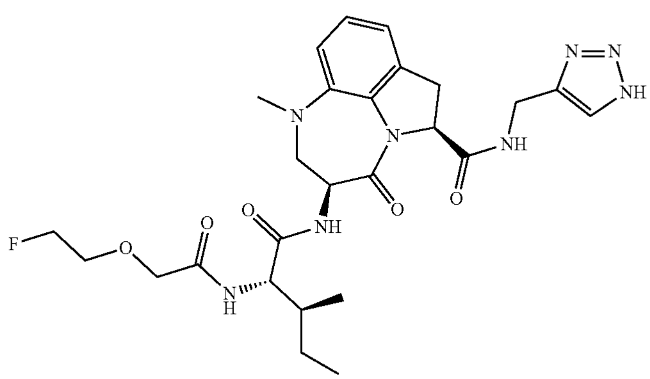 [SMILES: CC[C@H](C)[C@H](NC(=O)COCCF)C(=O)N[C@H]1CN(C)c2cccc3c2N(C1=O)[C@H](C(=O)NCc1c[nH]nn1)C3] | (3S,6S)-3-{(2S,3S)-2-[2-(2-Fluoro-ethoxy)-acetylamino]-3-methyl-pentanoylamino}-1-methyl-4-oxo-1,2,3,4,6,7-hexahydro-[1,4]diazepino[3,2,1-hi]indole-6-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C145 | 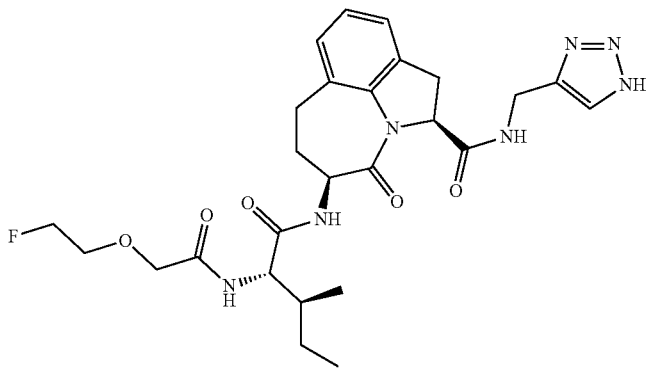 [SMILES: CC[C@H](C)[C@H](NC(=O)COCCF)C(=O)N[C@H]1CCc2cccc3c2N(C1=O)[C@H](C(=O)NCc1c[nH]nn1)C3] | (2S,5S)-5-{(2S,3S)-2-[2-(3-Fluoro-propoxy)-acetylamino]-3-methyl-pentanoylamino}-4-oxo-1,2,4,5,6,7-hexahydro-azepino[3,2,1-hi]indole-2-carboxylic acid (1H-[1,2,3]triazol-4-ylmethyl)-amide | ++++ |
| C146 | 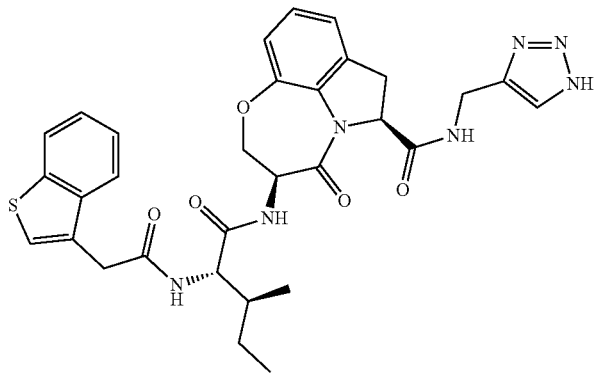 [SMILES: CC[C@H](C)[C@H](NC(=O)Cc1csc2ccccc12)C(=O)N[C@H]1COc2cccc3c2N(C1=O)[C@H](C(=O)NCc1c[nH]nn1)C3] | (1S,8S)-8-[(2S,3S)-2-(2-Benzo[b]thiophen-3-yl-acetylamino)-3-methyl-pentanoylamino]-9-oxo-1,2,8,9-tetrahydro-7H-6-oxa-9a-aza-benzo[cd]azulene-1-carboxylic acid (1H-[1,2,3]triazol-4-ylmethyl)-amide | ++++ |
| C147 | 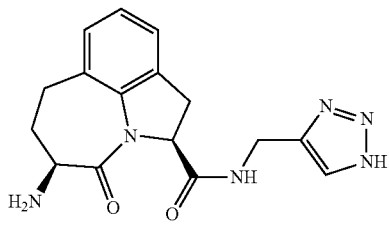 [SMILES: N[C@H]1CCc2cccc3c2N(C1=O)[C@H](C(=O)NCc1c[nH]nn1)C3] | (2S,5S)-5-Amino-4-oxo-1,2,4,5,6,7-hexahydro-azepino[3,2,1-hi]indole-2-carboxylic acid (1H-[1,2,3]triazol-4-ylmethyl)-amide | + |
| C148 | 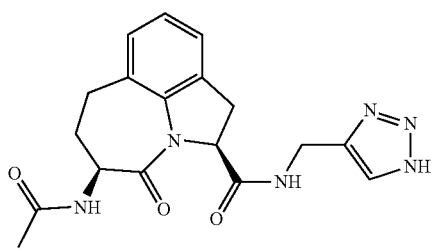 [SMILES: CC(=O)N[C@H]1CCc2cccc3c2N(C1=O)[C@H](C(=O)NCc1c[nH]nn1)C3] | (2S,5S)-5-Acetylamino-4-oxo-1,2,4,5,6,7-hexahydro-azepino[3,2,1-hi]indole-2-carboxylic acid (1H-[1,2,3]triazol-4-ylmethyl)-amide | + |

TABLE 5-continued

Compounds and IC$_{50}$ Values

| Compound Number | Structure | Name | IC$_{50}$ |
|---|---|---|---|
| C149 | 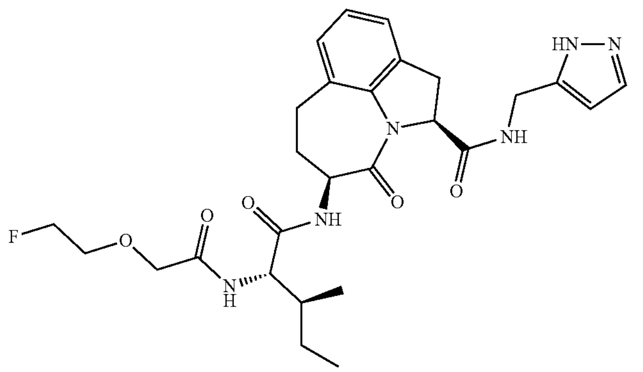 [SMILES: CC[C@H](C)[C@H](NC(=O)COCCF)C(=O)N[C@H]1CCc2cccc3c2N(C1=O)[C@H](C(=O)NCc1ccn[nH]1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (2H-pyrazol-3-ylmethyl)-amide | + |
| C158 | 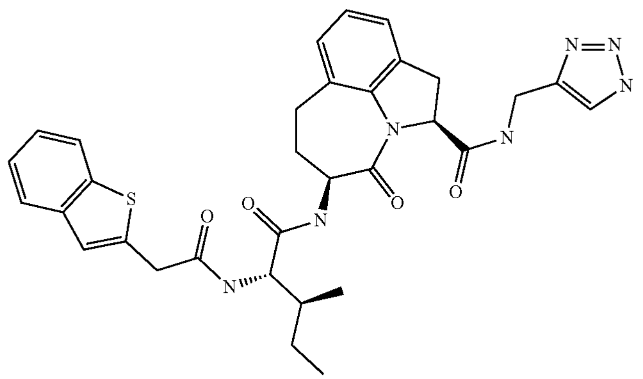 [SMILES: CC[C@H](C)[C@H](NC(=O)Cc1cc2ccccc2s1)C(=O)N[C@H]1CCc2cccc3c2N(C1=O)[C@H](C(=O)NCc1c[nH]nn1)C3] | (2S,5S)-5-[(2S,3S)-2-(2-Benzo[b]thiophen-2-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide | ++++ |
| C159 | 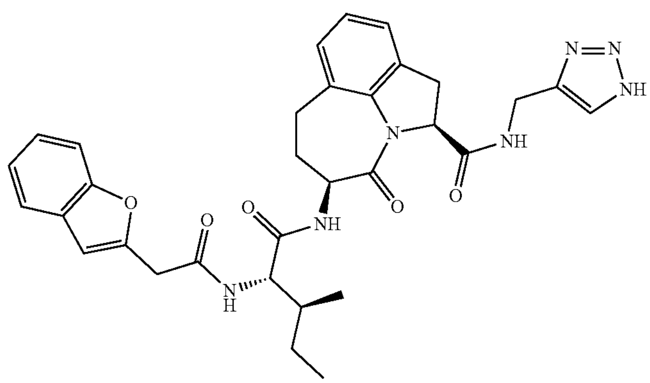 | (2S,5S)-5-[(2S,3S)-2-(2-Benzofuran-2-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide | ++++ |
| C160 | 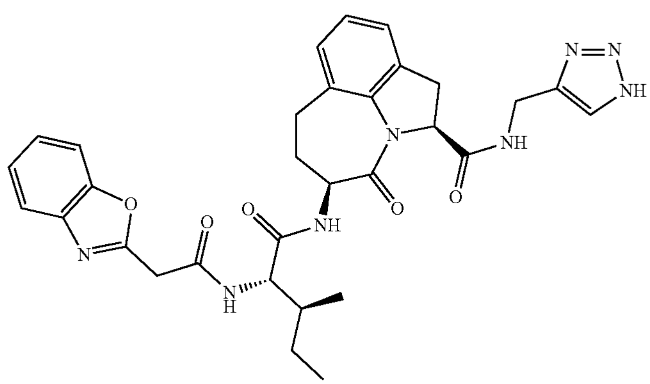 [SMILES: CC[C@H](C)[C@H](NC(=O)Cc1cc2ccccc2o1)C(=O)N[C@H]1CCc2cccc3c2N(C1=O)[C@H](C(=O)NCc1c[nH]nn1)C3] | (2S,5S)-5-[(2S,3S)-2-(2-Benzooxazol-2-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide | ++++ |

TABLE 5-continued

Compounds and IC$_{50}$ Values

| Compound Number | Structure | Name | IC$_{50}$ |
|---|---|---|---|
| C161 | 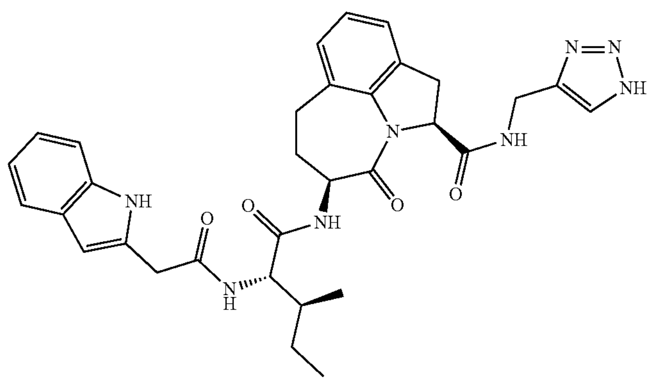 [SMILES: CC[C@H](C)[C@H](NC(=O)Cc1cc2ccccc2[nH]1)C(=O)N[C@H]1CCc2cccc3c2N(C1=O)[C@H](C(=O)NCc1c[nH]nn1)C3] | (2S,5S)-5-[(2S,3S)-2-(2-1H-Indol-2-yl-acetylamino)-3-methyl-pentanoylamino]-4-oxo-1,2,4,5,6,7-hexahydro-azepino[3,2,1-hi]indole-2-carboxylicacid (1H-[1,2,3]triazol-4-ylmethyl)-amide | ++++ |
| C162 | 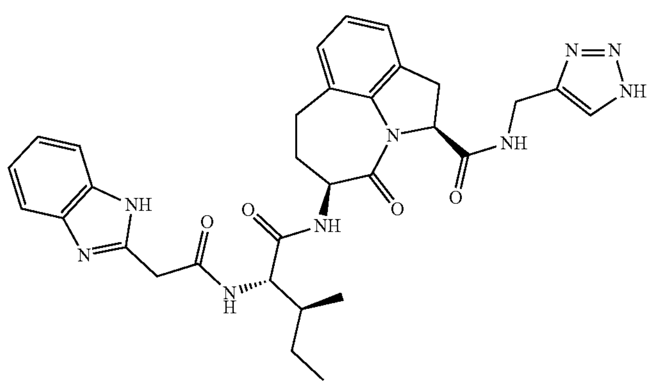 | (2S,5S)-5-[(2S,3S)-2-(2-1H-Benzoimidazol-2-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide | ++++ |
| C163 | 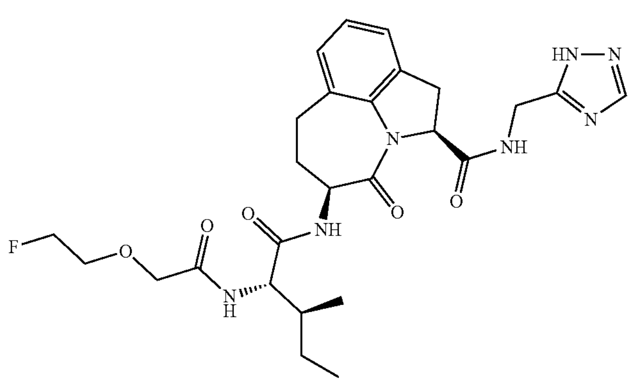 [SMILES: CC[C@H](C)[C@H](NC(=O)COCCF)C(=O)N[C@H]1CCc2cccc3c2N(C1=O)[C@H](C(=O)NCc1ncn[nH]1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (2H-[1,2,4]triazol-3-ylmethyl)-amide | + |

TABLE 5-continued

Compounds and IC$_{50}$ Values

| Compound Number | Structure | Name | IC$_{50}$ |
|---|---|---|---|
| C164 | 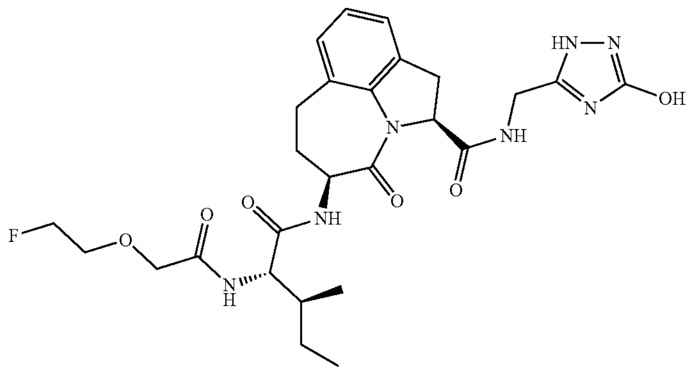 [SMILES: CC[C@H](C)[C@H](NC(=O)COCCF)C(=O)N[C@H]1CCc2cccc3c2N(C1=O)[C@H](C(=O)NCc1nc(O)n[nH]1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (5-hydroxy-2H-[1,2,4]triazol-3-ylmethyl)-amide | + |
| C165 | 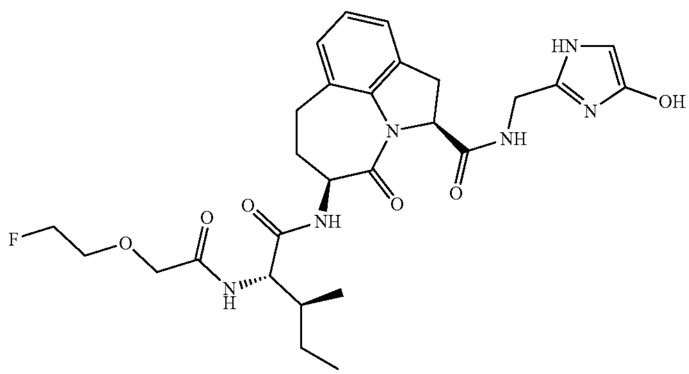 [SMILES: CC[C@H](C)[C@H](NC(=O)COCCF)C(=O)N[C@H]1CCc2cccc3c2N(C1=O)[C@H](C(=O)NCc1nc(O)c[nH]1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (4-hydroxy-1H-imidazol-2-ylmethyl)-amide | nd |
| C166 | 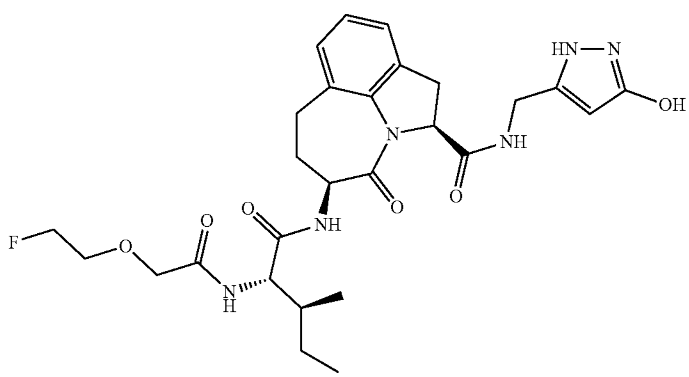 [SMILES: CC[C@H](C)[C@H](NC(=O)COCCF)C(=O)N[C@H]1CCc2cccc3c2N(C1=O)[C@H](C(=O)NCc1cc(O)n[nH]1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (5-hydroxy-2H-pyrazol-3-ylmethyl)-amide | ++ |
| C167 | 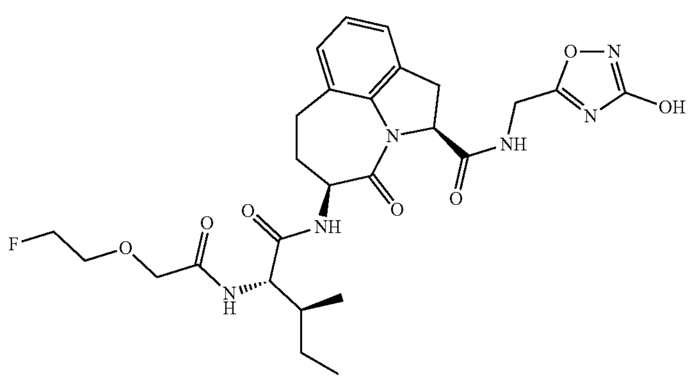 [SMILES: CC[C@H](C)[C@H](NC(=O)COCCF)C(=O)N[C@H]1CCc2cccc3c2N(C1=O)[C@H](C(=O)NCc1nc(O)no1)C3] | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (3-hydroxy-[1,2,4]oxadiazol-5-ylmethyl)-amide | nd |

TABLE 5-continued

Compounds and IC$_{50}$ Values

| Compound Number | Structure | Name | IC$_{50}$ |
|---|---|---|---|
| C168 | 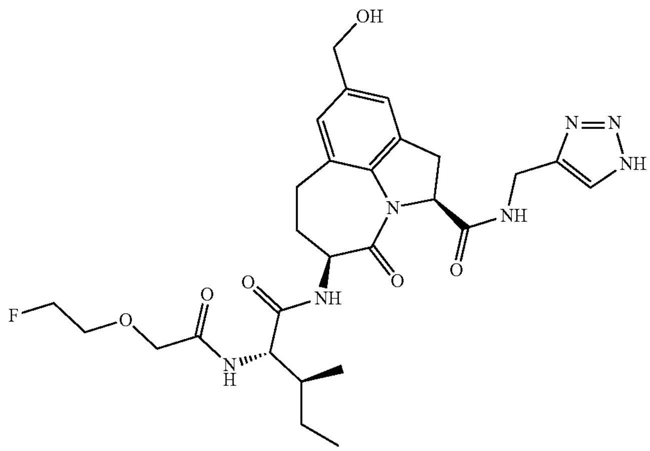 [SMILES: CC[C@H](C)[C@H](NC(=O)COCCF)C(=O)N[C@H]1CCc2cc(CO)cc3c2N(C1=O)[C@H](C(=O)NCc1c[nH]nn1)C3] | (2S,5S)-5-{(2S,3S)-2-[2-(2-Fluoro-ethoxy)-acetylamino]-3-methyl-pentanoylamino}-9-hydroxymethyl-4-oxo-1,2,4,5,6,7-hexahydro-azepino[3,2,1-hi]indole-2-carboxylic acid (1H-[1,2,3]triazol-4-ylmethyl)-amide | nd |
| C169 | 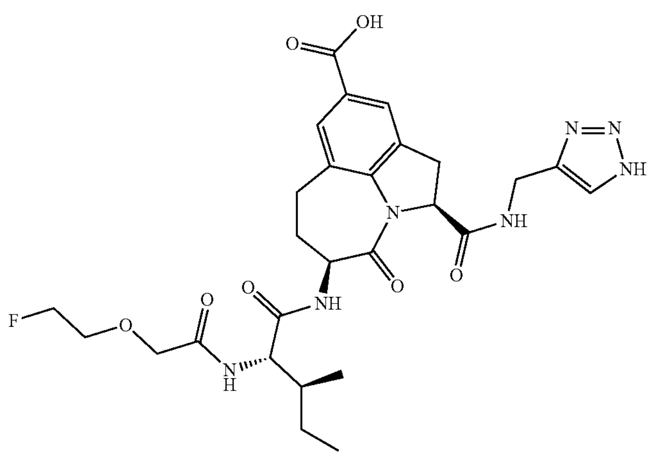 [SMILES: CC[C@H](C)[C@H](NC(=O)COCCF)C(=O)N[C@H]1CCc2cc(C(=O)O)cc3c2N(C1=O)[C@H](C(=O)NCc1c[nH]nn1)C3] | (2S,5S)-5-{(2S,3S)-2-[2-(2-Fluoro-ethoxy)-acetylamino]-3-methyl-pentanoylamino}-4-oxo-2-[(1H-[1,2,3]triazol-4-ylmethyl)-carbamoyl]-1,2,4,5,6,7-hexahydro-azepino[3,2,1-hi]indole-9-carboxylic acid | nd |
| C170 | 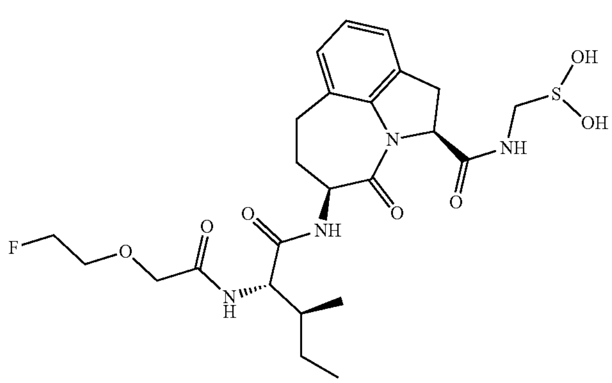 | {[((2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carbonyl)-amino]-methyl}-boronic acid | +++ |

TABLE 5-continued

Compounds and IC$_{50}$ Values

| Compound Number | Structure | Name | IC$_{50}$ |
|---|---|---|---|
| C171 | 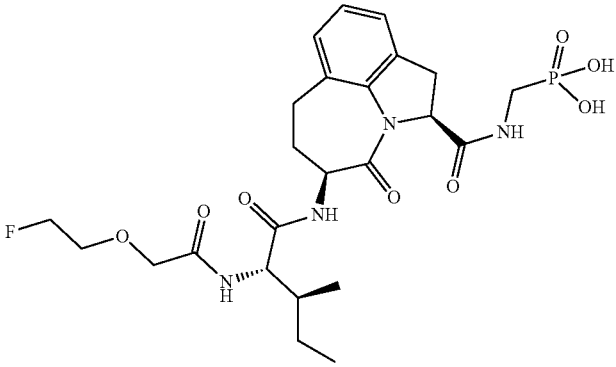 [SMILES: CC[C@H](C)[C@H](NC(=O)COCCF)C(=O)N[C@H]1CCc2cccc3c2N(C1=O)[C@H](C(=O)NCP(=O)(O)O)C3] | {[((2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carbonyl)-amino]-methyl}-phosphonic acid | nd |
| C172 | 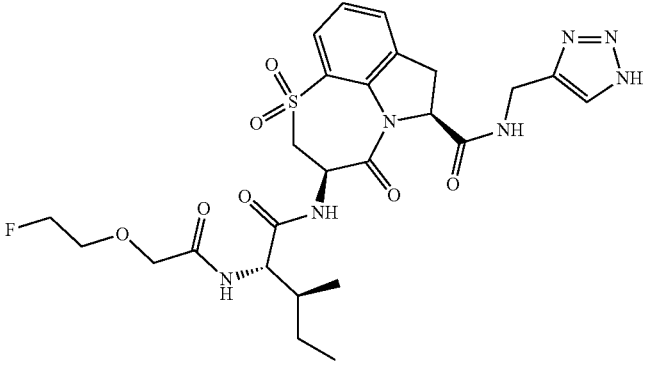 [SMILES: CC[C@H](C)[C@H](NC(=O)COCCF)C(=O)N[C@H]1CS(=O)(=O)c2cccc3c2N(C1=O)[C@H](C(=O)NCc1c[nH]nn1)C3] | (1S,8R)-8-{(2S,3S)-2-[2-(2-Fluoro-ethoxy)-acetylamino]-3-methyl-pentanoylamino}-6,6,9-trioxo-1,2,6,7,8,9-hexahydro-6lambda*6*-thia-9a-aza-benzo[cd]azulene-1-carboxylic acid (1H-[1,2,3]triazol-4-ylmethyl)-amide | +++ |
| C173 | 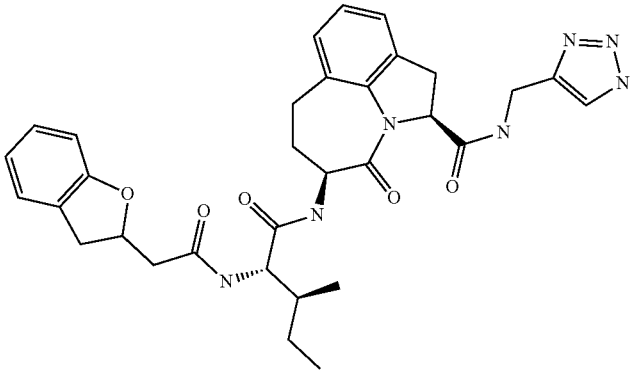 [SMILES: CC[C@H](C)[C@H](NC(=O)CC1Cc2ccccc2O1)C(=O)N[C@H]1CCc2cccc3c2N(C1=O)[C@H](C(=O)NCc1c[nH]nn1)C3] | (2S,5S)-5-[(2S,3S)-2-(2-2,3-Dihydro-benzofuran-2-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide | ++++ |
| C174 | 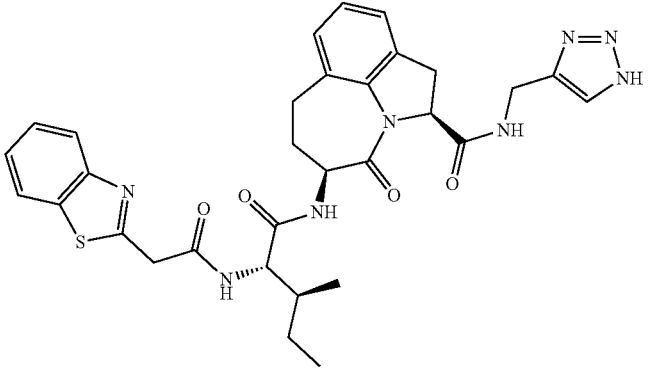 [SMILES: CC[C@H](C)[C@H](NC(=O)Cc1nc2ccccc2s1)C(=O)N[C@H]1CCc2cccc3c2N(C1=O)[C@H](C(=O)NCc1c[nH]nn1)C3] | (2S,5S)-5-[(2S,3S)-2-(2-Benzothiazol-2-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide | nd |

TABLE 5-continued

Compounds and IC$_{50}$ Values

| Compound Number | Structure | Name | IC$_{50}$ |
|---|---|---|---|
| C175 | 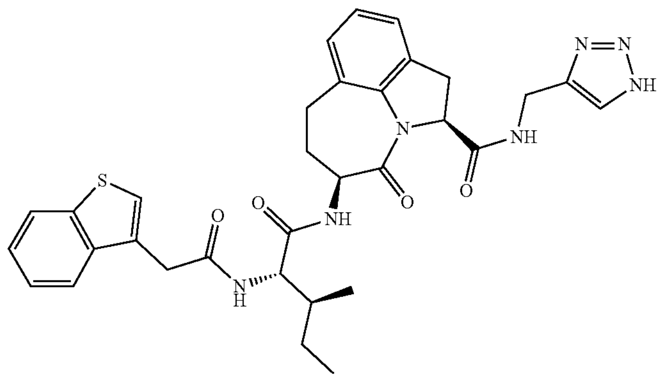 [SMILES: CC[C@H](C)[C@H](NC(=O)Cc1csc2ccccc12)C(=O)N[C@H]1CCc2cccc3c2N(C1=O)[C@H](C(=O)NCc1c[nH]nn1)C3] | (2S,5S)-5-[(2S,3S)-2-(2-Benzo[b]thiophen-3-yl-ethylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide | nd |

Described below are the procedures used to synthesize the above-described exemplary compounds.

All the reagents and solvents were purchased from commercial sources and used without further purification unless otherwise indication. All the reactions were carried out under dry nitrogen or argon atmosphere and monitored by thin layer chromatography (TLC) using Merck Silica gel 60 F$_{254}$ glass-backed plate. Column chromatography was performed by Merck silica gel 60 (0.040-0.063 mm, 230--400 mesh). $^1$H NMR and $^{13}$C NMR spectra were measured by Varian Mercury-300 and Varian Mercury-400 spectrometers, and the chemical shifts (δ) were reported in parts per million (ppm) relative to the resonance of the solvent peak. Multiplicities are reported with the following abbreviations: s (singlet), d (doublet), t (triplet), q (quartet), quin (quintet), m (multiplet), or br (broad). Low-resolution mass spectra were measured by HP Hewlett Packard 1100 series.

Example 1: Synthesis of Compounds with Carbocyclic Core

The following schemes were followed for synthesizing the compounds of formula I containing carbocyclic core.

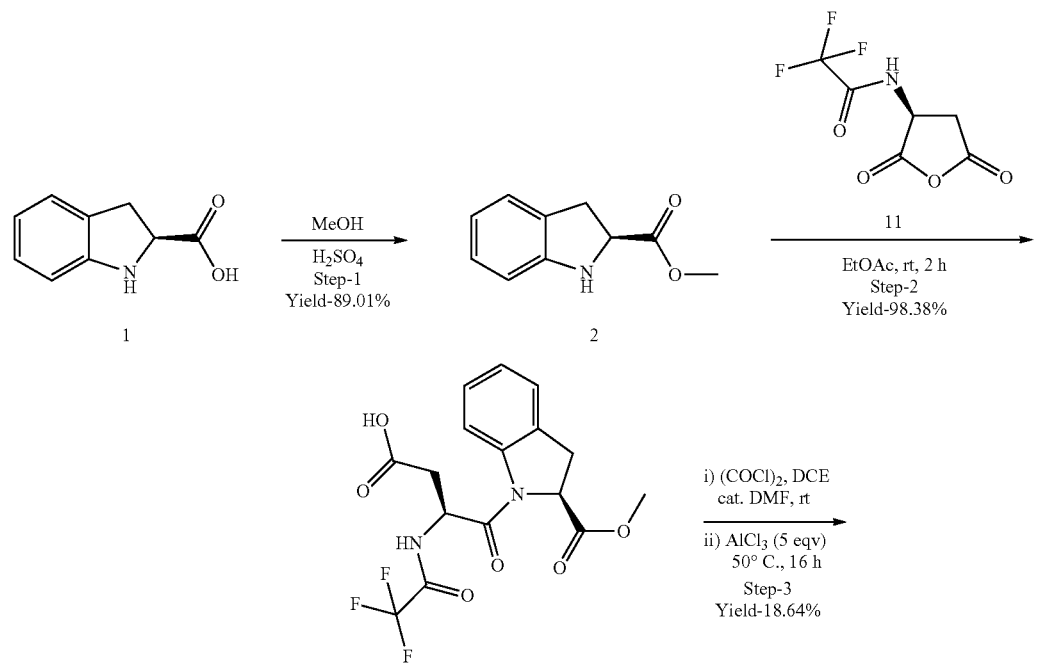

-continued

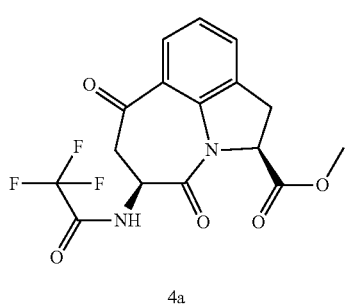

4a
reported SOR = (−)202.18
(DMSO, C = 0.67)

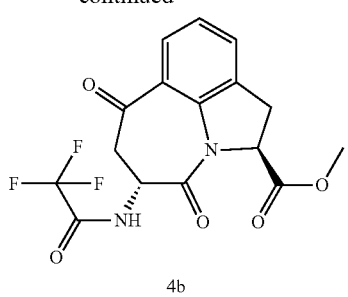

4b
reported SOR = (+)5.31
(DMSO, C = 0.9)
(slower eluting fraction)

Separation via NP column chromatography

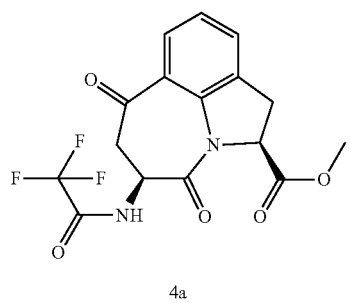

4a
reported SOR = (−)202.18
(DMSO, C = 0.67)
(faster eluting fraction)

H$_2$ (50 psi), Pd—C
AcOH, rt, 16 h
Step-4
Yield-99.85%

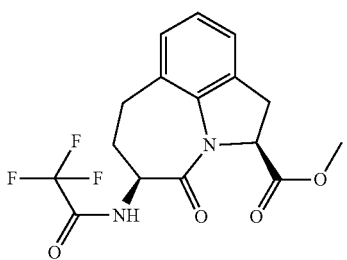

5
reported SOR = (−)124.07
(CHCl$_3$, C = 0.92)

i) aq. 1M LiOH
THF—H$_2$O, rt, 2 h
ii) H$^+$
Step-5

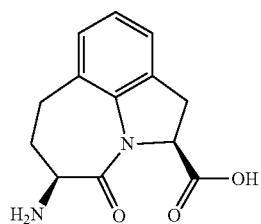

6

Boc$_2$O
NaHCO$_3$, H$_2$O
Step-6
Yield-98.68%

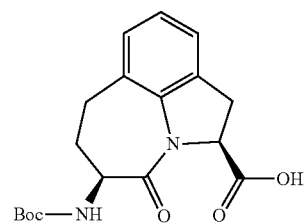

7

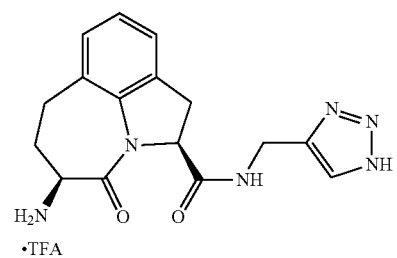

14

EDCl·HCl, HOBT,
DIPEA, DMF, rt 16 h
Step-7

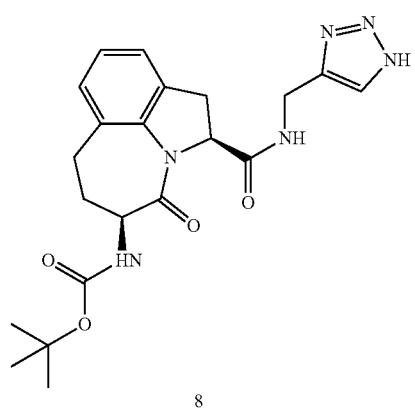

8

TFA, DCM
Step-8

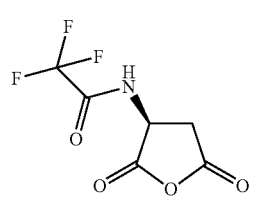

Central scaffold

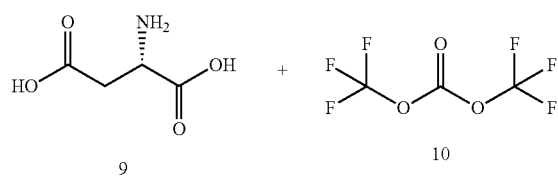

9 + 10

TFA
−10° C.
Step-9
Yield-94.58%

11

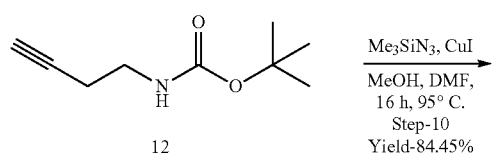 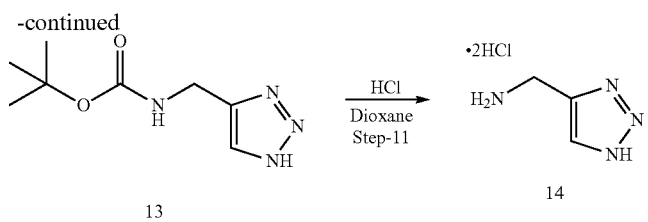

General remarks: Friedel Craft cyclization [step-4] is moisture sensitive and acid chloride preparation followed by addition of AlCl₃ should perform cautiously under argon atmosphere. SOR values are reported for initial intermediates and cross-checked. During isolation of compound 7, adjustment of pH should be done under cooling condition to avoid possibility of N-boc de-protection under acidic condition.

Experimentals

Synthesis of (S)-2,3-Dihydro-1H-indole-2-carboxylic acid methyl ester [Scheme 1, Step-1]: To a suspension of 1 (30.0 g, 184 mmol) in MeOH (300 mL) was added sulfuric acid (22.5 mL) drop wise at room temperature. After addition, resultant mixture was allowed to stir at 80° C. for 16 h. After completion, solvent was removed under vacuum and residue was neutralized with 15% aqueous NaOH solution. Then reaction mixture was extracted with EtOAc (2×150 mL). Combined organic part was further washed with 1N aqueous NaOH, brine (100 mL), dried (MgSO₄), filtered and evaporated under reduced pressure to afford compound 2 (29 g, 89%) as light brown gummy liquid. ¹H NMR complies.

Synthesis of (S)-1-[(S)-3-Carboxy-2-(2,2,2-trifluoro-acetylamino)-propionyl]-2,3-dihydro-1H-indole-2-carboxylic acid methyl ester [Scheme 1, Step-2]: To a clear solution of 2 (25.00 g, 130.9 mmol) in ethyl acetate [1.2 L] was added 11 (30.38 g, 144.0 mmol) at 0-5° C. and the resultant reaction mixture was stirred at room temperature for 2 h. After completion [monitored by LC-MS] reaction mixture was concentrated under reduced pressure and resultant crude was subjected for column chromatography under gradient elution of 10-25% EtOAc/hexane. The eluent was concentrated and azeotroped with toluene to afford compound 3 (50.0 g, 98.4%) as off white floppy solid. Mass [ESI]: m/z 388.3 [M⁺+1].

Synthesis of (2S,5S)-4,7-Dioxo-5-(2,2,2-trifluoro-acetylamino)-1,2,4,5,6,7-hexahydro-azepino[3,2,1-hi]indole-2-carboxylic acid methyl ester [Scheme 1, Step-3]: To a stirred solution of 3 [10.0 g, 25.8 mmol] in DCE [120 mL, freshly distilled] was added oxalyl chloride [8.85 mL, 103 mmol] drop wise followed by addition of catalytic amount of DMF and the resultant reaction mixture was allowed to stir at room temperature for 2 h. After completion [monitored by TLC, quenching with MeOH], reaction mixture was concentrated under reduced pressure. Crude acid chloride thus obtained was diluted with DCE [250 mL] followed by drop wise addition of AlCl₃ [16.40 g, 116.2 mmol] maintaining external temperature at 0-5° C. After addition, reaction mixture was allowed to stir at 50° C. for 16 h. After completion [monitored with TLC, 40% EtOAc/hexane, R_f 0.5], reaction mixture was quenched with water and extracted with DCM. Organic layer was further washed with saturated sodium bicarbonate solution and brine solution. Then organic part was dried (MgSO₄) and concentrated under reduced pressure. Resultant crude was purified by column chromatography (20-50% EtOAc/hexane, SiO₂) to afford desired compound 4a [1.70 g, 18.6%, non polar compound] as white solid and 2.5 g undesired isomer 4b [polar compound]. Mass [ESI]: m/z 370.28 [M⁺+1].

Synthesis of (2S,5S)-4-Oxo-5-(2,2,2-trifluoro-acetylamino)-1,2,4,5,6,7-hexahydro-azepino[3,2,1-hi]indole-2-carboxylic acid methyl ester [Scheme 1, Step-4]: To a solution of 4a [5.20 g, 14.1 mmol] in AcOH [300 mL] was added Pd—C [5 g, 50% wet] and resultant suspension was subjected to hydrogenation in parr shaker under 50 psi H₂ pressure for 16 h. After completion [30% EtOAc/hexane, R_f 0.5], reaction mixture was concentrated under reduced pressure, resultant crude was diluted with EtOAc and washed with saturated sodium bicarbonate solution. Organic layer was separated, dried (MgSO₄) and concentrated under reduced pressure to afford compound 5 (5.0 g, 99.8%) as off white solid. Mass [ESI]: m/z 356.3 [M⁺−1].

Synthesis of (2S, 5S)-5-tert-Butoxycarbonylamino-4-oxo-1,2,4,5,6,7-hexahydro-azepino[3,2,1-hi]indole-2-carboxylic acid [Scheme 1, Step-5 & 6]: Compound 5 [5.00 g, 14.0 mmol] was dissolved in THF [140 mL] and solution of LiOH [3.54 g, 84.3 mmol] in water [70 mL] was added to it, then reaction mixture was allowed to stir at room temperature for 2 h. After completion reaction mixture was concentrated under reduced pressure and residue was acidified with 1N aqueous HCl up to pH ~5. Then sodium carbonate [4.46 g, 42.1 mmol] was added to the reaction mixture and stirred for 5 min followed by addition of solution of Boc-anhydride [3.87 mL, 42.1 mmol] in dioxane [100 mL] and stirring was continued for 2 h. After completion [monitored by LC-MS] reaction mixture was concentrated under reduced pressure, resultant crude was diluted with water and pH of the reaction mixture was carefully adjusted to ~3 using 1N aqueous HCl solution under ice cold condition [external temperature should not >5-7° C.]. Reaction mixture was immediately extracted with EtOAc, organic part was further washed with water, brine, organic part was dried (MgSO₄) and concentrated under reduced pressure to afford desired compound 7 (4.8 g, 98.6%) as brown solid. Mass [ESI]: m/z 346.38 [M⁺+1].

Synthesis of [(2S,5S)-4-Oxo-2-[(1H-[1,2,3]triazol-4-ylmethyl)-carbamoyl]-1,2,4,5,6,7-hexahydro-azepino[3,2,1-hi] indol-5-yl}-carbamic acid tert-butyl ester [Scheme 1, Step-7]: To a stirred solution of compound 7 (4.65 g, 13.4 mmol) in DMF (20 mL) were added compound 14 (3.60 g, 26.90 mmol), hunig's base (12.04 mL, 67.19 mmol) at room temperature. Finally EDC.HCl (3.94 g, 20.6 mmol) and HOBT (2.36 g, 17.5 mmol) were added in one portion at ice cold condition and the reaction mixture was stirred for 16 h at room temperature. After completion [monitored by LC-MS] reaction mixture was diluted with ethyl acetate and washed with excess water. Organic layer was then washed with saturated aqueous solution of Na₂CO₃ (50 mL) and brine. Organic part was dried (MgSO₄) and concentrated to get crude material. The crude was purified through column chromatography (30-60% EtOAc/hexane, SiO2) to provide compound 8 (3.21 g, 55.8%) as white solid. Mass [ESI]: m/z 426.46 [M⁺+1].

Synthesis of (2S,5S)-5-Amino-4-oxo-1,2,4,5,6,7-hexahydro-azepino[3,2,1-hi]indole-2-carboxylic acid (1H-[1,2,3]triazol-4-ylmethyl)-amide[Scheme 1, Step-8]: To a stirred solution of compound 8 (3.21 g, 3.28 mmol) in DCM (4 mL) was added 50% TFA in DCM (10 mL) and the resultant reaction mixture was allowed to stir for 2 h at room temperature. After completion [monitored by LC-MS] reaction mixture was evaporated to dryness to provide crude central scaffold (1.6 g) as yellow semi solid. Mass [ESI]: m/z 326.35 [M⁺+1].

Synthesis of N—((S)-2,5-Dioxo-tetrahydro-furan-3-yl)-2,2,2-trifluoro-acetamide [Scheme 1, Step-9]: To a suspension of 9 (10.0 g, 75.1 mmol) in TFA (30 mL) was added TFAA [10] [29.45 mL, 210.4 mmol" ] maintaining the external temperature below −10° C. After addition reaction mixture was left to stir vigorously for half an hour under cold condition. Then reaction mixture was allowed to stir at 45° C. for 2 h. Finally reaction mixture was brought to room temperature and allowed to stir for 16 h. After completion reaction mixture was diluted with acetone and concentrated under reduced pressure. Resultant solid was triturated with hexane to afford compound 11 (15 g, 95%) as white solid. ¹H NMR complies.

Synthesis of (1H-[1,2,3]Triazol-4-ylmethyl)-carbamic acid tert-butyl ester [Scheme-1, Step-10]: To a stirred solution of 12 [5.00 g, 32.3 mmol] in DMF:MeOH [90:10 mL] was added trimethylsilyl azide [5.56 mL, 48.4 mmol] followed by addition of CuI [0.31 g, 1.61 mmol] and the resultant reaction mixture was allowed to stir at 95° C. in a sealed tube for 12 h. After completion reaction mixture was partitioned between EtOAc and water, organic layer was separated, dried (MgSO₄) and concentrated under reduced pressure. Resultant crude residue was diluted with DCM, insoluble part was filtered through glass sintered and filtrate was concentrated under reduced pressure to afford compound 13 (5.4 g, 84%) as yellow sticky liquid. ¹H NMR complies.

Synthesis of C-(1H-[1,2,3]Triazol-4-yl)-methylamine [Scheme-1, Step-11]: Solution of 13 [8.00 g, 40.4 mmol] in 4 (M) HCl in dioxane [120 mL] was allowed to stir at room temperature for 2 h. After completion [monitored by LC-MS], reaction mixture was concentrated under reduced pressure and resultant crude was triturated with hexane to afford crude compound 14 (5.35 g) as off white solid [HCl salt]. Mass [ESI]: m/z 98.11 [M⁺+1].

Scheme-2

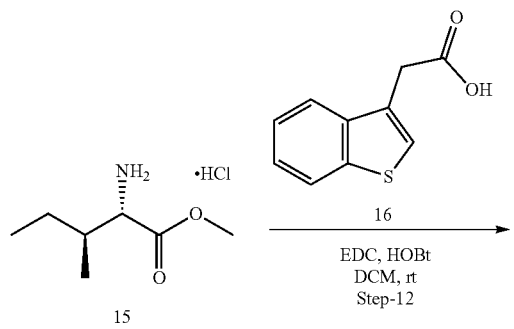

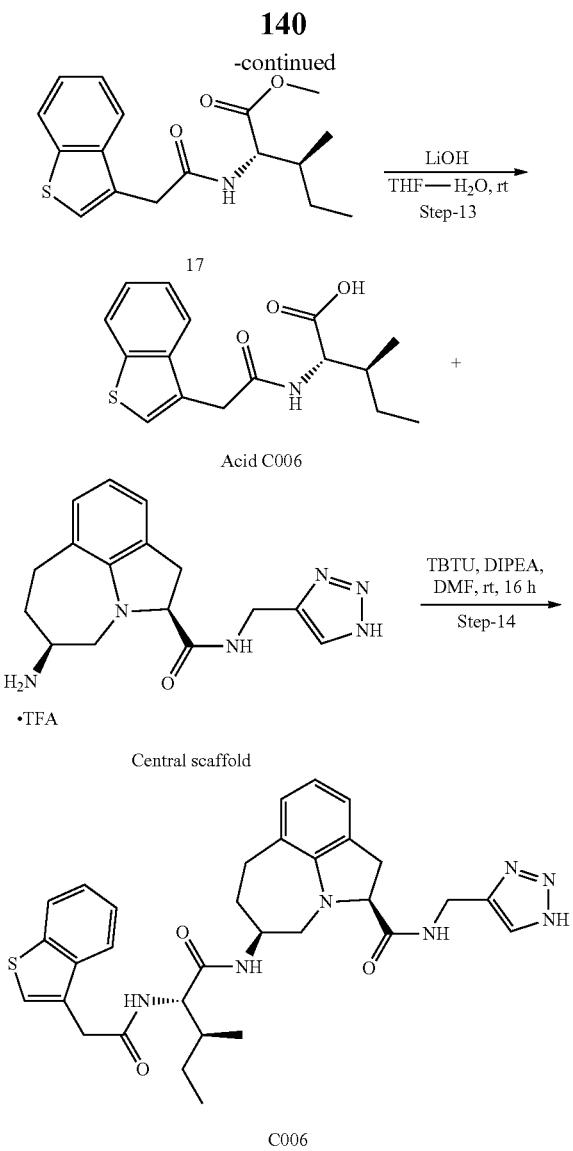

General remarks: All final compounds were purified by RP preparative HPLC, however, yield of final steps are very low because of poor solubility and separation of isomers were also difficult in RP.

Synthesis of (2S,3S)-2-(2-Benzo[b]thiophen-3-yl-acetylamino)-3-methyl-pentanoic acid methyl ester [Scheme 2, Step-12]: To a stirred solution of compound 16 (0.50 g, 2.60 mmol) in DCM (5 mL) was added compound 15 (0.52 g, 2.86 mmol), EDC.HCl (0.65 g, 3.38 mmol), HOBT (0.53 g, 3.90 mmol), DIPEA (2.4 mL, 13 mmol) and the reaction mixture was stirred for 16 h at room temperature. After completion [monitored by LC-MS and TLC (30% EtOAc-Hexane, R$_f$-0.3)] reaction mixture was partitioned between DCM (50 mL) and water (30 mL). Organic layer was separated, dried over sodium sulphate and concentrated under reduced pressure. The crude was purified through chromatography (0-20% EtOAc/Hexane, SiO₂) to provide compound 17 (490 mg, Yield: 55.8%) as white solid. Mass [ESI]: m/z 557.64 [M⁺+1].

Synthesis of (2S,3S)-2-(2-Benzo[b]thiophen-3-yl-acetylamino)-3-methyl-pentanoic acid [Scheme 2, Step-13]: To a stirred solution of compound 3 (490 mg, 1.53 mmol) in THF (5 mL):water (1 mL) was added LiOH·H₂O (90.0 mg, 2.29 mmol) under ice cold condition and the resultant reaction mixture was allowed to stir at room temperature for 3 h. After completion [monitored with LC-MS] reaction mixture was concentrated, resultant crude was diluted with water [50 mL] and washed with EtOAc [50 mL]. Aqueous layer was separated and acidified with 1(N) aqueous HCl up to pH 2-3 and extracted with EtOAc [50 mL×2]. Combined organic layer was washed with brine [30 mL], dried over sodium sulphate and concentrated under reduced pressure to afford Acid C006 (390 mg, Yield: quantitative]. Mass [ESI]: m/z 557.64 [M$^+$+1].

Synthesis of (2S,5S)-5-{(2S,3S)-2-[(Benzo[b]thiophen-3-ylmethyl)-amino]-3-methyl-pentanoylamino}-4-oxo-1,2,4,5,6,7-hexahydro-azepino[3,2,1-hi]indole-2-carboxylic acid (1H-[1,2,3]triazol-4-ylmethyl)-amide [Scheme 2, Step-14]: To a stirred solution of Acid A (224 mg, 0.73 mmol) and central scaffold (200 mg, 0.61 mmol) in DMF (5 mL) was added DIPEA (0.5 mL, 3.06 mmol), followed by the addition of TBTU (295 mg, 0.68 mmol) and reaction mixture was allowed to stir at room temperature for 16 h. On completion of the reaction (confirmed by LCMS), crude reaction mixture was submitted for reverse phase prep HPLC purification to afford two isomers [faster moving isomer 28 mg and slower moving isomer 5 mg] and the faster moving isomer was biologically potent i.e desired C006 (29 mg) as off white solid. Mass [ESI]: m/z 613.74 [M$^+$+1]

General condition for amidation the Final amidation: The below mentioned compounds were synthesized following the same condition as for C006.

(2S, 5S)-5-[2-(2-Benzo[b] thiophen-3-yl-acetylamino)-acetylamino]-4-oxo-1,2,4,5,6,7-hexahydro-azepino[3,2,1-hi]indole-2-carboxylic acid (1H-[1,2,3]triazol-4-ylmethyl)-amide [C001]: This compound was synthesized following same protocol as for C006. After completion reaction mixture was diluted with cold water [50 mL], resultant light brown precipitate was filtered through glass sintered. Solid was further triturated with pentane and dried under vacuum to afford C001 [15 mg, 11.85%] as off white solid. Mass [ESI]: m/z 557.64 [M$^+$+1].

(2S,5S)-5-[(S)-2-(2-Benzo[b]thiophen-3-yl-acetylamino)-propionylamino]-4-oxo-1,2,4,5,6,7-hexahydro-azepino[3,2,1-hi]indole-2-carboxylic acid(1H-[1,2,3]triazol-4-ylmethyl)-amide [C002]: This compound was synthesized following same protocol as for C006. Prep HPLC purification provided 16 mg of faster eluting as well as major isomer of C002 as white solid. Mass [ESI]: m/z 571.66 [M$^+$+1].

(2S,5S)-5-[(S)-2-(2-Benzo[b]thiophen-3-yl-acetylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide [C003]: This compound was synthesized following same protocol as for C006. Prep HPLC purification provided 5 mg of faster eluting as well as major isomer of C003 as white solid, 0.08 mg of slower eluting isomer was also isolated. Mass [ESI]: m/z 599.72 [M$^+$+1].

(2S,5S)-5-[(S)-2-(2-Benzo[b]thiophen-3-yl-acetylamino)-3-phenyl-propionylamino]-4-oxo-1,2,4,5,6,7-hexahydro-azepino[3,2,1-hi]indole-2-carboxylic acid (1H-[1,2,3]triazol-4-ylmethyl)-amide [C004]: This compound was synthesized following same protocol as for C006. Prep HPLC purification provided 12 mg of faster eluting as well as major isomer of C004 as off white solid. Mass [ESI]: m/z 647.76[M$^+$+1].

(2S,5S)-5-[(S)-2-(2-Benzo[b]thiophen-3-yl-acetylamino)-4-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide [C005]: This compound was synthesized following same protocol as for C006. Prep HPLC purification provided 12 mg of faster eluting as well as major isomer [Isomer1] of C005 as white solid and 2.5 mg of slower eluting isomer [Isomer2] of C005. Mass [ESI]: m/z 613.74[M$^+$+1].

(2S, 5S)-5-[(S)-2-(2-Benzo[b]thiophen-3-yl-acetylamino)-3-hydroxy-propionylamino]-4-oxo-1,2,4,5,6,7-hexahydro-azepino[3,2,1-hi]indole-2-carboxylic acid (1H-[1,2,3]triazol-4-ylmethyl)-amide [C007]: This compound was synthesized following same protocol as for C006. Prep HPLC purification provided 1 mg of faster eluting isomer [Isomer1] of C007 as white solid and 19 mg of slower eluting isomer [Isomer2] of C007. Mass [ESI]: m/z 587.66 [M$^+$+1].

(2S,5S)-5-[(S)-2-(2-Benzo[b]thiophen-3-yl-acetylamino)-2-phenyl-acetylamino]-4-oxo-1,2,4,5,6,7-hexahydro-azepino[3,2,1-hi]indole-2-carboxylic acid (1H-[1,2,3]triazol-4-ylmethyl)-amide [C009]: This compound was synthesized following same protocol as for C006. Prep HPLC purification provided 14 mg of faster eluting isomer [Isomer1] of C009 as white solid. Mass [ESI]: m/z 633.73 [M$^+$+1].

(2S,5S)-5-[(S)-2-(2-Benzo[b]thiophen-3-yl-acetylamino)-3-(4-hydroxy-phenyl)-propionylamino]-4-oxo-1,2,4,5,6,7-hexahydro-azepino[3,2,1-hi]indole-2-carboxylic acid (1H-[1,2,3]triazol-4-ylmethyl)-amide [C010]: This compound was synthesized following same protocol as for C006. Prep HPLC purification provided 33.4 mg of faster eluting isomer [Isomer1] of C010 as light yellow solid. Mass [ESI]: m/z 663.76[M$^+$+1].

(2S, 5S)-5-[(S)-2-(2-Benzo[b]thiophen-3-yl-acetylamino)-3-(4-fluoro-phenyl)-propionylamino]-4-oxo-1,2,4,5,6,7-hexahydro-azepino[3,2,1-hi]indole-2-carboxylic acid (1H-[1,2,3]triazol-4-ylmethyl)-amide [C011]: This compound was synthesized following same protocol as for C006. Prep HPLC purification provided 15 mg of faster eluting isomer [Isomer1] of C011 as white solid. Mass [ESI]: m/z 665.75[M$^+$+1].

(2S,5S)-4-Oxo-S-(2-phenylacetylamino-acetylamino)-1,2,4,5,6,7-hexahydro-azepino[3,2,1-hi]indole-2-carboxylic acid (1H-[1,2,3]triazol-4-ylmethyl)-amide [C012]: This compound was synthesized following same protocol as for C006. Prep HPLC purification provided 40 mg of C012 as white solid. Mass [ESI]: m/z 501.55[M$^+$+1].

(2S, 5S)-4-Oxo-5-((S)-2-phenylacetylamino-propionylamino)-1,2,4,5,6,7-hexahydro-azepino[3,2,1-hi]indole-2-carboxylic acid (1H-[1,2,3]triazol-4-ylmethyl)-amide [C013]: This compound was synthesized following same protocol as for C006. Prep HPLC purification provided 21 mg of faster eluting isomer [Isomer1] of C013 as white solid. Mass [ESI]: m/z 515.58[M$^+$+1].

(2S, 5S)-5-((S)-3-Methyl-2-phenylacetylamino-butyrylamino)-4-oxo-1,2,4,5,6,7-hexahydro-azepino[3,2,1-hi]indole-2-carboxylic acid (1H-[1,2,3]triazol-4-ylmethyl)-amide [C014]: This compound was synthesized following same protocol as for C006. Prep HPLC purification provided 7.7 mg of faster eluting isomer [Isomer1] of C014 as white solid and 5.7 mg of slower eluting isomer [Isomer2] of C014 as white solid. Mass [ESI]: m/z 543.63[M$^+$+1].

(2S, 5S)-4-Oxo-5-((S)-3-phenyl-2-phenylacetylamino-propionylamino)-1,2,4,5,6,7-hexahydro-azepino [3,2,1-hi] indole-2-carboxylic acid (1H-[1,2,3]triazol-4-ylmethyl)-amide [C015]: This compound was synthesized following same protocol as for C006. Prep HPLC purification provided 30 mg of faster eluting isomer [Isomer1] of C015 as white solid. Mass [ESI]: m/z 591.68[M$^+$+1].

(2S, 5S)-5-((S)-4-Methyl-2-phenylacetylamino-pentanoylamino)-4-oxo-1,2,4,5,6,7-hexahydro-azepino[3,2,1-hi]indole-2-carboxylic acid (1H-[1,2,3]triazol-4-ylmethyl)-amide [C016]: This compound was synthesized following same protocol as for C006. Prep HPLC purification provided 10.9 mg of faster eluting isomer [Isomer1] of C016 as white solid. Mass [ESI]: m/z 557.66[M$^+$+1].

(2S, 5S)-5-((2S,3S)-3-Methyl-2-phenylacetylamino-pentanoylamino)-4-oxo-1,2,4,5,6,7-hexahydro-azepino[3,2,1-hi]indole-2-carboxylic acid (1H-[1,2,3]triazol-4-ylmethyl)-amide [C017]: This compound was synthesized following same protocol as for C006. Prep HPLC purification provided 5.3 mg of faster eluting isomer [Isomer1] of C017 as white solid. Mass [ESI]: m/z 557.66[M$^+$+1].

(2S, 5 S)-5-((S)-3-Hydroxy-2-phenylacetylamino-propionylamino)-4-oxo-1,2,4,5,6,7-hexahydro-azepino[3,2,1-hi]indole-2-carboxylic acid (1H-[1,2,3]triazol-4-ylmethyl)-amide [C018]: This compound was synthesized following same protocol as for C006. Prep HPLC purification provided 14 mg of slower eluting isomer [Isomer 2] of C018 as white solid. Mass [ESI]: m/z 531.58[M$^+$+1].

(2S,5S)-4-Oxo-5-((S)-2-phenyl-2-phenylacetylamino-acetylamino)-1,2,4,5,6,7-hexahydro-azepino[3,2,1-hi]indole-2-carboxylic acid (1H-[1,2,3]triazol-4-ylmethyl)-amide [C020]: This compound was synthesized following same protocol as for C006. Prep HPLC purification provided 14 mg of faster eluting isomer [Isomer 1] of C020 as white solid. Mass [ESI]: m/z 577.65[M$^+$+1].

(2S,5S)-4-Oxo-5-((S)-2-phenyl-2-phenylacetylamino-acetylamino)-1,2,4,5,6,7-hexahydro-azepino[3,2,1-hi]indole-2-carboxylic acid (1H-[1,2,3]triazol-4-ylmethyl)-amide [C021]: This compound was synthesized following same protocol as for C006. Prep HPLC purification provided 20 mg of faster eluting isomer [Isomer 1] of C021 as white solid. Mass [ESI]: m/z 607.67[M$^+$+1].

(2S,5S)-5-[(S)-3-(4-Fluoro-phenyl)-2-phenylacetylamino-propionylamino]-4-oxo-1,2,4,5,6,7-hexahydro-azepino[3,2,1-hi]indole-2-carboxylic acid(1H-[1,2,3]triazol-4-ylmethyl)-amide [C022]: This compound was synthesized following same protocol as for C006. Prep HPLC purification provided 36 mg of faster eluting isomer [Isomer 1] of C022 as white solid. Mass [ESI]: m/z 609.67[M$^+$+1].

(2S,5S)-5-(2-Acetylamino-acetylamino)-4-oxo-1,2,4,5,6,7-hexahydro-azepino[3,2,1-hi]indole-2-carboxylic acid (1H-[1,2,3]triazol-4-ylmethyl)-amide [C023]: This compound was synthesized following same protocol as for C006. Prep HPLC purification provided 35 mg of C023 as white solid. Mass [ESI]: m/z 425.45[M$^+$+1].

(2S, 5 S)-5-((S)-2-Acetylamino-propionylamino)-4-oxo-1,2,4,5,6,7-hexahydro-azepino[3,2,1-hi]indole-2-carboxylic acid (1H-[1,2,3]triazol-4-ylmethyl)-amide [C024]: This compound was synthesized following same protocol as for C006. Preparative HPLC purification provided 14.2 mg of faster eluting isomer [Isomer 1] of C024 as white solid and 1.2 mg of slower eluting isomer [Isomer2] of C024. Mass [ESI]: m/z 439.48 [M$^+$+1].

(2S,5S)-5-((S)-2-Acetylamino-3-methyl-butyrylamino)-4-oxo-1,2,4,5,6,7-hexahydro-azepino[3,2,1-hi]indole-2-carboxylic acid (1H-[1,2,3]triazol-4-ylmethyl)-amide [C025]: This compound was synthesized following same protocol as for C006. Preparative HPLC purification provided 21 mg of faster eluting isomer [Isomer 1] of C025 Mass [ESI]: m/z 467.53 [M$^+$+1].

(2S,5S)-5-((S)-2-Acetylamino-3-phenyl-propionylamino)-4-oxo-1,2,4,5,6,7-hexahydro-azepino[3,2,1-hi]indole-2-carboxylic acid (1H-[1,2,3]triazol-4-ylmethyl)-amide [C026]: This compound was synthesized following same protocol as for C006. Preparative HPLC purification provided 21 mg of faster eluting isomer [Isomer 1] of C026 as white solid. Mass [ESI]: m/z 515.58[M$^+$+1].

(2S,5S)-5-((S)-2-Acetylamino-4-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide [C027]: This compound was synthesized following same protocol as for C006. Preparative HPLC purification provided 7.4 mg of faster eluting isomer [Isomer 1] of C027 as white solid. Mass [ESI]: m/z 481.56[M$^+$+1].

(2S, 5S)-5-((S)-2-Acetylamino-3-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide [C028]: This compound was synthesized following same protocol as for C006. Preparative HPLC purification provided 18.5 mg of faster eluting isomer [Isomer 1] of C028 as white solid. Mass [ESI]: m/z 481.56[M$^+$+1].

(2S,5S)-5-((S)-2-Acetylamino-3-hydroxy-propionylamino)-4-oxo-1,2,4,5,6,7-hexahydro-azepino[3,2,1-hi]indole-2-carboxylic acid (1H-[1,2,3]triazol-4-ylmethyl)-amide [C029]: This compound was synthesized following same protocol as for C006. Preparative HPLC purification provided 14 mg of slower eluting isomer [Isomer 2] of C029 as white solid. Mass [ESI]: m/z 455.48[M$^+$+1].

(2S,5S)-5-((S)-2-Acetylamino-2-phenyl-acetylamino)-4-oxo-1,2,4,5,6,7-hexahydro-azepino[3,2,1-hi]indole-2-carboxylic acid (1H-[1,2,3]triazol-4-ylmethyl)-amide [C031]: This compound was synthesized following same protocol as for C006. Prep HPLC purification provided 1.3 mg of faster eluting as well as major isomer of C031 as white solid. Mass [ESI]: m/z 501.55[M$^+$+1].

(2S,5S)-5-[(S)-2-Acetylamino-3-(4-hydroxy-phenyl)-propionylamino]-4-oxo-1,2,4,5,6,7-hexahydro-azepino[3,2,1-hi]indole-2-carboxylic acid (1H-[1,2,3]triazol-4-ylmethyl)-amide [C032]: This compound was synthesized following same protocol as for C006. Prep HPLC purification provided 3.2 mg of faster eluting as well as major isomer of C032 as white solid. Mass [ESI]: m/z 531.58[M$^+$+1].

(2S,5S)-5-[(S)-2-Acetylamino-3-(4-fluoro-phenyl)-propionylamino]-4-oxo-1,2,4,5,6,7-hexahydro-azepino[3,2,1-hi]indole-2-carboxylic acid (1H-[1,2,3]triazol-4-ylmethyl)-amide [C033]: This compound was synthesized following same protocol as for C006. Prep HPLC purification provided 10 mg of faster eluting as well as major isomer of C033 as white solid. Mass [ESI]: m/z 533.57[M$^+$+1].

(2S,5S)-5-(2-Benzoylamino-acetylamino)-4-oxo-1,2,4,5,6,7-hexahydro-azepino[3,2,1-hi]indole-2-carboxylic acid (1H-[1,2,3]triazol-4-ylmethyl)-amide [C034]: This compound was synthesized following same protocol as for C006. Prep HPLC purification provided 10 mg of C034 as white solid. Mass [ESI]: m/z 487.52[M$^+$+1].

(2S,5S)-5-((S)-2-Benzoylamino-propionylamino)-4-oxo-1,2,4,5,6,7-hexahydro-azepino[3,2,1-hi]indole-2-carboxylic acid (1H-[1,2,3]triazol-4-ylmethyl)-amide [C035]: This compound was synthesized following same protocol as for C006. Prep HPLC purification provided 9.6 mg of faster eluting as well as major isomer of C035 as white solid. Mass [ESI]: m/z 501.55[M$^+$+1].

(2S,5S)-5-((S)-2-Benzoylamino-3-methyl-butyrylamino)-4-oxo-1,2,4,5,6,7-hexahydro-azepino[3,2,1-hi]indole-2-carboxylic acid (1H-[1,2,3]triazol-4-ylmethyl)-amide [C036]: This compound was synthesized following same protocol as for C006. Prep HPLC purification provided 15 mg of faster eluting as well as major isomer [Isomer1] of C036 as white solid and 8 mg of slower eluting isomer [Isomer2] of C036. Mass [ESI]: m/z 529.60 [M$^+$+1].

(2S,5S)-5-((S)-2-Benzoylamino-3-phenyl-propionylamino)-4-oxo-1,2,4,5,6,7-hexahydro-azepino[3,2,1-hi]indole-2-carboxylic acid (1H-[1,2,3]triazol-4-ylmethyl)-amide [C037]: This compound was synthesized following same protocol as for C006. Prep HPLC purification provided 22.1 mg of faster eluting as well as major isomer [Isomer1] of C037 as white solid and 1.1 mg of slower eluting isomer [Isomer2] of C037. Mass [ESI]: m/z 577.65 [M$^+$+1].

(2S,5S)-5-((S)-2-Benzoylamino-4-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide [C038]: This compound was synthesized following same protocol as for C006. Prep HPLC purification provided 10 mg of faster eluting as well as major isomer of C038 as white solid. Mass [ESI]: m/z 543.63[M$^+$+1].

(2S,5S)-5-((S)-2-Benzoylamino-3-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide [C039]: This compound was synthesized following same protocol as for C006. Prep HPLC purification provided 15 mg of faster eluting as well as major isomer [Isomer1] of C039 as white solid and 13 mg of slower eluting isomer [Isomer2] of C039. Mass [ESI]: m/z 577.65 [M$^+$+1].

(2S,5S)-5-((S)-2-Benzoylamino-3-hydroxy-propionylamino)-4-oxo-1,2,4,5,6,7-hexahydro-azepino[3,2,1-hi]indole-2-carboxylic acid (1H-[1,2,3]triazol-4-ylmethyl)-amide [C040]: This compound was synthesized following same protocol as for C006. Prep HPLC purification provided 13 mg of slower eluting isomer of C040. Mass [ESI]: m/z 517.55 [M$^+$+1].

(2S,5S)-5-[(S)-2-Benzoylamino-3-(4-hydroxy-phenyl)-propionylamino]-4-oxo-1,2,4,5,6,7-hexahydro-azepino[3,2,1-hi]indole-2-carboxylic acid (1H-[1,2,3]triazol-4-ylmethyl)-amide [C042]: This compound was synthesized following same protocol as for C006. Prep HPLC purification provided 40 mg of faster eluting as well as major isomer of C042 as white solid. Mass [ESI]: m/z 593.65[M$^+$+1].

(2S,5S)-5-[(S)-2-Benzoylamino-3-(4-fluoro-phenyl)-propionylamino]-4-oxo-1,2,4,5,6,7-hexahydro-azepino[3,2,1-hi]indole-2-carboxylic acid (1H-[1,2,3]triazol-4-ylmethyl)-amide [C043]: This compound was synthesized following same protocol as for C006. Prep HPLC purification provided 15 mg of faster eluting as well as major isomer of C043 as white solid. Mass [ESI]: m/z 595.64[M$^+$+1].

(2S,5S)-5-(2-Methyl-2-phenylacetylamino-propionylamino)-4-oxo-1,2,4,5,6,7-hexahydro-azepino[3,2,1-hi]indole-2-carboxylic acid (1H-[1,2,3]triazol-4-ylmethyl)-amide [C044]: This compound was synthesized following same protocol as for C006. Prep HPLC purification provided 30 mg of C044 as white solid. Mass [ESI]: m/z 529.60[M$^+$+1].

(2S,5S)-5-((S)-2-Benzoylamino-butyrylamino)-4-oxo-1,2,4,5,6,7-hexahydro-azepino[3,2,1-hi]indole-2-carboxylic acid (1H-[1,2,3]triazol-4-ylmethyl)-amide [C045]: This compound was synthesized following same protocol as for C006. Prep HPLC purification provided 11 mg of faster eluting as well as major isomer [Isomer1] of C045 as white solid and 4 mg of slower eluting isomer [Isomer2] of C045. Mass [ESI]: m/z 515.58[M$^+$+1].

(2S,5S)-5-((S)-2-Benzoylamino-3,3-dimethyl-butyrylamino)-4-oxo-1,2,4,5,6,7-hexahydro-azepino[3,2,1-hi]indole-2-carboxylic acid (1H-[1,2,3]triazol-4-ylmethyl)-amide [C046]: To a stirred solution of Acid C046 (80.1 mg, 0.341 mmol) and central scaffold (150 mg, 0.341 mmol) in DMF (2 mL) was added DIPEA (0.237 mL, 1.36 mmol), followed by the addition of PyBOP (266 mg, 0.511 mmol) and reaction mixture was allowed to stir at room temperature for 16 h. On completion of the reaction (confirmed by LCMS), crude reaction mixture was submitted for reverse phase prep HPLC purification to afford 10 mg of faster eluting as well as major isomer of C046 as white solid. Mass [ESI]: m/z 543.63[M$^+$+1].

(2S,5S)-5-[(S)-2-(4-Fluoro-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide [C047]: This compound was synthesized following same protocol as for C006. Prep HPLC purification provided 3.1 mg of faster eluting as well as major isomer of C047 as white solid. Mass [ESI]: m/z 547.59[M$^+$+1].

(2S,5S)-5-[(S)-2-(3-Fluoro-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide [C048]: This compound was synthesized following same protocol as for C006. Prep HPLC purification provided 16.5 mg of faster eluting as well as major isomer [Isomer1] of C048 as white solid and 5 mg of slower eluting isomer [Isomer2] of C048. Mass [ESI]: m/z 547.59[M$^+$+1].

(2S,5S)-5-[(S)-2-(2-Fluoro-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide [C049]: This compound was synthesized following same protocol as for C006. Prep HPLC purification provided 6.1 mg of faster eluting as well as major isomer of C049 as white solid. Mass [ESI]: m/z 547.59[M$^+$+1].

(2S,5S)-5-[(S)-3-Methyl-2-(2-methyl-benzoylamino)-butyrylamino]-4-oxo-1,2,4,5,6,7-hexahydro-azepino[3,2,1-hi]indole-2-carboxylic acid (1H-[1,2,3]triazol-4-ylmethyl)-amide [C050]: This compound was synthesized following same protocol as for C006. Prep HPLC purification provided 4.3 mg of faster eluting as well as major isomer of C050 as white solid. Mass [ESI]: m/z 543.63[M$^+$+1].

(2S,5S)-5-[(S)-3-Methyl-2-(3-methyl-benzoylamino)-butyrylamino]-4-oxo-1,2,4,5,6,7-hexahydro-azepino[3,2,1-hi]indole-2-carboxylic acid (1H-[1,2,3]triazol-4-ylmethyl)-amide [C051]: This compound was synthesized following same protocol as for C006. Prep HPLC purification provided 4.8 mg of faster eluting as well as major isomer of C051 as white solid. Mass [ESI]: m/z 543.63[M$^+$+1].

(2S,5S)-5-[(S)-3-Methyl-2-(4-methyl-benzoylamino)-butyrylamino]-4-oxo-1,2,4,5,6,7-hexahydro-azepino[3,2,1-hi]indole-2-carboxylic acid (1H-[1,2,3]triazol-4-ylmethyl)-amide [C052]: This compound was synthesized following same protocol as for C006. Prep HPLC purification provided 3.5 mg of faster eluting as well as major isomer of C052 as white solid. Mass [ESI]: m/z 543.63[M$^+$+1].

(2S,5S)-5-((2S,3R)-2-Benzoylamino-3-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide [C053,]: To a stirred solution of Acid C053 (107 mg, 0.455 mmol) and central scaffold (200 mg, 0.455 mmol) in DMF (2 mL) was added DIPEA (0.396 mL, 2.27 mmol), followed by the addition of BOP (301 mg, 0.682 mmol) and reaction mixture was allowed to stir at room temperature for 16 h. On completion of the reaction (confirmed by LCMS), crude reaction mixture was submitted for reverse phase prep HPLC purification to afford 10 mg of faster eluting as well as major isomer [Isomer1] of C053 as white solid and 3.7 mg of slower eluting isomer [Isomer2] of C053. Mass [ESI]: m/z 543.63[M$^+$+1].

(2S,5S)-5-[(2S,3R)-2-(2-Benzo[b]thiophen-3-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide [C054]: This compound was synthesized following same protocol as for C053. Prep HPLC purification provided 7 mg of faster eluting as well as major isomer of C054 as white solid. Mass [ESI]: m/z 613.74[M+ +1].

(2S,5S)-5-((S)-2-Benzoylamino-4,4,4-trifluoro-3-methyl-butyrylamino)-4-oxo-1,2,4,5,6,7-hexahydro-azepino[3,2,1-hi]indole-2-carboxylic acid (1H-[1,2,3]triazol-4-ylmethyl)-amide [C055]: This compound was synthesized following same protocol as for C053. Prep HPLC purification provided 5 mg of faster eluting as well as major isomer of C055 as white solid. Mass [ESI]: m/z 583.58[M+ +1].

(2S,5S)-5-((S)-2-Benzoylamino-4,4,4-trifluoro-3-methyl-butyrylamino)-4-oxo-1,2,4,5,6,7-hexahydro-azepino[3,2,1-hi]indole-2-carboxylic acid (1H-[1,2,3]triazol-4-ylmethyl)-amide [C056]: This compound was synthesized following same protocol as for C053. Prep HPLC purification provided 15.2 mg of faster eluting as well as major isomer of C056 as white solid, 0.4 mg of slower eluting isomer was also isolated. Mass [ESI]: m/z 529.58[M+ +1].

(2S, 5S)-5-[(S)-2-(2-Fluoro-acetylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide [C057]: This compound was synthesized following same protocol as for C053. Prep HPLC purification provided 50 mg of faster eluting as well as major isomer of C057 as white solid. Mass [ESI]: m/z 485.52[M+ +1].

(2S, 5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (1H-[1,2,3]triazol-4-ylmethyl)-amide [C058]: This compound was synthesized following same protocol as for C053. Prep HPLC purification provided 9.2 mg of faster eluting as well as major isomer of C058 as white solid, 3.8 mg of slower eluting isomer was also isolated. Mass [ESI]: m/z 543.60 [M+ +1].

(2S, 5S)-5-[(2S,3S)-2-(2-Fluoro-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide [C059]: This compound was synthesized following same protocol as for C053. Prep HPLC purification provided 21 mg of faster eluting as well as major isomer of C059 as white solid. Mass [ESI]: m/z 499.55[M+ +1].

(2S,5S)-5-[(2S,3S)-2-(2-Methoxy-benzoylamino)-3-methyl-pentanoylamino]-4-oxo-1,2,4,5,6,7-hexahydro-azepino[3,2,1-hi]indole-2-carboxylic acid(1H-[1,2,3]triazol-4-ylmethyl)-amide [C060]: This compound was synthesized following same protocol as for C053. Prep HPLC purification provided 6.5 mg of faster eluting as well as major isomer of C060 as white solid, 2.1 mg of slower eluting isomer was also isolated. Mass [ESI]: m/z 573.66[M+ +1].

(2S, 5S)-5-[(2S,3S)-2-(3-Methoxy-benzoylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide [C061]: This compound was synthesized following same protocol as for C053. Prep HPLC purification provided 15 mg of faster eluting as well as major isomer of C061 as white solid. Mass [ESI]: m/z 573.66[M+ +1].

(2S,5S)-5-[(2S,3S)-2-(4-Methoxy-benzoylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide [C062]: This compound was synthesized following same protocol as for C053. Prep HPLC purification provided 21 mg of faster eluting as well as major isomer of C062 as white solid and 7 mg of slower eluting isomer [Isomer2] of C062. Mass [ESI]: m/z 573.66[M+ +1].

(2S, 5S)-5-[(S)-2-(2-Methoxy-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide [C063]: This compound was synthesized following same protocol as for C053. Prep HPLC purification provided 7 mg of faster eluting as well as major isomer of C063 as white solid, 0.4 mg of slower eluting isomer was also isolated. Mass [ESI]: m/z 573.66[M+ +1].

(2S,5S)-5-[(S)-2-(3-Methoxy-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide [C064]: This compound was synthesized following same protocol as for C053. Preparative HPLC purification provided 9 mg of faster eluting isomer [Isomer 1] of C064 as white solid. Mass [ESI]: m/z 559.63[M+ +1].

(2S,5S)-5-[(S)-2-(4-Methoxy-benzoylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide [C065]: This compound was synthesized following same protocol as for C053. Preparative HPLC purification provided 18 mg of faster eluting isomer [Isomer 1] of C065 as white solid. Mass [ESI]: m/z 559.63[M+ +1].

(2S, 5S)-5-{(2S,3S)-3-Methyl-2-[(pyridine-2-carbonyl)-amino]-pentanoylamino}-4-oxo-1,2,4,5,6,7-hexahydro-azepino[3,2,1-hi]indole-2-carboxylicacid (1H-[1,2,3]triazol-4-ylmethyl)-amide [C066]: This compound was synthesized following same protocol as for C053. Preparative HPLC purification provided 40 mg of faster eluting isomer [Isomer 1] of C066. Mass [ESI]: m/z 544.62[M+ +1].

(2S,5S)-5-{(2S,3S)-3-Methyl-2-[(pyridine-3-carbonyl)-amino]-pentanoylamino}-4-oxo-1,2,4,5,6,7-hexahydro-azepino[3,2,1-hi]indole-2-carboxylicacid (1H-[1,2,3]triazol-4-ylmethyl)-amide [C067]: This compound was synthesized following same protocol as for C053. Preparative HPLC purification provided 13 mg of faster eluting isomer [Isomer 1] of C067 as off white solid and 5 mg of slower eluting isomer [Isomer2] of C067 as off white solid. Mass [ESI]: m/z 544.62[M+ +1].

(2S,5S)-5-{(2S,3S)-3-Methyl-2-[(pyridine-4-carbonyl)-amino]-pentanoylamino}-4-oxo-1,2,4,5,6,7-hexahydro-azepino[3,2,1-hi]indole-2-carboxylicacid (1H-[1,2,3]triazol-4-ylmethyl)-amide [C068]: This compound was synthesized following same protocol as for C053. Preparative HPLC purification provided 9 mg of faster eluting isomer [Isomer 1] of C068 as white solid. Mass [ESI]: m/z 544.62[M+ +1].

(2S,5S)-5-{(S)-3-Methyl-2-[(pyridine-2-carbonyl)-amino]-butyrylamino}-4-oxo-1,2,4,5,6,7-hexahydro-azepino[3,2,1-hi]indole-2-carboxylic acid (1H-[1,2,3]triazol-4-ylmethyl)-amide [C069]: This compound was synthesized following same protocol as for C053. Preparative HPLC purification provided 40 mg of faster eluting isomer [Isomer 1] of C069 as off white solid. Mass [ESI]: m/z 530.59[M+ +1].

(2S,5S)-5-{(S)-3-Methyl-2-[(pyridine-3-carbonyl)-amino]-butyrylamino}-4-oxo-1,2,4,5,6,7-hexahydro-azepino[3,2,1-hi]indole-2-carboxylic acid (1H-[1,2,3]triazol-4-ylmethyl)-amide [C070]: This compound was synthesized following same protocol as for C053. Preparative HPLC purification provided 30 mg of faster eluting isomer [Isomer 1] of C070 as white solid and 15 mg of slower eluting isomer [Isomer-2] of C070 as white solid. Mass [ESI]: m/z 530.59 [M+ +1].

(2S, 5S)-5-{(S)-3-Methyl-2-[(pyridine-4-carbonyl)-amino]-butyrylamino}-4-oxo-1,2,4,5,6,7-hexahydro-azepino[3,2,1-hi]indole-2-carboxylic acid (1H-[1,2,3]triazol-4-ylmethyl)-amide [C071]: This compound was synthesized following same protocol as for C053. Preparative HPLC purification provided 9 mg of faster eluting isomer [Isomer 1] of C071 as white solid and 5 mg of slower eluting isomer [Isomer-2] of C071 as white solid. Mass [ESI]: m/z 530.59 [M$^+$+1].

(2S,5S)-5-[(S)-2-(2-Benzo[b]thiophen-3-yl-acetylamino)-3-ethyl-pentanoylamino]-4-oxo-1,2,4,5,6,7-hexahydro-azepino[3,2,1-hi]indole-2-carboxylic acid (1H-[1,2,3]triazol-4-ylmethyl)-amide [C072]: This compound was synthesized following same protocol as for C053. Preparative HPLC purification provided 26 mg of faster eluting isomer [Isomer 1] of C072 as off white solid. Mass [ESI]: m/z 627.77[M$^+$+1].

(2S, 5S)-5-((S)-2-Benzoylamino-3-ethyl-pentanoylamino)-4-oxo-1,2,4,5,6,7-hexahydro-azepino[3,2,1-hi]indole-2-carboxylic acid (1H-[1,2,3]triazol-4-ylmethyl)-amide [C073]: This compound was synthesized following same protocol as for C053. Preparative HPLC purification provided 17 mg of faster eluting isomer [Isomer 1] of C073 as white solid and 6 mg of slower eluting isomer [Isomer-2] of C073 as white solid. Mass [ESI]: m/z 557.66[M$^+$+1].

(2S,5S)-5-((S)-2-Acetylamino-3-ethyl-pentanoylamino)-4-oxo-1,2,4,5,6,7-hexahydro-azepino[3,2,1-hi]indole-2-carboxylic acid (1H-[1,2,3]triazol-4-ylmethyl)-amide [C074]: This compound was synthesized following same protocol as for C053. Preparative HPLC purification provided 30 mg of faster eluting isomer [Isomer 1] of C074 as white solid and 10 mg of slower eluting isomer [Isomer-2] of C074 as white solid. Mass [ESI]: m/z 495.59[M$^+$+1].

(2S,5S)-5-[(S)-2-(2-Benzo[b]thiophen-3-yl-acetylamino)-2-cyclopentyl-acetylamino]-4-oxo-1,2,4,5,6,7-hexahydro-azepino[3,2,1-hi]indole-2-carboxylic acid (1H-[1,2,3]triazol-4-ylmethyl)-amide [C075]: This compound was synthesized following same protocol as for C053. Preparative HPLC purification provided 26 mg of faster eluting isomer [Isomer 1] of C075 as white solid. Mass [ESI]: m/z 625.76[M$^+$+1].

(2S, 5S)-5-((S)-2-Benzoylamino-2-cyclopentyl-acetylamino)-4-oxo-1,2,4,5,6,7-hexahydro-azepino[3,2,1-hi]indole-2-carboxylic acid (1H-[1,2,3]triazol-4-ylmethyl)-amide [C076]: This compound was synthesized following same protocol as for C053. Preparative HPLC purification provided 8 mg of faster eluting isomer [Isomer 1] of C076 as white solid and 15 mg of slower eluting isomer [Isomer-2] of C076 as white solid. Mass [ESI]: m/z 555.64[M$^+$+1].

(2S, 5S)-5-((S)-2-Acetylamino-2-cyclopentyl-acetylamino)-4-oxo-1,2,4,5,6,7-hexahydro-azepino[3,2,1-hi]indole-2-carboxylic acid (1H-[1,2,3]triazol-4-ylmethyl)-amide [C077]: This compound was synthesized following same protocol as for C053. Preparative HPLC purification provided 32 mg of faster eluting isomer [Isomer 1] of C077 as white solid. Mass [ESI]: m/z 493.56[M$^+$+1].

(2S, 5S)-5-[(S)-2-(2-Benzo[b]thiophen-3-yl-acetylamino)-2-cyclohexyl-acetylamino]-4-oxo-1,2,4,5,6,7-hexahydro-azepino[3,2,1-hi]indole-2-carboxylic acid (1H-[1,2,3]triazol-4-ylmethyl)-amide [C078]: This compound was synthesized following same protocol as for C053. Preparative HPLC purification provided 16 mg of faster eluting isomer [Isomer 1] of C078 as white solid and 6 mg of slower eluting isomer [isomer2] of C078 as white solid. Mass [ESI]: m/z 639.78[M$^+$+1].

(2S, 5S)-5-((S)-2-Benzoylamino-2-cyclohexyl-acetylamino)-4-oxo-1,2,4,5,6,7-hexahydro-azepino[3,2,1-hi]indole-2-carboxylic acid (1H-[1,2,3]triazol-4-ylmethyl)-amide [C079]: This compound was synthesized following same protocol as for C053. Preparative HPLC purification provided 5 mg of faster eluting isomer [Isomer 1] of C079 as off white solid. Mass [ESI]: m/z 569.67 [M$^+$+1].

(2S, 5S)-5-((S)-2-Acetylamino-2-cyclohexyl-acetylamino)-4-oxo-1,2,4,5,6,7-hexahydro-azepino[3,2,1-hi]indole-2-carboxylic acid (1H-[1,2,3]triazol-4-ylmethyl)-amide [C080]: This compound was synthesized following same protocol as for C053. Preparative HPLC purification provided 40 mg of faster eluting isomer [Isomer 1] of C080 as off white solid. Mass [ESI]: m/z 507.6 [M$^+$+1].

(2S,5S)-5-((S)-2-Acetylamino-2-cyclopropyl-acetylamino)-4-oxo-1,2,4,5,6,7-hexahydro-azepino[3,2,1-hi]indole-2-carboxylic acid (1H-[1,2,3]triazol-4-ylmethyl)-amide [C081]: This compound was synthesized following same protocol as for C053. Preparative HPLC purification provided 18 mg of faster eluting isomer [Isomer 1] of C081 as off white solid. Mass [ESI]: m/z 465.52 [M$^+$+1].

(2S, 5S)-5-((S)-2-Benzoylamino-2-cyclopropyl-acetylamino)-4-oxo-1,2,4,5,6,7-hexahydro-azepino[3,2,1-hi]indole-2-carboxylic acid (1H-[1,2,3]triazol-4-ylmethyl)-amide [C082]: This compound was synthesized following same protocol as for C053. Preparative HPLC purification provided 11 mg of faster eluting isomer [Isomer 1] of C082 as white solid. Mass [ESI]: m/z 527.59 [M$^+$+1].

(2S, 5S)-5-((S)-2-Acetylamino-2-cyclobutyl-acetylamino)-4-oxo-1,2,4,5,6,7-hexahydro-azepino[3,2,1-hi]indole-2-carboxylic acid (1H-[1,2,3]triazol-4-ylmethyl)-amide [C083]: This compound was synthesized following same protocol as for C053. Preparative HPLC purification provided 40 mg of faster eluting isomer [Isomer 1] of C083 as white solid. Mass [ESI]: m/z 479.54 [M$^+$+1].

(2S, 5S)-5-((S)-2-Benzoylamino-2-cyclobutyl-acetylamino)-4-oxo-1,2,4,5,6,7-hexahydro-azepino[3,2,1-hi]indole-2-carboxylic acid (1H-[1,2,3]triazol-4-ylmethyl)-amide [C084]: This compound was synthesized following same protocol as for C053. Preparative HPLC purification provided 36 mg of faster eluting isomer [Isomer 1] of C084 as white solid and 5.6 mg of slower eluting isomer of C084 as white solid. Mass [ESI]: m/z 541.61 [M$^+$+1].

General Condition for Acid Counterpart Synthesis:
Synthesis of Acid Counterpart Following Scheme-2:
Synthesis of (2-Benzo[b]thiophen-3-yl-acetylamino)-acetic acid (Acid C001): This compound was synthesized following same protocol as for Acid C006 to afford Acid C001 (0.32 g, 99%) as white solid. Mass [ESI]: m/z 249.29 [M$^+$+1].

Synthesis of (S)-2-(2-Benzo[b]thiophen-3-yl-acetylamino)-propionic acid (Acid C002): This compound was synthesized following same protocol as for Acid C006 to afford Acid C002 (0.28 g, 89%) as white solid. Mass [ESI]: m/z 263.32[M$^+$+1].

Synthesis of (S)-2-(2-Benzo[b]thiophen-3-yl-acetylamino)-3-methyl-butyric acid (Acid C003): This compound was synthesized following same protocol as for Acid C006 to afford Acid C003 (0.20 g, 70%) as white solid. Mass [ESI]: m/z 291.37[M$^+$+1].

Synthesis of (S)-2-(2-Benzo[b]thiophen-3-yl-acetylamino)-3-phenyl-propionic acid (Acid C004): This compound was synthesized following same protocol as for Acid C006 to afford Acid C004 (0.17 g, 82%) as white solid. Mass [ESI]: m/z 339.4[M$^+$+1].

Synthesis of (S)-2-(2-Benzo[b]thiophen-3-yl-acetylamino)-4-methyl-pentanoic acid (Acid C005): This compound was synthesized following same protocol as for Acid C006 to afford Acid C005 (0.31 g, 93%) as white solid. Mass [ESI]: m/z 305.4[M$^+$+1].

Synthesis of (S)-(2-Benzo[b]thiophen-3-yl-acetylamino)-phenyl-acetic acid (Acid C009): This compound was synthesized following same protocol as for Acid C006 to afford Acid C009 (0.31 g, 92%) as white solid. Mass [ESI]: m/z 325.39[M$^+$+1].

Synthesis of (S)-2-(2-Benzo[b]thiophen-3-yl-acetylamino)-3-(4-hydroxy-phenyl)-propionic acid (Acid C010): This compound was synthesized following same protocol as for Acid C006 to afford Acid C010 (0.40 g, 87%) as white solid. Mass [ESI]: m/z 355.4[M$^+$+1].

Synthesis of (S)-2-(2-Benzo[b]thiophen-3-yl-acetylamino)-3-(4-fluoro-phenyl)-propionic acid (Acid C011): This compound was synthesized following same protocol as for Acid C006 to afford Acid C011 (0.40 g, 86%) as white solid. Mass [ESI]: m/z 357.41[M$^+$+1].

Synthesis of Phenylacetylamino-acetic acid (Acid C012): This compound was synthesized following same protocol as for Acid C006 to afford Acid C012 (0.52 g, 85%) as white solid. Mass [ESI]: m/z 193.20[M$^+$+1].

Synthesis of (S)-2-Phenylacetylamino-propionic acid (Acid C013): This compound was synthesized following same protocol as for Acid C006 to afford Acid C013 (0.66 g, 99%) as white solid. Mass [ESI]: m/z 207.23[M$^+$+1].

Synthesis of (S)-3-Methyl-2-phenylacetylamino-butyric acid (Acid C014): This compound was synthesized following same protocol as for Acid C006 to afford Acid C014 (0.60 g, 91%) as white solid. Mass [ESI]: m/z 235.29[M$^+$+1].

Synthesis of (S)-3-Phenyl-2-phenylacetylamino-propionic acid (Acid C015): This compound was synthesized following same protocol as for Acid C006 to afford Acid C015 (0.16 g, 88%) as white solid. Mass [ESI]: m/z 283.33 [M$^+$+1].

Synthesis of (S)-4-Methyl-2-phenylacetylamino-pentanoic acid (Acid C016): This compound was synthesized following same protocol as for Acid C006 to afford Acid C016 (0.22 g, 91%) as white solid. Mass [ESI]: m/z 249.31 [M$^+$+1].

Synthesis of (2S, 3S)-3-Methyl-2-phenylacetylamino-pentanoic acid (Acid C017): This compound was synthesized following same protocol as for Acid C006 to afford Acid C017 (0.56 g, 77%) as white solid. Mass [ESI]: m/z 249.31[M$^+$+1].

Synthesis of (S)-3-Hydroxy-2-phenylacetylamino-propionic acid (Acid C018): This compound was synthesized following same protocol as for Acid C006 to afford Acid C018 (0.12 g, 56%) as white solid. Mass [ESI]: m/z 223.23 [M$^+$+1].

Synthesis of (S)-Phenyl-phenylacetylamino-acetic acid (Acid C020): This compound was synthesized following same protocol as for Acid C006 to afford Acid C020 (0.54 g, 80%) as white solid. Mass [ESI]: m/z 269.30[M$^+$+1].

Synthesis of (S)-Phenyl-phenylacetylamino-acetic acid (Acid C021): This compound was synthesized following same protocol as for Acid C006 to afford Acid C021 (0.68 g, 94%) as white solid. Mass [ESI]: m/z 299.33[M$^+$+1].

Synthesis of (S)-2-Benzoylamino-3-(4-fluoro-phenyl)-propionic acid (Acid C022): This compound was synthesized following same protocol as for Acid C006 to afford Acid C022 (0.80 g, 94%) as white solid. Mass [ESI]: m/z 287.33[M$^+$+1].

Synthesis of (S)-2-Acetylamino-3-phenyl-propionic acid (Acid C026): This compound was synthesized following same protocol as for Acid C006 to afford Acid C026 (0.40 g, 66%) as white solid. Mass [ESI]: m/z 207.23[M$^+$+1].

Synthesis of (S)-2-Acetylamino-3-(4-hydroxy-phenyl)-propionic acid (Acid C032): This compound was synthesized following same protocol as for Acid C006 to afford Acid C032 (0.50 g, 62%) as white solid. Mass [ESI]: m/z 223.23[M$^+$+1].

Synthesis of Benzoylamino-acetic acid (Acid C034): This compound was synthesized following same protocol as for Acid C006 to afford Acid C034 (0.35 g, 75%) as white solid. Mass [ESI]: m/z 179.18[M$^+$+1].

Synthesis of (S)-2-Benzoylamino-propionic acid (Acid C035): This compound was synthesized following same protocol as for Acid C006 to afford Acid C035 (0.38 g, 77%) as white solid. Mass [ESI]: m/z 193.20[M$^+$+1].

Synthesis of (S)-2-Benzoylamino-3-methyl-butyric acid (Acid C036): This compound was synthesized following same protocol as for Acid C006 to afford Acid C036 (0.40 g, 85%) as white solid. Mass [ESI]: m/z 221.26[M$^+$+1].

Synthesis of (S)-2-Benzoylamino-3-phenyl-propionic acid (Acid C037): This compound was synthesized following same protocol as for Acid C006 to afford Acid C037 (0.38 g, 92%) as white solid. Mass [ESI]: m/z 269.30[M$^+$+1].

Synthesis of (S)-2-Benzoylamino-4-methyl-pentanoic acid (Acid C038): This compound was synthesized following same protocol as for Acid C006 to afford Acid C038 (0.56 g, 59%) as white solid. Mass [ESI]: m/z 235.29[M$^+$+1].

Synthesis of (S)-2-Benzoylamino-3-methyl-pentanoic acid (Acid C039): This compound was synthesized following same protocol as for Acid C006 to afford Acid C039 (0.80 g, 89%) as white solid. Mass [ESI]: m/z 235.29[M$^+$+1].

Synthesis of (S)-2-Benzoylamino-3-hydroxy-propionic acid (Acid C040): This compound was synthesized following same protocol as for Acid C006 to afford Acid C040 (0.13 g, 60%) as white solid. Mass [ESI]: m/z 209.20[M$^+$+1].

Synthesis of (S)-2-Benzoylamino-3-(4-hydroxy-phenyl)-propionic acid (Acid C042): This compound was synthesized following same protocol as for Acid C006 to afford Acid C042 (0.80 g, 94%) as white solid. Mass [ESI]: m/z 285.30[M$^+$+1].

Synthesis of (S)-2-Benzoylamino-3-(4-fluoro-phenyl)-propionic acid (Acid C043): This compound was synthesized following same protocol as for Acid C006 to afford Acid C043 (0.60 g, 94%) as white solid. Mass [ESI]: m/z 287.29[M$^+$+1].

Synthesis of 2-(2-Benzo[b]thiophen-3-yl-acetylamino)-2-methyl-propionic acid (Acid C044): This compound was synthesized following same protocol as for Acid C006 to afford Acid C044 (0.45 g, 92%) as white solid. Mass [ESI]: m/z 277.34[M$^+$+1].

Synthesis of (S)-2-Benzoylamino-butyric acid (Acid C045): This compound was synthesized following same protocol as for Acid C006 to afford Acid C045 (0.38 g, 84%) as white solid. Mass [ESI]: m/z 207.23[M$^+$+1].

Synthesis of (S)-2-Benzoylamino-3,3-dimethyl-butyric acid (Acid C046): This compound was synthesized following same protocol as for Acid C006 to afford Acid C046 (0.28 g, 81%) as white solid. Mass [ESI]: m/z 235.29[M$^+$+1].

Synthesis of (S)-2-(4-Fluoro-benzoylamino)-3-methyl-butyric acid (Acid C047): This compound was synthesized following same protocol as for Acid C006 to afford Acid C047 (0.28 g, 81%) as white solid. Mass [ESI]: m/z 239.25 [M$^+$+1].

Synthesis of (S)-2-(3-Fluoro-benzoylamino)-3-methyl-butyric acid (Acid C048): This compound was synthesized following same protocol as for Acid C006 to afford Acid C048 (0.63 g, 82%) as white solid. Mass [ESI]: m/z 239.25 [M$^+$+1].

Synthesis of (S)-2-(2-Fluoro-benzoylamino)-3-methyl-butyric acid (Acid C049): This compound was synthesized following same protocol as for Acid C006 to afford Acid C049 (0.39 g, 82%) as white solid. Mass [ESI]: m/z 239.25 [M$^+$+1].

Synthesis of (S)-3-Methyl-2-(2-methyl-benzoylamino)-butyric acid (Acid C050): This compound was synthesized following same protocol as for Acid C006 to afford Acid C050 (0.50 g, 95%) as white solid. Mass [ESI]: m/z 235.25 [M$^+$+1].

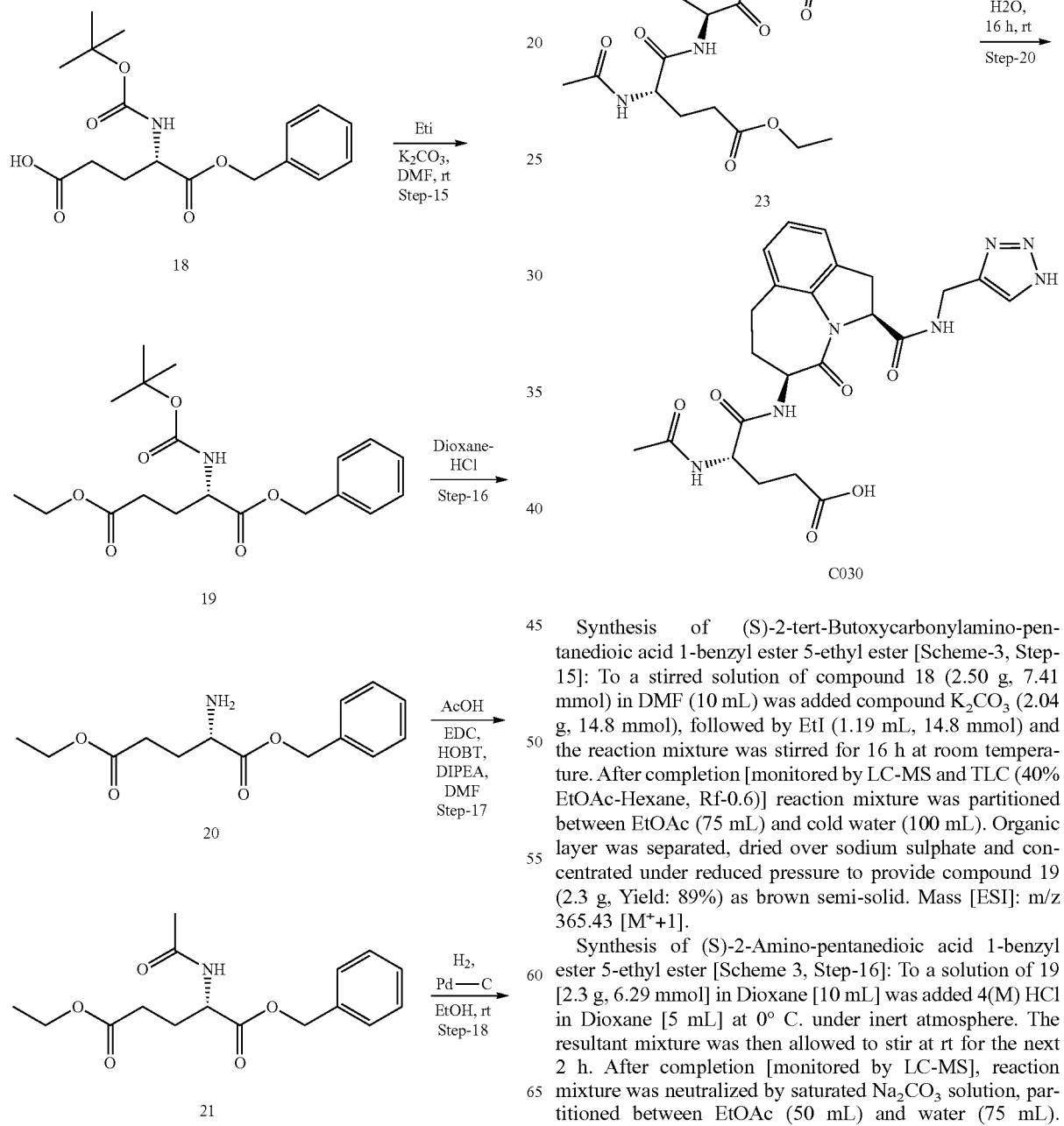

Synthesis of (S)-2-tert-Butoxycarbonylamino-pentanedioic acid 1-benzyl ester 5-ethyl ester [Scheme-3, Step-15]: To a stirred solution of compound 18 (2.50 g, 7.41 mmol) in DMF (10 mL) was added compound $K_2CO_3$ (2.04 g, 14.8 mmol), followed by EtI (1.19 mL, 14.8 mmol) and the reaction mixture was stirred for 16 h at room temperature. After completion [monitored by LC-MS and TLC (40% EtOAc-Hexane, Rf-0.6)] reaction mixture was partitioned between EtOAc (75 mL) and cold water (100 mL). Organic layer was separated, dried over sodium sulphate and concentrated under reduced pressure to provide compound 19 (2.3 g, Yield: 89%) as brown semi-solid. Mass [ESI]: m/z 365.43 [M$^+$+1].

Synthesis of (S)-2-Amino-pentanedioic acid 1-benzyl ester 5-ethyl ester [Scheme 3, Step-16]: To a solution of 19 [2.3 g, 6.29 mmol] in Dioxane [10 mL] was added 4(M) HCl in Dioxane [5 mL] at 0° C. under inert atmosphere. The resultant mixture was then allowed to stir at rt for the next 2 h. After completion [monitored by LC-MS], reaction mixture was neutralized by saturated $Na_2CO_3$ solution, partitioned between EtOAc (50 mL) and water (75 mL). Organic layer was separated, dried over sodium sulphate and concentrated under reduced pressure to provide compound 20 (1.5 g, Yield: 90%) as off-white gum. Mass [ESI]: m/z 265.31 [M$^+$+1]. The crude ester was used as such without further purification.

Synthesis of (S)-2-Acetylamino-pentanedioic acid 1-benzyl ester 5-ethyl ester [Scheme 3, Step-17]: To a stirred solution of compound 20 (1.50 g, 5.65 mmol) in DCM (20 mL) were added AcOH (0.286 g, 4.99 mmol), hunig's base (4.35 mL, 25.0 mmol) at room temperature. Finally EDC.HCl (1.24 g, 6.49 mmol) and HOBT (1.01 g, 7.49 mmol) were added in one portion at ice cold condition and the reaction mixture was stirred for 16 h at room temperature. After completion [monitored by LC-MS and TLC] reaction mixture was diluted with DCM and washed with excess water. Organic layer was then washed with water and brine. Organic part was dried (MgSO$_4$) and concentrated to get crude material. The crude was purified through column chromatography (25-35% EtOAc/hexane, SiO$_2$) to provide compound 21 (0.60 g, 39%) as colorless semi-solid. Mass [ESI]: m/z 307.35 [M$^+$+1].

Synthesis of (S)-2-Acetylamino-pentanedioic acid 5-ethyl ester [Scheme 3, step-18]: To a stirred solution of compound 21 (0.600 g, 1.37 mmol) in EtOH (10 mL), Pd/C powder (180 mg, 50% wet) was added and resultant reaction mixture was allowed to stir under H$_2$ balloon pressure for 16 h at room temperature. Then reaction mixture was filtered through celite bed and filtrate part was concentrated under reduced pressure to afford compound 22 (0.29 g, 98%) as white solid. The crude acid was used as such without further purification. [$^1$H NMR complies].

Synthesis of (S)-4-Acetylamino-4-{(2S,5S)-4-oxo-2-[(1H-[1,2,3]triazol-4-ylmethyl)-carbamoyl]-1,2,4,5,6,7-hexahydro-azepino[3,2,1-hi]indol-5-ylcarbamoyl}-butyric acid ethyl ester [Scheme 3, Step-19]: To a stirred solution of compound 22 (74 mg, 0.34 mmol) and central scaffold (150 mg, 0.341 mmol) in DMF (1 mL) was added DIPEA (0.36 mL, 2.0 mmol), followed by the addition of TBTU (164 mg, 0.511 mmol) and reaction mixture was allowed to stir at room temperature for 16 h. On completion of the reaction (confirmed by LC-MS and TLC), reaction mixture was diluted with DCM and washed with excess water. Organic layer was then washed with water and brine, dried (MgSO$_4$) and concentrated to get crude material. The crude was purified through column chromatography (1-5% MeOH-DCM, SiO$_2$) to provide compound 23 (80 mg, 39%) as white solid. Mass [ESI]: m/z 525.57 [M$^+$+1].

Synthesis of (S)-4-Acetylamino-4-{(2S,5S)-4-oxo-2-[(1H-[1,2,3]triazol-4-ylmethyl)-carbamoyl]-1,2,4,5,6,7-hexahydro-azepino[3,2,1-hi]indol-5-ylcarbamoyl}-butyric acid (C030) [Scheme 3, Step-20]: To a stirred solution of compound 23 (80 mg, 0.15 mmol) in THF (3 mL): water (1 mL): MeOH (1 mL) was added LiOH·H$_2$O (25.5 mg, 0.609 mmol) and the resultant reaction mixture was allowed to stir at room temperature for 16 hour. After completion [monitored with LC-MS and TLC (5% MeOH-DCM, Rf-0.1)] reaction mixture was concentrated, resultant crude was diluted with water and washed with EtOAc [15 mL]. Aqueous layer was separated and acidified with 1(N) aqueous HCl upto pH 2-3 and extracted with EtOAc [10 mL×2] and concentrated under reduced pressure. Crude reaction mixture was submitted for reverse phase prep HPLC purification to afford 5 mg of slower eluting isomer [Isomer 2] of C030 as white solid. Mass [ESI]: m/z 497.51 [M$^+$+1].

Synthesis of (S)-4-(2-Benzo[b]thiophen-3-yl-acetylamino)-4-{(2S,5S)-4-oxo-2-[(1H-[1,2,3]triazol-4-ylmethyl)-carbamoyl]-1,2,4,5,6,7-hexahydro-azepino[3,2,1-hi]indol-5-ylcarbamoyl}-butyric acid (C008): This compound was synthesized following same protocol as for C030. Preparative HPLC purification provided 1.2 mg of faster eluting isomer [Isomer 1] of C008 as white solid and 5 mg of slower eluting isomer of C008 [Isomer 2] as white solid. Mass [ESI]: m/z 629.70 [M$^+$+1].

Synthesis of (S)-4-{(2S,5S)-4-Oxo-2-[(1H-[1,2,3]triazol-4-ylmethyl)-carbamoyl]-1,2,4,5,6,7-hexahydro-azepino[3,2,1-hi]indol-5-ylcarbamoyl}-4-phenylacetylamino-butyric acid (C019): This compound was synthesized following same protocol as for C030. Preparative HPLC purification provided 2 mg of slower eluting isomer [Isomer 2] of C019 as white solid. Mass [ESI]: m/z 573.61 [M$^+$+1].

Synthesis of (S)-4-Benzoylamino-4-{(2S,5S)-4-oxo-2-[(1H-[1,2,3]triazol-4-ylmethyl)-carbamoyl]-1,2,4,5,6,7-hexahydro-azepino[3,2,1-hi]indol-5-ylcarbamoyl}-butyric acid (C041): This compound was synthesized following same protocol as for C030. Preparative HPLC purification provided 3 mg of slower eluting isomer [Isomer 2] of C0041 as white solid. Mass [ESI]: m/z 559.59 [M$^+$+1].

General Condition for Acid Counterpart Synthesis:

Below mentioned acid counterparts were synthesized following the same protocol as mentioned in Scheme-2 step no. 12 and 13.

Synthesis of (2-Benzo[b]thiophen-3-yl-acetylamino)-acetic acid (Acid C001): This compound was synthesized following same protocol as for Acid C006 to afford Acid C001 (0.32 g, 99%) as white solid. Mass [ESI]: m/z 249.29 [M$^+$+1].

Synthesis of (S)-2-(2-Benzo[b]thiophen-3-yl-acetylamino)-propionic acid (Acid C002): This compound was synthesized following same protocol as for Acid C006 to afford Acid C002 (0.28 g, 89%) as white solid. Mass [ESI]: m/z 263.32[M$^+$+1].

Synthesis of (S)-2-(2-Benzo[b]thiophen-3-yl-acetylamino)-3-methyl-butyric acid (Acid C003): This compound was synthesized following same protocol as for Acid C006 to afford Acid C003 (0.20 g, 70%) as white solid. Mass [ESI]: m/z 291.37[M$^+$+1].

Synthesis of (S)-2-(2-Benzo[b]thiophen-3-yl-acetylamino)-3-phenyl-propionic acid (Acid C004): This compound was synthesized following same protocol as for Acid C006 to afford Acid C004 (0.17 g, 82%) as white solid. Mass [ESI]: m/z 339.4[M$^+$+1].

Synthesis of (S)-2-(2-Benzo[b]thiophen-3-yl-acetylamino)-4-methyl-pentanoic acid (Acid C005): This compound was synthesized following same protocol as for Acid C006 to afford Acid C005 (0.31 g, 93%) as white solid. Mass [ESI]: m/z 305.4[M$^+$+1].

Synthesis of (S)-(2-Benzo[b]thiophen-3-yl-acetylamino)-phenyl-acetic acid (Acid C009): This compound was synthesized following same protocol as for Acid C006 to afford Acid C009 (0.31 g, 92%) as white solid. Mass [ESI]: m/z 325.39[M$^+$+1].

Synthesis of (S)-2-(2-Benzo[b]thiophen-3-yl-acetylamino)-3-(4-hydroxy-phenyl)-propionic acid (Acid C010): This compound was synthesized following same protocol as for Acid C006 to afford Acid C010 (0.40 g, 87%) as white solid. Mass [ESI]: m/z 355.4[M$^+$+1].

Synthesis of (S)-2-(2-Benzo[b]thiophen-3-yl-acetylamino)-3-(4-fluoro-phenyl)-propionic acid (Acid C011): This compound was synthesized following same protocol as for Acid C006 to afford Acid C011 (0.40 g, 86%) as white solid. Mass [ESI]: m/z 357.41[M$^+$+1].

Synthesis of Phenylacetylamino-acetic acid (Acid C012): This compound was synthesized following same protocol as for Acid C006 to afford Acid C012 (0.52 g, 85%) as white solid. Mass [ESI]: m/z 193.20[M$^+$+1].

Synthesis of (S)-2-Phenylacetylamino-propionic acid (Acid C013): This compound was synthesized following same protocol as for Acid C006 to afford Acid C013 (0.66 g, 99%) as white solid. Mass [ESI]: m/z 207.23[M$^+$+1].

Synthesis of (S)-3-Methyl-2-phenylacetylamino-butyric acid (Acid C014): This compound was synthesized following same protocol as for Acid C006 to afford Acid C014 (0.60 g, 91%) as white solid. Mass [ESI]: m/z 235.29[M$^+$+1].

Synthesis of (S)-3-Phenyl-2-phenylacetylamino-propionic acid (Acid C015): This compound was synthesized following same protocol as for Acid C006 to afford Acid C015 (0.16 g, 88%) as white solid. Mass [ESI]: m/z 283.33 [M$^+$+1].

Synthesis of (S)-4-Methyl-2-phenylacetylamino-pentanoic acid (Acid C016): This compound was synthesized following same protocol as for Acid C006 to afford Acid C016 (0.22 g, 91%) as white solid. Mass [ESI]: m/z 249.31 [M$^+$+1].

Synthesis of (2S, 3S)-3-Methyl-2-phenylacetylamino-pentanoic acid (Acid C017): This compound was synthesized following same protocol as for Acid C006 to afford Acid C017 (0.56 g, 77%) as white solid. Mass [ESI]: m/z 249.31[M$^+$+1].

Synthesis of (S)-Phenyl-phenylacetylamino-acetic acid (Acid C020): This compound was synthesized following same protocol as for Acid C006 to afford Acid C020 (0.54 g, 80%) as white solid. Mass [ESI]: m/z 269.30[M$^+$+1].

Synthesis of (S)-Phenyl-phenylacetylamino-acetic acid (Acid C021): This compound was synthesized following same protocol as for Acid C006 to afford Acid C021 (0.68 g, 94%) as white solid. Mass [ESI]: m/z 299.33[M$^+$+1].

Synthesis of (S)-2-Benzoylamino-3-(4-fluoro-phenyl)-propionic acid (Acid C022): This compound was synthesized following same protocol as for Acid C006 to afford Acid C022 (0.80 g, 94%) as white solid. Mass [ESI]: m/z 287.33[M$^+$+1].

Synthesis of (S)-2-Acetylamino-3-phenyl-propionic acid (Acid C026): This compound was synthesized following same protocol as for Acid C006 to afford Acid C026 (0.40 g, 66%) as white solid. Mass [ESI]: m/z 207.23[M$^+$+1].

Synthesis of (S)-Acetylamino-phenyl-acetic acid (Acid C031): This compound was synthesized following same protocol as for Acid C006 to afford Acid C031 (0.50 g, 76%) as white solid. Mass [ESI]: m/z 193.2[M$^+$+1].

Synthesis of (S)-2-Acetylamino-3-(4-hydroxy-phenyl)-propionic acid (Acid C032): This compound was synthesized following same protocol as for Acid C006 to afford Acid C032 (0.50 g, 62%) as white solid. Mass [ESI]: m/z 223.23[M$^+$+1].

Synthesis of (S)-2-Acetylamino-3-(4-fluoro-phenyl)-propionic acid (Acid C033): This compound was synthesized following same protocol as for Acid C006 to afford Acid C033 (0.6 g, 70%) as white solid. The crude acid was used as such without further purification. Mass [ESI]: m/z 225.21 [M$^+$+1].

Synthesis of Benzoylamino-acetic acid (Acid C034): This compound was synthesized following same protocol as for Acid C006 to afford Acid C034 (0.35 g, 75%) as white solid. Mass [ESI]: m/z 179.18[M$^+$+1].

Synthesis of (S)-2-Benzoylamino-propionic acid (Acid C035): This compound was synthesized following same protocol as for Acid C006 to afford Acid C035 (0.38 g, 77%) as white solid. Mass [ESI]: m/z 193.20[M$^+$+1].

Synthesis of (S)-2-Benzoylamino-3-methyl-butyric acid (Acid C036): This compound was synthesized following same protocol as for Acid C006 to afford Acid C036 (0.40 g, 85%) as white solid. Mass [ESI]: m/z 221.26[M$^+$+1].

Synthesis of (S)-2-Benzoylamino-3-phenyl-propionic acid (Acid C037): This compound was synthesized following same protocol as for Acid C006 to afford Acid C037 (0.38 g, 92%) as white solid. Mass [ESI]: m/z 269.30[M$^+$+1].

Synthesis of (S)-2-Benzoylamino-4-methyl-pentanoic acid (Acid C038): This compound was synthesized following same protocol as for Acid C006 to afford Acid C038 (0.56 g, 59%) as white solid. Mass [ESI]: m/z 235.29[M$^+$+1].

Synthesis of (S)-2-Benzoylamino-3-methyl-pentanoic acid (Acid C039): This compound was synthesized following same protocol as for Acid C006 to afford Acid C039 (0.80 g, 89%) as white solid. Mass [ESI]: m/z 235.29[M$^+$+1].

Synthesis of (S)-2-Benzoylamino-3-(4-hydroxy-phenyl)-propionic acid (Acid C042): This compound was synthesized following same protocol as for Acid C006 to afford Acid C042 (0.80 g, 94%) as white solid. Mass [ESI]: m/z 285.30[M$^+$+1].

Synthesis of (S)-2-Benzoylamino-3-(4-fluoro-phenyl)-propionic acid (Acid C043): This compound was synthesized following same protocol as for Acid C006 to afford Acid C043 (0.60 g, 94%) as white solid. Mass [ESI]: m/z 287.29[M$^+$+1].

Synthesis of 2-(2-Benzo[b]thiophen-3-yl-acetylamino)-2-methyl-propionic acid (Acid C044): This compound was synthesized following same protocol as for Acid C006 to afford Acid C044 (0.45 g, 92%) as white solid. Mass [ESI]: m/z 277.34[M$^+$+1].

Synthesis of (S)-2-Benzoylamino-butyric acid (Acid C045): This compound was synthesized following same protocol as for Acid C006 to afford Acid C045 (0.38 g, 84%) as white solid. Mass [ESI]: m/z 207.23[M$^+$+1].

Synthesis of (S)-2-Benzoylamino-3,3-dimethyl-butyric acid (Acid C046): This compound was synthesized following same protocol as for Acid C006 to afford Acid C046 (0.28 g, 81%) as white solid. Mass [ESI]: m/z 235.29[M$^+$+1].

Synthesis of (S)-2-(4-Fluoro-benzoylamino)-3-methyl-butyric acid (Acid C047): This compound was synthesized following same protocol as for Acid C006 to afford Acid C047 (0.28 g, 81%) as white solid. Mass [ESI]: m/z 239.25 [M$^+$+1].

Synthesis of (S)-2-(3-Fluoro-benzoylamino)-3-methyl-butyric acid (Acid C048): This compound was synthesized following same protocol as for Acid C006 to afford Acid C048 (0.63 g, 82%) as white solid. Mass [ESI]: m/z 239.25 [M$^+$+1].

Synthesis of (S)-2-(2-Fluoro-benzoylamino)-3-methyl-butyric acid (Acid C049): This compound was synthesized following same protocol as for Acid C006 to afford Acid C049 (0.39 g, 82%) as white solid. Mass [ESI]: m/z 239.25 [M$^+$+1].

Synthesis of (S)-3-Methyl-2-(2-methyl-benzoylamino)-butyric acid (Acid C050): This compound was synthesized following same protocol as for Acid C006 to afford Acid C050 (0.50 g, 95%) as white solid. Mass [ESI]: m/z 235.25 [M$^+$+1].

Synthesis of (S)-3-Methyl-2-(3-methyl-benzoylamino)-butyric acid (Acid C051): This compound was synthesized following same protocol as for Acid C006 to afford Acid C051 (0.65 g, 86%) as off-white gum. Mass [ESI]: m/z 235.29[M$^+$+1].

Synthesis of (S)-3-Methyl-2-(4-methyl-benzoylamino)-butyric acid (Acid C052): This compound was synthesized following same protocol as for Acid C006 to afford Acid C052 (0.60 g, 95%) as off-white gum. Mass [ESI]: m/z 235.29[M$^+$+1].

Synthesis of (2S,3R)-2-Benzoylamino-3-methyl-pentanoic acid (Acid C053): This compound was synthesized following same protocol as for Acid C006 to afford Acid C053 (0.63 g, 95%) as off-white gum. Mass [ESI]: m/z 235.29[M$^+$+1].

Synthesis of (2S,3R)-2-(2-Benzo[b]thiophen-3-yl-acetylamino)-3-methyl-pentanoic acid (Acid C054): This compound was synthesized following same protocol as for Acid C006 to afford Acid C054 (0.43 g, 90%) as off-white gum. Mass [ESI]: m/z 305.40[M$^+$+1].

Synthesis of (S)-2-(2-Fluoro-acetylamino)-3-methyl-butyric acid (Acid C057): This compound was synthesized following same protocol as for Acid C006 to afford Acid C057 (0.76 g, 99%) as off-white gum. Mass [ESI]: m/z 177.18[M$^+$+1].

Synthesis of (2S,3S)-2-(2-Fluoro-acetylamino)-3-methyl-pentanoic acid (Acid C59): This compound was synthesized following same protocol as for Acid C006 to afford Acid C059 (0.80 g, 98%) as off-white gum. Mass [ESI]: m/z 191.20[M$^+$+1].

Synthesis of (2S,3S)-2-(2-Methoxy-benzoylamino)-3-methyl-pentanoic acid (Acid C60): This compound was synthesized following same protocol as for Acid C006 to afford Acid C060 (0.63 g, 88%) as off-white gum. Mass [ESI]: m/z 265.31[M$^+$+1].

Synthesis of (2S,3S)-2-(4-Methoxy-benzoylamino)-3-methyl-pentanoic acid (Acid C61): This compound was synthesized following same protocol as for Acid C006 to afford Acid C061 (0.63 g, 83%) as off-white gum. Mass [ESI]: m/z 265.31[M$^+$+1].

Synthesis of (2S,3S)-2-(3-Methoxy-benzoylamino)-3-methyl-pentanoic acid (Acid C062): This compound was synthesized following same protocol as for Acid C006 to afford Acid C062 (0.70 g, 93%) as off-white gum. Mass [ESI]: m/z 265.31[M$^+$+1].

Synthesis of (S)-2-(2-Methoxy-benzoylamino)-3-methyl-butyric acid (Acid C063): This compound was synthesized following same protocol as for Acid C006 to afford Acid C063 (0.46 g, 81%) as off-white gum. Mass [ESI]: m/z 251.28[M$^+$+1].

Synthesis of (S)-2-(3-Methoxy-benzoylamino)-3-methyl-butyric acid (Acid C064): This compound was synthesized following same protocol as for Acid C006 to afford Acid C064 (0.43 g, 61%) as off-white gum. Mass [ESI]: m/z 251.28[M$^+$+1].

Synthesis of (S)-2-(4-Methoxy-benzoylamino)-3-methyl-butyric acid (Acid C065): This compound was synthesized following same protocol as for Acid C006 to afford Acid C065 (0.58 g, 96%) as off-white gum. Mass [ESI]: m/z 251.28[M$^+$+1].

Scheme-4 [Synthesis of Acid C025]

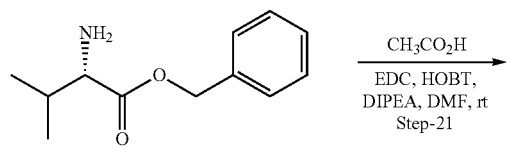

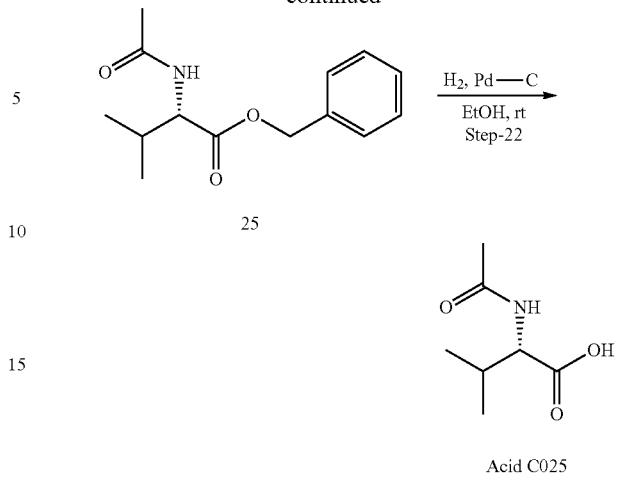

Synthesis of (S)-2-Acetylamino-3-methyl-butyric acid benzyl ester [Scheme-4, Step-21]: To the stirred solution of compound 24 (3.79 g, 9.99 mmol) and AcOH (0.50 g, 8.33 mmol) in DCM (15 ml) was added EDC.HCl (2.075 g, 10.82 mmol), HOBT (1.69 g, 12.5 mmol), DIPEA (7.25 ml, 41.6 mmol) and resultant reaction mixture was allowed to stir at room temperature for 16 h. After completion [monitored with TLC and LC-MS]reaction mixture was partitioned between EtAOc [200 mL] and water [100 mL]. Organic layer was separated, dried (MgSO$_4$) and concentrated under reduced pressure. Resultant crude was purified via column chromatography using silica gel 100-200 mesh as absorbent and 50-60% EtOAc-Hexane as eluting solvent to afford compound 25 as off white solid (1.50 g, 72.3%). Mass [ESI]: m/z 250.3 [M$^+$+1]

Synthesis of (S)-2-Acetylamino-3-methyl-butyric acid (Acid C025) [Scheme-4, step-22]: To a stirred solution of compound 25 (1.50 g, 6.04 mmol) in EtOH (25 ml), Pd/C powder (400 mg, 50% wet) was added and resultant reaction mixture was allowed to stir under H$_2$ balloon pressure for 16 h at room temperature. Then reaction mixture was filtered through celite bed and filtrate part was concentrated under reduced pressure to afford Acid C025 (0.50 g, 52%) as white solid. The crude acid was used as such without further purification. [$^1$H NMR complies].

Synthesis of Acetylamino-acetic acid (Acid C023): This compound was synthesized following same protocol as for Acid C025 to afford Acid C023 (0.25 g, 62%) as off-white solid. The crude acid was used as such without further purification. [$^1$H NMR complies].

Synthesis of (S)-2-Acetylamino-propionic acid (Acid C024): This compound was synthesized following same protocol as for Acid C025 to afford Acid C024 (0.21 g, 89%) as white solid. The crude acid was used as such without further purification. [$^1$H NMR complies].

Synthesis of (S)-2-Acetylamino-4-methyl-pentanoic acid (Acid C027): This compound was synthesized following same protocol as for Acid C025 to afford Acid C027 (0.65 g, 98%) as white solid. The crude acid was used as such without further purification. [$^1$H NMR complies].

Synthesis of (2S,3S)-2-Acetylamino-3-methyl-pentanoic acid (Acid C028): This compound was synthesized following same protocol as for Acid C025 to afford Acid C028 (0.45 g, 40%) as white solid. The crude acid was used as such without further purification. [$^1$H NMR complies].

Synthesis of (S)-2-Acetylamino-3-hydroxy-propionic acid (Acid C029): This compound was synthesized following same protocol as for Acid C025 to afford Acid C029 (0.45 g, 85%) as white solid. The crude acid was used as such without further purification. [¹H NMR complies].

Synthesis of (2S,3S)-3-Methyl-2-[(pyridine-2-carbonyl)-amino]-pentanoic acid (Acid C066): This compound was synthesized following same protocol as for Acid C025 to afford Acid C066 (0.57 g, 68%) as white solid. The crude acid was used as such without further purification. [¹H NMR complies].

Synthesis of (2S,3S)-3-Methyl-2-[(pyridine-3-carbonyl)-amino]-pentanoic acid (Acid C067): This compound was synthesized following same protocol as for Acid C025 to afford Acid C067 (0.14 g, 97%) as white solid. The crude acid was used as such without further purification. [¹H NMR complies].

Synthesis of (2S,3S)-3-Methyl-2-[(pyridine-4-carbonyl)-amino]-pentanoic acid (Acid C068): This compound was synthesized following same protocol as for Acid C025 to afford Acid C068 (0.65 g, 99%) as white solid. The crude acid was used as such without further purification. [¹H NMR complies].

Synthesis of (S)-3-Methyl-2-[(pyridine-2-carbonyl)-amino]-butyric acid (Acid C69): This compound was synthesized following same protocol as for Acid C025 to afford Acid C069 (0.70 g, 98%) as white solid. The crude acid was used as such without further purification. [¹H NMR complies].

Synthesis of (S)-3-Methyl-2-[(pyridine-3-carbonyl)-amino]-butyric acid (Acid C70): This compound was synthesized following same protocol as for Acid C025 to afford Acid C070 (0.16 g, 90%) as white solid. The crude acid was used as such without further purification. [¹H NMR complies].

Synthesis of (S)-3-Methyl-2-[(pyridine-4-carbonyl)-amino]-butyric acid (Acid C71): This compound was synthesized following same protocol as for Acid C025 to afford Acid C071 (0.71 g, 99%) as white solid. The crude acid was used as such without further purification. [¹H NMR complies].

Scheme-5: [Synthesis of Acid C007]

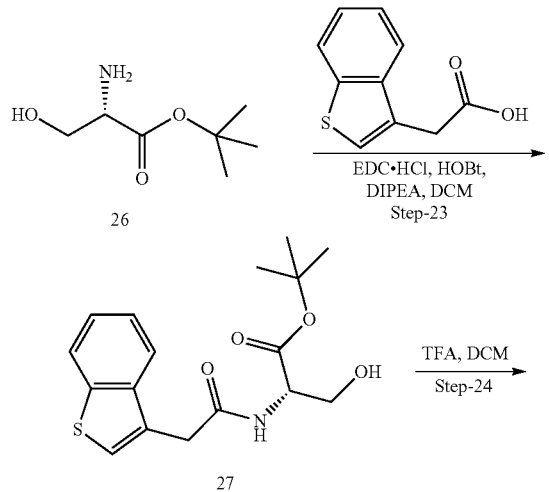

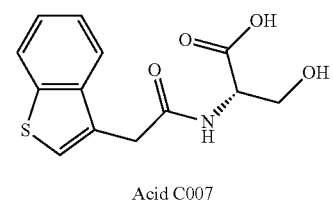

Acid C007

Synthesis of (S)-2-(2-Benzo[b]thiophen-3-yl-acetylamino)-3-hydroxy-propionic acid tert-butyl ester [Scheme-5, Step-23]: To the stirred solution of commercial amino ester (26) (432 mg, 2.19 mmol) and Benzothiophene2-acetic acid (300 mg, 1.56 mmol) in DCM (15 ml) was added EDC.HCl (389 mg, 2.03 mmol), HOBT (316 mg, 2.34 mmol), DIPEA (1.36 ml, 7.80 mmol) and resultant reaction mixture was allowed to stir at room temperature for 16 h. After completion [monitored with TLC and LC-MS] reaction mixture was partitioned between EtOAc [200 mL] and water [100 mL]. Organic layer was separated, dried (MgSO₄) and concentrated under reduced pressure. Resultant crude was purified via column chromatography using silica gel 100-200 mesh as absorbent and 50-60% EtOAc-hexane as eluting solvent to afford compound 27 as off white solid (400 mg, 76.4%). Mass [ESI]: m/z 335.41 [M⁺+1]

Synthesis of (S)-2-(2-Benzo[b]thiophen-3-yl-acetylamino)-3-hydroxy-propionic acid (Acid C007) [Scheme-5, step-24]: To a stirred solution of intermediate (27) (150 mg, 0.45 mmol) in DCM (6 ml), TFA (2 mL) was added and resultant reaction mixture was allowed to stir under inert atmosphere for 1 h at room temperature. Then reaction mixture was concentrated under reduced pressure and washed with n-pentane to afford Acid C007 (130 mg, TFA salt) as sticky solid. [¹H NMR complies].

Scheme-6 [Synthesis of Acid C040]

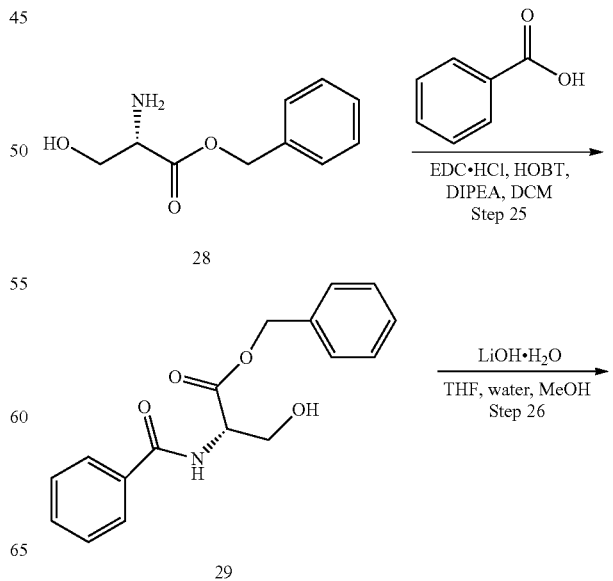

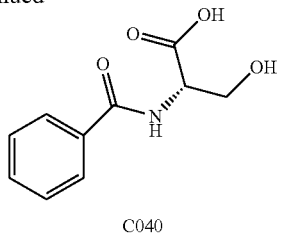

C040

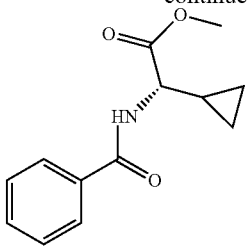

32

Synthesis of (S)-2-(2-Benzo[b]thiophen-3-yl-acetylamino)-3-hydroxy-propionic acid benzyl ester [Scheme-6, Step-25]: To the stirred solution of L-Serine benzyl ester (28) (1.33 g, 5.73 mmol) and Benzoic Acid (2a)(0.50 g, 4.09 mmol) in DCM (15 ml) was added EDC.HCl (1.02 g, 5.32 mmol), HOBT (0.830 g, 6.14 mmol), DIPEA (3.57 ml, 20.46 mmol) and resultant reaction mixture was allowed to stir at room temperature for 16 h. After completion [monitored with TLC and LC-MS] reaction mixture was partitioned between EtAOc [200 mL] and water [100 mL]. Organic layer was separated, dried (MgSO$_4$) and concentrated under reduced pressure. Resultant crude was purified via column chromatography using silica gel 100-200 mesh as absorbent and 50-60% EtOAc-hexane as eluting solvent to afford (29) (1.00 g, 81.6%) as off white solid. Mass [ESI]: m/z 369.44 [M$^+$+1]

Synthesis of (S)-2-(2-Benzo[b]thiophen-3-yl-acetylamino)-3-hydroxy-propionic acid [Scheme-6, Step-26]: To a stirred solution of compound 29 (300 mg, 1.00 mmol) in THF (6 mL):methanol (2 mL):water (2 mL) was added LiOH·H$_2$O (96.1 mg, 4.01 mmol) under ice cold condition and the resultant reaction mixture was allowed to stir at room temperature for 3 hours. After completion [monitored with LC-MS] reaction mixture was concentrated, resultant crude was diluted with water [50 mL] and washed with EtOAc [50 mL]. Aqueous layer was separated and acidified with 1(N) aqueous HCl upto pH 2-3 and extracted with EtOAc [50 mL×2]. Combined organic layer was washed with brine [30 mL], dried over sodium sulphate and concentrated under reduced pressure to afford Acid C040 (125 mg, 59.6%1. Mass [ESI]: m/z 279.32 [M$^+$+1].

Synthesis of (S)-3-Hydroxy-2-phenylacetylamino-propionic acid (C018): This compound was synthesized following same protocol as for Acid C040 to afford Acid C018 (0.12 g, 56.1%) as white solid. Mass [ESI]: m/z 223.23[M$^+$+1].

Scheme-7 [Synthesis of Acid C082]

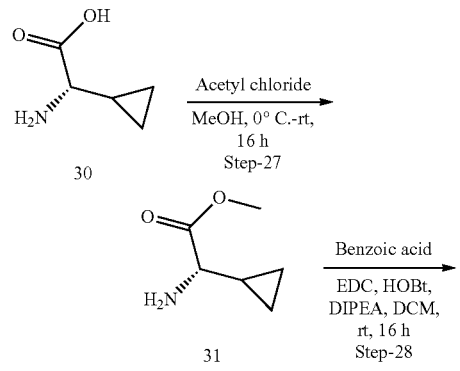

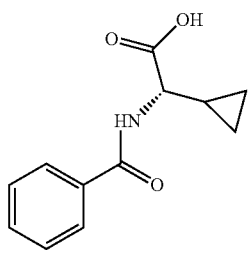

Acid C082

Synthesis of (S)-2-Acetylamino-3-methyl-butyric acid benzyl ester [Scheme 7, Step-27]: To the stirred solution of compound 30 (400 mg, 3.47 mmol) in MeOH [10 mL] was added acetyl chloride [3.72 mL, 52.1 mmol] at 0-5° C. and stirred for 45 minutes. Then temperature was raised to 50° C. and reaction mixture was allowed to stir for 16 h. After completion [monitored with TLC] reaction mixture was partitioned basified with saturated sodium carbonate [100 mL] and extracted with EtOAc [3×100 mL]. Combined organic part was separated, dried [MgSO$_4$] and concentrated under reduced pressure to afford 180 mg compound 31 as yellow solid. [$^1$H NMR complies].

Synthesis of (S)-Benzoylamino-cyclopropyl-acetic acid methyl ester [Scheme 7, step-28]: To the stirred solution of commercial amino ester (31) (180 mg, 1.39 mmol) and Benzoic acid (170 mg, 1.39 mmol) in DCM (10 ml) was added EDC.HCl (347 mg, 1.81 mmol), HOBT (282 mg, 2.09 mmol), DIPEA (1.21 ml, 6.97 mmol) and resultant reaction mixture was allowed to stir at room temperature for 16 h. After completion [monitored with TLC and LC-MS] reaction mixture was partitioned between DCM [200 mL] and water [100 mL]. Organic layer was separated, dried (MgSO$_4$) and concentrated under reduced pressure. Resultant crude was purified via column chromatography using silica gel 100-200 mesh as absorbent and 10-20% EtOAc-hexane as eluting solvent to afford compound 32 (80 mg, 24%) as off white gum. Mass [ESI]: m/z 233.26 [M$^+$+1]

Synthesis of (S)-Benzoylamino-cyclopropyl-acetic acid [Scheme 7, Step 29]: To a stirred solution of compound 32 (80 mg, 1.53 mmol) in THF:Water:MeOH {10 mL, 3:1:1] was added LiOH·H$_2$O (40 mg, 1.0 mmol) under ice cold condition and the resultant reaction mixture was allowed to stir at room temperature for 3 h. After completion reaction mixture was acidified with 1(N) aqueous HCl upto pH 2-3 and extracted with EtOAc [50 mL×2]. Combined organic layer was washed with brine [30 mL], dried over sodium sulphate and concentrated under reduced pressure to afford Acid C082 (65 mg, 86%). Mass [ESI]: m/z 219.23 [M$^+$+1].

Synthesis of (S)-2-(2-Benzo[b]thiophen-3-yl-acetylamino)-3-ethyl-pentanoic acid (Acid C072): This compound was synthesized following same protocol as for Acid C082 to afford Acid C072 (0.20 g, 84%) as white solid. Mass [ESI]: m/z 319.43[M$^+$+1].

Synthesis of (S)-2-Benzoylamino-3-ethyl-pentanoic acid (Acid C073): This compound was synthesized following same protocol as for Acid C082 to afford Acid C073 (0.13 g, 76%) as white solid. Mass [ESI]: m/z 249.31[M$^+$+1].

Synthesis of (S)-(2-Benzo[b]thiophen-3-yl-acetylamino)-cyclopentyl-acetic acid (Acid C075): This compound was synthesized following same protocol as for Acid C082 to afford Acid C075 (0.35 g, 91%) as white solid. Mass [ESI]: m/z 317.41[M$^+$+1].

Synthesis of (S)-Benzoylamino-cyclopentyl-acetic acid (Acid C076): This compound was synthesized following same protocol as for Acid C082 to afford Acid C076 (0.50 g, 81%) as white solid. Mass [ESI]: m/z 247.30[M$^+$+1].

Synthesis of (S)-(2-Benzo[b]thiophen-3-yl-acetylamino)-cyclohexyl-acetic acid (Acid C078): This compound was synthesized following same protocol as for Acid C082 to afford Acid C078 (0.76 g, 92%) as white solid. Mass [ESI]: m/z 331.44[M$^+$+1].

Synthesis of (S)-Benzoylamino-cyclopropyl-acetic acid (Acid C084): This compound was synthesized following same protocol as for Acid C080 to afford Acid C084 (0.07 g, 86%) as white solid. Mass [ESI]: m/z 219.24[M$^+$+1].

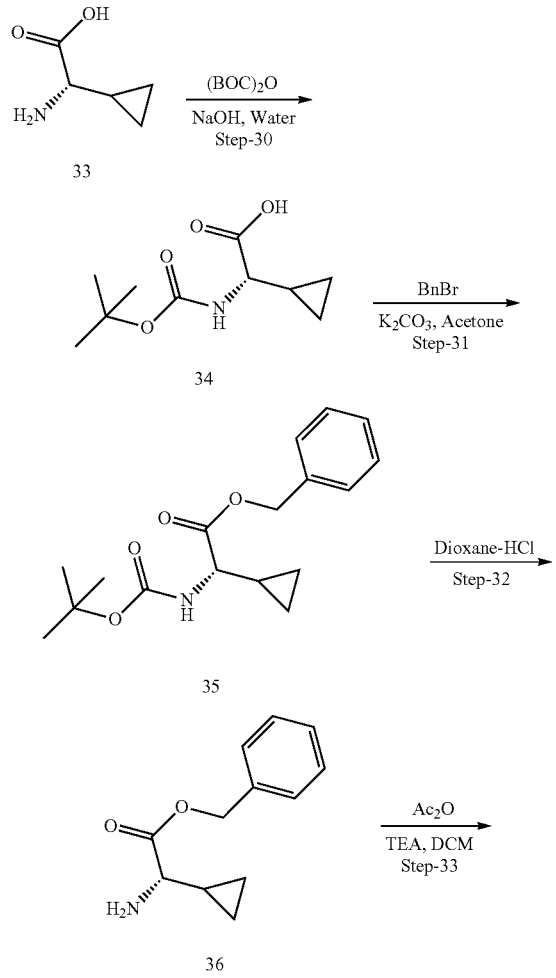

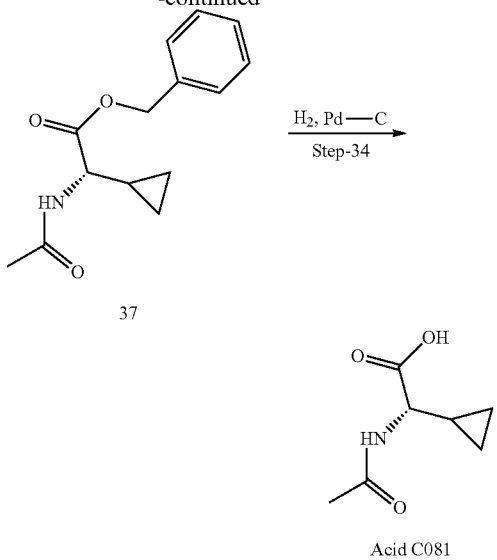

Synthesis of (S)-Amino-cyclopropyl-acetic acid [Scheme 8, Step-30]: To the stirred solution of compound 33 (300 mg, 2.60 mmol) in 2 (M) aqueous NaOH [8 mL] was added boc anhydride (0.72 mL, 3.1 mmol) under 0-5° C. Then reaction mixture was gradually warmed to room temperature and stirred for 16 h. After completion pH of the reaction mixture was adjusted to 3-4 using 1 (N) aqueous HCl and reaction mixture was immediately extracted with EtOAc [3×50 mL]. Organic layer was separated; dried [MgSO$_4$] and concentrated to afford compound 34 [280 mg, 49.9%] as off white solid. [$^1$H NMR complies].

Synthesis of (5)-tert-Butoxycarbonylamino-cyclopropyl-acetic acid benzyl ester [Scheme 8, step-31]: To a stirred solution of compound 34 (280 mg, 1.30 mmol) in acetone (10 mL) was added K$_2$CO$_3$ (435 mg, 3.15 mmol) followed by slow addition of BnBr (389 mg, 2.28 mmol) at room temperature under argon atmosphere. Then the resultant reaction mixture was gradually warmed to reflux, and stirred for 16 h. On completion (confirmed by TLC and LCMS) reaction mixture was evaporated to dryness, partitioned between water [50 mL] and EtOAc (3×50 mL). Organic layer was separated, dried [MgSO$_4$] and concentrated under reduced pressure. Resultant crude was purified by column chromatography using silica gel 100-200 mesh as absorbent and 0-10% EtOAc-Hexane as eluent to afford compound 35 [270 mg, 67.9%] as off white gum. Mass [ESI]: m/z 305.36 [M$^+$+1].

Synthesis of (S)-Amino-cyclopropyl-acetic acid benzyl ester [Scheme 8, Step no-32]: To a stirred solution of compound 35 (280 mg, 0.917 mmol) in 3 mL Dioxane was added 6 mL of 4 (M) HCl in dioxane, at room temperature under argon atmosphere and allowed to stir at room temperature for 2 h. After completion (confirmed by TLC and LCMS), reaction mixture was basified with saturated aqueous Na$_2$CO$_3$ solution [50 mL] and extracted with EtOAc (3×75 mL). Organic layer was separated, washed with water [50 mL], brine [50 mL], then dried [MgSO$_4$] and concentrated under reduced pressure to afford compound 36 [180 mg, 95.6%] as yellow liquid. Mass [ESI]: m/z 205.25 [M$^+$+1].

Synthesis of (S)-Amino-cyclopropyl-acetic acid benzyl ester [Scheme 8, Step no-33]: To a stirred solution of compound 36 (130 mg, 0.633 mmol) in 10 mL DCM, was added Et₃N (0.15 mL, 1.07 mmol) at room temperature under nitrogen atmosphere. The resulting mixture was cooled to 0° C. and Ac₂O (0.15 mL, 1.6 mmol) was slowly added to the reaction mixture. After addition reaction mixture was warmed to room temperature and stirred for 16 h. After completion [confirmed by LC-MS and TLC] reaction mixture was partitioned between water [100 mL] and DCM [3×75 mL]. Organic layer was separated; washed with brine [50 mL], dried [MgSO₄] and evaporated. Resultant crude was purified by column chromatography (eluent: 30-60% EtOAc-hexane, absorbent silica gel-100-200 mesh) to afford compound 37 [80 mg, 51%] as off-white solid. Mass [ESI]: m/z 247.29 [M⁺+1].

Synthesis of (S)-Amino-cyclopropyl-acetic acid benzyl ester [Scheme 8, Step no-34]: To a stirred solution of compound 37 (90 mg, 0.36 mmol) in 8 mL EtOH, 50 mg of 10% by weight Pd/C (wet) powder was added and resultant suspension was allowed to stir under H2 balloon pressure at room temperature for 13 h. After completion (confirmed by TLC), reaction mixture was filtered through a celite bed, bed was further washed with EtOAc [50 mL] and EtOH [50 mL]. Filtrate was concentrated under reduced pressure to afford Acid C081 [60 mg, crude compound] as off white gum. [¹H NMR complies].

Synthesis of (S)-Benzoylamino-cyclopropyl-acetic acid (Acid C083): This compound was synthesized following same protocol as for Acid C081 to afford Acid C083 (0.07 g, 86%) as white solid. Mass [ESI]: m/z 219.24[M⁺+1].

Scheme-9 [Synthesis of Acid C077]

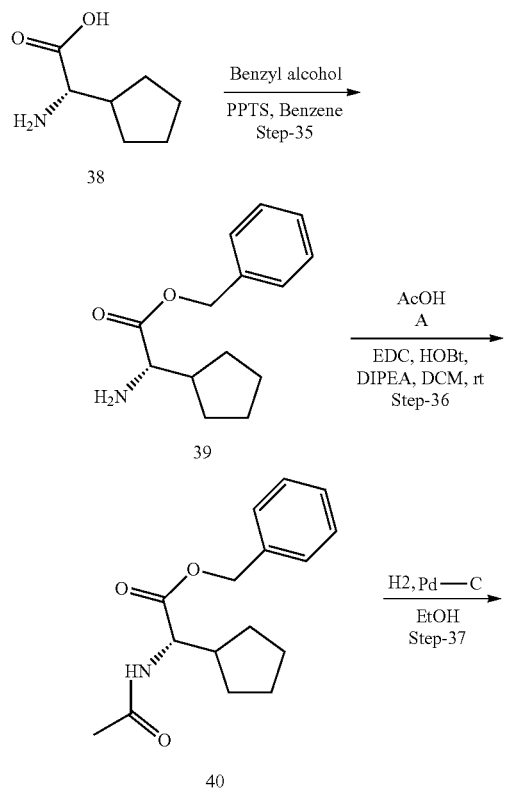

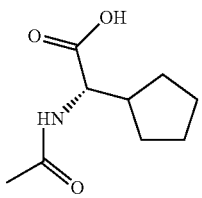

Acid C077

Synthesis of (S)-Amino-cyclopentyl-acetic acid benzyl ester [Scheme 9, Step-35]: To a stirred solution of compound 38 (500 mg, 3.49 mmol) in 10 mL Benzene was added p-TsOH (721 mg, 4.19 mmol) and benzyl alcohol (1.08 mL, 10.5 mmol) at rt under nitrogen atmosphere. The resultant reaction mixture was then heated to reflux and continued at the same for 16 h. After completion (confirmed by TLC and LCMS), reaction mixture was concentrated under reduced pressure and resultant crude was partitioned between water [10 mL] and EtOAc (3×75 mL). Organic layer was separated, washed with brine and dried over sodium sulphate and concentrated under reduced pressure to afford crude compound 39 [750 mg] as pale yellow liquid. [¹H NMR complies].

Synthesis of (S)-Amino-cyclopentyl-acetic acid benzyl ester [Scheme 9, step-36]: To a stirred solution of compound 39 (450 mg, 1.93 mmol), AcOH (0.11 mL, 1.93 mmol) and HOBt (391 mg, 2.89 mmol) in 15 mL DCM, was added DIPEA (1.68 mL, 9.64 mmol) drop-wise and stirred at 0° C. for 10 min under inert atmosphere. To the resulting mixture EDC-HCl (480.667 mg, 2.507 mmol) was added and the reaction was allowed to stir at rt for 16 h. After completion (confirmed by TLC and LCMS), reaction mixture was partitioned between water [100 mL] and DCM [3×70 mL]. Organic layer was separated, washed with brine [50 mL], dried [MgSO₄] and concentrated. Resultant crude was purified by column chromatography (eluent: 20-30% EA-hexane, absorbent SiO2) to provide of compound 40 [350 mg, 65.9%] as white solid. Mass [ESI]: m/z 275.34 [M⁺+1].

Synthesis of (S)-Acetylamino-cyclopentyl-acetic acid [Scheme 9, Step no-37]: To a stirred solution of compound 40 (350 mg, 1.27 mmol) in 5 mL EtOH, 80 mg of 10% by weight Pd/C (wet) powder was added and resultant suspension was allowed to stir under H2 balloon pressure at room temperature for 13 h. After completion (confirmed by TLC), reaction mixture was filtered through a celite bed, bed was further washed with EtOAc [50 mL] and EtOH [50 mL]. Filtrate was concentrated under reduced pressure to afford Acid C077 [200 mg, crude compound] as white solid. [¹H NMR complies].

Synthesis of (S)-Acetylamino-cyclohexyl-acetic acid (Acid C080): This compound was synthesized following same protocol as for Acid C077 to afford Acid C080 (151 mg, 99.5%) as white solid. [¹H NMR complies].

Scheme 10 [Synthesis acid Acid C074]

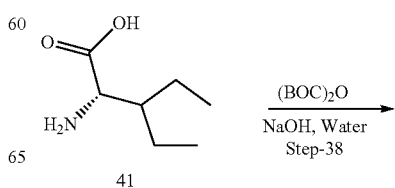

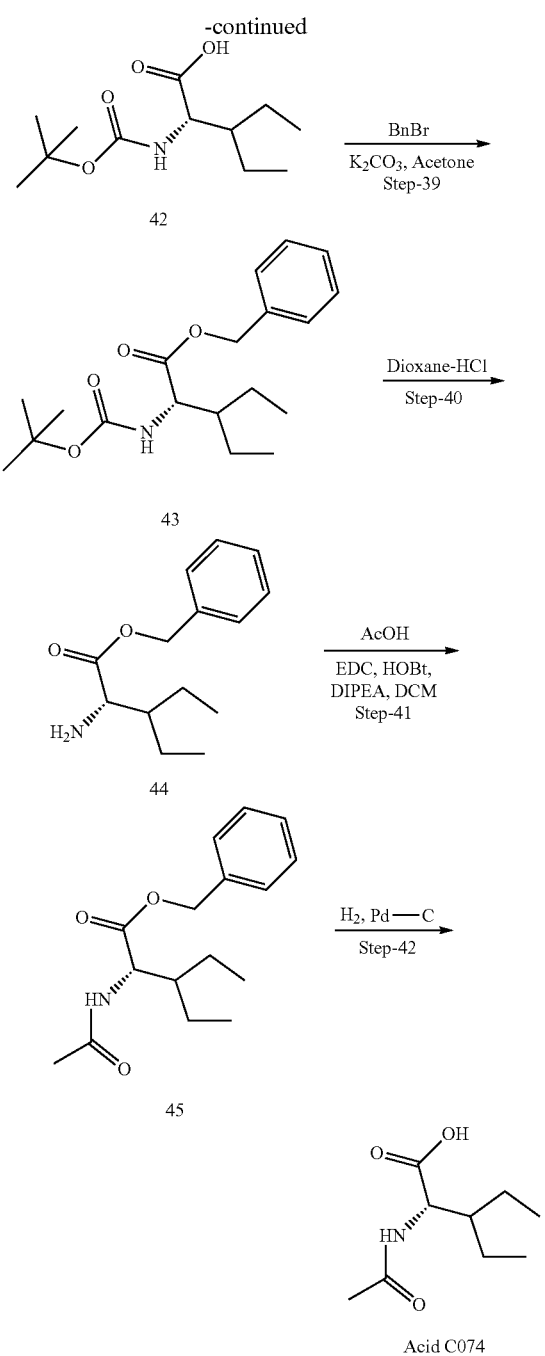

Synthesis of (S)-2-tert-Butoxycarbonylamino-3-ethyl-pentanoic acid [Scheme 10, Step-38]: To the stirred solution of compound 41 (200 mg, 1.38 mmol) in 2 (M) aqueous NaOH [4 mL] was added boc anhydride (0.38 mL, 1.65 mmol) under 0-5° C. Then reaction mixture was gradually warmed to room temperature and stirred for 16 h. After completion pH of the reaction mixture was adjusted to 3-4 using 1 (N) aqueous HCl and reaction mixture was immediately extracted with EtOAc [3×50 mL]. Organic layer was separated; dried [MgSO4] and concentrated to afford compound 42 [250 mg, 74%] as off white solid. [$^1$H NMR complies].

Synthesis of (S)-2-tert-Butoxycarbonylamino-3-ethyl-pentanoic acid benzyl ester [Scheme 10, step-39]: To a stirred solution of compound 42 (250 mg, 1.02 mmol) in acetone (5 mL) was added K2CO3 (341 mg, 2.47 mmol) followed by slow addition of BnBr (0.21 mL, 1.78 mmol) at room temperature under argon atmosphere. Then the resultant reaction mixture was gradually warmed to reflux, and stirred for 16 h. On completion (confirmed by TLC and LCMS) reaction mixture was evaporated to dryness, partitioned between water [50 mL] and EtOAc (3×50 mL). Organic layer was separated, dried [MgSO4] and concentrated under reduced pressure. Resultant crude was purified by column chromatography using silica gel 100-200 mesh as absorbent and 0-10% EtOAc-Hexane as eluent to afford compound 43 [200 mg, 51.5%] as off white gum. Mass [ESI]: m/z 335.45 [M$^+$+1].

Synthesis of (S)-2-Amino-3-ethyl-pentanoic acid benzyl ester [Scheme 10, Step no-40]: To a stirred solution of compound 43 (0.20 g 0.60 mmol) in 3 mL Dioxane was added 6 mL of 4 (M) HCl in dioxane, at room temperature under argon atmosphere and allowed to stir at room temperature for 2 h. After completion (confirmed by TLC and LCMS), reaction mixture was basified with saturated aqueous Na2CO3 solution [50 mL] and extracted with EtOAc (3×75 mL). Organic layer was separated, washed with water [50 mL], brine [50 mL], then dried [MgSO4] and concentrated under reduced pressure to afford compound 44 [200 mg] as HCl salt. Mass [ESI]: m/z 235.33 [M$^+$+1].

Synthesis of (S)-2-Acetylamino-3-ethyl-pentanoic acid benzyl ester [Scheme 10, Step no-41]: To a stirred solution of compound 44 (200 mg, 0.85 mmol) in DCM (5 mL) was added compound AcOH (0.05 mL, 0.85 mmol), EDC.HCl (212 mg, 1.11 mmol), HOBT (172 mg, 1.28 mmol), DIPEA (0.74 mL, 1.25 mmol) and the reaction mixture was stirred for 16 h at room temperature. After completion [monitored by LC-MS and TLC (30% EtOAc-Hexane, Rf-0.3)] reaction mixture was partitioned between DCM (50 mL) and water (30 mL). Organic layer was separated, dried over sodium sulphate and concentrated under reduced pressure. The crude was purified through chromatography (0-20% EtOAc/Hexane, SiO2) to provide compound 45 (100 mg, Yield: 42.4%) as white solid. Mass [ESI]: m/z 277.37 [M$^+$+1].

Synthesis of (S)-2-Acetylamino-3-ethyl-pentanoic acid [Scheme 10, Step no-42]: To a stirred solution of compound 45 (100 mg, 0.36 mmol) in 5 mL EtOH, 30 mg of 10% by weight Pd/C (wet) powder was added and resultant suspension was allowed to stir under H2 balloon pressure at room temperature for 13 h. After completion (confirmed by TLC), reaction mixture was filtered through a celite bed, bed was further washed with EtOAc [50 mL] and EtOH [50 mL]. Filtrate was concentrated under reduced pressure to afford Acid C074 [30 mg, 67.5%] as off white gum. [$^1$H NMR complies].

Scheme-11 [Synthesis of Acid C055]

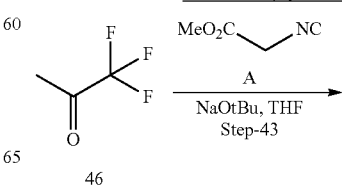

46

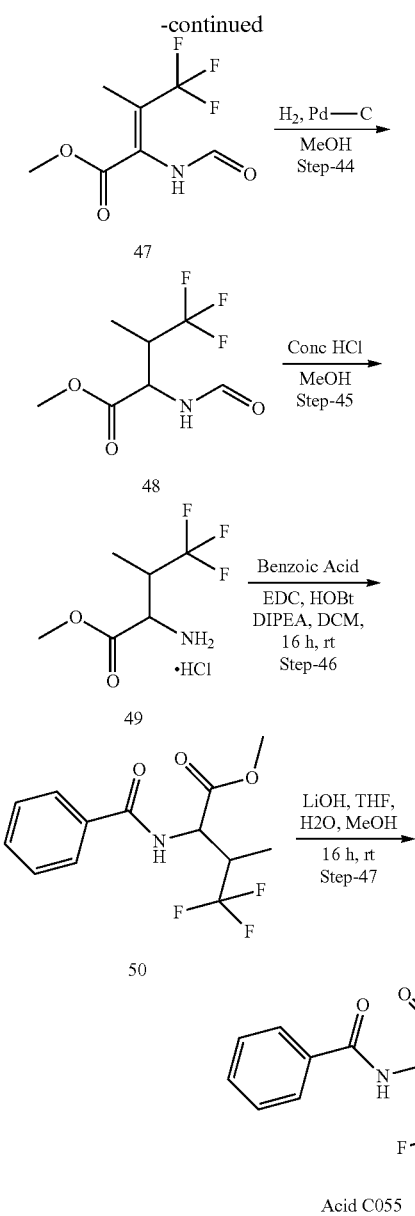

Synthesis of (Z)-4,4,4-Trifluoro-2-formylamino-3-methyl-but-2-enoic acid methyl ester [Scheme-11, step-43]: To a stirred solution of dry NaOtBu (2.13 gm, 22.2 mmol) in THF (20 ml) at −60° C. under inert atmosphere, methyl-2-isocyanoacetate (1.83 ml, 20.2 mmol) in 5 ml THF was added dropwise for 5 min at the same temperature and the reaction mixture was stirred for 30 mins. After that compound 46 (2.33 ml, 25.6 mmol) in ml THF was added to the reaction mixture at −60° C. and the reaction mixture was stirred for another 1 hour and then temp was gradually increased to room temperature. After completion [monitored with TLC (40% EtOAc-Hexane, Rf-0.4) and LC-MS]; reaction mixture was quenched with 1(N) aqueous HCl solution up to pH of 4-5 and the mixture was stirred for an hour. Then reaction mixture was partitioned between EtOAc [5×50 mL] and water [75 mL]. Organic layer was separated, dried (MgSO₄) and concentrated under reduced pressure. Resultant crude was purified via column chromatography using silica gel 100-200 mesh as absorbent and 20-30% EtOAc-hexane as eluting solvent to afford compound 47 (1.4 g, 33%) as colorless oil. Mass [ESI]: m/z 211.14 [M⁺+1].

Synthesis of 4,4,4-Trifluoro-2-formylamino-3-methyl-butyric acid methyl ester [Scheme 11, step-44]: To a suspended solution of compound 47 (1.40 g, 6.63 mmol) in MeOH (20 mL), 10% Pd/C powder (750 mg, wet) was added and the reaction mixture was subjected to a parr shaker at 55 Psi $H_2$ pressure for 16 h. After completion [monitored by TLC (70% EtOAc-Hexane, Rf-0.1) and LC-MS], the reaction mixture was filtered through celite bed and filtrate part was concentrated under reduced pressure to afford compound 48 (1.2 g, 85%) as white solid. Mass [ESI]: m/z 213.16 [M⁺+1].

Synthesis of 4,4,4-Trifluoro-2-formylamino-3-methyl-butyric acid methyl ester (HCl Salt) [Scheme-11, Step-45]: To the stirred solution of compound 48 (1.00 g, 4.68 mmol) in MeOH (10 mL), conc. HCl (0.187 ml, 6.09 mmol) was added and the reaction mixture was heated at 55° C. for 4 hours under inert atmosphere. After completion [monitored by TLC and LC-MS], the reaction mixture was evaporated under reduced pressure to obtain the solid material which was washed by ether to get the crude compound 49 (1.1 g) as HCl salt.

Synthesis of 2-Benzoylamino-4,4,4-trifluoro-3-methyl-butyric acid methyl ester [Scheme 11, Step-46]: To a stirred solution of Benzoic acid (0.10 g, 0.82 mmol) and compound 49 (0.17 g, 0.90 mmol) in DCM (4 mL), DIPEA (0.71 mL, 4.1 mmol) was added, followed by the addition of HOBT (0.15 g, 1.1 mmol) and EDC.HCl (0.24 g, 1.3 mmol) and the reaction mixture was stirred for 16 h at room temperature. After completion [monitored by LC-MS and TLC (30% EtOAc-Hexane, Rf-0.4)], reaction mixture was partitioned between DCM (25 mL) and water (15 mL). Organic layer was separated, washed with water and brine, dried over Na2SO4 and concentrated under reduced pressure. The resultant crude was purified through column chromatography (30% EtOAc/Hexane, SiO2) to provide compound 51 (0.15 mg, Yield: 62%) as white solid. Mass [ESI]: m/z 289.26 [M⁺+1].

Synthesis of 2-Benzoylamino-4,4,4-trifluoro-3-methyl-butyric acid [Scheme 11, Step-47]: To a stirred solution of compound 50 (0.15 g 0.51 mmol) in THF (3 mL):MeOH (1 mL):H2O (1 mL), was added LiOH·H₂O (64.1 mg, 1.54 mmol), and the resultant reaction mixture was stirred for 3 hours at ambient temperature. After completion [monitored by LC-MS], methanol was evaporated under reduced pressure. The resultant crude was diluted with water [25 mL] and washed with EtOAc [25 mL]. Aqueous layer was separated and acidified with 1(N) aqueous HCl upto pH 2-3 and extracted with EtOAc [25 mL×2]. Combined organic layer was washed with water and brine, dried over solid anhydrous Na2SO4 and concentrated under reduced pressure to afford Acid C055 (13 mg, Yield: 92%) as white solid. Mass [ESI]: m/z 275.23 [M⁺+1].

Scheme-12 [Synthesis of acid Acid C058]

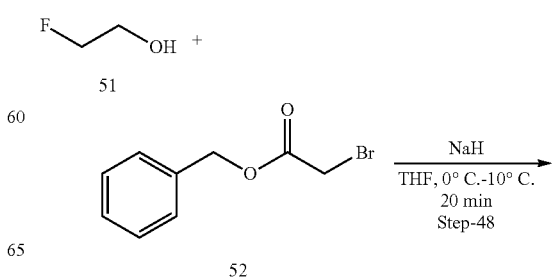

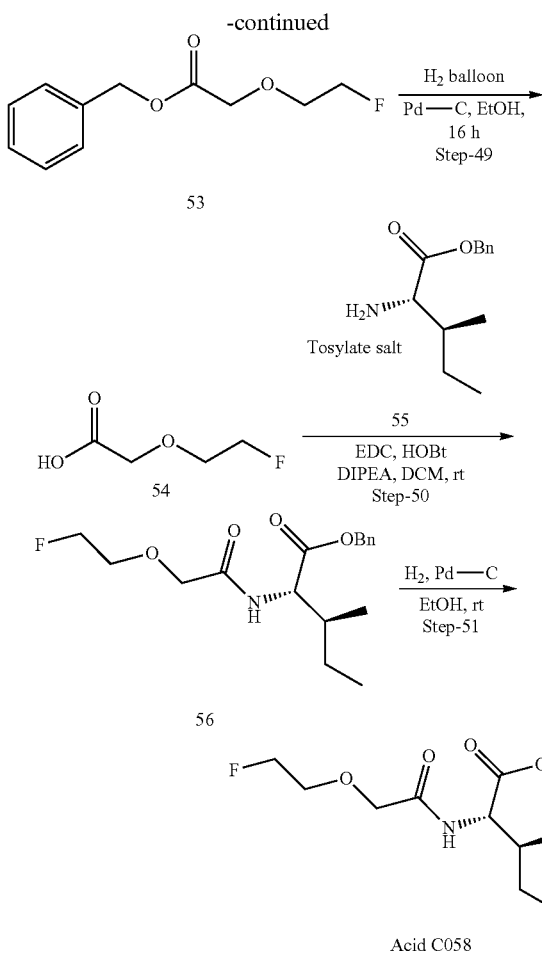

53

54

56

Acid C058

Synthesis of (2-Fluoro-ethoxy)-acetic acid benzyl ester [Scheme 12, Step-48]: To a stirred solution of compound 51 (0.26 mL, 4.37 mmol) in 5 mL THF, was added NaH (60%, 262 mg, 6.55 mmol) portion-wise at 0° C. under argon atmosphere and allowed to stir at the same temperature for 10 min Compound 52 (0.69 mL, 4.36 mmol) was added to the reaction mixture and stirred for 10 min at 10-15° C. After TLC analysis [10% EtOAc/hexane, $R_f$ 0.5, total reaction time: maximum 15-20 min] reaction mixture was concentrated under reduced pressure and resultant crude was partitioned between EtOAc [150 mL] and water [100 mL]. Organic part was separated, dried (MgSO$_4$) and concentrated under reduced pressure. Crude residue thus obtained was purified by column purification under gradient elution of 2-8% EtOAc/hexane to afford desired compound i.e. compound 53 (350 mg, 35.3%) as colorless liquid. Mass [ESI]: m/z 212.22 [M$^+$+1]

Synthesis of (2-Fluoro-ethoxy)-acetic acid [Scheme 12, Step-49]: To a stirred solution of compound 53 (1.6 g, 7.539 mmol) in 10 mL EtOH, 10% Pd/C (480 mg, wet) powder was added and resultant reaction mixture was allowed to stir under H$_2$ balloon pressure for 16 h at room temperature. Then reaction mixture was filtered through celite bed and filtrate part was concentrated under reduced pressure to afford compound 54 (830 mg, 90%) as pale brown gummy liquid. [$^1$H NMR complies]

Synthesis of 2-[2-(2-Fluoro-ethoxy)-acetylamino]-3-methyl-pentanoic acid benzyl ester [Scheme 12, Step-50]: To a stirred solution of compound 54 (415 mg, 3.40 mmol), compound 55 (1.34 g, 3.40 mmol) and HOBt (689 mg, 5.10 mmol) in DCM (10 mL) was added DIPEA (2.96 mL, 16.99 mmol) and stirred at 0° C. for 10 min under inert atmosphere. To the resulting mixture EDC.HCl (847 mg, 4.42 mmol) was added and the reaction was continued at room temperature for 16 h. On completion of the reaction (confirmed by TLC and LCMS), the mixture was extracted by DCM (2×10 mL), washed with water, brine, dried (MgSO$_4$) and concentrated. It was then purified by column chromatography (10-35% EtOAc/hexane, SiO$_2$) to provide compound 56 (670 mg, 63.2%) as colorless liquid. Mass [ESI]: m/z 325.38 [M$^+$+1]

Synthesis of 2-[2-(2-Fluoro-ethoxy)-acetylamino]-3-methyl-pentanoic acid [Scheme 12, Step-51]: To a stirred solution of compound 56 (400 mg, 1.23 mmol) in EtOH (8 mL), 10% Pd/C(wet) (120 mg) powder was added and resultant reaction mixture was allowed to stir under H$_2$ balloon pressure for 16 h at room temperature. Then reaction mixture was filtered through celite bed and filtrate part was concentrated under reduced pressure to afford Acid C058 (270 mg, 93.3%) as off white gummy liquid. [$^1$H NMR complies].

Synthesis of (S)-2-[2-(2-Fluoro-ethoxy)-acetylamino]-3-methyl-butyric acid (Acid C056): This compound was synthesized following same protocol as for Acid C058 to afford Acid C056 (0.45 g, 97%) as off-white gum. [$^1$H NMR complies].

Scheme-13 [Synthesis of C086]

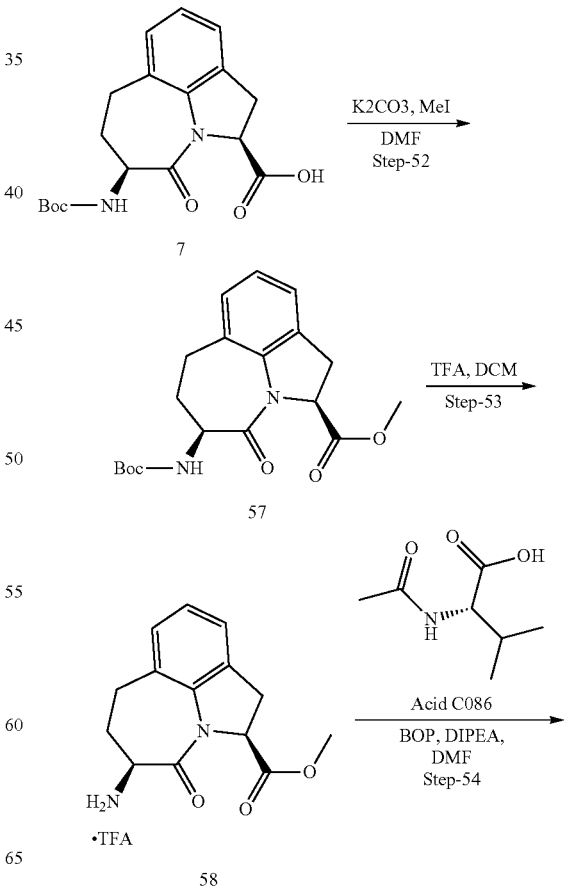

7

57

58

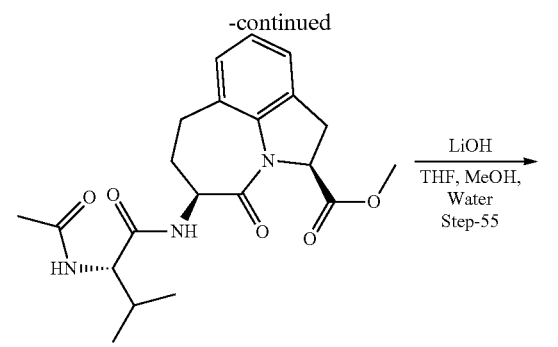

59

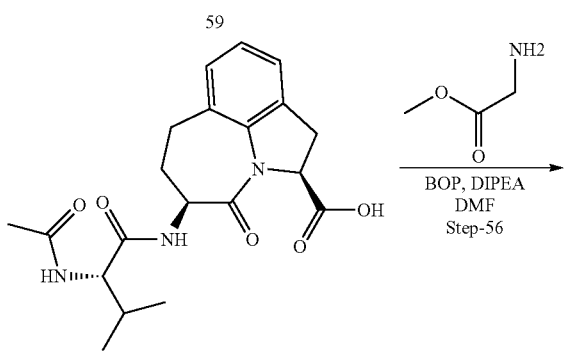

60

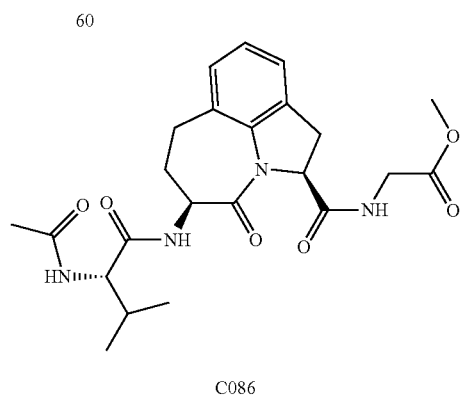

C086

Synthesis of (2S,5S)-5-tert-Butoxycarbonylamino-4-oxo-1,2,4,5,6,7-hexahydro-azepino[3,2,1-hi]indole-2-carboxylic acid methyl ester [Scheme 13, Step-52]: To a stirred solution of compound 7 (10.0 g, 28.9 mmol) in DMF (30.0 mL), was added K$_2$CO$_3$ (11.98 g, 86.71 mmol) followed by slow addition of MeI (3.60 mL, 57.8 mmol) and the resultant reaction mixture was stirred for 16 h at room temperature. After completion [monitored by LC-MS and TLC (20% EtOAc-Hexane, Rf-0.7)] reaction mixture was partitioned between EtOAc (150 mL) and water (75 mL). Organic layer was separated, washed with water and brine, dried (MgSO$_4$) and concentrated under reduced pressure. The resultant crude was purified through chromatography (eluent 0-10% EtOAc-Hexane, Absorbent-SiO2) to provide compound 57 (8.0 g, 77%) as white solid. [$^1$H NMR complies].

Synthesis of (2S,5S)-5-Amino-4-oxo-1,2,4,5,6,7-hexahydro-azepino[3,2,1-hi]indole-2-carboxylic acid methyl ester (TFA Salt) [Scheme 13, Step-53]: To a stirred solution of compound 57 (5.00 g, 13.9 mmol) in 5 mL DCM was added 15 mL TFA:DCM (1:1) at room temperature under nitrogen atmosphere and stirred for 2 h. On completion of the reaction [confirmed by LC-MS and TLC (20% EtOAc-Hexane, Rf-0.1)], reaction mixture was concentrated under reduced pressure and azeotroped with toluene (3-4 times) to afford compound 58 (5.50 g, crude compound) as brown gum. Mass [ESI]: m/z 260.28 [M$^+$+1].

Synthesis of (2S,5S)-5-((S)-2-Acetylamino-3-methyl-butyrylamino)-4-oxo-1,2,4,5,6,7-hexahydro-azepino[3,2,1-hi]indole-2-carboxylic acid methyl ester [Scheme 13, Step-54]: To a stirred solution of compound 58 (200 mg, 0.77 mmol) and Acid C086 (134 mg, 0.85 mmol) in 2 mL DMF, was added DIPEA (0.80 mL, 4.62 mmol) dropwise, followed by the addition of BOP reagent (680 mg, 1.54 mmol) and allowed to stir at room temperature for 16 h. After completion [monitored with TLC] reaction mixture was partitioned between EtOAc (50 mL) and water (50 mL). Organic layer was separated, washed with water and brine, dried [MgSO$_4$] and concentrated under reduced pressure to provide compound 59 (0.18 g, Yield: 58.3%) as white solid. Mass [ESI]: m/z 401.47 [M$^+$+1].

Synthesis of (2S,5S)-5-((S)-2-Acetylamino-3-methyl-butyrylamino)-4-oxo-1,2,4,5,6,7-hexahydro-azepino[3,2,1-hi]indole-2-carboxylic acid [Scheme 13, Step-55]: To a solution of compound 59 (180 mg, 0.45 mmol) in THF:MeOH:WATER (6:2:2 ml) was added LiOH·H$_2$O (75 mg, 1.80 mmol) at ice cold condition and the resultant solution was stirred for 3 h at room temperature. After completion [monitored with LC-MS] reaction mixture was concentrated, resultant crude was diluted with water [20 mL] and washed with EtOAc [20 mL]. Aqueous layer was separated and acidified with 1(N) aqueous HCl upto pH 2-3 and extracted with EtOAc [50 mL×2]. Combined organic layer was washed with brine [30 mL], dried [MgSO$_4$] and concentrated under reduced pressure to afford compound 60 [140 mg, Yield—80.5%] as white solid. Mass [ESI]: m/z 387.44 [M$^+$+1].

Synthesis of {[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-acetic acid methyl ester [Scheme 13, Step-56]: To a stirred solution of compound 60 (140 mg, 0.36 mmol) and amino-acetic acid methyl ester (49.7 mg, 0.40 mmol) in 1.5 mL DMF, was added DIPEA (0.38 mL, 2.17 mmol) drop-wise, followed by addition of BOP reagent (319 mg, 0.72 mmol) under argon atmosphere at room temperature and stirred for 16 h. After completion (confirmed by LCMS), crude reaction mixture was submitted for reverse phase prep HPLC purification to afford faster moving as major isomer C086 [25 mg] as white solid. Mass [ESI]: m/z 458.52 [M$^+$+1].

Synthesis of (R)-2-{[(2S,5 S)-5-((S)-2-Acetylamino-3-methyl-butyrylamino)-4-oxo-1,2,4,5,6,7-hexahydro-azepino[3,2,1-hi]indole-2-carbonyl]-amino}-propionic acid methyl ester [C088]: This compound was synthesized following same protocol as for C086. Prep HPLC purification provided 12 mg of faster eluting as major isomer of C088 [12 mg] as white solid. Mass [ESI]: m/z 472.55[M$^+$+1].

Synthesis of (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-propionic acid methyl ester [C090]: This compound was synthesized following same protocol as for C086. Prep HPLC purification provided 12 mg of faster eluting as major isomer of C090 [12 mg] as white solid. Mass [ESI]: m/z 472.55[M$^+$+1].

Synthesis of 2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-3-hydroxy-propionic acid methyl ester [C091]: This compound was synthesized following same protocol as for C086. Prep HPLC purification provided faster eluting as major isomer of C091 [4 mg] as white solid. Mass [ESI]: m/z 488.55[M$^+$+1].

Synthesis of (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-succinic acid dimethyl ester [C093]: This compound was synthesized following same protocol as for C086. Prep HPLC purification provided faster eluting as major isomer of C093 [20 mg] as white solid. Mass [ESI]: m/z 530.58[M$^+$+1].

Synthesis of (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-pentanedioic acid dimethyl ester [C095]: This compound was synthesized following same protocol as for C086. Prep HPLC purification provided 4.5 mg of faster eluting as major isomer of C095 [4.5 mg] as white solid. Mass [ESI]: m/z 544.61[M$^+$+1].

Synthesis of (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-propionic acid [C089]: This compound was synthesized following same protocol as for C085. Prep HPLC purification provided faster eluting as major isomer of C089 [3.8 mg] as white solid. Mass [ESI]: m/z 458.52[M$^+$+1].

Synthesis of (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-succinic acid [C092]: This compound was synthesized following same protocol as for C085. Prep HPLC purification provided faster eluting as major isomer of C092 [10 mg] as white solid. Mass [ESI]: m/z 502.53[M$^+$+1].

Synthesis of (S)-2-{[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-pentanedioic acid [C094]: This compound was synthesized following same protocol as for C085. Prep HPLC purification provided faster eluting as major isomer of C094 [10 mg] as white solid. Mass [ESI]: m/z 502.53[M$^+$+1].

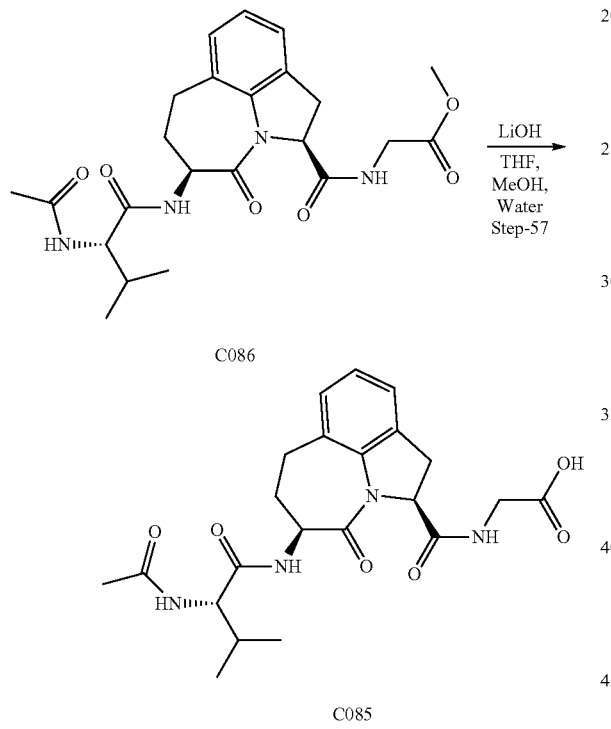

Scheme-14 [Synthesis of C085]

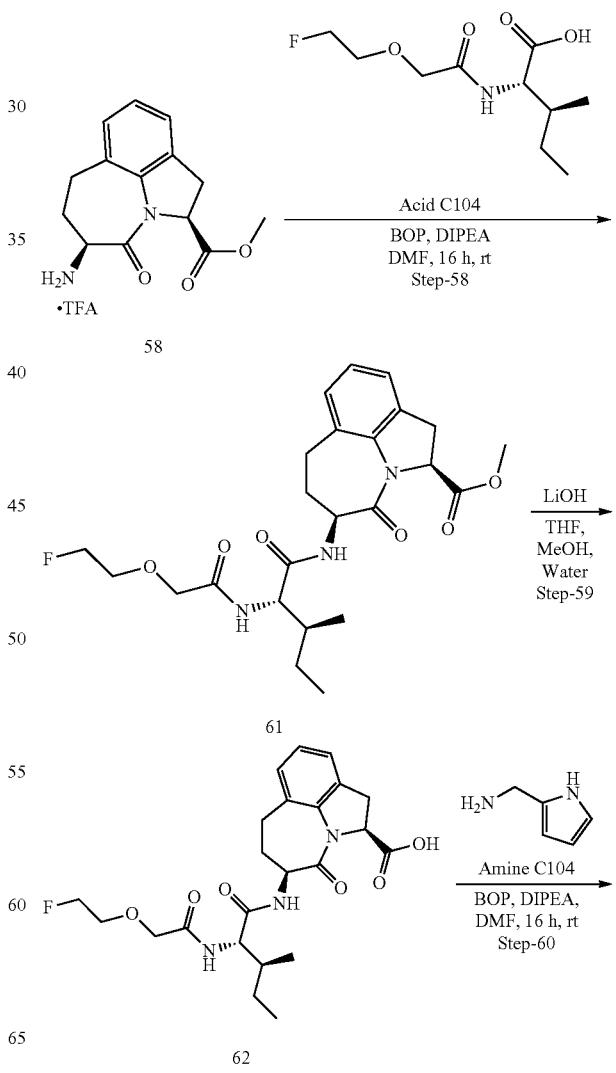

Scheme-15 [Sythesis of C104]

Synthesis of {[(2S,5S)-5-((S)-2-Acetylamino-3-methyl-butyrylamino)-4-oxo-1,2,4,5,6,7-hexahydro-azepino[3,2,1-hi]indole-2-carbonyl]-amino}-acetic acid [C085]: To the stirred solution of C086 (100 mg, 0.26 mmol) in THF:Methanol:H2O=3:1:1 (5 ml), LiOH·H$_2$O (16.3 mg, 0.39 mmol) was added at OC and the reaction mixture was stirred for 3 h at room temperature. As per LCMS, SM was consumed and desired product was formed. On completion of the reaction (confirmed by LCMS), crude reaction mixture was submitted for reverse phase prep HPLC purification to afford faster moving as major isomer C085 [7 mg] as white solid. Mass [ESI]: m/z 444.49 [M$^+$+1].

Synthesis of (R)-2-{[(2S,5 S)-5-((S)-2-Acetylamino-3-methyl-butyrylamino)-4-oxo-1,2,4,5,6,7-hexahydro-azepino[3,2,1-hi]indole-2-carbonyl]-amino}-propionic acid [C087]: This compound was synthesized following same protocol as for C085. Prep HPLC purification provided faster eluting as major isomer of C087 [7.7 mg] as white solid. Mass [ESI]: m/z 458.52[M$^+$+1].

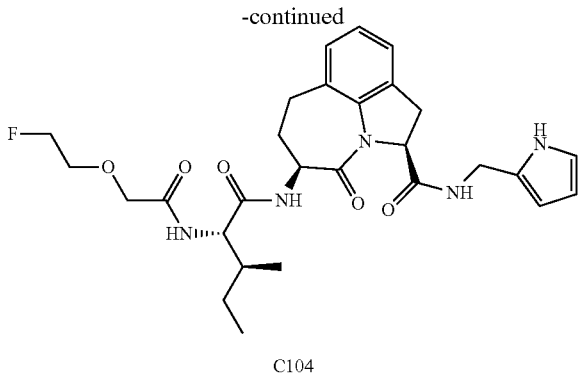

C104

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid methyl ester [Scheme-15, Step-58]: To a stirred solution of compound 58 (4.00 g, 10.7 mmol), Acid C104 (2.52 g, 10.7 mmol) in 10 mL DMF, was added DIPEA (9.28 mL, 53.5 mmol) drop-wise and stirred at room temperature for 10 min under inert atmosphere. Then BOP (9.46 g, 21.4 mmol) was added to the reaction mixture and allowed to stir at room temperature for 16 h. After completion[confirmed by TLC (70% EtOAc-Hexane, Rf-0.3) and LC-MS], reaction mixture was partitioned between EtOAc (150 mL) and water (75 mL). Organic layer was separated brine [50 mL], dried [MgSO₄] and concentrated under reduced pressure. The resultant crude was purified through chromatography (50-75% EtOAc-Hexane, SiO2) to afford compound 61 (3.25 g, 77.1%) as off-white solid.

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid [Scheme-15, Step-59]: To a stirred solution of compound 61 (3.90 g, 8.18 mmol) in THF (24 mL):MeOH (8 mL):water (8 mL) was added LiOH·H₂O (343 mg, 2.29 mmol) under ice cold condition and the resultant reaction mixture was allowed to stir at room temperature for 2 hour. After completion [monitored by LC-MS and TLC 10% MeOH-DCM, Rf-0.2] reaction mixture was concentrated, resultant crude was diluted with water [50 mL] and washed with EtOAc [50 mL]. Aqueous layer was separated and acidified with 1(N) aqueous HCl upto pH 2-3 and extracted with EtOAc [50 mL×2]. Combined organic layer was washed with brine, dried [MgSO₄] and concentrated under reduced pressure to afford compound 62 (3.2 g, 84%) as white solid.

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (1H-pyrrol-2-ylmethyl)-amide (C104) [Scheme-15, Step-60]: To a stirred solution of compound 62 (100 mg, 0.216 mmol) and Amine C104 (26.6 mg, 0.238 mmol) in DMF (2 mL) was added DIPEA (0.23 mL, 1.3 mmol), followed by the addition of BOP (191 mg, 0.432 mmol) and resultant reaction mixture was allowed to stir at room temperature for 16 h. After completion (confirmed by LC-MS), crude reaction mixture was submitted for reverse phase prep HPLC purification to afford 20 mg of faster eluting as major isomer [Isomer 1] of C104 as white solid. Mass [ESI]: m/z 541.63 [M⁺+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (furan-2-ylmethyl)-amide [C105""]: This compound was synthesized following same protocol as for C104. Preparative HPLC purification provided 25 mg of faster eluting isomer [Isomer 1] of C105 as white solid. Mass [ESI]: m/z 542.61 [M⁺+1]

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (thiophen-2-ylmethyl)-amide [C106""]: This compound was synthesized following same protocol as for C104. Preparative HPLC purification provided 40 mg of faster eluting isomer [Isomer 1] of C106 as white solid. Mass [ESI]: m/z 558.68 [M⁺+1].

Synthesis of (2S, 5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (1H-pyrrol-3-ylmethyl)-amide [C107""]: This compound was synthesized following same protocol as for C104. Preparative HPLC purification provided 40 mg of faster eluting isomer [Isomer 1] of C107 as white solid. Mass [ESI]: m/z 541.63 [M⁺+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (furan-3-ylmethyl)-amide [C108""]: This compound was synthesized following same protocol as for C104. Preparative HPLC purification provided 40 mg of faster eluting isomer [Isomer 1] of C108 as white solid. Mass [ESI]: m/z 542.61 [M⁺+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (thiophen-3-ylmethyl)-amide [C109]: This compound was synthesized following same protocol as for C104. Prep HPLC purification provided 40 mg of faster eluting as major isomer of C109 as white solid. Mass [ESI]: m/z 558.68[M⁺+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (3H-imidazol-4-ylmethyl)-amide [C110]: This compound was synthesized following same protocol as for C104. Prep HPLC purification provided 25 mg of faster eluting as major isomer of C110 as white solid. Mass [ESI]: m/z 542.62[M⁺+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (oxazol-5-ylmethyl)-amide [C111]: This compound was synthesized following same protocol as for C104. Prep HPLC purification provided 40 mg of faster eluting as major isomer of C111 as white solid. Mass [ESI]: m/z 543.60[M⁺+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (thiazol-5-ylmethyl)-amide [C112]: This compound was synthesized following same protocol as for C104. Prep HPLC purification provided 30 mg of faster eluting as major isomer of C112 as white solid. Mass [ESI]: m/z 559.66[M⁺+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (oxazol-4-ylmethyl)-amide [C114]: This compound was synthesized following same protocol as for C104. Prep HPLC purification provided 45 mg of faster eluting as major isomer of C114 as white solid. Mass [ESI]: m/z 543.60[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (thiazol-4-ylmethyl)-amide [C115]: This compound was synthesized following same protocol as for C104. Prep HPLC purification provided 35 mg of faster eluting as major isomer of C115 as white solid. Mass [ESI]: m/z 559.66[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (1H-pyrazol-4-ylmethyl)-amide [C116]: This compound was synthesized following same protocol as for C104. Prep HPLC purification provided 20 mg of faster eluting as major isomer of C116 as white solid. Mass [ESI]: m/z 542.62[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (isoxazol-4-ylmethyl)-amide [C117]: This compound was synthesized following same protocol as for C104. Prep HPLC purification provided 40 mg of faster eluting as major isomer of C117 as white solid. Mass [ESI]: m/z 543.60[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (isothiazol-4-ylmethyl)-amide [C118]: This compound was synthesized following same protocol as for C104. Prep HPLC purification provided 40 mg of faster eluting as major isomer of C118 as white solid. Mass [ESI]: m/z 559.66[M$^+$+1].

Synthesis of (2S, 5S)-5-[(2S, 3S)-2-(4-Methoxy-benzoylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide [C119]: This compound was synthesized following same protocol as for C104. Prep HPLC purification provided 40 mg of faster eluting as major isomer of C119 as white solid and 5 mg of slower eluting isomer [Isomer 2] of C119. Mass [ESI]: m/z 573.66[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid [2-(3H-[1,2,3]triazol-4-yl)-ethyl]-amide [C120]: This compound was synthesized following same protocol as for C104. Prep HPLC purification provided 30 mg of faster eluting as major isomer of C120 as white solid. Mass [ESI]: m/z 557.63[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (pyridin-2-ylmethyl)-amide [C121]: This compound was synthesized following same protocol as for C104. Prep HPLC purification provided 25 mg of faster eluting as major isomer of C121 as white solid. Mass [ESI]: m/z 553.64[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (pyridin-3-ylmethyl)-amide [C122]: This compound was synthesized following same protocol as for C104. Prep HPLC purification provided 20 mg of faster eluting as major isomer of C122 as white solid. Mass [ESI]: m/z 553.64[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (pyridin-4-ylmethyl)-amide [C123]: This compound was synthesized following same protocol as for C104. Prep HPLC purification provided 25 mg of faster eluting as major isomer of C123 as white solid. Mass [ESI]: m/z 553.64[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 2-methyl-benzylamide [C127]: This compound was synthesized following same protocol as for C104. Prep HPLC purification provided 111 mg of faster eluting as major isomer of C127 as white solid, 20 mg of slower eluting isomer was also isolated. Mass [ESI]: m/z 566.68[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 3-methyl-benzylamide [C128]: This compound was synthesized following same protocol as for C104. Prep HPLC purification provided 130 mg of faster eluting as major isomer of C128 as white solid and 10 mg of slower eluting isomer [Isomer2] of C128. Mass [ESI]: m/z 566.68[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 4-methyl-benzylamide [C129]: This compound was synthesized following same protocol as for C104. Prep HPLC purification provided 36 mg of faster eluting as major isomer of C129 as white solid and 10 mg of slower eluting isomer [Isomer2] of C129. Mass [ESI]: m/z 566.68[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 2-chloro-benzylamide [C130]: This compound was synthesized following same protocol as for C104. Prep HPLC purification provided 25 mg of faster eluting as major isomer of C130 as white solid. Mass [ESI]: m/z 587.10[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 3-chloro-benzylamide [C131]: This compound was synthesized following same protocol as for C104. Prep HPLC purification provided 45 mg of faster eluting as major isomer of C131 as white solid, 3 mg of slower eluting isomer was also isolated. Mass [ESI]: m/z 587.10[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid 4-chloro-benzylamide [C132]: This compound was synthesized following same protocol as for C104. Prep HPLC purification provided 90 mg of faster eluting as major isomer of C132 as white solid, 2 mg of slower eluting isomer was also isolated. Mass [ESI]: m/z 587.10[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (pyridin-3-ylmethyl)-amide [C133]: This compound was synthesized following same protocol as for C104. Prep HPLC purification provided 32 mg of faster eluting as major isomer of C133 as white solid, 8 mg of slower eluting isomer was also isolated. Mass [ESI]: m/z 621.53[M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (2H-pyrazol-3-ylmethyl)-amide [C149]: This compound was synthesized following same protocol as for C104. Prep HPLC purification provided 32 mg of faster eluting as major isomer of C149 as white solid, 8 mg of slower eluting isomer was also isolated. Mass [ESI]: m/z 542.62[M⁺+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (2H-[1,2,4]triazol-3-ylmethyl)-amide [C163]: This compound was synthesized following same protocol as for C104. Prep HPLC purification provided 30 mg of faster eluting as major isomer of C163 as white solid. Mass [ESI]: m/z 543.60[M⁺+1].

C104. Prep HPLC purification provided 8.5 mg of faster eluting as major isomer of C164 as white solid. Mass [ESI]: m/z 559.60[M⁺+1].

Synthesis of (2S,5S)-5-{(2S,3S)-2-[2-(3-Fluoro-propoxy)-acetylamino]-3-methyl-pentanoylamino}-4-oxo-1,2,4,5,6,7-hexahydro-azepino[3,2,1-hi]indole-2-carboxylic acid (1H-[1,2,3]triazol-4-ylmethyl)-amide [C145]: This compound was synthesized following same protocol as for C104. Prep HPLC purification provided 39 mg of faster eluting as major isomer of C145 as white solid. Mass [ESI]: m/z 559.60[M⁺+1].

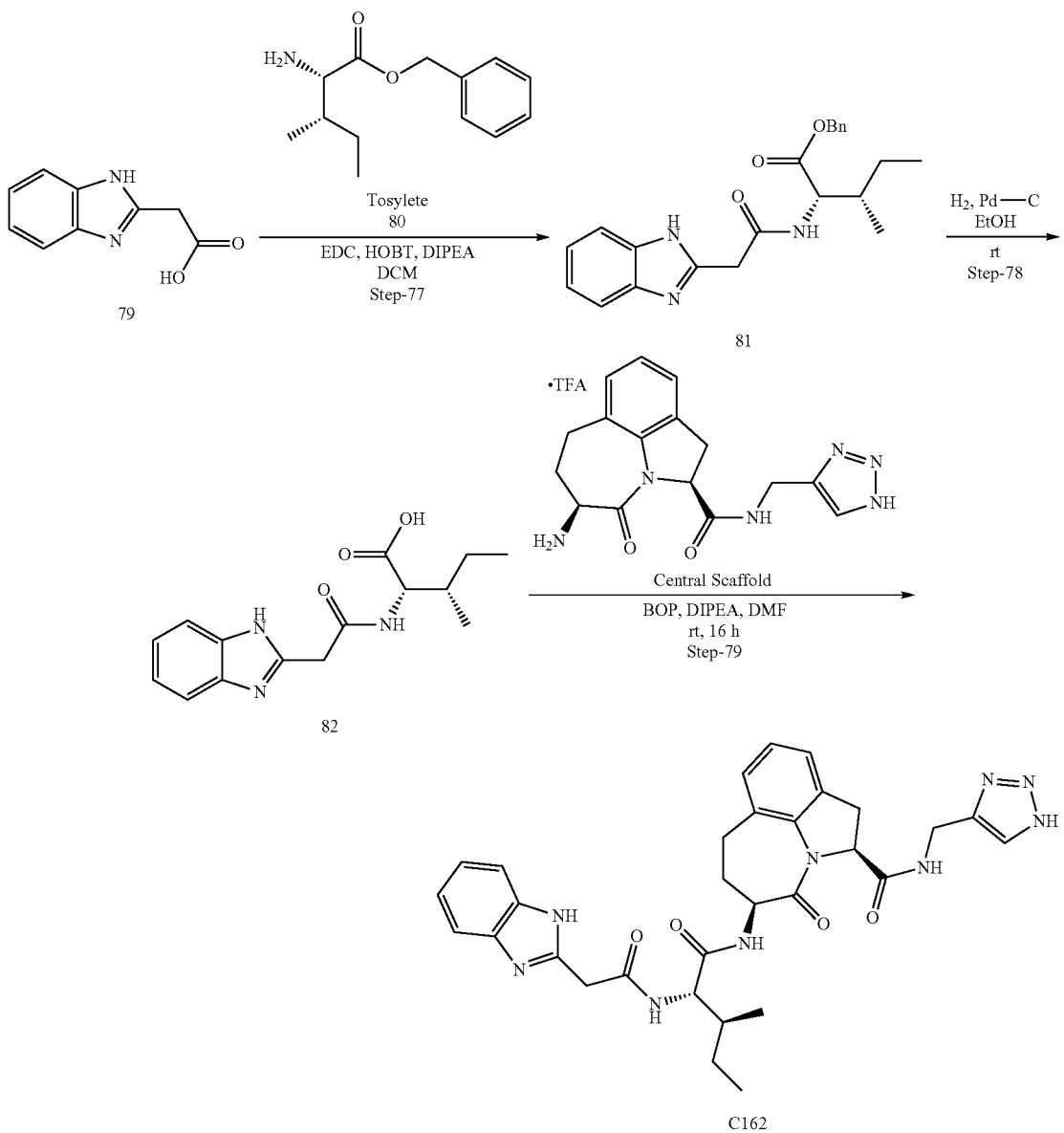

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid (5-hydroxy-2H-[1,2,4]triazol-3-ylmethyl)-amide [C164]: This compound was synthesized following same protocol as for Synthesis of (2S,3S)-2-(2-1H-Benzoimidazol-2-yl-acetylamino)-3-methyl-pentanoic acid benzyl ester [Scheme-16, Step-77]: To a stirred solution of compound 80 (tosylate) (536 mg, 1.36 mmol), compound 79 (200 mg, 1.13 mmol) and HOBt (230 mg, 1.70 mmol) in 5 mL DCM, was added DIPEA (0.99 mL, 5.7 mmol) drop-wise and stirred at 0° C. for 10 min under inert atmosphere. Then EDC-HCl (283 mg, 1.48 mmol) was added to the reaction mixture and allowed to stir at room temperature for 16 h. After completion [confirmed by TLC (70% EtOAc-Hexane, Rf-0.4) and LC-MS] reaction mixture was partitioned between water (70 mL) and DCM (3×60 mL). Organic layer was separated, dried (MgSO$_4$) and concentrated. Resultant crude was purified by column chromatography (eluent: 30-65% EtOAc-hexane, SiO$_2$) to yield compound 81 (210 mg, 48.8%) as white solid. Mass [ESI]: m/z 379.45 [M$^+$+1].

Synthesis of (2S,3S)-2-(2-1H-Benzoimidazol-2-yl-acetylamino)-3-methyl-pentanoic acid [Scheme-16, Step-78]: To a stirred solution of compound 81 (210 mg, 0.553 mmol) in 4 mL EtOH was added 65 mg of 10% by weight Pd/C (wet) powder and the resultant suspension was allowed to stir under ordinary hydrogen pressure (balloon) at room temperature for 16 h. After completion [confirmed by TLC (70% EtOAc-Hexane, Rf-0.1 and LC-MS] reaction mixture was filtered through celite bed, filtrate part was concentrated under reduced pressure to afford compound 82 (0.15 g, 94%) as white solid. Mass [ESI]: m/z 379.45 [M$^+$+1].

Synthesis of (2S,5S)-5-[(2S,3S)-2-(2-1H-Benzoimidazol-2-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide [Scheme-16, Step-79]: To a stirred solution of 82 (72 mg, 0.325 mmol) and central scaffold (100 mg, 0.227 mmol) in DMF (2 mL) was added DIPEA (0.198 mL, 1.14 mmol), followed by the addition of BOP reagent (201 mg, 0.454 mmol) and resultant reaction mixture was allowed to stir at room temperature for 16 h. After completion [monitored with LC-MS], crude reaction mixture was submitted for reverse phase prep HPLC purification to afford 20 mg of faster eluting as major isomer [Isomer1] of C162 as white solid. Mass [ESI]: m/z 597.68 [M$^+$+1].

Synthesis of (2S,5S)-5-[(2S,3S)-2-(2-1H-Indol-2-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide: [(C161)]: This compound was synthesized following the same protocol as for C162. Prep HPLC purification provided 20 mg of faster eluting as major isomer [Isomer1] of C161 as pale orange solid. Mass [ESI]: m/z 596.69[M$^+$+1].

Synthesis of (2S,5S)-5-[(2S,3S)-2-(2-Benzo[b]thiophen-2-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide: [(C158)]: This compound was synthesized following the same protocol as for C162. Prep HPLC purification provided 7 mg of faster eluting as major isomer [Isomer1] of C158 as pale orange solid. Mass [ESI]: m/z 613.74[M$^+$+1].

Synthesis of (2S,5S)-5-[(2S,3S)-2-(2-Benzo[b]thiophen-2-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide: [(C160)]: This compound was synthesized following the same protocol as for C162. Prep HPLC purification provided 8 mg of faster eluting as major isomer [Isomer1] of C160 as pale orange solid. Mass [ESI]: m/z 598.65[M$^+$+1].

Synthesis of (2S,5S)-5-{(2S,3S)-2-[(6-Fluoro-pyridine-3-carbonyl)-amino]-3-methyl-pentanoylamino}-4-oxo-1,2,4,5,6,7-hexahydro-azepino[3,2,1-hi]indole-2-carboxylic acid (1H-[1,2,3]triazol-4-ylmethyl)-amide: [(C140)]: This compound was synthesized following the same protocol as for C162. Prep HPLC purification provided 5.1 mg of faster eluting as major isomer [Isomer1] of C140 as pale yellow solid. Mass [ESI]: m/z 562.59[M$^+$+1].

Synthesis of (2S,5S)-5-{(2S,3S)-2-[(6-Fluoro-pyridine-4-carbonyl)-amino]-3-methyl-pentanoylamino}-4-oxo-1,2,4,5,6,7-hexahydro-azepino[3,2,1-hi]indole-2-carboxylic acid (1H-[1,2,3]triazol-4-ylmethyl)-amide: [(C141)]: This compound was synthesized following the same protocol as for C162. Prep HPLC purification provided 5 mg of faster eluting as major isomer [Isomer1] of C141 as pale yellow solid. Mass [ESI]: m/z 562.59[M$^+$+1].

Scheme-17: [Synthesis of C171]

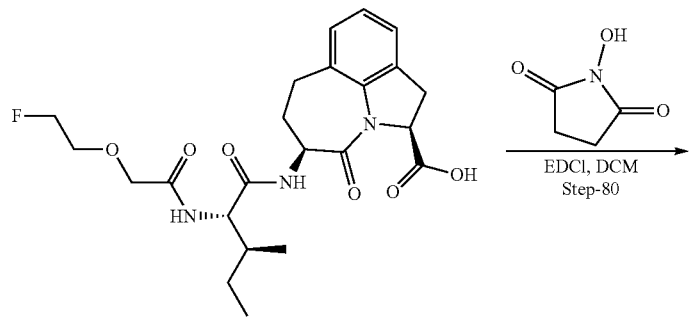

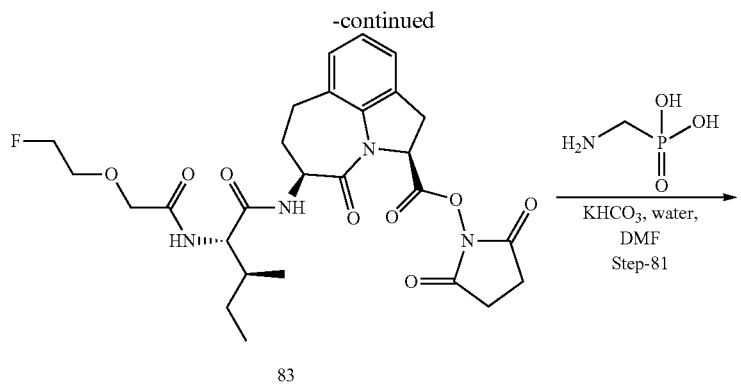

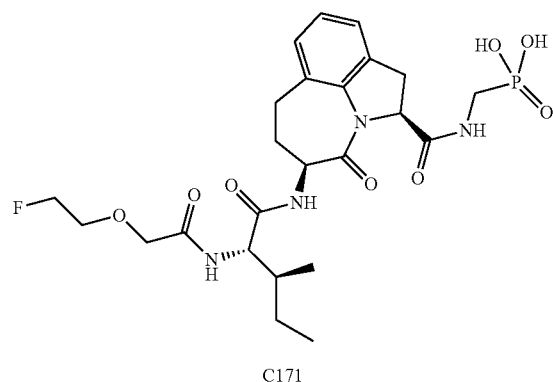

C171

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid [Scheme-17, Step-80]: To the stirred solution of 62 (100 mg, 0.22 mmol) in DCM (3 ml), N-hydroxy succinimide (24.8 mg, 0.22 mmol) was added followed by the addition of EDC.HCl (124.2 mg, 0.648 mmol) and the resultant reaction mixture was allowed to stir at room temperature for 2 h. After completion [monitored with TLC and LC-MS], reaction mixture was partitioned between water (50 mL) and DCM (2×50 mL). Organic layer was separated, dried (MgSO$_4$) and concentrated under reduced pressure to afford compound 83 (70 mg, 58%) as white solid. Mass [ESI]: m/z 560.58 [M$^+$+1]

Synthesis of {[((2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carbonyl)-amino]-methyl}-phosphonicacid (C171) [Scheme-17, Step-81] To a stirred solution of compound 83 (50.0 mg, 0.09 mmol) 1 mL DMF was added solution of aminomethyl-phosphonic acid (9.91 mg, 0.09 mmol) and KHCO$_3$ (22.0 mg, 0.22 mmol) in water (1 mL). Then reaction mixture was allowed to stir at room temperature for 16 h. After completion (confirmed by LCMS), crude reaction mixture was submitted for reverse phase prep HPLC purification to afford faster moving as major isomer of C171 [12 mg] as white solid. Mass [ESI]: m/z 556.53 [M$^+$+1].

Synthesis of (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi] indole-2-carboxylic acid (5-hydroxy-2H-pyrazol-3-ylmethyl)-amide [C166]: This compound was synthesized following same protocol as for C171 however, in the final step DIPEA (5 eq) was used instead of KHCO$_3$ and only DMF was used as a solvent. Prep HPLC purification provided faster eluting as major isomer of C166 [12 mg] as white solid. Mass [ESI]: m/z 558.62[M$^+$+1].

Scheme-18 [synthesis of C170]

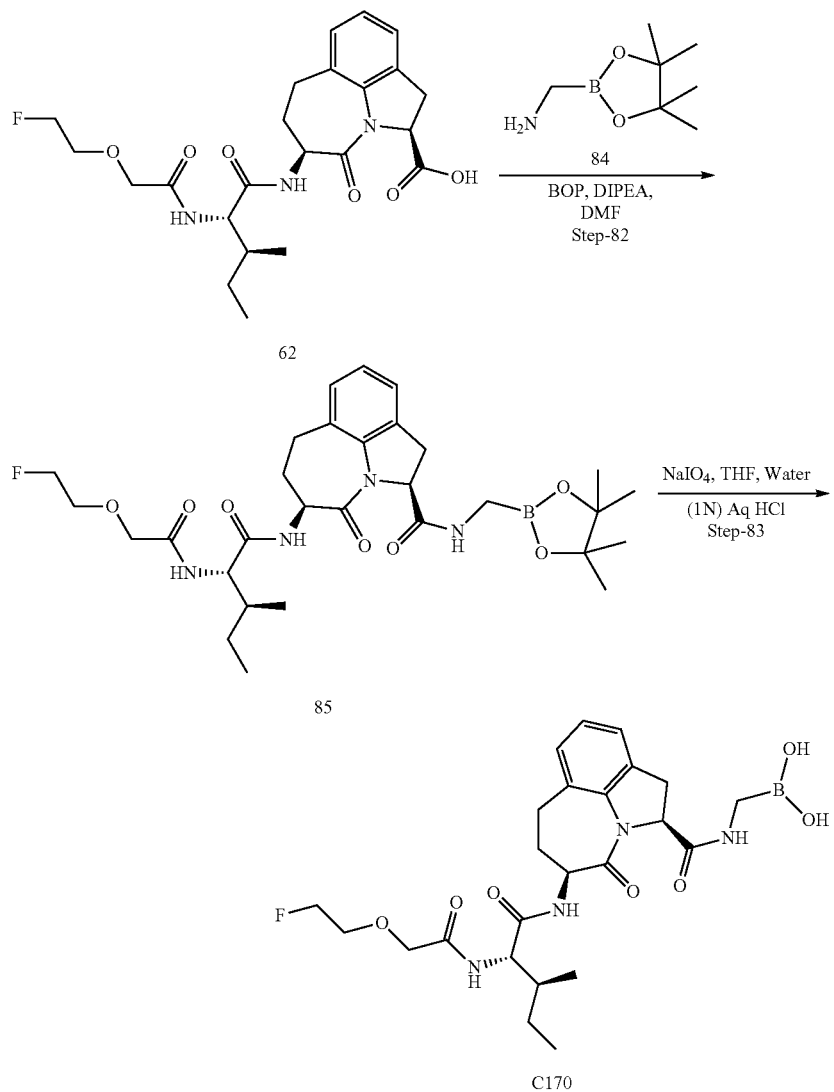

Synthesis of (2S, 5S)-5-{(2S, 3S)-2-[2-(2-Fluoro-ethoxy)-acetylamino]-3-methyl-pentanoylamino}-4-oxo-1, 2, 4, 5, 6, 7-hexahydro-azepino [3, 2, 1-hi] indole-2-carboxylic acid (4,4,5,5-tetramethyl-[1,3,2]dioxaborolan-2-ylm-ethyl)-amide [Scheme-18, Step-82]: To a stirred solution of 62 (100 mg, 0.216 mmol) and 84 (46 mg, 0.24 mmol) in DMF (2 mL) was added DIPEA (0.23 mL, 1.3 mmol), followed by the addition of BOP reagent (191 mg, 0.432 mmol) and resultant reaction mixture was allowed to stir at room temperature for 16 h. Then reaction mixture was partitioned between EtOAc [200 mL] and water [100 mL]. Organic layer was separated, dried [MgSO₄] and concentrated under reduced pressure to afford compound 85 [100 mg, crude] as off white solid. ¹H NMR complies.

Synthesis of {[((2S,5S)-5-{(2S,3S)-2-[2-(2-Fluoro-ethoxy)-acetylamino]-3-methyl-pentanoylamino}-4-oxo-1, 2,4,5,6,7-hexahydro-azepino[3,2,1-hi]indole-2-carbonyl)-amino]-methyl}-boronic acid (C170) [Scheme-18, Step-83]: To a stirred solution of 85 (100 mg, 0.166 mmol) in THF [2 mL] was slowly added water [1 mL], NaIO₄ (106 mg, 0.498 mmol) and allowed to stir at room temperature for 3 hour.

Then (1M) aqueous HCl [0.34 mL] was added to the reaction mixture and stirred for 1 hour. Reaction mixture was partitioned between EtOAc [150 mL] and water [100 mL], organic layer was separated, dried [MgSO₄] and concentrated. Resultant crude was purified by reverse phase preparative HPLC to provide 5 mg of C170 as white solid. Mass [ESI]: m/z 520.35 [M⁺–1].

Scheme-19 [synthesis of C147 & C148]

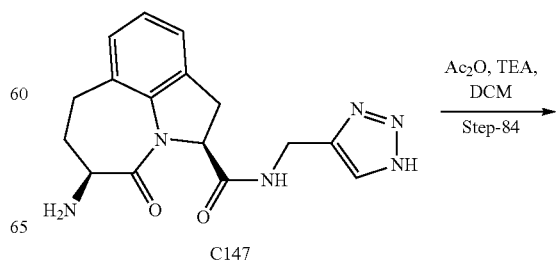

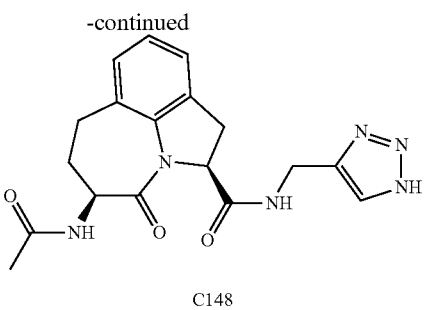

C148

Synthesis of (2S,5S)-5-Amino-4-oxo-1,2,4,5,6,7-hexahydro-azepino[3,2,1-hi]indole-2-carboxylic acid (1H-[1,2,3]triazol-4-ylmethyl)-amide (C147) [Scheme-1, Step-8]: C147 is actually central scaffold from Scheme 1 [step-8]. 100 mg of the crude compound was further purified by RP preparative HPLC to provide 15 mg of C147 as white solid. Mass [ESI]: m/z 326.35 [M$^+$−1].

Synthesis of (2S,5S)-5-Acetylamino-4-oxo-1,2,4,5,6,7-hexahydro-azepino[3,2,1-hi]indole-2-carboxylic acid (1H-[1,2,3]triazol-4-ylmethyl)-amide (C148) [Scheme-19, Step-84]: To a stirred solution of 84 (100 mg, 0.227 mmol) in DCM [5 mL], TEA (0.08 mL, 0.6 mmol) was slowly added followed by addition of acetic anhydride (0.02 mL, 0.22 mL) and allowed to stir at room temperature for 16 h. After completion [Monitored by LC-MS]reaction mixture was directly submitted for RP preparative HPLC purification to afford 20 mg of C148 as white solid. Mass [ESI]: m/z 368.38 [M$^+$+1].

Example 2: Synthesis of Compounds with Oxygen-Containing Core

Synthesis of Oxa-Azepinone Central Scaffold

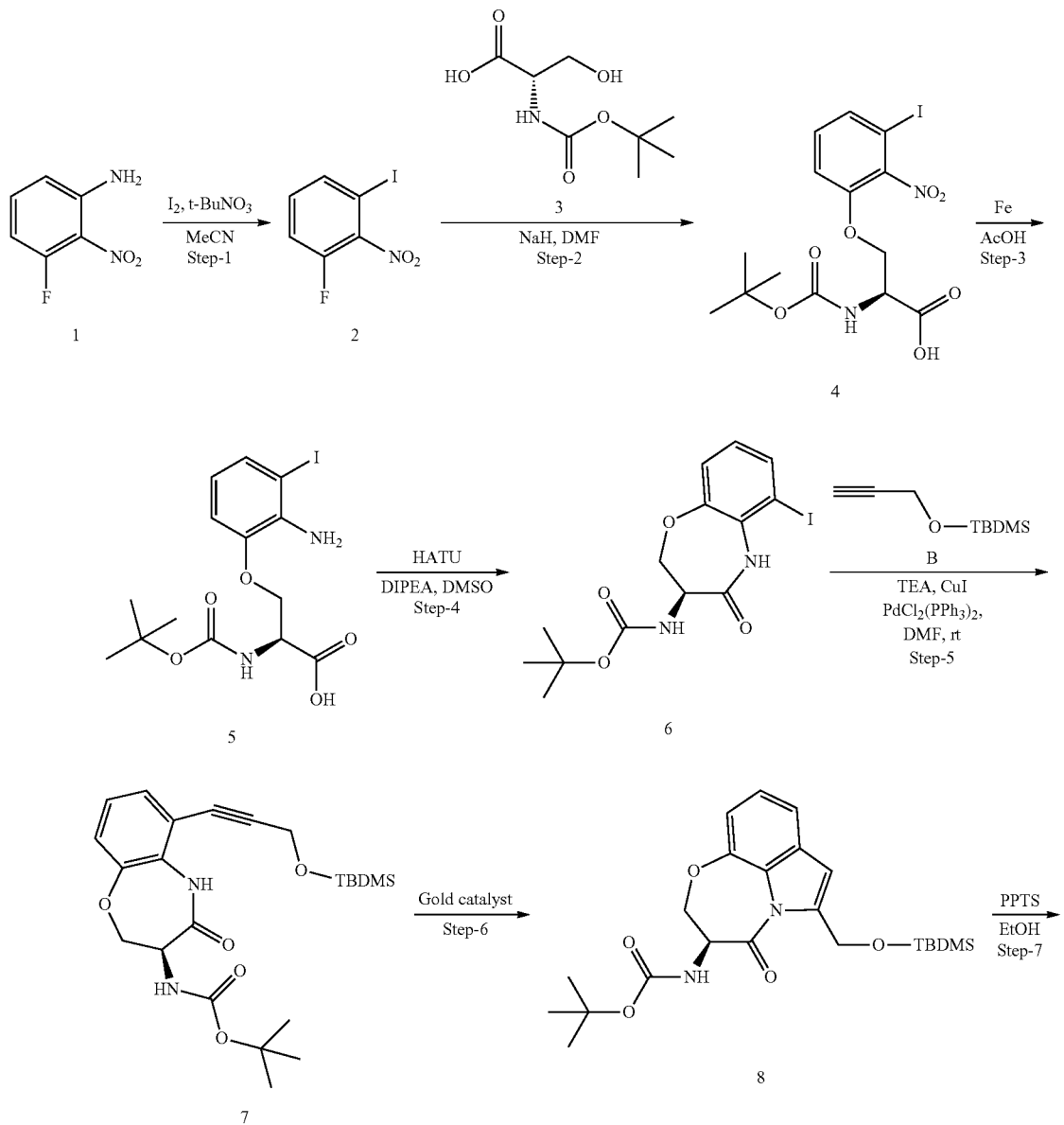

-continued
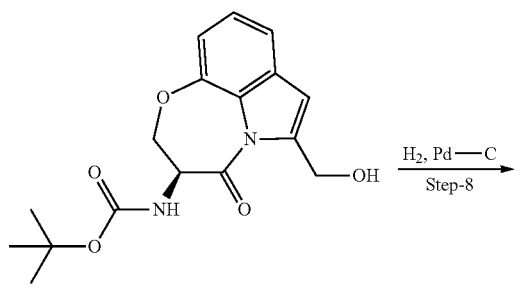
9
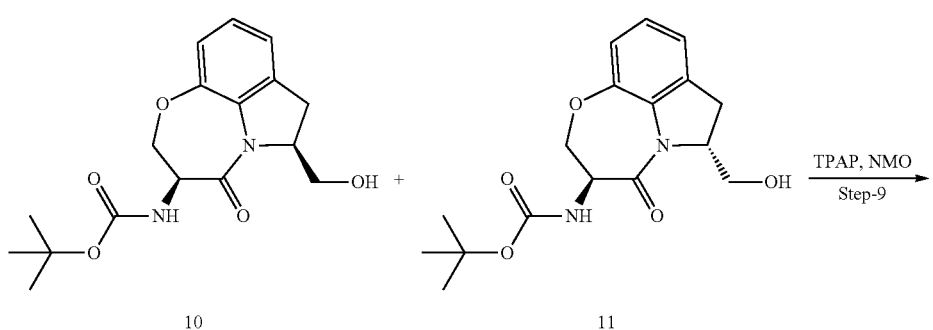
10      11
Absolute stereochemistry unknown
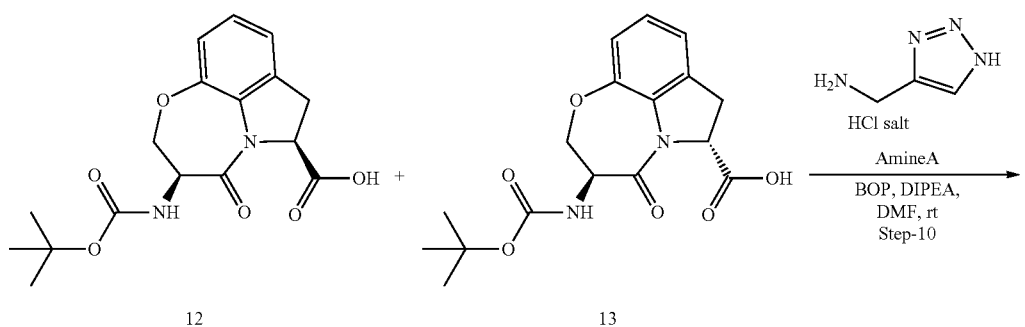
12      13
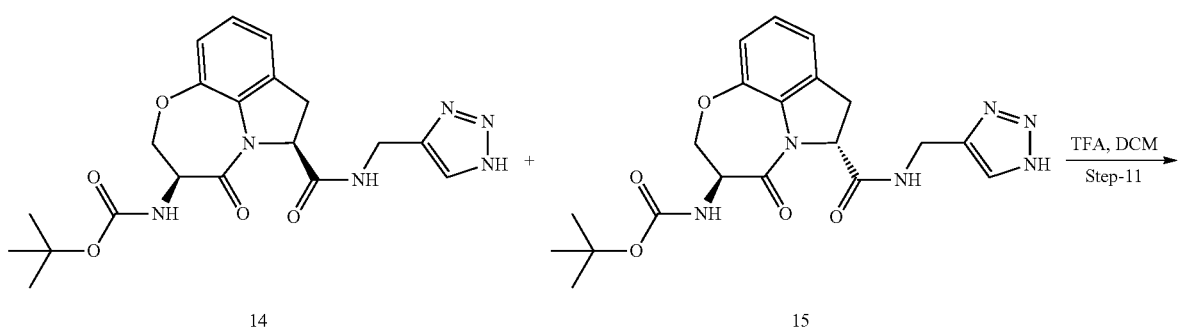
14      15
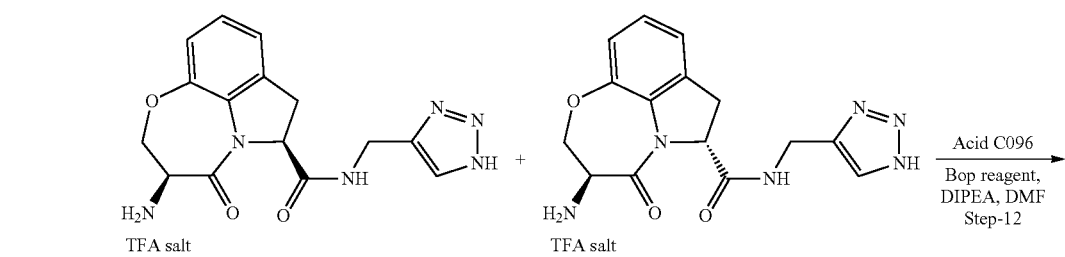
16      17
Absolute stereochemistry unknown -continued

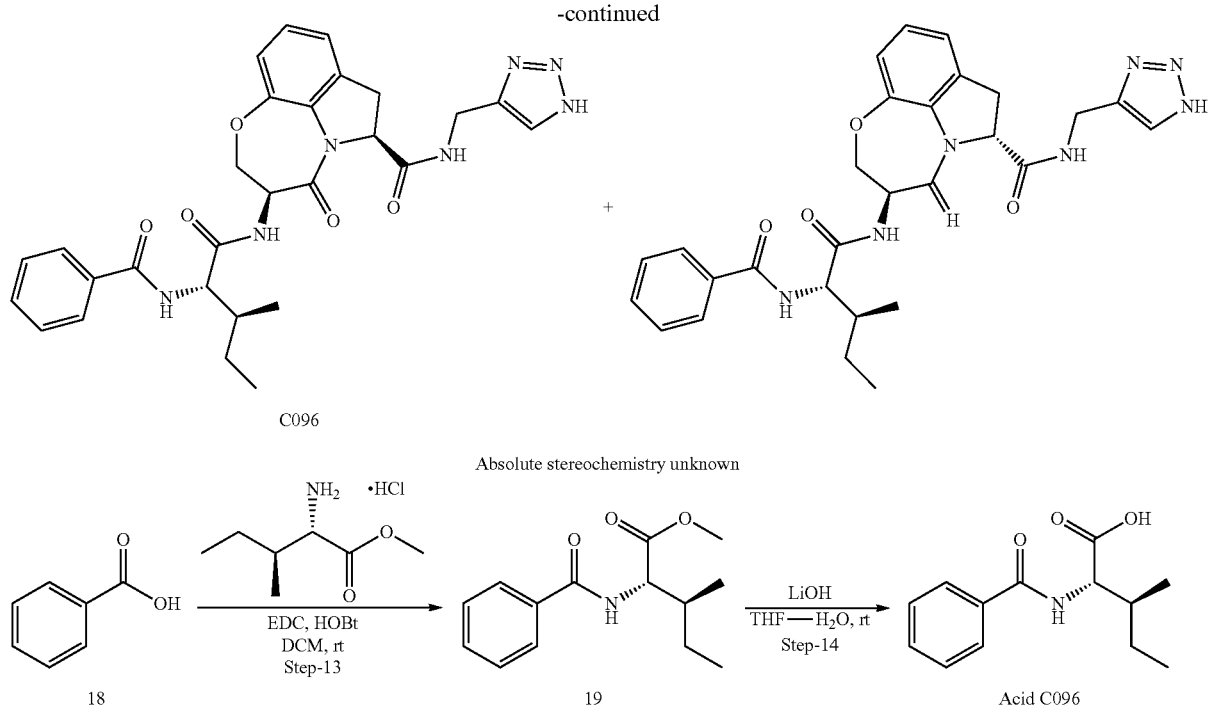

General remarks: We have separated both isomers after indole to indoline reduction reaction [Scheme-20, step-8], however, absolute stereochemistry is unknown for the separated isomers. We have forwarded both isomers [polar and no polar] separately till final amidation. Final compound synthesized from non polar isomer always became potent in the assay. We captured protocol for the conversion of upper isomer [non polar] in the experimental and analogues protocol was followed for the conversion of lower isomer [polar].

Experimentals

Synthesis of 1-Fluoro-3-iodo-2-nitro-benzene [Scheme-20, Step-1]: To a pre heated solution of iodine [244.23 g, 1923.1 mmol] and tert butyl nitrite [114.2 ml, 961.5 mmol] in MeCN (300 mL) at 60° C., was added a solution of compound 1 [30.00 g, 192.3 mmol] in MeCN (300 mL). The reaction mixture was stirred for an additional 2 h at 60° C. and allowed to stir at room temperature for another 16 h. After completion [monitored by TLC [10% EtOAc-Hexane, $R_f$=0.5], the mixture was quenched with saturated aqueous $Na_2S_2O_3$ [300 mL] solution at ice cool condition and extracted with EtOAc [3×500 mL]. The combined organic layers were dried ($Na_2SO_4$), filtered, and concentrated under reduced pressure. The residue was purified through silica gel column chromatography using 0-3% EtOAc-hexane as eluting solvent to afford compound 2 [39 g, 76%] as a yellow solid. [$^1$H NMR is consistent].

Synthesis of (S)-2-tert-Butoxycarbonylamino-3-(3-iodo-2-nitro-phenoxy)-propionic acid [Scheme-20, Step-2]: To a stirred suspension of NaH (50%) [3.60 g, 74.9 mmol] in DMF [60 mL] was added slowly a solution of compound 3 [15.3 g, 74.9 mmol] in DMF [30 mL] maintaining the external temperature below −10° C. After addition, reaction mixture was left stirring vigorously for half an hour under cold condition. A solution of compound 2 [20.0 g, 74.9 mmol] in DMF [30 mL] was slowly added to the reaction mixture under ice cold condition, after addition reaction mixture was allowed to warm at room temperature and stirred for 16 h. Then reaction mixture was quenched with water [500 mL] and aqueous part was extracted with EtOAc [2×100 mL]. Organic part was separated; pH of the aqueous part was slowly adjusted to 2-3 using 1N aqueous HCl under ice cooled condition and immediately extracted with EtOAc [2×300 mL]. Organic part was separated, dried ($MgSO_4$) and concentrated under reduced pressure to afford 7.2 g of compound 4. 15 g of un-reacted starting material was also recovered; this material was further treated under the same condition to afford 8.5 g compound 4 [total 16.1 g, 47.6%]. Mass [ESI]: m/z 452.21 [M$^+$−1]

Synthesis of (S)-3-(2-Amino-3-iodo-phenoxy)-2-tert-butoxycarbonylamino-propionic acid [Scheme-20, Step-3,]: To a stirred solution of 4 [16.1 g, 35.6 mmol] in AcOH [105 mL] was added Fe powder [19.89 g, 356.2 mmol] and resultant heterogeneous mixture was refluxed at 80° C. for 3.5 h. After completion, reaction mixture was partitioned between EtOAc [2×500 mL] and water [500 mL]. Organic layer was separated, dried ($MgSO_4$) and concentrated under reduced pressure. Resultant crude was further azetropped with toluene to afford 5 [13.2 g, 87.8%] as brown floppy solid. Mass [ESI]: m/z 422.22 [M$^+$+1].

Synthesis of ((S)-1-Iodo-8-oxo-6,7,8,9-tetrahydro-5-oxa-9-aza-benzocyclohepten-7-yl)-carbamic acid tert-butyl ester [Scheme-20, Step-4]: To a stirred solution of compound 5 [13.2 g, 31.3 mmol] in DMSO [130 mL] was added DIPEA [8.42 mL, 46.9 mmol] at room temperature under inert atmosphere followed by HATU [13.0 g, 34.4 mmol] in two portions at ice-cold condition. It was allowed to stir at room temperature for 16 h. After completion [monitored by TLC (30% EtOAc-hexane, $R_f$=0.5) and LC-MS], reaction mixture was extracted with EtOAc [3×100 mL], washed with excess water [150 mL] and brine [100 ml]. The combined organic part was dried ($Na_2SO_4$), filtered and concentrated under reduced pressure to afford crude reaction mixture. Resultant crude was subjected to column chromatography [using silica gel 100-200 mesh under gradient elution of 5-10% EtOAc-hexane] to afford compound 6 [8.30 g, 65.6%] as light brown solid. Mass [ESI]: m/z 404.21 [M$^+$+1].

Synthesis of {(S)-1-[3-(tert-Butyl-dimethyl-silanyloxy)-prop-1-ynyl]-8-oxo-6,7,8,9-tetrahydro-5-oxa-9-aza-benzocyclohepten-7-yl}-carbamic acid tert-butylester [Scheme-20, Step-5]: A stirred solution of compound 6 [8.30 g, 20.5 mmol] in DMF [35 mL] was purged with argon for 10 min. To the resultant mixture was added compound B [17.46 g, 102.7 mmol], TEA [10.1 mL, 71.9 mmol], CuI [0.39 g, 2.10 mmol] and Pd(PPh$_3$)$_2$Cl$_2$ [1.4 g, 2.1 mmol] under argon atmosphere and stir for 16 h. After completion [monitored by TLC (20% EtOAc-hexane, $R_f$=0.4) and LC-MS], the reaction mixture was diluted with water [300 mL] and extracted with EtOAc [3×100 mL]. The combined organic part was dried (Na$_2$SO$_4$), filtered and concentrated under reduced pressure to afford crude reaction mixture. Resultant crude was purified by column chromatography [using silica gel 100-200 mesh under gradient elution of 0-6% EtOAc-hexane] to afford compound 7 [7.40 g, 80.6%] as deep red semi-solid. Mass [ESI]: m/z 446.62 [M$^+$+1].

Synthesis of [(S)-1-(tert-Butyl-dimethyl-silanyloxymethyl)-9-oxo-8,9-dihydro-7H-6-oxa-9a-aza-benzo[cd]azulen-8-yl]-carbamic acid tert-butyl ester [Scheme-20, Step-6]: A stirred solution of compound 7 [6.60 g, 16.6 mmol] in DCM [660 mL] was purged with Argon for 10 min. To the resultant mixture was added Gold catalyst (Cas no: 866641-66-9) [1.14 g, 1.50 mmol] portion-wise at ice-cold condition and was stirred for 6 h at 0° C. The reaction mixture was then kept in the refrigerator for the next 16 h. After completion [monitored by TLC (10% EtOAc-hexane, $R_f$=0.3) and LC-MS], the reaction mixture was concentrated under reduced pressure. Resultant crude was purified by column chromatography [using silica gel 100-200 mesh under gradient elution of 0-5% EtOAc-Hexane] to yield compound 8 [2.00 g, 30.3%] as gummy liquid and 2.5 g of un-reacted starting material [compound 7] was also recovered. Mass [ESI]: m/z 446.62 [M$^+$+1].

Synthesis of [(S)-1-Hydroxymethyl-9-oxo-8,9-dihydro-7H-6-oxa-9a-aza-benzo[cd]azulen-8-yl)]-carbamicacid tert-butyl ester [Scheme-20, Step-7]: To a stirred solution of compound 8 [3.7 g, 8.3 mmol] in EtOH [45 mL] was added pyridinium p-toluene sulfonate [0.62 g, 2.50 mmol] at 0° C. and reaction mixture was brought to room temperature and stirred for 16 h. After LC-MS and TLC analysis [20% EtOAc-Hexane, $R_f$=0.2] pyridinium p-toluene sulfonate [0.62 g, 2.50 mmol] was again added to the reaction mixture and allowed to stir at room temperature for additional 30 h. After completion [monitored by TLC (20% EtOAc-Hexane, $R_f$-0.7) and LC-MS], reaction mixture was concentrated to dryness. The crude residue was partitioned between water [50 mL] and EtOAc [3×75 mL]. Organic layer was separated, washed with brine [50 mL], dried (MgSO$_4$), filtered and concentrated under reduced pressure to afford crude reaction mixture. Resultant crude was purified by column chromatography [using silica gel 100-200 mesh under gradient elution of 20-30% EtOAc-hexane] to yield compound 9 [2.20 g, 79.8%] as floppy solid. Mass [ESI]: m/z 332.36 [M$^+$+1].

Synthesis of ((1S,8S)-1-Hydroxymethyl-9-oxo-1,2,8,9-tetrahydro-7H-6-oxa-9a-aza-benzo[cd]azulen-8-yl)-carbamic acid tert-butyl ester [Scheme-20, Step-8]: A stirred solution of compound 9 [2.20 g, 6.60 mmol] in EtOH [40 mL] was purged with Argon for 10 minutes. Then 880 mg of Pd/C powder [10% by weight, wet] was added to the reaction mixture and resultant suspension was allowed to stir under H2 balloon pressure at room temperature for 16 h. After completion [monitored by TLC (30% EtOAc-hexane, $R_f$=0.4 & 0.3) and LC-MS], the mixture was filtered through a celite bed, washed with EtOH [40 mL] and concentrated under reduced pressure. Resultant crude was purified via column chromatography [using silica gel 100-200 mesh under gradient elution of 20-35% EtOAc-DCM] to afford ~compound 10 [1.07 g, 48.3%, non polar spot; absolute stereo chemistry is unknown] as white floppy solid and ~compound 11 [[500 mg, polar spot; absolute stereochemistry is unknown]. We proceeded with both upper isomer and lower isomer separately however, the final compounds obtained from the upper isomer was biologically active. Mass [ESI]: m/z 334.38 [M$^+$+1].

Synthesis of (1S,8S)-8-tert-Butoxycarbonylamino-9-oxo-1,2,8,9-tetrahydro-7H-6-oxa-9a-aza-benzo[cd]azulene-1-carboxylicacid [Scheme-20, Step-9]: To a stirred solution of compound 10 (and 11) [1.00 g, 2.99 mmol] in ACN [12 mL] and DMF [4 mL] was added NMO [1.4 g, 12 mmol] and TPAP [105 mg, 0.29 mmol] portion-wise at room temperature and allowed to stir for 2 h. After completion [monitored by LC-MS] solvent was evaporated to dryness. Resultant crude reaction mixture was diluted with EtOAc [50 mL] and acidified with 1(N) aqueous HCl. The organic part was separated, dried (MgSO$_4$) and concentrated under reduced pressure to provide ~compound 12 [1.00 g, Yield: 95.9%] as floppy off white solid. [Absolute stereochemistry was unknown] Mass [ESI]: m/z 348.36 [M$^+$+1].

Synthesis of {(1S,8S)-9-Oxo-1-[(1H-[1,2,3]triazol-4-ylmethyl)-carbamoyl]-1,2,8,9-tetrahydro-7H-6-oxa-9a-azabenzo[cd]azulen-8-yl}-carbamic acid tert-butyl ester [Scheme-20, Step-10]: To a stirred solution of ~compound 12 [1.00 g, 2.99 mmol] and HCl salt of Amine A [442 mg, 3.28 mmol] in DMF [10 mL] was added DIPEA [3.21 mL, 17.9 mmol] at 0° C. under argon atmosphere. To the resultant reaction mixture was added BOP reagent [2.64 g, 5.97 mmol] in one portion at 0° C., and finally allowed to stir at room temperature for 16 h. After completion [monitored by TLC (100% EtOAc-$R_f$-0.5) and LC-MS], the reaction mixture was diluted with water [500 mL] and extracted with EtOAc [3×75 mL]. Organic layer was separated dried (MgSO$_4$), filtered and concentrated under reduced pressure to afford crude reaction mixture. Resultant crude was purified by column chromatography [using silica gel 100-200 mesh under gradient elution of 50-70% EtOAc-hexane] to afford ~compound 14 [0.54 g, 42.2%] as white solid. [The absolute stereochemistry was unknown] Mass [ESI]: m/z 428.45 [M$^+$+1].

Synthesis of (1S, 8S)-8-Amino-9-oxo-1,2,8,9-tetrahydro-7H-6-oxa-9a-aza-benzo[cd]azulene-1-carboxylicacid (1H-[1,2,3]triazol-4-ylmethyl)-amide [Scheme-20, Step-11]: To a stirred solution of compound 14 [0.54 g, 1.26 mmol] in DCM [3 mL] was added solution of TFA in DCM (1:1) [8 mL] at 0° C. and resultant reaction mixture was allowed to stir at room temperature for 3 h. After completion [monitored by LC-MS] reaction mixture was concentrated under reduced pressure, resultant residue was azeotroped with toluene to afford crude compound 16 [TFA salt (550 mg), crude compound] as brown semi-solid. Mass [ESI]: m/z 328.33 [M$^+$+1].

Synthesis of (2S, 3S)-2-Benzoylamino-3-methyl-pentanoic acid methyl ester [Scheme-20, Step-13]: To a stirred solution of compound 18 [0.50 g, 4.09 mmol] and L-isoleucine methyl ester. HCl [1.04 g, 5.73 mmol] in DCM [20 mL] was added DIPEA [3.56 mL, 129 mmol], HOBT [829.84 mg, 6.14 mmol] and EDC.HCl [1.02 g, 5.32 mmol]

maintaining external temperature under 5-10° C. Then reaction mixture was allowed to stir at room temperature for 16 h. After completion [monitored with LCMS and TLC (30% EtOAc-Hexane, R$_f$-0.4)] reaction mixture was partitioned between EtOAc [100 mL] and water [50 mL], organic layer was separated, dried (MgSO$_4$) and concentrated under reduced pressure. Resultant crude was purified by column chromatography using Silica gel 100-200 mesh as absorbent and 25-35% EtOAc-hexane as eluting solvent to afford compound 18 [0.95 g, 94%] as colorless semi solid. Mass [ESI]: m/z 249.31 [M$^+$+1].

Synthesis of (2S, 3S)-2-Benzoylamino-3-methyl-pentanoic acid [Scheme-20, Step-14]: To a stirred solution of compound 19 [955 mg, 3.83 mmol] in THF:Water:MeOH [10 mL, in 3:1:1 ratio] was added LiOH·H$_2$O [367 mg, 15.3 mmol] and allowed to stir at ambient temperature for 16 h. After completion [monitored with LCMS and TLC (5% MeOH-DCM, Rf=0.2)] reaction mixture was concentrated, resultant crude was acidified with 1 (N) aqueous HCl upto pH 2-3 and extracted with EtOAc [2×50 mL]. Combined organic part was further washed with brine [30 mL], organic layer was separated, dried over sodium sulphate and concentrated under reduced pressure to afford Acid A [802 mg, 90.0%] as white solid. Mass [ESI]: m/z 235.29 [M$^+$+1].

Synthesis of (1S,8S)-8-((2S,3S)-2-Benzoylamino-3-methyl-pentanoylamino)-9-oxo-1,2,8,9-tetrahydro-7H-6-oxa-9a-aza-benzo[cd]azulene-1-carboxylic acid (1H-[1,2,3] triazol-4-ylmethyl)-amide [Scheme-20, Step-12]: To a stirred solution of ~compound 16 [350 mg, 0.79 mmol] and Acid A [205 mg, 0.870 mmol] in DMF [3 mL] was added DIPEA [0.4 mL, 3.16 mmol] at 0° C. under argon atmosphere. To the resultant reaction mixture was added TBTU [381 mg, 1.19 mmol] and allowed to stir under RT for 16 h. After completion [monitored by LC-MS] reaction mixture was purified by RP preparative HPLC to afford 30 mg isomer 1 [faster moving compound] and 10 mg isomer 2 [slower moving compound]. Faster moving major isomer was biologically potent. Mass [ESI]: m/z 545.60 [M$^+$+1].

TABLE 6

List of compounds with oxygen-containing tri-cyclic ring:

| Compound No | Structure | Name |
|---|---|---|
| C096 | 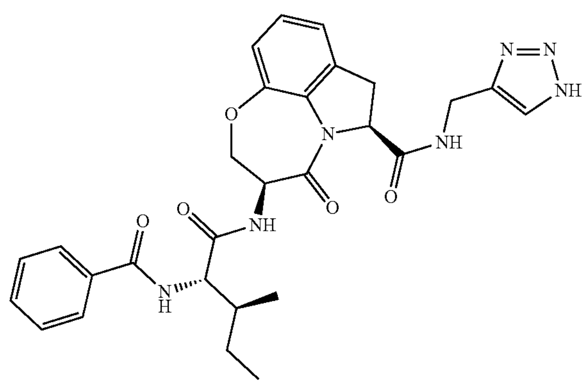 [SMILES: CC[C@H](C)[C@H](NC(=O)c1ccccc1)C(=O)N[C@H]1COc2cccc3c2N(C1=O)[C@H](C(=O)NCc1c[nH]nn1)C3] | (1S,8S)-8-((2S,3S)-Benzoylamino-3-methyl-pentanoylamino)-9-oxo-1,2,8,9-tetrahydro-7H-6-oxa-9a-aza-benzo[cd]azulene-1-carboxylic acid (1H-[1,2,3]triazol-4-ylmethyl)-amide |
| C097 | 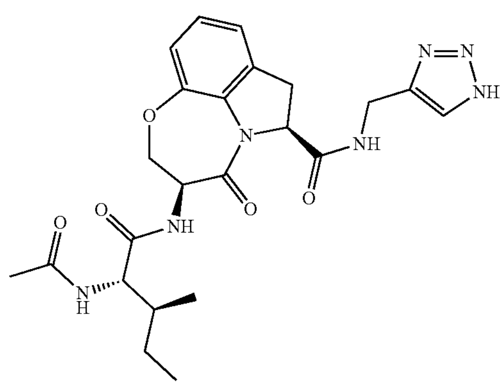 | (1S,8S)-8-((2S,3S)-2-Acetylamino-3-methyl-pentanoylamino)-9-oxo-1,2,8,9-tetrahydro-7H-6-oxa-9a-aza-benzo[cd]azutene-1-carboxylic acid (1H-[1,2,3]triazol-4-ylmethyl)-amide |

TABLE 6-continued

List of compounds with oxygen-containing tri-cyclic ring:

| Compound No | Structure | Name |
|---|---|---|
| C098 | 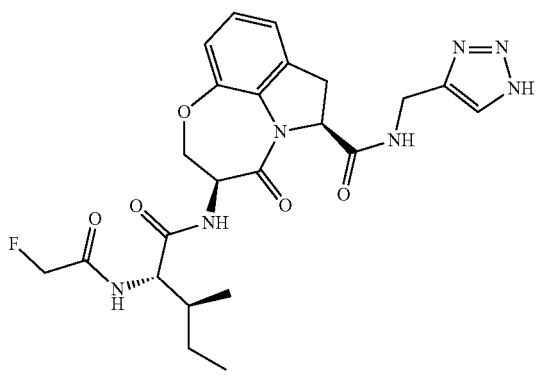 | (1S,8S)-8-[(2S,3S)-2-(2-Fluoro-acetylamino)-3-methyl-pentanoylamino]-9-oxo-1,2,8,9-tetrahydro-7H-6-oxa-9a-aza-benzo[cd]azilene-1-carboxylic acid (1H-[1,2,3]triazol-4-ylmethyl)-amide |
| C099 | 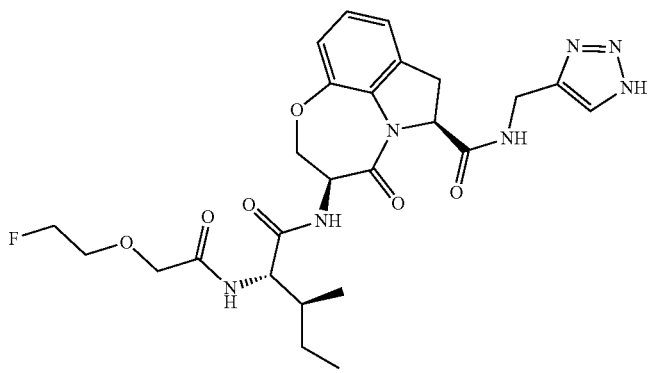 | (1S,8S)-8-{(2S,3S)-2-[2-(2-Fluoro-ethoxy)-acetylamino]-3-methyl-pentanoylamino}-9-oxo-1,2,8,9-tetrahydro-7H-6-oxa-9a-aza-benzo[cd]azulene-1-carboxylic acid (1H-[1,2,3]triazol-4-ylmethyl)-amide |
| C100 | 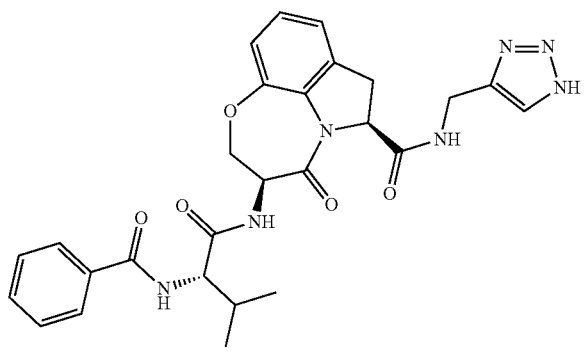 [SMILES: CC(C)[C@H](NC(=O)c1ccccc1)C(=O)N[C@H]1COc2cccc3c2N(C1=O)[C@H](C(=O)NCc1c[nH]nn1)C3] | (1S,8S)-8-((S)-2-Benzoylamino-3-methyl-butyrylamino)-9-oxo-1,2,8,9-tetrahydro-7H-6-oxa-9a-aza-benzo[cd]azulene-1-carboxylic acid (1H-[1,2,3]triazol-4-ylmethyl)-amide |
| C101 | 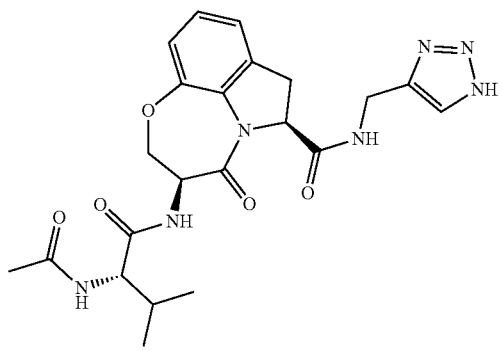 [SMILES: CC(=O)N[C@H](C(=O)N[C@H]1COc2cccc3c2N(C1=O)[C@H](C(=O)NCc1c[nH]nn1)C3)C(C)C] | (1S,8S)-8-((S)-2-Acetylamino-3-methyl-butyrylamino)-9-oxo-1,2,8,9-tetrahydro-7H-6-oxa-9a-aza-benzo[cd]azulene-1-carboxylic acid (1H-[1,2,3]triazol-4-ylmethyl)-amide |

TABLE 6-continued

List of compounds with oxygen-containing tri-cyclic ring:

| Compound No | Structure | Name |
| --- | --- | --- |
| C102 | 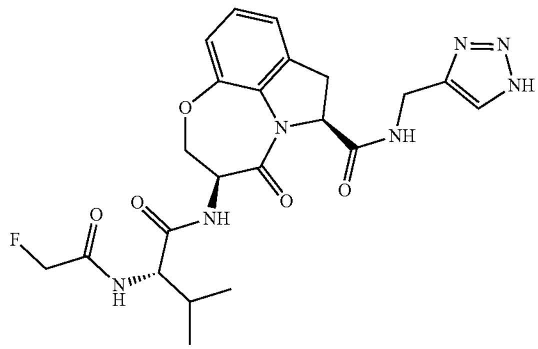 | (1S,8S)-8-[(S)-2-(2-Fluoro-acetylamino)-3-methyl-butyrylamino]-9-oxo-1,2,8,9-tetrahydro-7H-6-oxa-9a-aza-benzo[cd]azulene-1-carboxylic acid (1H-[1,2,3]triazol-4-ylmethyl)-amide |
| C103 | 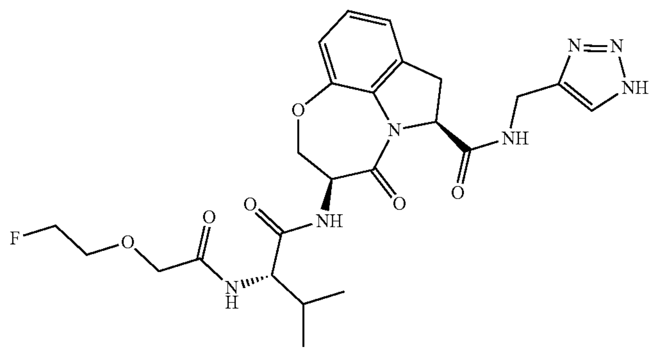 | (1S,8S)-8-{(S)-2-[2-(2-Fluoro-ethoxy)-acetylamino]-3-methyl-butyrylamino}-9-oxo-1,2,8,9-tetrahydro-7H-6-oxa-9a-aza-benzo[cd]azulene-1-carboxylic acid (1H-[1,2,3]triazol-4-ylmethyl)-amide |
| C146 | 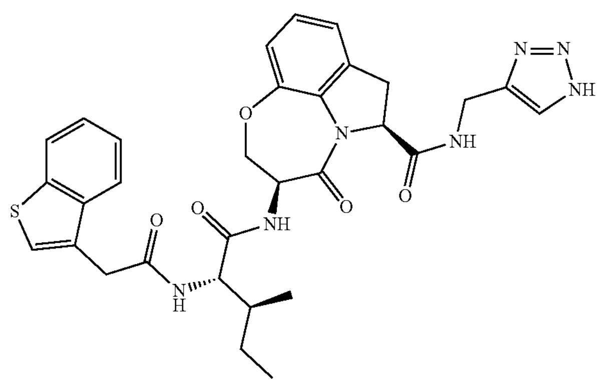 [SMILES: CC[C@H](C)[C@H](NC(=O)Cc1csc2ccccc12)C(=O)N[C@H]1COc2cccc3c2N(C1=O)[C@H](C(=O)NCc1c[nH]nn1)C3] | (1S,8S)-8-[(2S,3S)-2-(2-Benzo[b]thiophen-3-yl-acetylamino)-3-methyl-pentanoylamino]-9-oxo-1,2,8,9-tetrahydro-7H-6-oxa-9a-aza-benzo[cd]azulene-1-carboxylic acid (1H-[1,2,3]triazol-4-ylmethyl)-amide |

General condition for amidation the final amidation: The above mentioned compounds have been synthesized following the same protocol as mentioned for the synthesis of C096 and all compounds were purified by RP preparative HPLC.

Synthesis of (1S,8S)-8-((2S,3S)-2-Acetylamino-3-methyl-pentanoylamino)-9-oxo-1,2,8,9-tetrahydro-7H-6-oxa-9a-aza-benzo[cd]azulene-1-carboxylic acid (1H-[1,2,3]triazol-4-ylmethyl)-amide [C097]: This compound was synthesized following same protocol as C096. Prep HPLC purification provided 12 mg of faster eluting as well as major isomer of C097 as white solid. Mass [ESI]: m/z 484.3 [M$^+$+1].

Synthesis of (1 S,8S)-8-[(2S,3S)-2-(2-Fluoro-acetylamino)-3-methyl-pentanoylamino]-9-oxo-1,2,8,9-tetrahydro-7H-6-oxa-9a-aza-benzo[cd]azulene-1-carboxylic acid (1H-[1,2,3]triazol-4-ylmethyl)-amide [C098]: This compound was synthesized following same protocol as for C096. Prep HPLC purification provided 12.4 mg of faster eluting as well as major isomer of C098 as white solid. Mass [ESI]: m/z 501.52 [M$^+$+1].

Synthesis of (1 S,8S)-8-{(2S,3S)-2-[2-(2-Fluoro-ethoxy)-acetylamino]-3-methyl-pentanoylamino}-9-oxo-1,2,8,9-tetrahydro-7H-6-oxa-9a-aza-benzo[cd]azulene-1-carboxylic acid (1H-[1,2,3]triazol-4-ylmethyl)-amide [C099]: This compound was synthesized following the same protocol as for C096. Prep HPLC purification provided 13 mg of faster eluting as well as major isomer of C099 as white solid and 0.3 mg of slower eluting isomer as isomer2. Mass [ESI]: m/z 545.56 [M$^+$+1].

Synthesis of (1S,8S)-8-((S)-2-Benzoylamino-3-methyl-butyrylamino)-9-oxo-1,2,8,9-tetrahydro-7H-6-oxa-9a-aza-benzo[cd]azulene-1-carboxylic acid (1H-[1,2,3]triazol-4-yl-methyl)-amide [C100]: This compound was synthesized following the same protocol as for C096. Prep HPLC purification provided 5.1 mg of faster eluting as well as major isomer of C100 as white solid. Mass [ESI]: m/z 531.56 [M⁺+1].

Synthesis of (1S,8S)-8-((S)-2-Acetylamino-3-methyl-butyrylamino)-9-oxo-1,2,8,9-tetrahydro-7H-6-oxa-9a-aza-benzo[cd]azulene-1-carboxylic acid (1H-[1,2,3]triazol-4-ylmethyl)-amide [C101]: This compound was synthesized following the same protocol as for C096. Prep HPLC purification provided 18 mg of faster eluting as well as major isomer of C101 as white solid. Mass [ESI]: m/z 469.49 [M⁺+1].

Synthesis of (1S,8S)-8-[(S)-2-(2-Fluoro-acetylamino)-3-methyl-butyrylamino]-9-oxo-1,2,8,9-tetrahydro-7H-6-oxa-9a-aza-benzo[cd]azulene-1-carboxylic acid (1H-[1,2,3]triazol-4-ylmethyl)-amide [C102]: This compound was synthesized following the same protocol as for C096. Prep HPLC purification provided 16 mg of faster eluting as well as major isomer of C102 as white solid. Mass [ESI]: m/z 487.48 [M⁺+1].

Synthesis of (1S,8S)-8-[(S)-2-(2-Fluoro-acetylamino)-3-methyl-butyrylamino]-9-oxo-1,2,8,9-tetrahydro-7H-6-oxa-9a-aza-benzo[cd]azulene-1-carboxylic acid (1H-[1,2,3]triazol-4-ylmethyl)-amide [C103]: This compound was synthesized following the same protocol as for C096. Prep HPLC purification provided 20 mg of faster eluting as well as major isomer of C103-Isomer 1 and 10 mg slower eluting isomer C103-Isomer 2 as white solid. Mass [ESI]: m/z 531.54 [M⁺+1].

Synthesis of (1S,8S)-8-[(2S,3S)-2-(2-Benzo[b]thiophen-3-yl-acetylamino)-3-methyl-pentanoylamino]-9-oxo-1,2,8,9-tetrahydro-7H-6-oxa-9a-aza-benzo[cd]azulene-1-carboxylic acid (1H-[1,2,3]triazol-4-ylmethyl)-amide [C146]: This compound was synthesized following the same protocol as for C096. Prep HPLC purification provided 3 mg of faster eluting isomer [Isomer-1] of C146 as white solid and 5 mg slower eluting isomer [Isomer-2] C103 as white solid. Mass [ESI]: m/z 531.54 [M⁺+1].

General Condition for Acid Counterpart Synthesis:
(i) Acid counter part of C100 and C146 was synthesized following same protocol as mentioned in Step-13 and Step-14 of Scheme-20.
(ii) Protocol for synthesis of Acid counterpart of C099 is depicted below. Same protocol was followed for the synthesis of acid counter part of C103.
(iiI) Protocol for synthesis of Acid counterpart of C101 is depicted below. Same protocol was followed for the synthesis of acid counter part of C097, C098 and C102.

Synthesis of (S)-2-Benzoylamino-3-methyl-butyric acid [Acid C100,]: This compound was synthesized following the same protocol as for Acid C096 to afford of Acid C100 [400 mg, 85.0%] as white solid. Mass [ESI]: m/z 221.26 [M⁺+1].

Synthesis of (2S, 3S)-2-(2-Benzo[b]thiophen-3-yl-acetylamino)-3-methyl-pentanoic acid [Acid C146, "LNB no-12169, Page no-7"]: This compound was synthesized following the same protocol as for Acid C096 to afford of Acid C146 [390 mg, quantitative] as white solid. Mass [ESI]: m/z 305.39 [M⁺+1].

Scheme-21: [Synthesis of Acid C099]

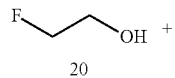
20

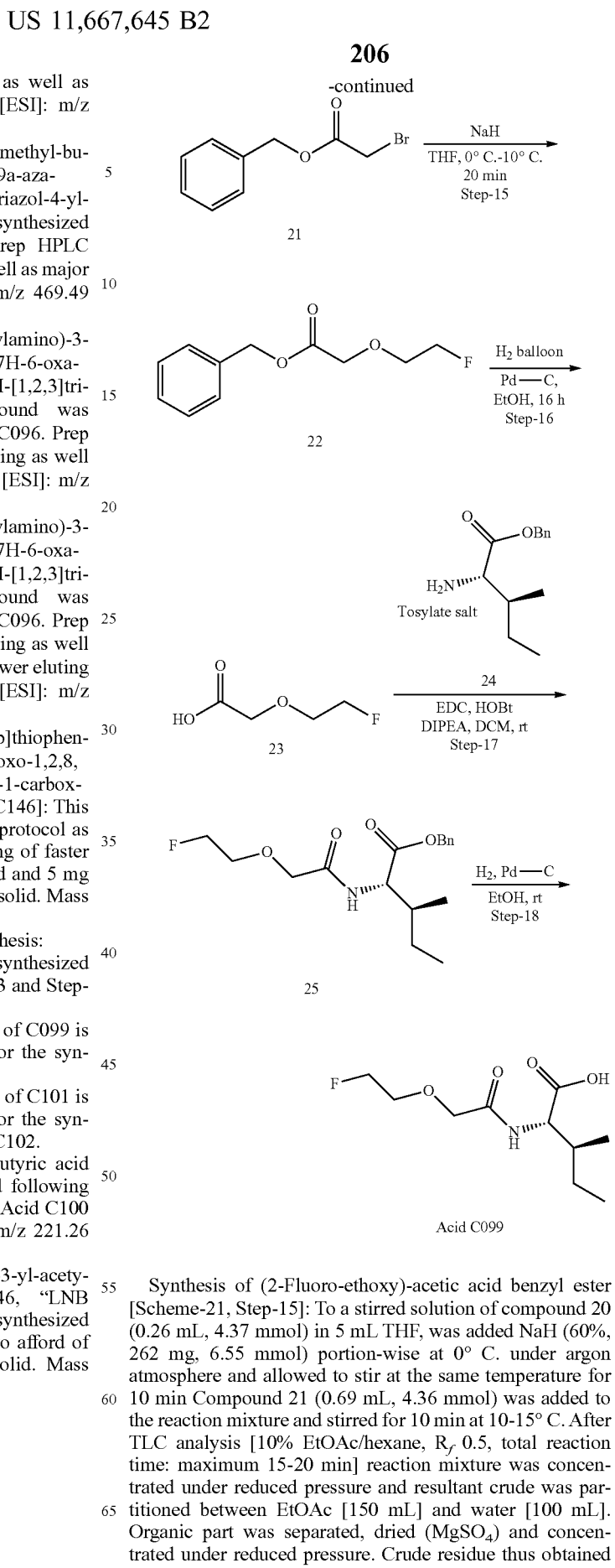

Synthesis of (2-Fluoro-ethoxy)-acetic acid benzyl ester [Scheme-21, Step-15]: To a stirred solution of compound 20 (0.26 mL, 4.37 mmol) in 5 mL THF, was added NaH (60%, 262 mg, 6.55 mmol) portion-wise at 0° C. under argon atmosphere and allowed to stir at the same temperature for 10 min Compound 21 (0.69 mL, 4.36 mmol) was added to the reaction mixture and stirred for 10 min at 10-15° C. After TLC analysis [10% EtOAc/hexane, R_f 0.5, total reaction time: maximum 15-20 min] reaction mixture was concentrated under reduced pressure and resultant crude was partitioned between EtOAc [150 mL] and water [100 mL]. Organic part was separated, dried (MgSO₄) and concentrated under reduced pressure. Crude residue thus obtained was purified by column purification under gradient elution of 2-8% EtOAc/hexane to afford desired compound i.e. compound 22 (350 mg, 35.3%) as colorless liquid. Mass [ESI]: m/z 212.22 [M$^+$+1]

Synthesis of (2-Fluoro-ethoxy)-acetic acid [Scheme-21, Step-16]: To a stirred solution of compound 22 (1.6 g, 7.539 mmol) in 10 mL EtOH, Pd/C (480 mg, 10%) powder was added and resultant reaction mixture was allowed to stir under H$_2$ balloon pressure for 16 h at room temperature. Then reaction mixture was filtered through celite bed and filtrate part was concentrated under reduced pressure to afford compound 23 (830 mg, 90%) as pale brown gummy liquid. [$^1$H NMR complies]

Synthesis of 2-[2-(2-Fluoro-ethoxy)-acetylamino]-3-methyl-pentanoic acid benzyl ester [Scheme-21, Step-17]: To a stirred solution of compound 23 (415 mg, 3.40 mmol), compound 24 (1.34 g, 3.40 mmol) and HOBt (689 mg, 5.10 mmol) in DCM (10 mL) was added DIPEA (2.96 mL, 16.99 mmol) and stirred at 0° C. for 10 min under inert atmosphere. To the resulting mixture EDC.HCl (847 mg, 4.42 mmol) was added and the reaction was continued at room temperature for 16 h. On completion of the reaction (confirmed by TLC and LCMS), the mixture was extracted by DCM (2×10 mL), washed with water, brine, dried (MgSO$_4$) and concentrated. It was then purified by column chromatography (10-35% EtOAc/hexane, SiO$_2$) to provide compound 25 (670 mg, 63.2%) as colorless liquid. Mass [ESI]: m/z 325.38 [M$^+$+1]

Synthesis of 2-[2-(2-Fluoro-ethoxy)-acetylamino]-3-methyl-pentanoic acid [Scheme-21, Step-18]: To a stirred solution of compound 25 (400 mg, 1.23 mmol) in EtOH (8 mL), 10% Pd/C(wet) (120 mg) powder was added and resultant reaction mixture was allowed to stir under H2 balloon pressure for 16 h at room temperature. Then reaction mixture was filtered through celite bed and filtrate part was concentrated under reduced pressure to afford Acid C099 (270 mg, 93.3%) as off white gummy liquid. Mass [ESI]: m/z 235.25 [M$^+$+1]

Synthesis of (S)-2-[2-(2-Fluoro-ethoxy)-acetylamino]-3-methyl-butyric acid [Acid C103]: This compound was synthesized following the same protocol as for Acid C099 to afford of Acid C103 [450 mg, 97.4%] as white solid. Mass [ESI]: m/z 221.23 [M$^+$+1].

Scheme-22: [Synthesis of Acid C101]

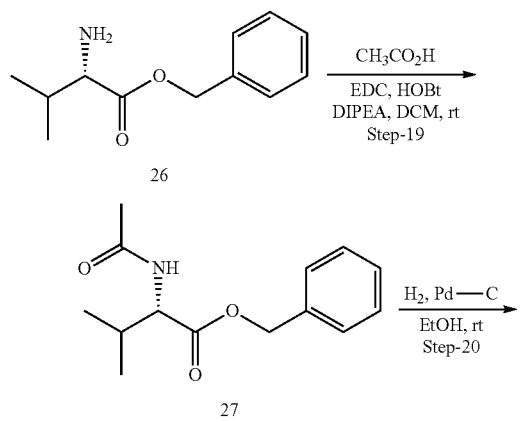

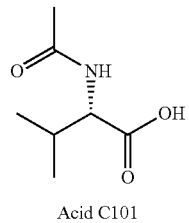

Acid C101

Synthesis of (S)-2-Acetylamino-3-methyl-butyric acid benzyl ester [Scheme-22, Step-19]: To the stirred solution of commercial amino ester (1a) (3.79 g, 9.99 mmol) and AcOH (0.50 g, 8.33 mmol) in DCM (15 ml) was added EDC.HCl (2.075 g, 10.82 mmol), HOBT (1.69 g, 12.5 mmol), DIPEA (7.25 ml, 41.6 mmol) and resultant reaction mixture was allowed to stir at room temperature for 16 h. After completion [monitored with TLC and LC-MS] reaction mixture was partitioned between EtAOc [200 mL] and water [100 mL]. Organic layer was separated, dried (MgSO$_4$) and concentrated under reduced pressure. Resultant crude was purified via column chromatography using silica gel 100-200 mesh as absorbent and 50-60% EtOAc-Hexane as eluting solvent to afford compound 27 as off white solid (1.50 g, 72.3%). Mass [ESI]: m/z 250.3 [M$^+$+1].

Synthesis of (S)-2-Acetylamino-3-methyl-butyric acid [Scheme-22, step-20]: To a stirred solution of intermediate (3a) (1.50 g, 6.04 mmol) in EtOH (25 ml), Pd—C powder (400 mg, 50% wet) was added and resultant reaction mixture was allowed to stir under H$_2$ balloon pressure for 16 h at room temperature. Then reaction mixture was filtered through celite bed and filtrate part was concentrated under reduced pressure to afford Acid C101 (0.50 g, 52%). The crude acid was used as such without further purification. [$^1$H NMR complies].

Synthesis of (2S, 3S)-2-(2-Fluoro-acetylamino)-3-methyl-pentanoic acid [Acid C098]: This compound was synthesized following the same protocol as for Acid C101 to afford Acid C098 [800 mg, 98.1%] as white solid. [$^1$H NMR complies].

Synthesis of (2S, 3S)-2-Acetylamino-3-methyl-pentanoic acid [Acid C097]: This compound was synthesized following the same protocol as for Acid C101 to afford Acid C097 [450 mg, 40.1%] as white solid. [$^1$H NMR complies].

Synthesis of (S)-2-(2-Fluoro-acetylamino)-3-methyl-butyric acid [Acid C102]: This compound was synthesized following the same protocol as for Acid C101 to afford Acid C102 [758 mg, 99.3%] as white solid. [$^1$H NMR complies].

Example 3: Synthesis of Compounds with Sulphur-Containing Core
Scheme-23 [Synthesis of C172]
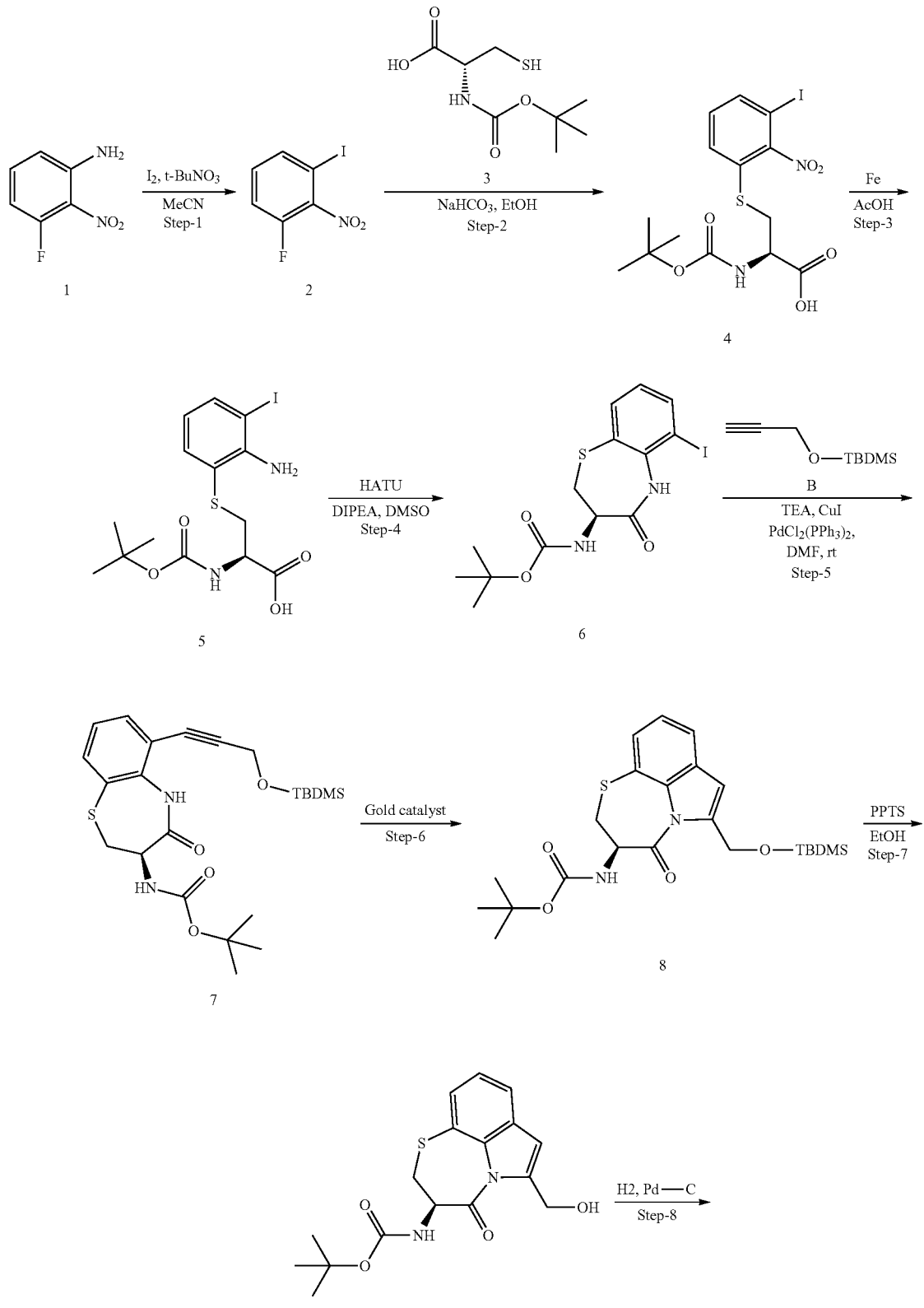

-continued
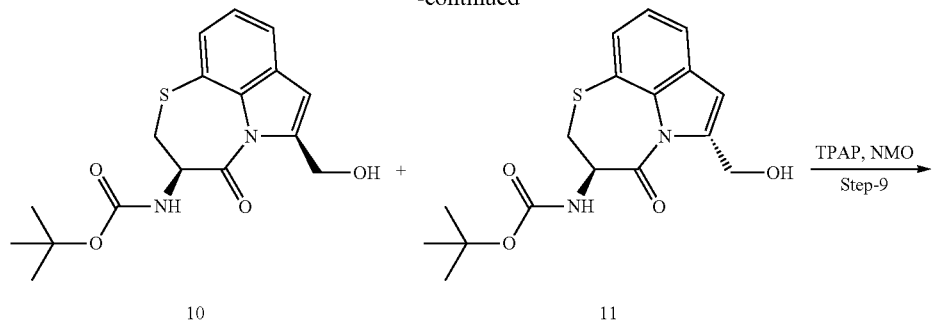
Absolute stereochemistry unknown
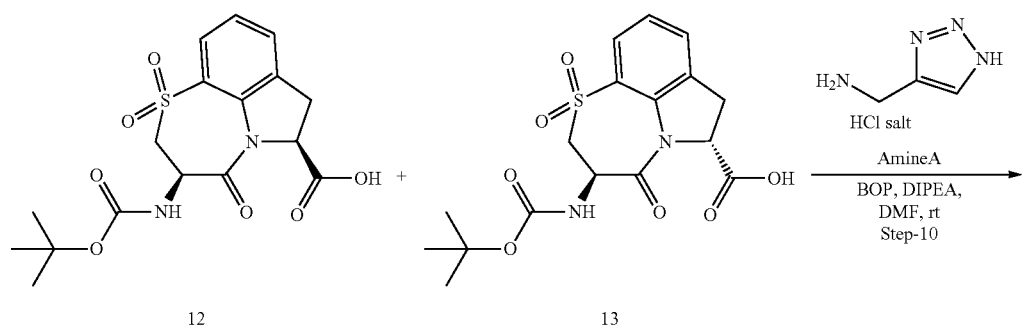
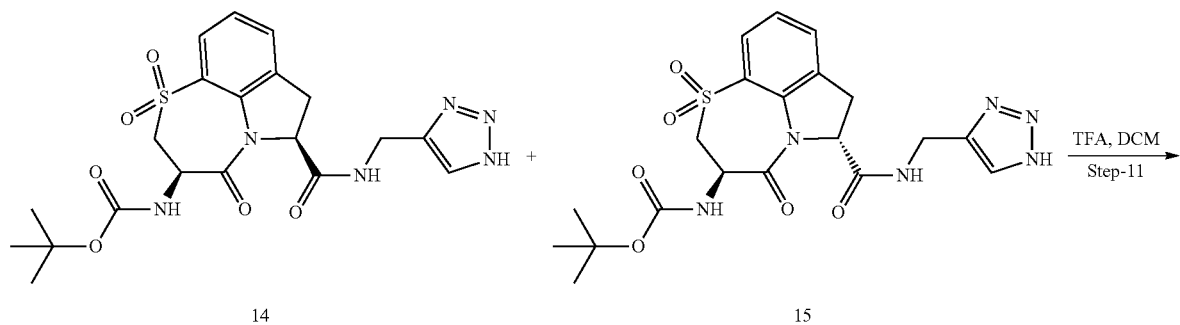
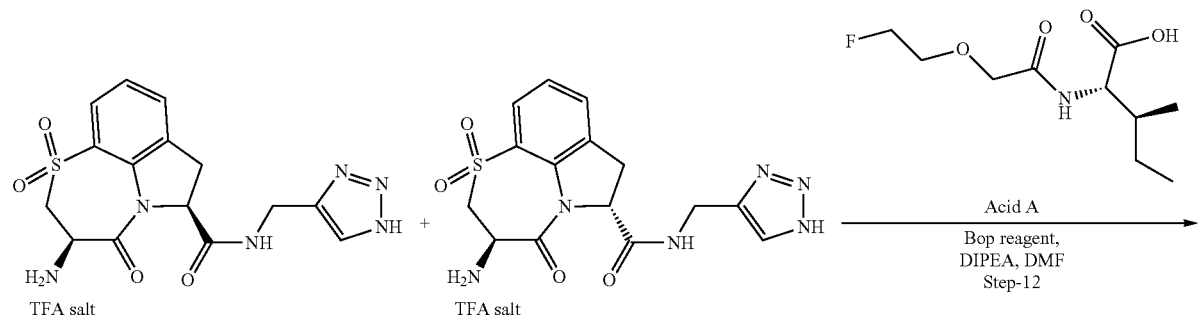

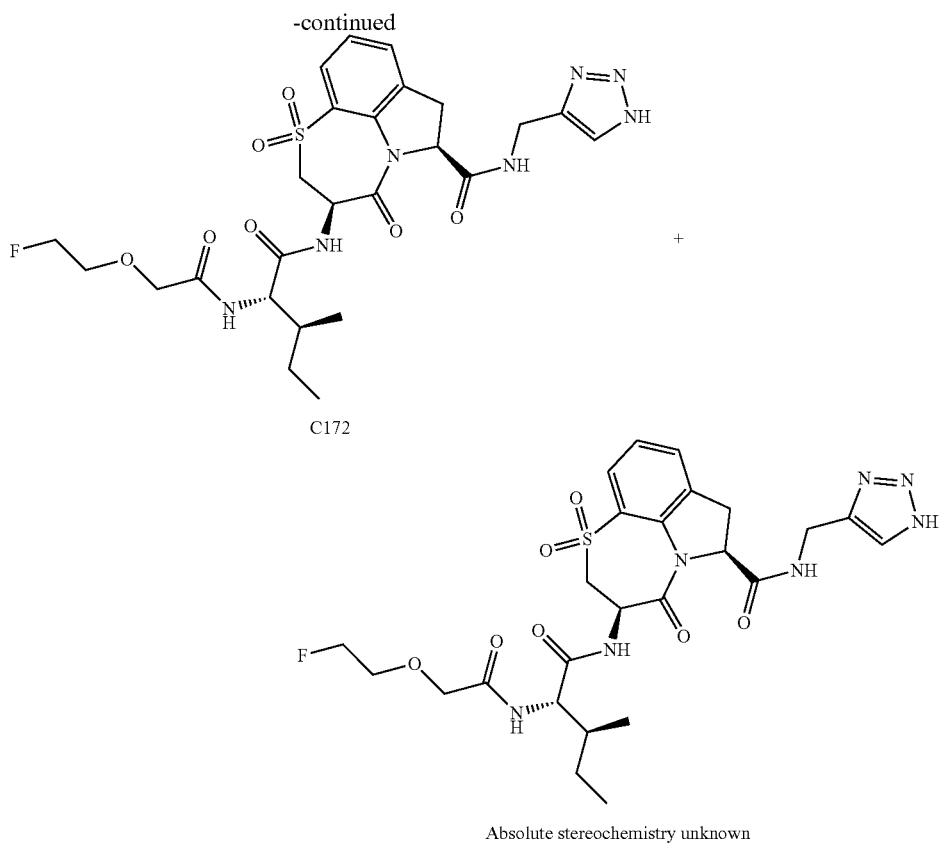

C172

Absolute stereochemistry unknown

General remarks: We were unable to separate diastereomers after indole to indoline reduction reaction [step-8] and we forwarded diastereomeroic mixture of compound 10 and 11 till the final step and from reverse phase prep HPLC we were able to isolate two isomers of C172. Because of the atom priority changes in the "S" based tricycle, stereochemistry of the tricyclic core is S, R instead of S, S.

Synthesis of 1-Fluoro-3-iodo-2-nitro-benzene [Scheme-23, Step-1]: Solution of compound 1 [30.0 g, 192 mmol] in MeCN [300 mL] was added to a pre heated solution of iodine [244.2 g, 1923 mmol] and tert butyl nitrite [114 mL, 961 mmol] in MeCN [300 mL] at 60° C. The reaction mixture was stirred for an additional 2 h at 60° C. and then stirred at room temperature for another 16 h. After completion [monitored by TLC] reaction mixture was quenched with saturated aqueous $Na_2S_2O_3$ [300 mL] solution maintaining the external temperature below 10° C. and extracted with EtOAc [3×500 mL]. The organic layer was dried [$MgSO_4$], concentrated under reduced pressure. Crude residue was purified through silica gel column chromatography using 0-3% EtOAc-hexane as eluting solvent to afford compound 2 [39 g, Yield: 76%] as a yellow solid. ($^1$H NMR complies).

Synthesis of (R)-2-tert-Butoxycarbonylamino-3-(3-iodo-2-nitro-phenylsulfanyl)-propionic acid [Scheme-23, Step-2]: $NaHCO_3$[5.70 g, 67.8 mmol] was added to a stirred solution of compound 3 [5.00 g, 22.6 mmol] in water (30 mL) at room temperature under argon atmosphere and stirred for 10 minutes. Finally, solution of compound 2 [4.22 g, 15.8 mmol] in EtOH (40 mL) was added to the reaction mixture and stirred at 80° C.; for 4 h. After completion, solvent was evaporated, crude was diluted with water [200 mL] and extracted with $Et_2O$ [200 mL]. Organic part was separated; pH of the aqueous part was slowly adjusted to 2-3 using 1 (N) aqueous HCl under ice cooled condition and immediately extracted with EtOAc [2×100 mL]. Organic part was separated, dried [$Na_2SO_4$] and concentrated under reduced pressure to afford compound 4 [4.5 g, 43%]. Mass [ESI]: m/z 468.27 [M$^+$+1].

Synthesis of (R)-3-(2-Amino-3-iodo-phenylsulfanyl)-2-tert-butoxycarbonylamino-propionic acid [Scheme-23, Step-3]: To a stirred solution of 4 [4.50 g, 9.61 mmol] in AcOH [40 mL] was added Fe powder [5.36 g, 96.1 mmol] and resultant reaction mixture was allowed to reflux at 80° C. for 4 h. After completion [monitored by LC-MS] reaction mixture was partitioned between EtOAc [2×200 mL] and water [150 mL]. Organic layer was separated, dried over sodium sulphate and concentrated under reduced pressure. Resultant crude was further azetroped with toluene to provide compound 5 [4.0 g, 95%] as light brown solid. Mass [ESI]: m/z 438.29 [M$^+$+1].

Synthesis of ((R)-6-Iodo-4-oxo-2,3,4,5-tetrahydro-benzo[b][1,4]thiazepin-3-yl)-carbamic acid tert-butyl ester [Scheme-23, Step-4]: To a stirred solution of compound 5 [8.00 g, 18.3 mmol] in DMSO [30 mL] was added DIPEA [4.77 mL, 27.4 mmol] at room temperature under inert atmosphere. To the resultant reaction mixture was added HATU [7.64 g, 20.1 mmol] in two portions and finally allowed to stir at room temperature for 16 h. After completion [monitored by TLC (40% EtOAc-Hexane, $R_f$=0.4) and LC-MS], reaction mixture was partitioned between water [500 mL] and EtOAc [3×100 mL]. Organic layer was separated, washed with brine [50 mL], dried [$MgSO_4$] and concentrated under reduced pressure. Resultant crude was purified by column chromatography [using silica gel 100-200 mesh as absorbent under gradient elution of 0-20% EtOAc-hexane] to afford compound 6 [3.6 g, 46%] as white solid. Mass [ESI]: m/z 420.27 [M$^+$+1].

Synthesis of {(R)-6-[3-(tert-Butyl-dimethyl-silanyloxy)-prop-1-ynyl]-4-oxo-2,3,4,5-tetrahydro-benzo[b][1,4]thiazepin-3-yl}-carbamic acid tert-butyl ester [Scheme-23, Step-5]: A stirred solution of compound 6 [3.56 g, 8.47 mmol] in DMF [15 mL] was purged with Argon for 10 minutes. To the resultant mixture was added TBDMS protected propargyl alcohol [7.20 g, 42.4 mmol], TEA [4.13 mL, 29.7 mmol], CuI [161 mg, 0.847 mmol] and Pd(PPh$_3$)$_2$Cl$_2$[595 mg, 0.847 mmol] under argon atmosphere and stirred at room temperature for 16 h. After completion [monitored by TLC (30% EtOAc-hexane, R$_f$=0.6) and LC-MS], reaction mixture was diluted with excess water [300 mL] and extracted with EtOAc [3×100 mL]. Organic layer was dried (MgSO$_4$) and concentrated under reduced pressure. Resultant crude was purified by column chromatography [gradient elution of 0-9% EtOAc-hexane, absorbent SiO$_2$] to afford compound 7 [3.1 g, 79%] as deep red gummy liquid. Mass [ESI]: m/z 462.69 [M$^+$+1].

Synthesis of [(R)-1-(tert-Butyl-dimethyl-silanyloxymethyl)-9-oxo-8,9-dihydro-7H-6-thia-9a-aza-benzo[cd]azulen-8-yl]-carbamic acid tert-butyl ester [Scheme-23, Step-6]: Solution of compound 7 [160 mg, 0.346 mmol] in DCM [13 mL] was degassed with nitrogen for 10 minutes. To the resultant mixture was added Gold catalyst [26.7 mg, 0.035 mmol] portion-wise under ice-cold condition and was stirred for 6 hour at 0° C. The reaction mixture was then kept in the refrigerator for next 72 h. After completion [monitored by TLC (20% EtOAc-hexane, R$_f$=0.6) and LC-MS], reaction mixture was filtered, then concentrated under reduced pressure. Resultant crude was purified by column chromatography [using silica gel 100-200 mesh under gradient elution of 5% EtOAc-hexane] to provide compound 8 [110 mg, 68.7%] as white solid. Mass [ESI]: m/z 462.69 [M$^+$+1].

Synthesis of ((R)-1-Hydroxymethyl-9-oxo-8,9-dihydro-7H-6-thia-9a-aza-benzo[cd]azulen-8-yl)-carbamic acid tert-butyl ester [Scheme-23, Step-7]: To a stirred solution of compound 8 [100 mg, 0.216 mmol] in EtOH [3 mL] was added pyridinium p-toluene sulfonate [21.8 mg, 0.087 mmol] at 0° C. and then reaction mixture was allowed to stir at room temperature for 16 h. After completion [monitored by TLC (50% EtOAc-Hexane, R$_f$=0.2 and LC-MS], reaction mixture was concentrated to dryness. Resultant crude was purified by column chromatography [under gradient elution of 0-50% EtOAc-hexane, SiO$_2$] to yield compound 9 [50 mg, 66%] as floppy solid. Mass [ESI]: m/z 348.42 [M$^+$+1].

Synthesis of ((1S,8R)-1-Hydroxymethyl-9-oxo-1,2,8,9-tetrahydro-7H-6-thia-9a-aza-benzo[cd]azulen-8-yl)-carbamic acid tert-butyl ester [Scheme-23, Step-8]: Solution of compound 9 [1.20 g, 3.44 mmol] in EtOH [100 mL] was degassed with argon for 15 minutes. Then 232 mg of Pd/C powder [10% by weight, wet] was added to the reaction mixture and resultant suspension was allowed to stir for 6 hour under 40 psi hydrogen pressure in a parr shaker. After completion [monitored by TLC (50% EtOAc-Hexane, R$_f$=0.2) and LC-MS], reaction mixture was filtered through a celite bed, washed with EtOH [3×10 mL] and concentrated under reduced pressure. Resultant crude was purified by column chromatography [using silica gel as absorbent, under gradient elution of 30-60% EtOAc-Hexane] to afford diastereomeric mixture of compound 10 and compound 11 [840 mg, disteromeric mixture]. Mass [ESI]: m/z 350.44 [M$^+$+1].

Synthesis of (1S,8R)-8-tert-Butoxycarbonylamino-6,6,9-trioxo-1,2,6,7,8,9-hexahydro-6lambda*6*-thia-9a-aza-benzo[cd]azulene-1-carboxylic acid [Scheme-23, Step-9]: To a stirred solution of compound 10 & compound 11)[50 mg, 0.14 mmol] in ACN [0.5 mL] was added NMO [67.5 mg, 0.576 mmol] and TPAP [5.06 mg, 0.014 mmol] portionwise at room temperature and stirred for 2 hour. After completion [monitored by TLC (20% EtOAc-Hexane, R$_f$=0.1) and LC-MS] solvent was evaporated to dryness. Resultant crude was diluted with EtOAc [30 mL] and acidified with (1N) aqueous HCl upto pH=2. Organic part was separated, dried over anhydrous Na$_2$SO$_4$ and concentrated under reduced pressure to afford diastereomeric mixture of compound 12 and compound 13 [50 mg, 88%, absolute stereochemistry was unknown] as floppy solid. Mass [ESI]: m/z 396.42 [M$^+$+1].

Synthesis of {(1S,8R)-6,6,9-Trioxo-1-[(1H-[1,2,3]triazol-4-ylmethyl)-carbamoyl]-1,2,6,7,8,9-hexahydro-6lambda*6*-thia-9a-aza-benzo[cd]azulen-8-yl}-carbamic acid tert-butyl ester [Scheme-23, Step-10]: To a stirred solution of compound 12 & compound 13 [0.590 g, 1.49 mmol] in DMF [6 mL] was added HCl salt of Amine A [220 mg, 1.64 mmol], DIPEA [1.60 mL, 8.94 mmol] and BOP reagent [1.32 g, 2.98 mmol] at 0° C. and resultant reaction mixture was allowed to stir at room temperature for 16 hour. After completion [monitored by TLC and LC-MS], reaction mixture was partitioned between water [50 mL] and EtOAc [3×25 mL]. Organic layer was separated, washed with brine, dried [MgSO$_4$] and concentrated under reduced pressure. Resultant crude was purified by column chromatography [under gradient elution of 90-92% EtOAc-hexane] to afford compound 14 and compound 15[140 mg, 19.7%, absolute stereochemistry was unknown] as white solid. Mass [ESI]: m/z 476.51 [M$^+$+1].

Synthesis of (1S, 8R)-8-Amino-6,6,9-trioxo-1,2,6,7,8,9-hexahydro-6lambda*6*-thia-9a-aza-benzo[cd]azulene-1-carboxylic acid (1H-[1,2,3]triazol-4-ylmethyl)-amide [Scheme-23, Step-11]: To a stirred solution of compound 14 and compound 15 [140 mg, 0.327 mmol] in DCM [0.5 mL] was added TFA in DCM (1:1) [1.5 mL] at 0° C. under argon atmosphere. The resultant reaction mixture was allowed to stir at room temperature for 2 hour. After completion [monitored by TLC (EtOAc, R$_f$=0.1) and LC-MS], reaction mixture was concentrated under reduced pressure, resultant residue was azeotroped with toluene to afford compound 16 and compound 17 [123 mg, crude TFA salt] as gummy liquid. Mass [ESI]: m/z 376.39 [M$^+$+1].

Synthesis of (1S,8R)-8-{(2S,3S)-2-[2-(2-Fluoro-ethoxy)-acetylamino]-3-methyl-pentanoylamino}-6,6,9-trioxo-1,2,6,7,8,9-hexahydro-6lambda*6*-thia-9a-aza-benzo[cd]azulene-1-carboxylic acid (1H-[1,2,3]triazol-4-ylmethyl)-amide [C172][Scheme-23, Step-12]: To a stirred solution of compound 16 & compound 17 [TFA salt][144 mg, 0.294 mmol] and acid A (69.1 mg, 0.294 mmol) in 1.5 mL DMF, was added DIPEA [0.263 mL, 1.47 mmol] followed by addition of BOP reagent [260 mg, 0.588 mmol] and resultant reaction mixture was allowed to stir at ambient temperature for 16 h. After completion [monitored by LC-MS], reaction mixture was submitted for reverse phase prep HPLC purification to afford 9 mg of C172-Isomer1 [faster moving isomer] as white solid and 5 mg of C172-Isomer2 [slower moving isomer] as white solid. Though we have drawn (S, S) configuration here but the absolute stereochemistry was unknown. Mass [ESI]: m/z 593.63 [M$^+$+1].

Example 4: Synthesis of Compounds with Nitrogen-Containing Core
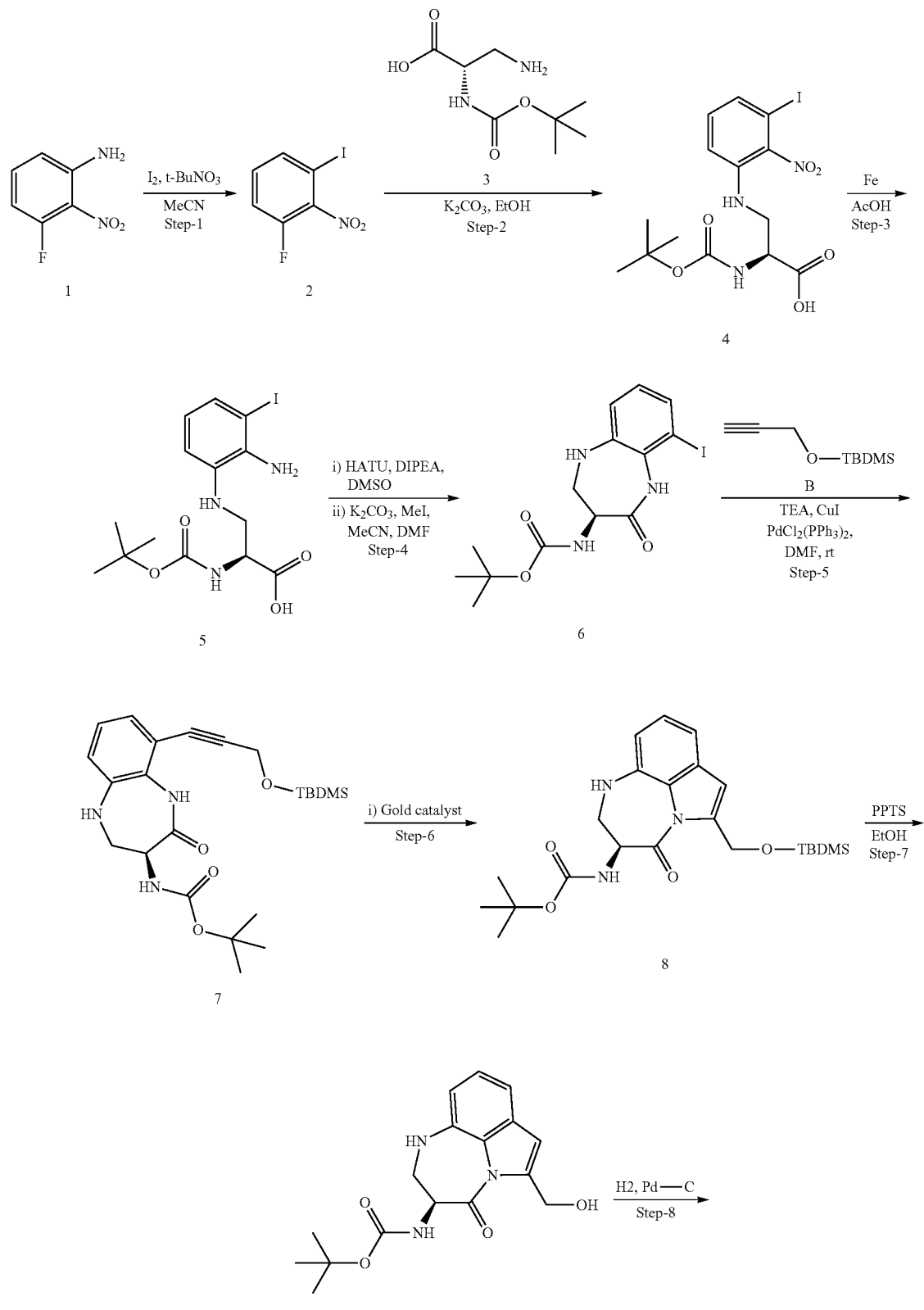

-continued
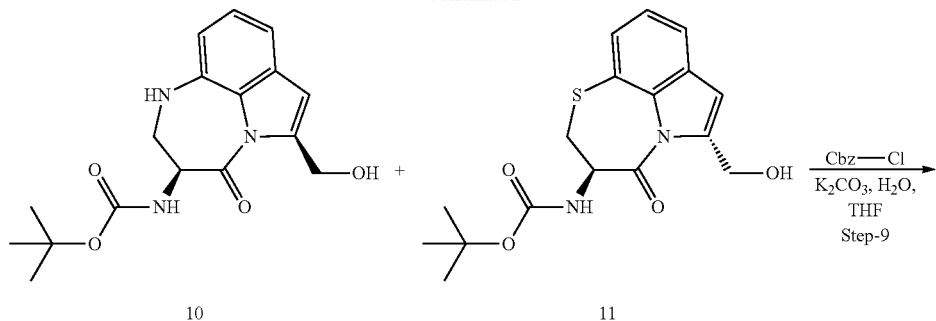
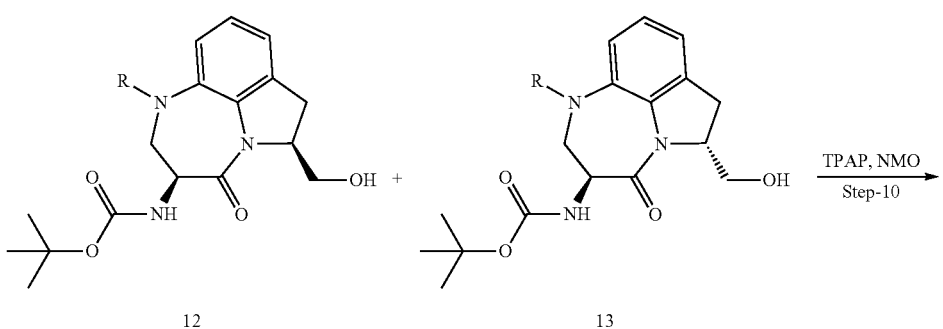
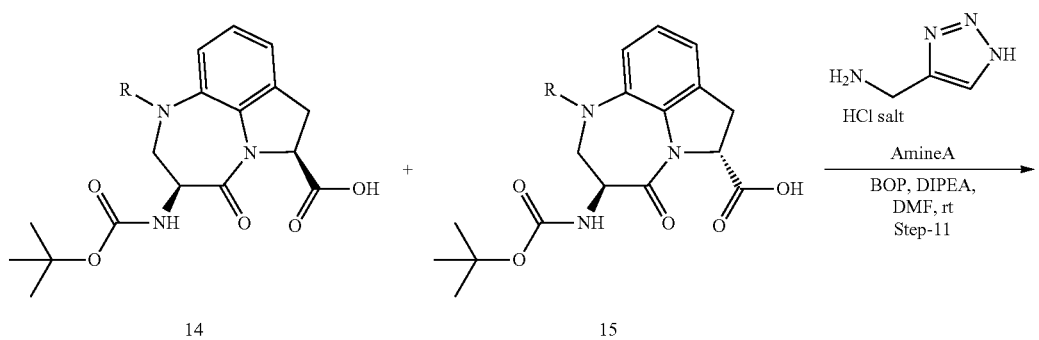
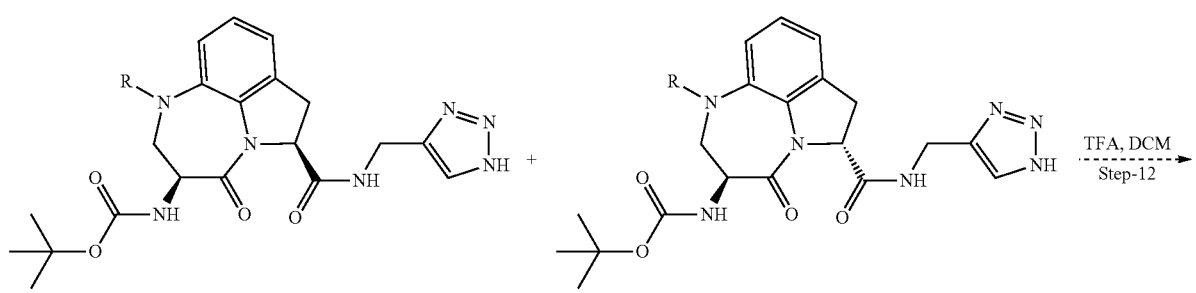
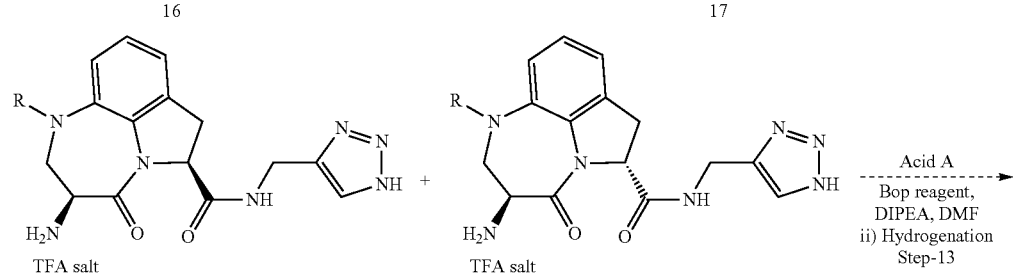

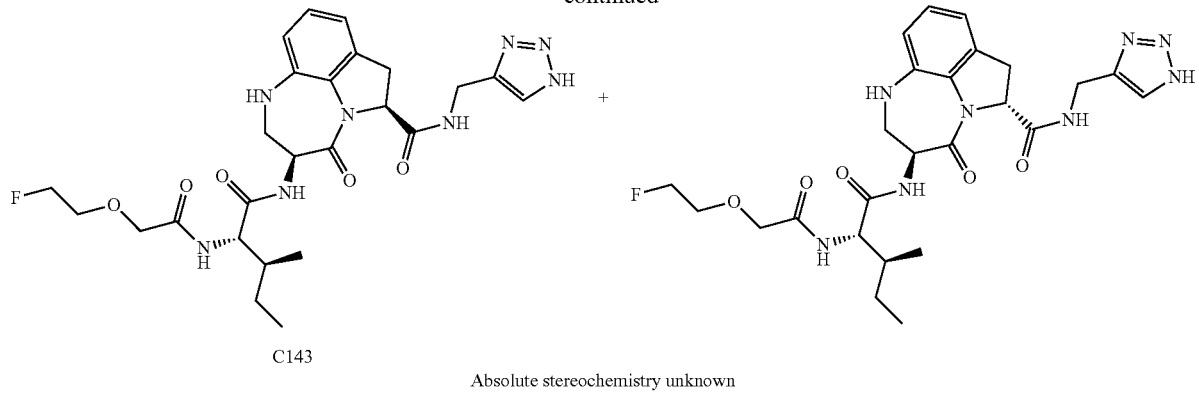

221  222

-continued

C143
R = CBz

Absolute stereochemistry unknown

General remarks: We have separated both isomer after indole to indoline reduction reaction however the absolute stereochemistry is unknown for the separated isomers. We have forwarded both isomers till final step. We captured protocol for the conversion of upper isomer [non polar] in the experimental and analogues protocol was followed for the conversion of lower isomer [polar].

Experimentals

Synthesis of 1-Fluoro-3-iodo-2-nitro-benzene [Scheme-24, Step-1]: Solution of compound 1 [30.0 g, 192 mmol] in MeCN [300 mL] was added to a pre heated solution of iodine [244.2 g, 1923 mmol] and tert butyl nitrite [114 mL, 961 mmol] in MeCN [300 mL] at 60° C. The reaction mixture was stirred for an additional 2 h at 60° C. and then stirred at room temperature for another 16 h. After completion [monitored by TLC] reaction mixture was quenched with saturated aqueous $Na_2S_2O_3$ [300 mL] solution maintaining the external temperature below 10° C. and extracted with EtOAc [3×500 mL]. The organic layer was dried [$MgSO_4$], concentrated under reduced pressure. Crude residue was purified through silica gel column chromatography using 0-3% EtOAc-hexane as eluting solvent to afford compound 2 [39 g, Yield: 76%] as a yellow solid. ($^1$H NMR complies)

Synthesis of (S)-2-tert-Butoxycarbonylamino-3-(3-iodo-2-nitro-phenylamino)-propionic acid [Scheme-24, Step-2]: $K_2CO_3$ [5.20 g, 37.7 mmol] was added to a stirred suspension of compound 3 [7.0 g, 34 mmol] in EtOH (230 mL) under ice cold condition. After addition reaction mixture was left to stir vigorously for half an hour under cold condition. Finally, compound 2 [9.16 g, 34.3 mmol] was added portion wise to the reaction mixture at 0° C., after addition reaction mixture was brought to room temperature and heated at 80° C. for 40 h. After completion, EtOH were evaporated, crude was diluted with water [200 mL] and extracted with $Et_2O$ [200 mL]. Organic part was separated; pH of the aqueous part was slowly adjusted to 2-3 using 1 (N) aqueous HCl under ice cooled condition and immediately extracted with EtOAc [2×200 mL]. Organic part was separated, dried [$MgSO_4$] and concentrated under reduced pressure to afford compound 4 [10.6 g, 68.4%] as dark red floppy solid. Mass [ESI]: m/z 451.21 [M$^+$−1].

Synthesis of (S)-3-(2-Amino-3-iodo-phenylamino)-2-tert-butoxycarbonylamino-propionic acid [Scheme-24, Step-3]: To a stirred solution of 4 [10.6 g, 23.5 mmol] in AcOH [70 mL] was added Fe powder [13.1 g, 235 mmol] and resultant reaction mixture was allowed to reflux at 80° C. for 3.5 h. After completion [monitored by LC-MS] reaction mixture was partitioned between EtOAc [2×300 mL] and water [300 mL]. Organic layer was separated, dried over sodium sulphate and concentrated under reduced pressure. Resultant crude was further azetroped with toluene to provide compound 5 [8.96 g, 90.5%] as brown floppy solid. Mass [ESI]: m/z 421.23 [M$^+$+1].

Synthesis of ((S)-9-Iodo-2-oxo-2,3,4,5-tetrahydro-1H-benzo[b][1,4]diazepin-3-yl)-carbamic acid tert-butyl ester [Scheme-24, Step-4]: To a stirred solution of compound 5 [8.76 g, 20.8 mmol] in DMSO [87 mL] was added DIPEA [5.59 mL, 31.2 mmol] at room temperature under inert atmosphere. To the resultant reaction mixture was added HATU [8.70 g, 22.9 mmol] in two portions under ice-cold condition and finally allowed to stir at room temperature for 16 h. After completion [monitored by TLC (30% EtOAc-Hexane, $R_f$=0.5) and LC-MS], reaction mixture was partitioned between water [500 mL] and EtOAc [3×100 mL]. Organic layer was separated, washed with brine [50 mL], dried [$MgSO_4$] and concentrated under reduced pressure. Resultant crude was purified by column chromatography [using silica gel 100-200 mesh as absorbent under gradient elution of 10-20% EtOAc-hexane] to afford compound 6 [4.9 g, 59%] as light brown solid. Mass [ESI]: m/z 403.21 [M$^+$+1].

{(S)-9-[3-(tert-Butyl-dimethyl-silanyloxy)-prop-1-ynyl]-2-oxo-2, 3, 4, 5-tetrahydro-1H-benzo [b][1,4]diazepin-3-yl}-carbamic acid tert-butyl ester [Scheme-24, Step-5]: A stirred solution of compound 6 [4.41 g, 10.9 mmol] in DMF [18 mL] was purged with Argon for 10 minutes. To the resultant mixture was added TBDMS protected propargyl alcohol [9.28 g, 54.6 mmol], TEA [5.37 mL, 38.21 mmol], CuI [208 mg, 1.09 mmol] and Pd(PPh$_3$)$_2$Cl$_2$ [766 mg, 1.09 mmol] under argon atmosphere and stirred at room temperature for 16 h. After completion [monitored by TLC (20% EtOAc-hexane, $R_f$=0.4) and LC-MS], reaction mixture was diluted with water [300 mL] and extracted with EtOAc [3×100 mL]. Organic layer was dried (MgSO$_4$) and concentrated under reduced pressure. Resultant crude was purified by column chromatography [gradient elution of 10-14% EtOAc-hexane, absorbent SiO$_2$] to afford compound 7 [4.0 g, 82.21%] as deep red semi solid. Mass [ESI]: m/z 445.62 [M$^+$+1].

[(S)-6-(tert-Butyl-dimethyl-silanyloxymethyl)-1-methyl-4-oxo-1,2,3,4-tetrahydro-[1,4]diazepino[3,2,1-hi]indol-3- yl]-carbamic acid tert-butyl ester i) [Scheme-24, Step-6]: Solution of compound 7 [4.0 g, 8.9 mmol] in DCM [400 mL] was degassed with nitrogen for 10 minutes. To the resultant mixture was added Gold catalyst [0.69 g, 0.89 mmol] portion-wise under ice-cold condition and was stirred for 6 hour at 0° C. The reaction mixture was then kept in the refrigerator for next 16 h. After completion [monitored by TLC (10% EtOAc-hexane, $R_f$=0.2) and LC-MS], reaction mixture was concentrated under reduced pressure. Resultant crude was purified by column chromatography [using silica gel 100-200 mesh under gradient elution of 0-9% EtOAc-hexane] to provide cyclized intermediate (1.50 g, 37.4%) as gummy liquid and 800 mg of un-reacted starting material was also recovered.

((S)-6-Hydroxymethyl-4-oxo-1,2,3,4-tetrahydro-[1,4]diazepino[3,2,1-hi]indol-3-yl)-carbamic acid tert-butyl ester i) [Scheme-24, Step-7]: To a clear solution of compound 8 (1.20 g, 2.61 mmol) in ethanol (5 mL) was added pyridinium p-toluene sulfonate (197 mg, 0.78 mmol) at 0° C. Reaction mixture was slowly raised to room temperature and stir for 16 h at room temperature. LCMS showed, starting material was consumed completely. Again, another portion of pyridinium p-toluene sulfonate (197 mg, 0.78 mmol) was added to it and allowed to stir for 16 h. After completion, solvent was removed and the residue was dissolved in ethyl acetate. The organic solution was washed with brine solution, water and then dried over $MgSO_4$. The solvent was evaporated to get crude. Crude was purified through silica gel column chromatography using 42% ethyl acetate in hexane as eluting solvent to get desired product as floppy solid (750 mg, 86.6%). Mass [ESI]: m/z 331.37 [M$^+$+1]

((3S,6S)-6-Hydroxymethyl-4-oxo-1,2,3,4,6,7-hexahydro-[1,4]diazepino[3,2,1-hi]indol-3-yl)-carbamic acid tert-butyl ester [Scheme-24, Step-8]: Compound 9 (750 mg, 2.17 mmol) were dissolved in 15 ml of ethanol, mixed with 232 mg of palladium on carbon (wet 10%), and the mixture was stirred for 2 h at room temperature under hydrogen (balloon pressure). The reaction solution was filtered through celite and washed three times with ethanol (5 mL). Filtrate was concentrated to get crude. Crude was purified through silica gel column chromatography using 15% ethyl acetate in DCM as eluting solvent to get desired product as floppy solid. The next step was forwarded with upper isomer. Exact stereochemistry was unknown. Upper isomer was obtained as major (260 mg, 35.9%) and lower isomer was referred as minor compound. Mass [ESI]: m/z 333.39 [M$^+$+1]

(3S, 6S)-3-tert-Butoxycarbonylamino-6-hydroxymethyl-4-oxo-3,4,6,7-tetrahydro-2H-[1,4] diazepino[3,2,1-hi]indole-1-carboxylic acid benzyl ester: [Scheme-24, Step-9] To a stirred solution of ~compound 10 (160 mg, 0.48 mmol) in THF (1.6 ml) was added $K_2CO_3$ (66.3 mg, 0.48 mmol) followed by $H_2O$ (1 ml). Finally, Cbz chloride (0.08 ml, 0.58 mmol) was added at ice cool condition. The resultant mixture was stirred at room temperature for 16 h. After overnight LCMS analysis of the reaction mixture showed that the starting was not fully consumed. So, again 66.3 mg of $K_2CO_3$ and 0.08 ml of Cbz chloride added and reaction was continued for overnight. After completion, (confirmed by LCMS) resulting mixture was diluted with EtOAc (150 mL) and washed with water (100 mL). Organic layer was separated, dried [$Na_2SO_4$] and concentrated. Resultant crude was purified by column chromatography [using silica gel 100-200 mesh as absorbent and 30-53% EtOAc-hexane as eluting solvent] as afford ~compound 12 as floppy solid (140 mg, 62.3%). Mass [ESI]: m/z 467.53 [M$^+$+1]

(3S,6S)-3-tert-Butoxycarbonylamino-4-oxo-3,4,6,7-tetrahydro-2H-[1,4]diazepino[3,2,1-hi]indole-1,6-dicarboxylic acid 1-benzyl ester: [Scheme-24, Step-10] To a stirred solution of ~compound 12 (140 mg, 0.30 mmol) in ACN (3.5 ml), NMO (141 mg, 1.20 mmol) and TPAP (10.5 mg, 0.03 mmol) was added in portion wise at ice cool condition. The resulting mixture was stirred at RT for 2 h. After completion (confirmed by LCMS monitoring) solvent was evaporated, diluted with water and acidified with 1 N HCl upto pH=3-4 at ice cool condition. The combined organic layer was diluted with Ethyl acetate and washed with water. The organic layer was separated, dried over $Na_2SO_4$ and concentrated to provide ~compound 14 (144 mg, 99.9%) as floppy solid. Mass [ESI]: m/z 481.51 [M$^+$+1]

(3S,6S)-3-tert-Butoxycarbonylamino-4-oxo-6-[(1H-[1,2,3]triazol-4-ylmethyl)-carbamoyl]-3,4,6,7-tetrahydro-2H-[1,4]diazepino[3,2,1-hi]indole-1-carboxylic acid benzyl ester: [Scheme-24, Step-11] To a stirred solution of ~Compound 14 (160 mg, 0.33 mmol) and HCl salt of triazolo amine (49.0 mg, 0.37 mmol) in DMF (2.0 ml) were added hunig's base (0.35 ml, 1.99 mmol) at 0° C. Finally Bop reagent (294 mg, 0.67 mmol) was added portion wise at ice cold condition and the reaction mixture was stirred at room temperature for 16 h. After completion, (monitored by LCMS) reaction mixture was diluted with ethyl acetate (40 mL) and washed with excess water (4×30 mL), organic part dried over $Na_2SO_4$, evaporated to get crude material. Crude was purified through silica gel column chromatography using 0-1% MeOH-DCM as eluting solvent to provide ~compound 16 (100 mg, 53.6%) as white solid. Mass [ESI]: m/z 561.60 [M$^+$+1]

(3S, 6S)-3-Amino-4-oxo-6-[(1H-[1, 2, 3]triazol-4-ylmethyl)-carbamoyl]-3, 4, 6, 7-tetrahydro-2H-[1,4]diazepino[3,2,1-hi]indole-1-carboxylic acid benzyl ester(TFA salt): [Scheme-24, Step-12] To a stirred solution of ~compound 16 (100 mg 0.18 mmol) in 1.5 ml DCM, was added 2.15 ml of DCM in TFA (1:1) at ice cold condition. The resultant mixture was allowed to stir for 3 hours. After completion of reaction (monitored by LCMS) TFA was removed under reduced pressure. The residue was azeotroped with toluene to provide compound 18 as TFA salt (82.2 mg, 100%). Mass [ESI]: m/z 461.48 [M$^+$+1]

(3S,6S)-3-{(2S,3S)-2-[2-(2-Fluoro-ethoxy)-acetylamino]-3-methyl-pentanoylamino}-4-oxo-1,2,3,4,6,7-hexahydro-[1,4]diazepino[3,2,1-hi]indole-6-carboxylic acid (1H-[1,2,3]triazol-4-ylmethyl)-amide: i) [Scheme-24, Step-13] To a stirred solution of compound 18 (82.2 mg, 0.18 mmol) and Acid A (41.9 mg, 0.18 mmol) in DMF (0.8 ml) were added Hunig's base (0.19 ml, 1.07 mmol) at 0° C. Finally Bop reagent (157.5 mg, 0.357 mmol) was added portion wise at ice cold condition and the reaction mixture was stirred at room temperature for 16 h. After 16 h, as the starting was not fully consumed 22 mg of Acid A, 80 mg BOP and 0.1 ml DIPEA was further added and the reaction was continued for another 16 hours. After completion (monitored by LCMS), reaction mixture was diluted with ethyl acetate (40 ml) at ice cool condition and washed with excess water (3×20 ml), organic layer was separated, dried over $Na_2SO_4$ and evaporated to afford 130 mg of crude amidation product. Mass [ESI]: m/z 678.73 [M$^+$+1]

ii) Amidation product (121 mg, 0.18 mmol) was dissolved in 10 ml of ethanol, and 50 mg of 10% palladium on carbon (wet) was added and resultant suspension was allowed to stir under hydrogen balloon pressure for 16 h. After completion (monitored by LCMS), reaction mixture was filtered through celite and washed three times with ethyl acetate (50 mL). Filtrate was concentrated and resultant crude was submitted for preparative HPLC purification to afford 3 mg of faster eluting isomer of C143 as off white solid. Mass [ESI]: m/z 544.59 [M$^+$+1].

Scheme-25 [Synthesis of C144]
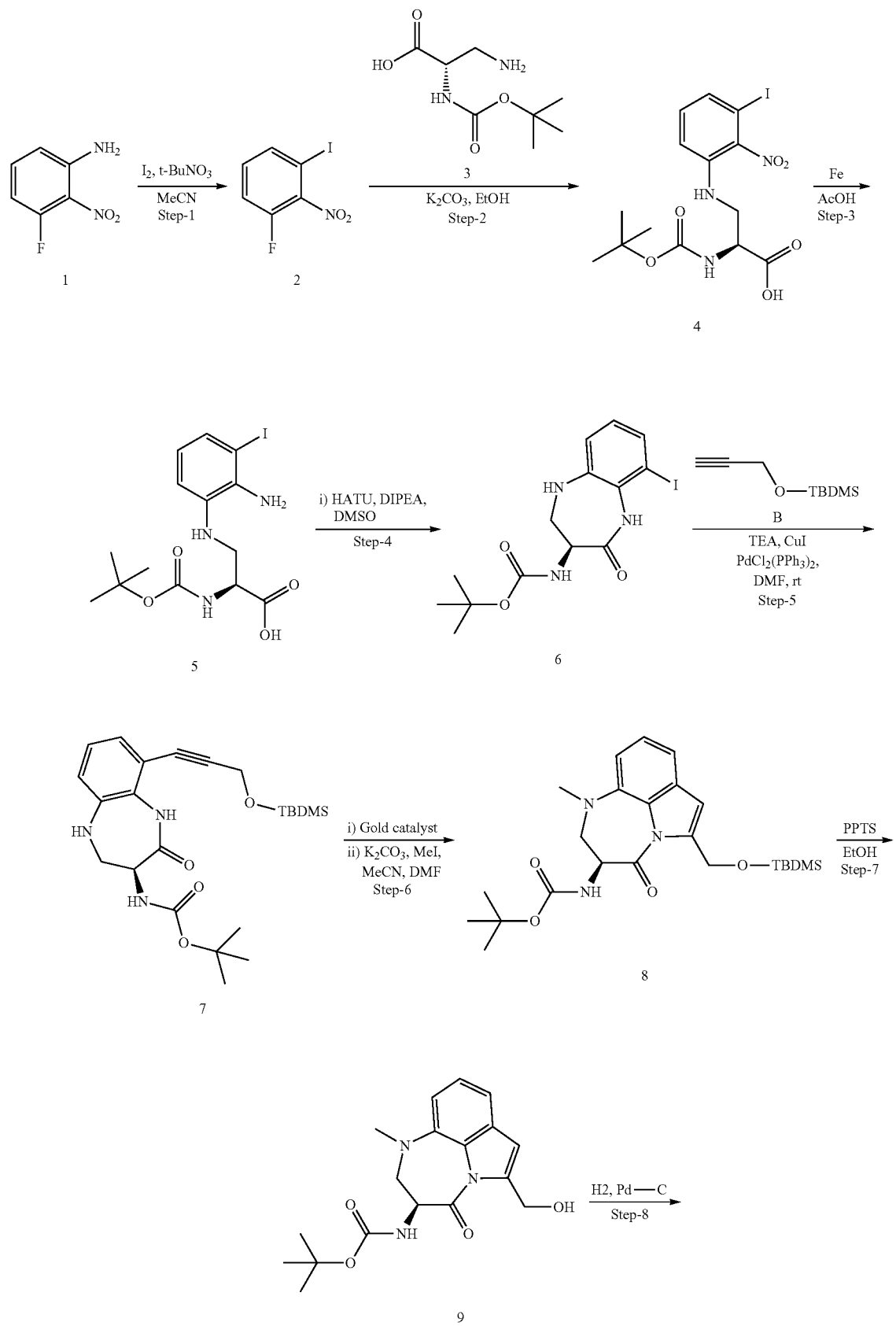

-continued
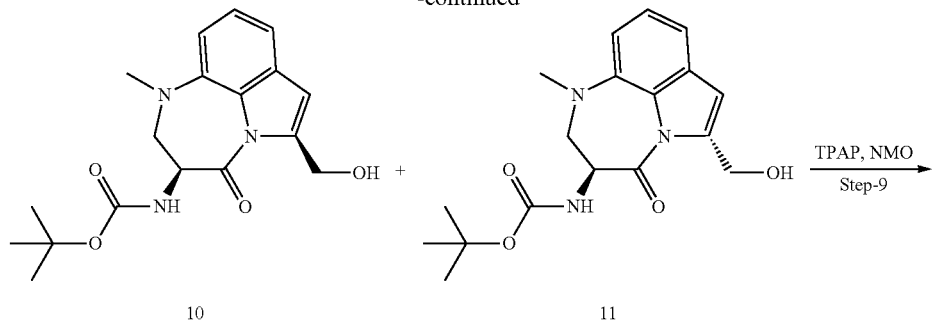
10
11
Absolute structure unknown
TPAP, NMO
Step-9
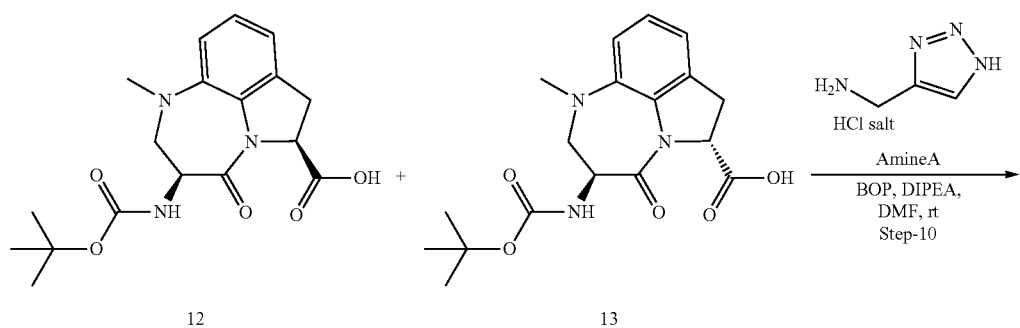
12
13
AmineA
BOP, DIPEA,
DMF, rt
Step-10
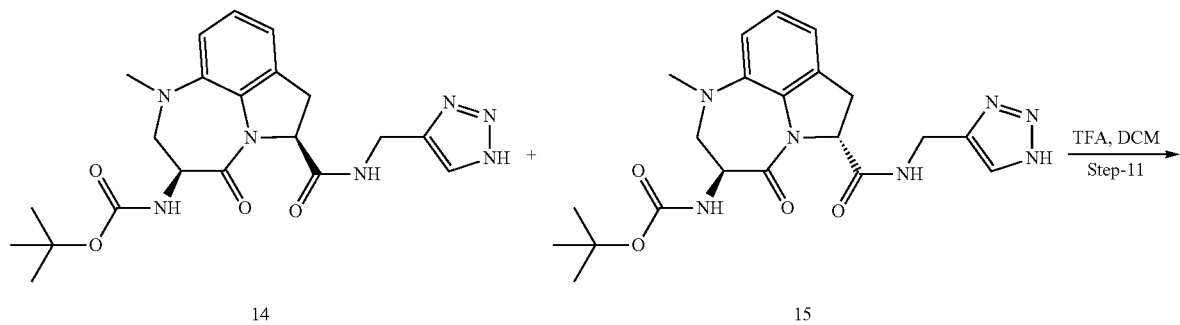
14
15
TFA, DCM
Step-11
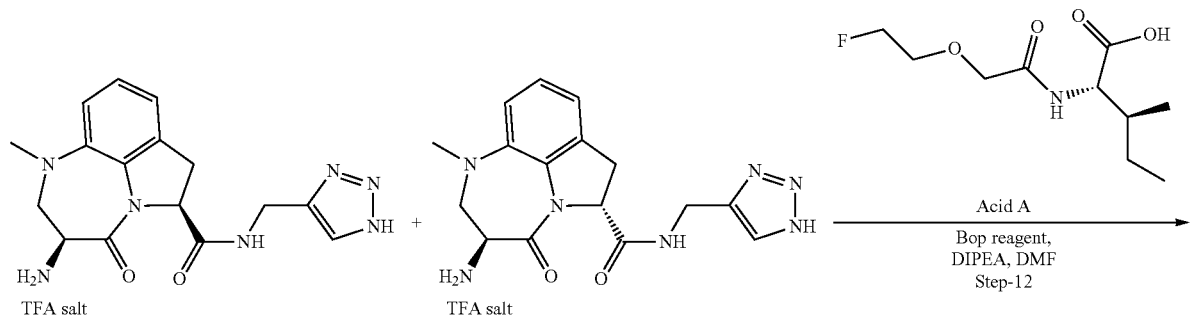
16
TFA salt
17
TFA salt
Absolute structure unknown
Acid A
Bop reagent,
DIPEA, DMF
Step-12

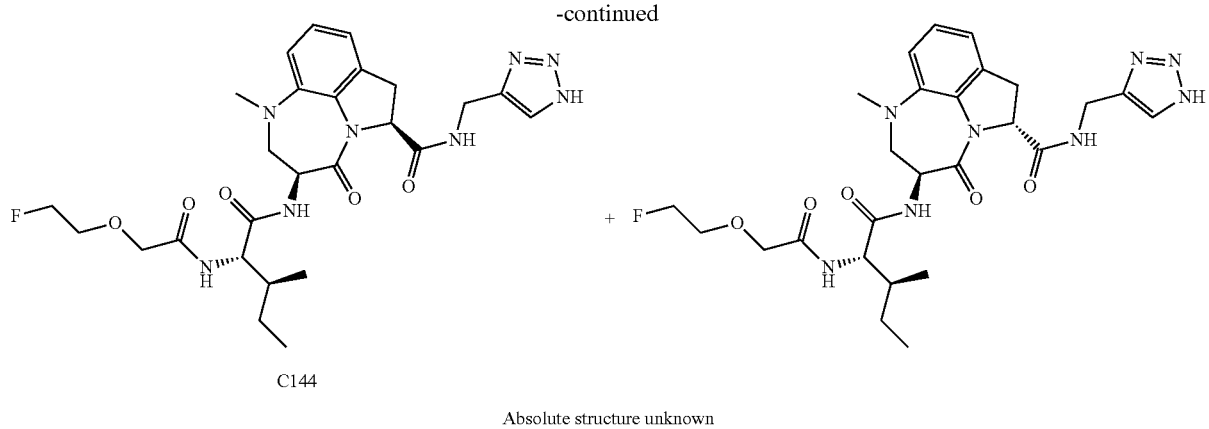

C144

Absolute structure unknown

General remarks: We have separated both isomer after indole to indoline reduction reaction however the absolute stereochemistry is unknown for the separated isomers. We have forwarded both isomers till final step. We captured protocol for the conversion of upper isomer [non polar] in the experimental and analogues protocol was followed for the conversion of lower isomer [polar].

Experimentals

Synthesis of 1-Fluoro-3-iodo-2-nitro-benzene [Scheme-25, Step-1]: Solution of compound 1 [30.0 g, 192 mmol] in MeCN [300 mL] was added to a pre heated solution of iodine [244.2 g, 1923 mmol] and tert butyl nitrite [114 mL, 961 mmol] in MeCN [300 mL] at 60° C. The reaction mixture was stirred for an additional 2 h at 60° C. and then stirred at room temperature for another 16 h. After completion [monitored by TLC] reaction mixture was quenched with saturated aqueous $Na_2S_2O_3$ [300 mL] solution maintaining the external temperature below 10° C. and extracted with EtOAc [3×500 mL]. The organic layer was dried [$MgSO_4$], concentrated under reduced pressure. Crude residue was purified through silica gel column chromatography using 0-3% EtOAc-hexane as eluting solvent to afford compound 2 [39 g, Yield: 76%] as a yellow solid. ($^1$H NMR complies)

Synthesis of (S)-2-tert-Butoxycarbonylamino-3-(3-iodo-2-nitro-phenylamino)-propionic acid [Scheme-25, Step-2]: $K_2CO_3$ [5.20 g, 37.7 mmol] was added to a stirred suspension of compound 3 [7.0 g, 34 mmol] in EtOH (230 mL) under ice cold condition. After addition reaction mixture was left to stir vigorously for half an hour under cold condition. Finally, compound 2 [9.16 g, 34.3 mmol] was added portion wise to the reaction mixture at 0° C., after addition reaction mixture was brought to room temperature and heated at 80° C. for 40 h. After completion, EtOH were evaporated, crude was diluted with water [200 mL] and extracted with $Et_2O$ [200 mL]. Organic part was separated; pH of the aqueous part was slowly adjusted to 2-3 using 1 (N) aqueous HCl under ice cooled condition and immediately extracted with EtOAc [2×200 mL]. Organic part was separated, dried [$MgSO_4$] and concentrated under reduced pressure to afford compound 4 [10.6 g, 68.4%] as dark red floppy solid. Mass [ESI]: m/z 451.21 [M$^+$−1].

Synthesis of (S)-3-(2-Amino-3-iodo-phenylamino)-2-tert-butoxycarbonylamino-propionic acid [Scheme-25, Step-3]: To a stirred solution of 4 [10.6 g, 23.5 mmol] in AcOH [70 mL] was added Fe powder [13.1 g, 235 mmol] and resultant reaction mixture was allowed to reflux at 80° C. for 3.5 h. After completion [monitored by LC-MS] reaction mixture was partitioned between EtOAc [2×300 mL] and water [300 mL]. Organic layer was separated, dried over sodium sulphate and concentrated under reduced pressure. Resultant crude was further azetroped with toluene to provide compound 5 [8.96 g, 90.5%] as brown floppy solid. Mass [ESI]: m/z 421.23 [M$^+$+1].

Synthesis of ((S)-9-Iodo-2-oxo-2,3,4,5-tetrahydro-1H-benzo[b][1,4]diazepin-3-yl)-carbamic acid tert-butyl ester [Scheme-25, Step-4]: To a stirred solution of compound 5 [8.76 g, 20.8 mmol] in DMSO [87 mL] was added DIPEA [5.59 mL, 31.2 mmol] at room temperature under inert atmosphere. To the resultant reaction mixture was added HATU [8.70 g, 22.9 mmol] in two portions under ice-cold condition and finally allowed to stir at room temperature for 16 h. After completion [monitored by TLC (30% EtOAc-Hexane, $R_f$=0.5) and LC-MS], reaction mixture was partitioned between water [500 mL] and EtOAc [3×100 mL]. Organic layer was separated, washed with brine [50 mL], dried [$MgSO_4$] and concentrated under reduced pressure. Resultant crude was purified by column chromatography [using silica gel 100-200 mesh as absorbent under gradient elution of 10-20% EtOAc-hexane] to afford compound 6 [4.9 g, 59%] as light brown solid. Mass [ESI]: m/z 403.21 [M$^+$+1].

{(S)-9-[3-(tert-Butyl-dimethyl-silanyloxy)-prop-1-ynyl]-2-oxo-2, 3, 4, 5-tetrahydro-1H-benzo [b][1,4]diazepin-3-yl}-carbamic acid tert-butyl ester [Scheme-25, Step-5]: A stirred solution of compound 6 [4.41 g, 10.9 mmol] in DMF [18 mL] was purged with Argon for 10 minutes. To the resultant mixture was added TBDMS protected propargyl alcohol [9.28 g, 54.6 mmol], TEA [5.37 mL, 38.21 mmol], CuI [208 mg, 1.09 mmol] and Pd(PPh$_3$)$_2$Cl$_2$ [766 mg, 1.09 mmol] under argon atmosphere and stirred at room temperature for 16 h. After completion [monitored by TLC (20% EtOAc-hexane, $R_f$=0.4) and LC-MS], reaction mixture was diluted with water [300 mL] and extracted with EtOAc [3×100 mL]. Organic layer was dried (MgSO$_4$) and concentrated under reduced pressure. Resultant crude was purified by column chromatography [gradient elution of 10-14% EtOAc-hexane, absorbent SiO$_2$] to afford compound 7 [4.0 g, 82.21%] as deep red semi solid. Mass [ESI]: m/z 445.62 [M$^+$+1].

[(S)-6-(tert-Butyl-dimethyl-silanyloxymethyl)-1-methyl-4-oxo-1,2,3,4-tetrahydro-[1,4]diazepino[3,2,1-hi]indol-3-yl]-carbamic acid tert-butyl ester i) [Scheme-25, Step-6]: Solution of compound 7 [4.0 g, 8.9 mmol] in DCM [400 mL]

was degassed with nitrogen for 10 minutes. To the resultant mixture was added Gold catalyst [0.69 g, 0.89 mmol] portion-wise under ice-cold condition and was stirred for 6 hour at 0° C. The reaction mixture was then kept in the refrigerator for next 16 h. After completion [monitored by TLC (10% EtOAc-hexane, $R_f$=0.2) and LC-MS], reaction mixture was concentrated under reduced pressure. Resultant crude was purified by column chromatography [using silica gel 100-200 mesh under gradient elution of 0-9% EtOAc-hexane] to provide cyclized intermediate (1.5 g, 37.4%) as gummy liquid and 800 mg of un-reacted starting material was also recovered.

ii) To a clear solution of cyclized intermediate [1.5 g, 3.4 mmol] in MeCN [25 mL] and DMF [10 mL] was added potassium carbonate [0.69 g, 5.05 mmol] followed by methyl iodide [0.63 mL, 10.1 mmol] drop-wise under ice cold condition in a sealed tube and stirred for 16 h. After LC-MS analysis again methyl iodide [1.26 mL, 10.1 mmol] was added to the reaction mixture and stirred for another 48 h at ambient temperature. After completion, reaction mixture was diluted with EtOAc [200 mL] and washed with water [150 mL] followed by brine solution [100 mL]. Organic layer was separated, dried over $MgSO_4$ and concentrated. Crude residue was purified through silica gel column chromatography using 0-4% EtOAc-hexane as eluting solvent to provide compound 8 [0.9 g, 58%] as gummy liquid. Mass [ESI]: m/z 459.65 [M$^+$+1].

((S)-6-Hydroxymethyl-1-methyl-4-oxo-1,2,3,4-tetrahydro-[1,4]diazepino[3,2,1-hi]indol-3-yl)-carbamic acid tert-butyl ester [Scheme-25, Step-7]: To a stirred solution of compound 8 [0.9 g, 1.9 mmol] in EtOH [10 mL] was added pyridinium p-toluene sulfonate [0.15 g, 0.59 mmol] at 0° C. and then reaction mixture was allowed to stir at room temperature for 16 h. After LC-MS and TLC analysis [20% EtOAc-hexane, $R_f$=0.2], another portion of pyridinium p-toluene sulfonate [0.15 g, 0.59 mmol] was added to the reaction mixture and allowed to stir at room temperature for additional 30 h. After completion [monitored by TLC and LC-MS], reaction mixture was concentrated to dryness. Then crude was partitioned between EtOAc [3×75 mL] and water [100 mL]. Organic layer was separated, washed with brine [50 mL], dried [MgSO$_4$] and concentrated. Resultant crude was purified by column chromatography [under gradient elution of 30-42% EtOAc-hexane, SiO$_2$] to yield compound 9 [0.58 g, 85.6%] as floppy solid. Mass [ESI]: m/z 345.39 [M$^+$+1].

((3 S, 6S)-6-Hydroxymethyl-1-methyl-4-oxo-1,2,3,4,6,7-hexahydro-[1,4]diazepino[3,2,1-hi]indol-3-yl)-carbamic acid tert-butyl ester [Scheme-25, Step-8]: Solution of compound 9 [0.58 g, 1.68 mmol] in EtOH [20 mL] was degassed with argon for 10 minutes. Then 232 mg of Pd/C powder [10% by weight, wet] was added to the reaction mixture and resultant suspension was allowed to stir at for 2 h under H$_2$ balloon pressure. After completion [monitored by TLC and LC-MS], reaction mixture was filtered through a celite bed, washed with EtOH [3×10 mL] and concentrated under reduced pressure. Resultant crude was purified by column chromatography [using silica gel as absorbent, under gradient elution of 10-18% EtOAc-DCM] to afford ~compound 10 [0.24 g, non polar spot; absolute stereo chemistry is unknown] as white floppy solid and ~compound 11 [0.15 g, polar spot; absolute stereochemistry is unknown]. We proceeded with both upper isomer and lower isomer separately however the absolute stereochemistry was unknown. Mass [ESI]: m/z 347.4 [M$^+$+1].

(3S,6S)-3-tert-Butoxycarbonylamino-1-methyl-4-oxo-1,2,3,4,6,7-hexahydro-[1,4]diazepino[3,2,1-hi]indole-6-carboxylic acid [Scheme-25, Step-9]: To a stirred solution of ~compound 10 [0.24 g, 0.69 mmol] in MeCN [2.7 mL] and DMF [1 mL] was added NMO [324 mg, 2.76 mmol] and TPAP [24.3 mg, 0.07 mmol] portion-wise at room temperature and stirred for 2 hour at room temperature. After completion [monitored by TLC and LC-MS] solvent was evaporated to dryness. Resultant crude was diluted with EtOAc [50 mL] and acidified with (1N) aqueous HCl. Organic part was separated, dried over anhydrous Na$_2$SO$_4$ and concentrated under reduced pressure to afford ~compound 12 [0.249 g, crude compound, absolute stereochemistry was unknown] as light brown floppy solid. Mass [ESI]: m/z 361.39 [M$^+$+1].

{(3S,6S)-1-Methyl-4-oxo-6-[(1H-[1,2,3]triazol-4-ylmethyl)-carbamoyl]-1,2,3,4,6,7-hexahydro-[1,4]diazepino[3,2,1-hi]indol-3-yl}-carbamic acid tert-butyl ester [Scheme-25, Step-10]: To a stirred solution of ~compound 12 [0.25 g, 0.69 mmol] in DMF [2.5 mL] was added HCl salt of Amine A [102 mg, 0.76 mmol], DIPEA [0.74 mL, 4.15 mmol] and BOP reagent [0.61 g, 1.38 mmol] at 0° C. and resultant reaction mixture was allowed to stir at room temperature for 16 hour. After completion [monitored by TLC and LC-MS], reaction mixture was partitioned between water [250 mL] and EtOAc [3×75 mL]. Organic layer was separated, washed with brine [50 mL], dried [MgSO$_4$] and concentrated under reduced pressure. Resultant crude was purified by column chromatography [under gradient elution of 50-70% EtOAc-hexane] to afford ~compound 14 [100 mg, 32.5%, absolute stereochemistry was unknown] as white solid. Mass [ESI]: m/z 441.48 [M$^+$+1].

Synthesis of (3S,6S)-3-Amino-1-methyl-4-oxo-1,2,3,4,6,7-hexahydro-[1,4]diazepino[3,2,1-hi]indole-6-carboxylic acid (1H-[1,2,3]triazol-4-ylmethyl)-amide [Scheme-25, Step-11]: To a stirred solution of compound 14 [100 mg, 0.227 mmol] in DCM [0.2 mL] was added TFA in DCM (1:1) [1 mL] at 0° C. under argon atmosphere. The resultant reaction mixture was allowed to stir at room temperature for 3 hour. After completion [monitored by LC-MS], reaction mixture was concentrated under reduced pressure, resultant residue was azeotroped with toluene to afford ~compound 16 [100 mg, crude TFA salt] as brown semi-solid. Mass [ESI]: m/z 341.36 [M$^+$+1].

Synthesis of (3S,6S)-3-{(2S,3S)-2-[2-(2-Fluoro-ethoxy)-acetylamino]-3-methyl-pentanoylamino}-1-methyl-4-oxo-1,2,3,4,6,7-hexahydro-[1,4]diazepino[3,2,1-hi]indole-6-carboxylic acid (1H-[1,2,3]triazol-4-ylmethyl)-amide [Scheme-25, Step-12]: To a stirred solution of ~compound 16 [TFA salt] [100 mg, 0.22 mmol] and acid A (51.64 mg, 0.22 mmol] in 1 mL DMF, was added DIPEA [0.197 mL, 1.09 mmol] followed by addition of BOP reagent [194 mg, 0.44 mmol] and resultant reaction mixture was allowed to stir at ambient temperature for 16 h. After completion [monitored by LC-MS], reaction mixture was submitted for reverse phase prep HPLC purification to afford 9 mg of C144-isomer1 [faster moving isomer] as white solid and 5.5 mg of C144-Isomer2 [slower moving isomer] as white solid. Though we have drawn (S, S) configuration here but the absolute stereochemistry was unknown. Mass [ESI]: m/z 558.60 [M$^+$+1].

Polar isomer isolated after step-8 was also forwarded following the same protocol and RP preparative HPLC purification provided two more isomers of C144 [5.9 mg (faster moving isomer i.e. isomer 3) and 1.2 mg (slower moving isomer i.e. isomer 4)].

Example 5: Evaluation of Compounds in Microsomal Stability Assay

Certain compounds of this disclosure were tested in the microsomal stability assay provided above. Results are shown in Table 7 below.

TABLE 7

Compounds Stability in Human Microsomes

| Compound | Name | $IC_{50}{}^a$ | $HLM^b$ % remaining @ 30 min |
|---|---|---|---|
| C003 | (2S,5S)-5-[(S)-2-(2-Benzo[b]thiophen-3-yl-acetylamino)-3-methyl-butyrylamino]-4-oxo-1,2,4,5,6,7-hexahydro-azepino[3,2,1-hi] indole-2-carboxylic acid (1H-[1,2,3]triazol-4-ylmethyl)-amide | ++++ | * |
| C006 | (2S,5S)-5-[(2S,3S)-2-(2-Benzo[b]thiophen-3-yl-acetylamino-3-methyl-pentanoylamino]-4-oxo-1,2,4,5,6,7-hexahydro-azepino[3,2,1hi]indole-2-carboxylic acid (1H-[1,2,3]triazol-4-ylmethyl)-amide | ++++ | * |
| C025 | (2S,5S)-5-((S)-2-Acetylamino-3-methyl-butyrylamino)-4-oxo-1,2,4,5,6,7-hexahydro-azepino[3,2,1-hi]indole-2-carboxylic acid (1H-[1,2,3]triazol-4-ylmethyl)-amide | ++++ | *** |
| C028 | (2S,5S)-5-((2S,3S)-2-Acetylamino-3-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide | ++++ | *** |
| C036 | (2S,5S)-5-((S)-2-Benzoylamino-3-methyl-butyrylamino)-4-oxo-1,2,4,5,6,7-hexahydro-azepino[3,2,1-hi]indole-2-carboxylic acid (1H-[1,2,3]triazol-4-ylmethyl)-amide | ++++ | *** |
| C039 | (2S,5S)-5-((2S,3S)-2-Benzoylamino-3-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide | ++++ | ** |
| C053 | (2S,5S)-5-((2S,3R)-2-Benzoylamino-3-methyl-pentanoylamino)-4-oxo-1,2,4,5,6,7-hexahydro-azepino[3,2,1-hi]indole-2-carboxylic acid (1H-[1,2,3]triazol-4-ylmethyl)-amide | ++++ | ** |
| C054 | (2S,5S)-5-[(2S,3R)-2-(2-Benzo[b]thiophen-3-yl-acetylamino)-3-methyl-pentanoylamino]-4-oxo-1,2,4,5,6,7-hexahydro-azepino[3,2,1-hi]indole-2-carboxylic acid (1H-[1,2,3]triazol-4-ylmethyl)-amide | ++++ | * |
| C056 | (2S,5S)-5-{(S)-2-[2-(2-Fluoro-ethoxy)-acetylamino]-3-methyl-butyrylamino}-4-oxo-1,2,4,5,6,7-hexahydro-azepino[3,2,1-hi]indole-2-carboxylic acid (1H-[1,2,3]triazol-4-ylmethyl)-amide | ++++ | *** |
| C057 | (2S,5S)-5-[(S)-2-(2-Fluoro-acetylamino)-3-methyl-butyrylamino]-4-oxo-1,2,4,5,6,7-hexahydro-azepino[3,2,1-hi]indole-2-carboxylic acid (1H-[1,2,3]triazol-4-ylmethyl)-amide | ++++ | *** |
| C058 | (2S,5S)-5-{(2S,3S)-2-[2-(2-Fluoro-ethoxy)-acetylamino]-3-methyl-pentanoylamino}-4-oxo-1,2,4,5,6,7-hexahydro-azepino[3,2,1-hi]indole-2-carboxylic acid(1H-[1,2,3]triazol-4-ylmethyl)-amide | ++++ | *** |
| C059 | (2S,5S)-5-[(2S,3S)-2-(2-Fluoro-acetylamino)-3-methyl-pentanoylamino]-4-oxo-1,2,4,5,5,6,7-hexahydro-azepino[3,2,1-hi]indole-2-carboxylic acid (1H-[1,2,3]triazol-4-ylmethyl)-amide | ++++ | *** |
| C096 | (1S,8S)-8-((2S,3S)-2-Benzoylamino-3-methyl-pentanoylamino)-9-oxo-1,2,8,9-tetrahydro-7H-6-oxa-9a-aza-benzo[cd]azulene-1-carboxylic acid (1H-[1,2,3]triazol-4-ylmethyl)-amide | ++++ | ** |
| C097 | (1S,8S)-8-((2S,3S)-2-Acetylamino-3-methyl-pentanoylamino)-9-oxo-1,2,8,9-tetrahydro-7H-6-oxa-9a-aza-benzo[cd]azulene-1-carboxylic acid (1H-[1,2,3]triazol-4-ylmethyl)-amide | ++++ | *** |
| C098 | (1S,8S)-8-[2S,3S)-2-(2-Fluoro-acetylamino)-3-methyl-pentanoylamino]-9-oxo-1,2,8,9-tetrahydro-7H-6-oxa-9a-aza-benzo[cd]azulene-1-carboxylic acid (1H-[1,2,3]triazol-4-ylmethyl)-amide | ++++ | *** |
| C099 | (1,S,8S)-8-{((2S,3S)-2-[2-(2-Fluoro-ethoxy)-acetylamino]-3-methyl-pentanoylamino}-9-oxo-1,2,8,9-tetrahydro-7H-6-oxa-9a-aza-benzo[cd]azulene-1-carboxylic acid (1H-[1,2,3]triazol-4-ylmethyl)-amide | ++++ | *** |
| C103 | (1S,8S)-8-{(S)-2-[2-(2-Fluoro-ethoxy)-acetylamino]-3-methyl-butyrylamino}-9-oxo-1,2,8,9-tetrahydro-7H-6-oxa-9a-aza-benzo[cd]azulene-1-carboxylic acid (1H-[1,2,3]triazol-4-ylmethyl)-amide | ++++ | *** |
| C140 | (2S,5S)-5-{(2S,3S)-2-[(6-Fluoro-pyridine-3-carbonyl)-amino]-3-methyl-pentanoylamino}-4-oxo-1,2,4,5,6,7-hexahydro-azepino[3,2,1-hi]indole-2-carboxylic acid (1H-[1,2,3]triazol-4-ylmethyl)-amide | ++++ | *** |
| C141 | (2S,5S)-5-{(2S,3S)-2-[(2-Fluoro-pyridine-4-carbonyl)-amino]-3-methyl-pentanoylamino}-4-oxo-1,2,4,5,6,7-hexahydro-azepino[3,2,1-hi]indole-2-carboxylic acid (1H-[1,2,3]triazol-4-ylmethyl)-amide | ++++ | *** |

$^a$The symbol "++++" indicates an $IC_{50}$ value of 0.001-0.300 μM.
$^b$HLM represents human liver microsomes; the symbol "*" indicates a remaining percentage of 71-100%, "" indicates a remaining percentage of 31-70%, and "*" indicates a remaining percentage of 0-30%.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A compound of Formula (I):

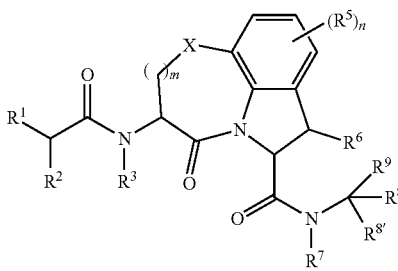

or a pharmaceutically acceptable salt thereof, or a stereoisomer or tautomer thereof,
wherein:
  m is 1;
  n is 1,2, or 3;
  $R^1$ is $NR^{10}R^{12}$, and at least one of $R^{10}$ and $R^{12}$ is —C(O)$C_{6-10}$ aryl, —C(O)$C_{6-10}$ cycloalkyl or —C(O)HET;
  $R^2$ is selected from the group consisting of: hydrogen, $C_{1-6}$ alkyl, $C_{1-6}$ alkoxy, $C_{3-6}$ cycloalkyl, $C_{6-10}$ aryl, HET and $NR^{10}R^{12}$, wherein each $C_{1-6}$ alkyl, $C_{1-6}$ alkoxy, $C_{3-6}$ cycloalkyl, are optionally substituted with 1, 2, or 3 substituents independently selected from the group consisting of halo and hydroxy, and $C_{6-10}$ aryl is optionally substituted with 1, 2, or 3 substituents independently selected from the group consisting of oxo, halo, hydroxy, $C_{1-4}$ alkyl and $C_{1-4}$ haloalkyl;
  each $R^3$ and $R^7$ is independently selected from the group consisting of hydrogen, $C_{1-4}$ alkyl and $C_{1-4}$ haloalkyl;
  X is $CH_2$;
  each $R^5$, $R^6$, $R^{8'}$ and $R^8$ is independently selected from the group consisting of hydrogen, halo, COOH, hydroxy, $OC_{1-4}$ alkyl, $C_{1-4}$ alkyl and $C_{1-4}$ haloalkyl;
  $R^9$ is 1,2,4-triazolyl, 1,2,3-triazolyl, or tetrazolyl;
  $R^{10}$ is selected from the group consisting of hydrogen, $C_{1-4}$ alkyl, —C(O)$C_{6-10}$ aryl, —C(O)$C_{6-10}$ cycloalkyl, —C(O)HET and —C(O)$C_{1-4}$ alkyl; wherein the $C_{1-4}$ alkyl is optionally substituted with 1, 2, or 3 halo groups; wherein the —C(O)$C_{1-4}$ alkyl is optionally substituted with 1, 2, or 3 substituents independently selected from the group consisting of halo, oxo, —N($R^{11}$)$_2$, HET, —O—$C_{1-4}$ alkyl and $C_{6-10}$ aryl; wherein the —O—$C_{1-4}$ alkyl is optionally substituted with 1, 2, or 3 substituents independently selected from the group consisting of halo, oxo, —N($R^{11}$)$_2$ and $C_{6-10}$ aryl; wherein the $C_{6-10}$ aryl is optionally substituted with 1, 2, or 3 halo groups and wherein the —C(O)$C_{6-10}$ aryl, and —C(O)$C_{6-10}$ cycloalkyl is optionally substituted with 1, 2, or 3 substituents independently selected from the group consisting of $C_{1-4}$ alkyl, $C_{1-4}$ haloalkyl, —O—$C_{1-4}$ alkyl, —O—$C_{1-4}$ haloalkyl and halo groups;
  each HET is independently a mono- or bicyclic 5-10-membered heteroaryl or a mono- or bicyclic 5-10 membered heterocycloalkyl group, wherein each HET comprises 1, 2, 3, or 4 heteroatoms selected from O, S and N and is optionally substituted with 1 or 2 substituents independently selected from the group consisting of $C_{1-4}$ alkyl, $C_{1-4}$ haloalkyl, —O—$C_{1-4}$ alkyl, —O—$C_{1-4}$ haloalkyl, halo, hydroxy and oxo groups;
  $R^{11}$ is selected from hydrogen, $C_{1-4}$ alkyl and $C_{1-4}$ haloalkyl; and
  $R^{12}$ is selected from the group consisting of $C_{1-4}$ alkyl, —C(O)$C_{6-10}$ aryl, —C(O)$C_{6-10}$ cycloalkyl, —C(O)HET and —C(O)$C_{1-4}$ alkyl; wherein the $C_{1-4}$ alkyl is substituted with 1, 2, or 3 halo groups; wherein the —C(O)$C_{1-4}$ alkyl is substituted with 1, 2, or 3 substituents independently selected from the group consisting of halo, —O—$C_{1-4}$ alkyl and $C_{6-10}$ aryl; wherein the —O—$C_{1-4}$ alkyl is substituted with 1, 2, or 3 halo; wherein the $C_{6-10}$ aryl is substituted with 1, 2, or 3 halo groups and wherein the —C(O)$C_{6-10}$ aryl, and —C(O)$C_{6-10}$ cycloalkyl is substituted with 1, 2, or 3 halo groups.

2. The compound of claim 1, wherein $R^2$ is $C_{1-6}$ alkyl.

3. The compound of claim 1, wherein each of $R^3$, $R^6$, $R^7$, $R^8$, and $R^{8'}$ is H.

4. The compound of claim 1, wherein $R^1$ is —$NR^{10}R^{12}$, and at least one of $R^{10}$ and $R^{12}$ is —C(O)$C_{6-10}$ aryl, —C(O)$C_{6-10}$ cycloalkyl, or —C(O)HET; $R^2$ is $C_{1-6}$ alkyl; each of $R^3$, $R^6$, $R^7$, $R^8$, and $R^{8'}$ is H; and $R^9$ is 1,2,4-triazolyl, 1,2,3-triazolyl, or tetrazolyl.

5. The compound of claim 4, wherein $R^1$ is $NR^{10}R^{12}$, in which $R^{10}$ is H and $R^{12}$ is —C(O)$C_{6-10}$ aryl or —C(O)HET.

6. The compound of claim 4, wherein $R^2$ is butyl.

7. The compound of claim 4, wherein $R^{10}$ is H and $R^{12}$ is —C(O)$C_{6-10}$ aryl, or —C(O)HET; $R^2$ is butyl; and $R^9$ is 1,2,4-triazolyl, 1,2,3-triazolyl, or tetrazolyl.

8. The compound of claim 7, wherein $R^2$ is

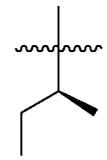

and $R^9$ is

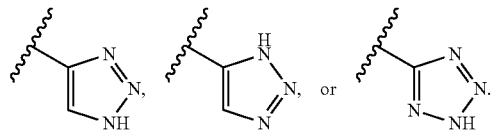 [SMILES: *c1c[nH]nn1 ; *c1cnn[nH]1 ; *c1nn[nH]n1]

9. The compound of claim 1, wherein the compound is:

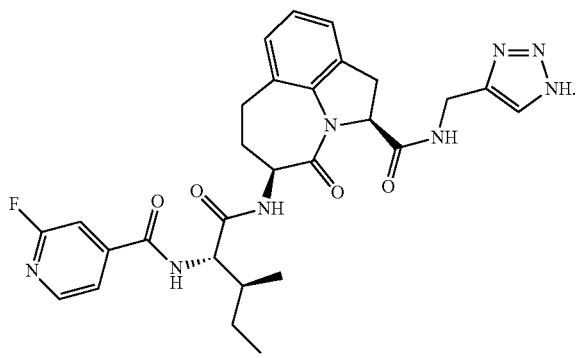 [SMILES: CC[C@H](C)[C@H](NC(=O)c1ccnc(F)c1)C(=O)N[C@H]1CCc2cccc3c2N(C1=O)[C@H](C(=O)NCc1c[nH]nn1)C3]

10. The compound according to claim 1, wherein at least one of $R^1$, $R^2$, and $R^5$ comprises fluorine or an isotope thereof.

11. The compound according to claim 10, wherein at least one of $R^1$, $R^2$, and $R^5$ comprises $^{18}F$.

12. A compound of or a pharmaceutically acceptable salt thereof, or a stereoisomer or tautomer thereof, wherein the compound is one of the following:

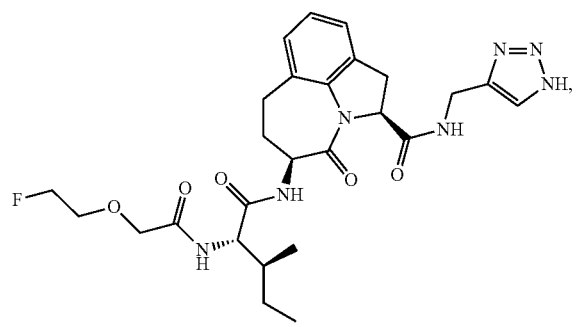

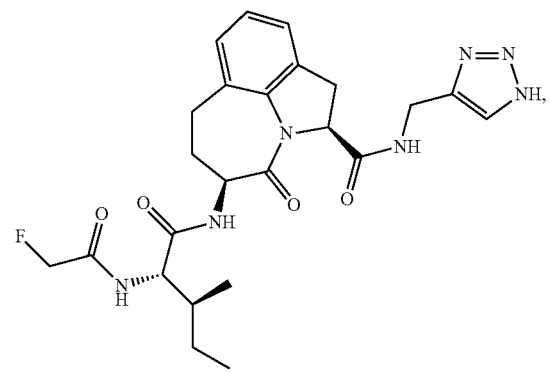

and

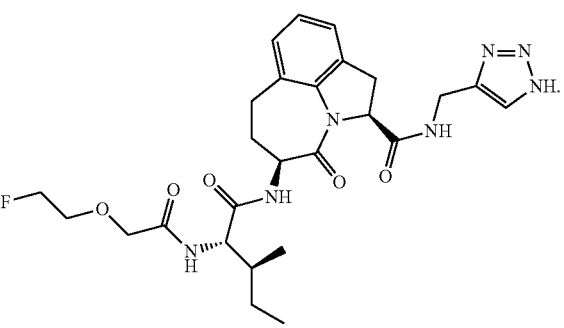

13. A pharmaceutical composition comprising a compound according to claim 1 and a pharmaceutically acceptable carrier.

14. A method for imaging Granzyme B in a subject in need thereof, the method comprising administering to said subject a compound according to claim 10 in an amount effective for imaging Granzyme B in the subject.

* * * * *